United States Patent
Arasappan et al.

(10) Patent No.: US 12,195,445 B2
(45) Date of Patent: Jan. 14, 2025

(54) 2-AMINO-N-HETEROARYL-NICOTINAMIDES AS $Na_v1.8$ INHIBITORS

(71) Applicant: Merck Sharp & Dohme LLC, Rahway, NJ (US)

(72) Inventors: Ashok Arasappan, Bridgewater, NJ (US); Ian M. Bell, Harleysville, PA (US); Michael J. Breslin, Drexel Hill, PA (US); Christopher James Bungard, Lansdale, PA (US); Christopher S. Burgey, Ambler, PA (US); Harry R. Chobanian, Westfield, NJ (US); Jason M. Cox, Rancho Santa Fe, CA (US); Anthony T. Ginnetti, Perkasie, PA (US); Deodial Guy Guiadeen, Chesterfield, NJ (US); Kristen L. G. Jones, Oreland, PA (US); Mark E. Layton, Harleysville, PA (US); Hong Liu, Hillsborough, NJ (US); Jian Liu, Norristown, PA (US); James J. Perkins, Churchville, PA (US); Shawn J. Stachel, Perkasie, PA (US); Linda M. Suen-Lai, Philadelphia, PA (US); Zhe Wu, Blue Bell, PA (US)

(73) Assignee: Merck Sharp & Dohme LLC, Rahway, NJ (US)

(*) Notice: Subject to any disclaimer, the term of this patent is extended or adjusted under 35 U.S.C. 154(b) by 0 days.

(21) Appl. No.: 17/752,419

(22) Filed: May 24, 2022

(65) Prior Publication Data
US 2022/0289710 A1 Sep. 15, 2022

Related U.S. Application Data

(62) Division of application No. 16/669,598, filed on Oct. 31, 2019, now Pat. No. 11,377,438.

(60) Provisional application No. 62/754,742, filed on Nov. 2, 2018.

(51) Int. Cl.
| | | |
|---|---|---|
| C07D 401/12 | (2006.01) | |
| C07D 401/14 | (2006.01) | |
| C07D 409/14 | (2006.01) | |
| C07D 413/14 | (2006.01) | |
| C07D 417/14 | (2006.01) | |
| C07D 471/04 | (2006.01) | |
| C07D 471/08 | (2006.01) | |
| C07D 487/04 | (2006.01) | |
| C07D 491/04 | (2006.01) | |
| C07D 491/048 | (2006.01) | |
| C07D 495/04 | (2006.01) | |

(52) U.S. Cl.
CPC ......... *C07D 401/12* (2013.01); *C07D 401/14* (2013.01); *C07D 409/14* (2013.01); *C07D 413/14* (2013.01); *C07D 417/14* (2013.01); *C07D 471/04* (2013.01); *C07D 471/08* (2013.01); *C07D 487/04* (2013.01); *C07D 491/04* (2013.01); *C07D 491/048* (2013.01); *C07D 495/04* (2013.01)

(58) Field of Classification Search
CPC .. C07D 401/12; C07D 401/14; C07D 413/14; C07D 409/14; C07D 471/04
USPC ....................................... 514/210.2
See application file for complete search history.

(56) References Cited

U.S. PATENT DOCUMENTS

| | | | |
|---|---|---|---|
| 8,202,877 B2 | 6/2012 | Maechling et al. | |
| 8,519,137 B2 | 8/2013 | Joshi et al. | |
| 8,703,768 B2 * | 4/2014 | Bleicher | C07D 417/14 |
| | | | 544/122 |
| 9,051,270 B2 | 6/2015 | Hadida-Ruah et al. | |

(Continued)

FOREIGN PATENT DOCUMENTS

| | | |
|---|---|---|
| BR | 112020000553 A2 | 7/2020 |
| EP | 3470404 A1 | 4/2019 |

(Continued)

OTHER PUBLICATIONS

Hanisak et al. Bioorganic and Medicinal Chemistry Letters (2016), 26(17), 4250-4255.*

(Continued)

*Primary Examiner* — Kahsay Habte
(74) *Attorney, Agent, or Firm* — Baerbel R. Brown; Catherine D. Fitch

(57) ABSTRACT

Novel compounds of the structural formula (I), and the pharmaceutically acceptable salts thereof, are inhibitors of $Na_v1.8$ channel activity and may be useful in the treatment, prevention, management, amelioration, control and suppression of diseases mediated by $Na_v1.8$ channel activity. The compounds of the present invention may be useful in the treatment, prevention or management of pain disorders, cough disorders, acute itch disorders, and chronic itch disorders.

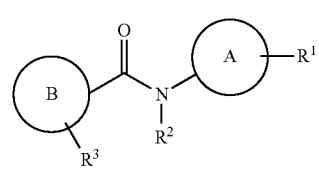

I

15 Claims, No Drawings

(56) References Cited

U.S. PATENT DOCUMENTS

| | | | |
|---|---|---|---|
| 9,108,903 | B2 | 8/2015 | Hadida-Ruah et al. |
| 9,163,042 | B2 | 10/2015 | Anderson et al. |
| 9,783,501 | B2 | 10/2017 | Tadida-Ruah et al. |
| 2007/0249579 | A1 | 10/2007 | Wang et al. |
| 2010/0298267 | A1 | 11/2010 | Maechling et al. |
| 2014/0213592 | A1 | 7/2014 | Chilov et al. |

FOREIGN PATENT DOCUMENTS

| | | | | |
|---|---|---|---|---|
| JP | | 6431779 | A | 2/1989 |
| JP | | 2008519034 | A | 6/2008 |
| JP | | 2012517966 | A | 8/2012 |
| JP | | 2017522346 | A | 8/2017 |
| JP | | 2017214290 | A | 12/2017 |
| JP | | 2020526561 | A | 8/2020 |
| WO | | 2005013914 | A2 | 2/2005 |
| WO | | 2006016316 | A1 | 2/2006 |
| WO | | 2006050476 | A2 | 5/2006 |
| WO | | 2007127635 | A2 | 11/2007 |
| WO | | 2009049180 | A2 | 4/2009 |
| WO | | 2009049181 | A1 | 4/2009 |
| WO | | 2009049183 | A1 | 4/2009 |
| WO | | 2010043315 | A1 | 4/2010 |
| WO | WO-2010043052 | A1 * | 4/2010 | ........... A61K 31/497 |
| WO | | 2010094406 | A1 | 8/2010 |
| WO | WO-2011043371 | A1 * | 4/2011 | ................ A61P 1/02 |
| WO | WO-2011154327 | A1 * | 12/2011 | ........... A61K 31/506 |
| WO | | 2012085650 | A1 | 6/2012 |
| WO | | 2013061205 | A2 | 5/2013 |
| WO | | 2014058691 | A1 | 4/2014 |
| WO | | 2014068988 | A1 | 5/2014 |
| WO | | 2014120808 | A1 | 8/2014 |
| WO | | 2014120815 | A1 | 8/2014 |
| WO | | 2014120820 | A1 | 8/2014 |
| WO | | 2014209841 | | 12/2014 |
| WO | | 2015010065 | A1 | 1/2015 |
| WO | | 2015089361 | A1 | 6/2015 |
| WO | | 2016016316 | A1 | 2/2016 |
| WO | | 2016039448 | A1 | 3/2016 |
| WO | | 2017209322 | A1 | 12/2017 |
| WO | | 2018050677 | A1 | 3/2018 |
| WO | | 2018213426 | A1 | 11/2018 |
| WO | | 2019014352 | A1 | 1/2019 |

OTHER PUBLICATIONS

Bagal, Sharan K. et al., Discovery and Optimization of Selective Nav1.8 Modulator Series That Demonstrate Efficacy in Preclinical Models of Pain, ACS Med. Chem. Lett., 2015, 650-654, 6.

Baker et al., Involvement of Na + Channels in Pain Pathways, Trends in Pharmacological Sciences, 2001, 27-31, 22, No. 1.

Bashford, Katherine E. et al., The Bohlmann-Rahtz route to functionalised pyridine scaffolds and their use in library synthesis, Tetrahedron Letters, 2003, 1627-1629, 44(8).

Belkouch, Mounir et al., Functional up-regulation of Nav1.8 sodium channel in Aβ afferent fibers subjected to chronic peripheral inflammation, Journal of Neuroinflammation, 2014, 1-17, 11:45.

Bennett, David L. et al., Painful and painless channelopathies, Lancet Neurol., 2014, 587-599, 13(6).

Black, Joel A. et a., Multiple Sodium Channel Isoforms and Mitogen-Activated Protein Kinases Are Present in Painful Human Neuromas, Ann Neurol, 2008, 644-653, 64(6).

Black, Joel A. et al., Sensory neuron-specific sodium channel SNS is abnormally expressed in the brains of mice with experimental allergic encephalomyelitis and humans with multiple sclerosis, Proc. Natl. Acad. Sci. USA, 2000, 11598-11602, 97(21).

Carter et al., Advances in the Management of Neuropathic Pain, Physical Medicine and Rehabilitation Clinics of North America, 2001, 447-459, 12(2).

Catterall, William A. et al., The chemical basis for electrical signaling, Nature Chemical Biology, 2017, 455-463, 13(5).

Colloca, Luana et al., Neuropathic pain, Nature Reviews Disease Primers, 2017, 1-19, 3:17002.

Coward, K et al., Immunolocalization of SNS/PN3 and NaN/SNS2 sodium channels in human pain states, Pain, 2000, 41-50, 85.

Emery, Edward C. et al., Novel SCN9A Mutations Underlying Extreme Pain Phenotypes: Unexpected Electrophysiological and Clinical Phenotype Correlations, Journal of Neuroscience, 2015, 7674-7681, 35(20).

Flaxman et al., Years Lived with Disability (YLDs) for 1160 Sequelae of 289 Diseases and Injuries 1990-2010: A Systematic Analysis for the Global Burden of Disease Study 2010, Lancet, 2012, 2163-2196, 380.

Goldin et al., Nomenclature of Voltage-Gated Sodium Channels, Neuron, 2000, 365-368, 28.

Goldin, Diveristy of Mammalian Voltage-Gated Sodium Channels, Ann NY Acad Sci., 1999, 38-50, 30, 868.

Han, Chongyang et al., The G1662S NaV1.8 mutation in small fibre neuropathy: impaired inactivation underlying DRG neuron hyperexcitability, J Neurol Neurosurg Psychiatry, 2014, 499-505, 85(5).

Han, Chongyang, et al., Sodium channel Nav1.8, Emerging links to human disease, Neurology, 2016, 473-483, 86.

Huang, Jianying et al., Small-Fiber Neuropathy Nav1.8 Mutation Shifts Activation to Hyperpolarized Potentials and Increases Excitability of Dorsal Root Ganglion Neurons, Journal of Neuroscience, 2013, 14087-14097, 33(35).

Ikoma et al., The Neurobiology of Itch, Nature Reviews, 2006, 535-547, 7.

Jarvis, Michael F. et al., A-803467, a potent and selective Nav1.8 sodium channel blocker, attenuates neuropathic and inflammatory pain in the rat, PNAS, 2007, 8520-8525, 104.

Kers, Inger et al., Structure and activity relationship in the (S)-N-chroman-3-ylcarboxamide series of voltage-gated sodium channel blockers, Bioorganic & Medicinal Chemistry Letters, 2012, 5618-5624, 22(17).

Kist, Andreas M. et al., SCN10A Mutation in a Patient with Erythromelalgia Enhances C-Fiber Activity Dependent Slowing, PLOS One, 2016, pp. 1-19, 11(9):e0161789.

Kort, Michael E. et al., Discovery and Biological Evaluation of 5-Aryl-2-furfuramides, Potent and Selective Blockers of the Nav1.8 Sodium Channel with Efficacy in Models of Neuropathic and Inflammatory Pain, J. Med. Chem., 2008, 407-416, 51.

Liu, Yang et al., VGLUT2-Dependent Glutamate Release from Nociceptors Is Required to Sense Pain and Suppress Itch, Neuron, 2010, 543-556, 68(3).

Luo, Jialie et al., Molecular and cellular mechanisms that initiate pain and itch, Cellular and Molecular Life Sciences, 2015, 3201-3223, 72.

McGaraughty, Steve et al., A Selective Nav1.8 Sodium Channel Blocker, A-803467 [5-(4-Chlorophenyl-N-(3,5-dimethoxyphenyl)furan-2-carboxamide], Attenuates Spinal Neuronal Activity in Neuropathic Rats, JPET, 2008, 1204-1211, 324.

McMahon et al., Itching for an Explanation, Trends Neuroscience, 1992, 497-501, 15.

Miyazaki, Tohru et al., Discovery of novel 4-phenyl-2-(pyrrolidinyl)nicotinamide derivatives as potent Nav1.1 activators, Bioorganic & Medicinal Chemistry Letters, 2019, 815-820, 29(23).

Nair, Parameswaran et al., Airway Hyperresponsiveness in Asthma: Measurement and Clinical Relevance, J Allergy Clin Immunol Pract, 2017, 649-659, 5(3).

Notification of Transmittal of the International Search Report and the Written Opinion of the International Searching Authority, or the Declaration, mailed Feb. 3, 2020, 7 pages.

Payne, Claire Elizabeth et al., A novel selective and orally bioavailable NAv1.8 channel blocker, PF-01247324, attenuates nociception and sensory neuron excitability, British Journal of Pharmacology, 2015, 2654-2670, 172.

Riol-Blanco, Lorena et al., Nociceptive sensory neurons drive interleukin-23-mediated psoriasiform skin inflammation, Nature, 2014, 157-161, 510.

Roostaei, Tina et al., Channelopathy-related SCN10A gene variants predict cerebellar dysfunction in multiple sclerosis, Neurology, 2016, 410-417, 86(5).

(56) References Cited

OTHER PUBLICATIONS

Schmelz et al., Specific C-Receptors for Itch in Human Skin, J. of Neuroscience, 1997, 8003-8008, 17(20).
Schreiber, Anne K. et al., Diabetic neuropathic pain: Physiopathology and treatment, World Journal of Diabetes, 2015, 432-444, 6(3).
Shields, Shannon D. et al., A Channelopathy Contributes to Cerebellar Dysfunction in a Model of Multiple Sclerosis, Ann Neurol, 2012, 186-194, 71(2).
Shields, Shannon D. et al., Oral Administration of PF-01247324, a Subtype-Selective Nav1.8 Blocker, Reverses Cerebellar Deficits in a Mouse Model of Multiple Sclerosis, PLoS One, 2015, 1-8, 10(3).
Sun, Shaoyi et al., The discovery of benzenesulfonamide-based potent and selective inhibitors of voltage-gated sodium channel Nav1.7, Bioorganic & Medicinal Chemistry Letters, 2014, 4397-4401, 24(18).
Talbot, Sebastien et al., Silencing Nociceptor Neurons Reduces Allergic Airway Inflammation, Neuron, 2015, 341-354, 87(2).
Van Loey et al., Itching Following Burns: Epidemiology and Predictors, British J. Dermatology, 2008, 95-100, 158.
Wood, John N et al., Voltage-gated sodium channels, Current Opinion in Pharmacolgoy, 2001, 17-21, 1.
Yiangou, Y. et al., SNS/PN3 and SNS2/NaN sodium channel-like immunoreactivity in human adult and neonate injured sensory nerves, FEBS Letters, 2000, 249-252, 467.
Yu et al., Overview of the Voltage-Gated Sodium Channel Family, Genome Biology, 2003, 207, 4.
Zeng, Chao et al., Relative efficacy and safety of topical non-steroidal anti-inflammatory drugs for osteoarthritis: a systematic review and network meta-analysis of randomised controlled trials and observational studies, Br J Sports Med, 2018, 642-650, 52.
Zhang, Xu-Feng et al., A-887826 is a structurally novel, potent and voltage-dependent Nav1.8 sodium channel blocker that attenuates neuropathic tactile allodynia in rats, Neuropharmacology, 2010, 201-207, 59.
Meurice, Nathalie et al., Structural Conservation in Band 4.1, Ezrin, Radixin, Moesin (FERM) Domains as a Guide to Identify Inhibitors of the Proline-Rich Tyrosine Kinase 2, J. Med. Chem., 2010, 669-677, 53.
Meurice, Nathalie et al., Supporting Information—Structural conservation in FERM domains as a guide to identify inhibitors of the focal adhesion kinase Pyk2, Journal of Medicinal Chemistry, 2010, S1-S18, 53.
Vlaar, Cornelis P. et al., Design, synthesis and biological evaluation of new carbazole derivatives as anti-cancer and anti-migratory agents, Bioorganic & Medicinal Chemistry Letters, 2018, 884-890, 26.
CAS RN. 1022814-74-9 (May 27, 2008 Entered STN), 1 page.
Camille G. Wermuth, Molecular Variations Based on Isosteric Replacements, The Practice of Medicinal Chemistry, Chapter 13, 189-214, 2003.
RN-2176589-55-0 dated Feb. 20, 2018, RN-2186126-31-6 dated Mar. 7, 2018, RN-2190063-54-6 dated Mar. 13, 2018, RN-2209817-54-7 dated Apr. 10, 2018, RN-2061218-61-7 dated Jan. 29, 2017 (3 pages).
Search result of STN:RN 21753353-22-5 dated Feb. 18, 2018, RN 2175797-30-3 dated Feb. 19, 2018, RN 2176276-62-1 dated Feb. 19, 2018, RN 2177313-40-3 dated Feb. 21, 2018, RN 2177393-26-7 dated Feb. 21, 2018, RN 1192603-96-5 dated Nov. 17, 2009, RN 1416243-57-6 dated Jan. 9, 2013, RN 1427851-84-0 dated Apr. 10, 2013, RN 1427851-94-2 dated Apr. 10, 2013, RN 1427851-98-6 dated Apr. 10, 2013, RN 1801148-86-6 dated Jul. 31, 2015 (6 pages).

\* cited by examiner

2-AMINO-N-HETEROARYL-NICOTINAMIDES AS $Na_v1.8$ INHIBITORS

CROSS-REFERENCE TO RELATED APPLICATIONS

This patent application is a Divisional Application of U.S. patent application Ser. No. 16/669,598, which claims priority from and the benefit of U.S. Provisional Application No. 62/754,742, filed Nov. 2, 2018.

BACKGROUND OF THE INVENTION

Voltage-gated sodium channels (VGSC) mediate the selective influx of sodium ions in excitable cells and play a central role in initiating and propagating action potentials (Yu et al., Genome Biology 4:207 (2003)). Voltage-gated sodium channels are ubiquitous in the central and peripheral nervous system where they play a central role in the initiation and propagation of action potentials, and also in skeletal and cardiac muscle where the action potential triggers cellular contraction (Goldin et al., Ann N Y Acad Sci. 1999 Apr. 30; 868:38-50). Alterations in VGSC function or their expression can profoundly affect normal cell excitability (Huang et al., J Neurosci. 2013 Aug. 28; 33 (35):14087-97; Emery et al., J Neurosci. 2015 May 20; 35(20):7674-81; Kist et al., PLoS One. 2016 Sep. 6; 11(9):e0161789; and Schreiber et al., World J Diabetes. 2015 Apr. 15; 6(3):432-44).

Voltage-gated sodium channels are multimeric complexes characterized by one α-subunit, which forms an ion-conducting aqueous pore, and at least one β-subunit that modifies the kinetics and voltage-dependence of the channel gating. Nine different α-subunits have been identified and characterized in mammalian voltage-gated sodium channels, including $Na_v1.8$, also known as SNS, PN3 or $Na_v1.8$ (Goldin et al., Neuron. 2000 November; 28 (2):365-8).

Expression of sodium channels can be tissue specific. $Na_v1.8$ voltage-gated sodium ion channels are expressed primarily in sensory neurons, which are responsible for conveying information from the periphery (e.g. skin, muscle and joints) to the central nervous system via the spinal cord. Sodium channels are integral to this process as sodium channel activity is required for initiation and propagation of action potentials triggered by noxious stimuli (thermal, mechanical and chemical) activating peripheral nociceptors (Catterall et al., Nat Chem Biol. 2017 Apr. 13; 13(5):455-463). An increase in VGSC protein level at the cell surface or an alteration in activity of the VGSC channels can result in disease states such as migraine, neurodegeneration following ischemia, epilepsies, and chronic neuropathic and inflammatory pain states. Gain of function mutations in Nav1.7, Nav1.8, and Nav1.9 manifest in a variety of pain syndromes where patients experience spontaneous pain without an external stimulus (Bennett et al., Lancet Neurol. 2014 June; 13(6):587-99; Huang et al., J Neurosci. 2013 Aug. 28; 33(35):14087-97; Kist et al., PLoS One. 2016 Sep. 6; 11(9):e0161789; Emery et al., J Neurosci. 2015 May 20; 35(20):7674-81; and Schreiber et al., World J Diabetes. 2015 Apr. 15; 6(3):432-44).

$Na_v1.8$ voltage-gated sodium ion channels are believed to play a role in various maladies, including neuropathic pain, chronic itch, and inflammatory pain perception (Belkouch et al., J Neuroinflammation. 2014 Mar. 7; 11:45; Coward et al., Pain. 2000 March; 85(1-2):41-50; Yiangou et al., FEBS Lett. 2000 Feb. 11; 467(2-3):249-52; Black et al., Ann Neurol. 2008 December; 64(6):644-53; Bird et al., Br J Pharmacol. 2015 May; 172(10):2654-70; Liu et al., Neuron. 2010 Nov. 4; 68(3):543-56; and Zhao et al., J Clin Invest. 2013).

Large portions of the voltage gated sodium ion channels are conserved among the various subtypes, therefore there is a potential for producing serious side effects when utilizing therapeutic agents that do not demonstrate subtype selectivity. Therefore, therapeutic agents suitable for use in addressing nociception, cough, or itch disorders, require specificity in their action, for example, discriminating between action upon $Na_v1.5$ sodium ion channels, thought to be important in regulation of cardiac function, and action upon $Na_v1.8$ sodium ion channels, thought to be central in inflammatory nociception, or itch and disorders arising from dysfunctional and/or upregulated $Na_v1.8$ sodium ion channels.

Accordingly, it is believed that inhibitors of $Na_v1.8$ voltage-gated sodium ion channel activity may useful to treat or prevent diseases, disorders and conditions involving $Na_v1.8$ receptors and/or stemming specifically from dysfunction of $Na_v1.8$ voltage-gated sodium ion channels (Han et al., J Neurol Neurosurg Psychiatry 2014 May; 85(5):499-505), including but not limited to, migraine, neurodegeneration following ischemia, epilepsy, inflammatory pain, spontaneous pain, acute pain, preoperative pain, perioperative pain, post-operative pain, neuropathic pain, chronic itch, and itch disorders.

There remains a need for potent $Na_v1.8$ sodium ion channel activity inhibitors with selective activity for $Na_v1.8$ sodium ion channels. As a result, the compounds of the present invention are useful for the treatment and prevention of diseases, disorders and conditions involving $Na_v1.8$ receptors and $Na_v1.8$ voltage-gated sodium ion channels.

The role of Nav1.8 sodium ion channels is discussed in: Bennett et al., Physical Medicine and Rehabilitation Clinics of North America, 2001, 12(2):447-459; Meissner et al., Br J Sports Med. 2018 May; 52(10):642-650; Legroux-Crespel et al., Neurology. 2016 Feb. 2; 86(5):473-83; and Flaxman et al., Lancet, 380:2163-2196 (2012).

Compounds useful to treat $Na_v1.8$ sodium ion channel related conditions are disclosed in: ACS Med. Chem. Lett. 2015, 6, 650; BJP 2015, 172, 2654; PNAS 2007, 104, 8520; J. Med. Chem. 2008, 51, 407; JPET 2008, 324, 1204; and Neuropharmacology 2010, 59, 201.

$Na_v1.8$ compounds are also disclosed in: WO 2009/049180, WO 2009/049181, WO 2009/049183, WO 2014/120808; WO 2014/120815; WO 2014/120820; WO 2015/010065; and WO 2015/089361; WO 2017/209322; U.S. Pat. Nos. 8,519,137; 9,051,270; 9,108,903; 9,163,042; and 9,783,501.

SUMMARY OF THE INVENTION

The present invention relates to novel compounds of structural formula I:

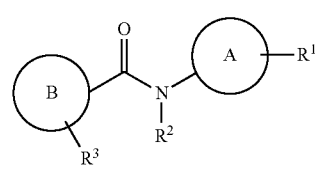

and pharmaceutically acceptable salts thereof. The compounds of structural formula I, and embodiments thereof, are inhibitors of $Na_v1.8$ sodium ion channel activity (or $Na_v1.8$ inhibitors) and may be useful in the treatment and prevention of diseases, disorders and conditions mediated by $Na_v1.8$ sodium ion channel activity, such as nociception, osteoarthritis, peripheral neuropathy, inherited erythromelalgia, multiple sclerosis, asthma, itch, atopy, allergic or contact dermatitis, renal failure, cholestasis, pruritus, acute itch, chronic itch, migraine, neurodegeneration following ischemia, epilepsy, pain, inflammatory pain, spontaneous pain, acute pain, acute pain due to fractures, musculoskeletal damage, pancreatitis and renal colic, peri-operative pain, post-operative pain, neuropathic pain, postherpetic neuralgia, trigeminal neuralgia, diabetic neuropathy, chronic lower back pain, phantom limb pain, sciatica, pain caused by 2° or 3° burn injury, optic neuritis, pain resulting from cancer and chemotherapy, chronic pelvic pain, pain syndromes, and complex regional pain syndromes. In one embodiment of the present invention, the condition, disease or disorder is a pain disorder, an acute pain disorder or chronic pain disorder. In another embodiment of the present invention, the condition, disease or disorder is an acute pain disorder.

The present invention also relates to pharmaceutical compositions comprising the compounds of the present invention and a pharmaceutically acceptable carrier.

The present invention also relates to methods for the treatment, management, prevention, alleviation, amelioration, suppression or control of disorders, diseases, and conditions that may be responsive to inhibition of $Na_v1.8$ sodium ion channel activity in a subject in need thereof by administering the compounds and pharmaceutical compositions of the present invention.

The present invention also relates to the use of compounds of the present invention for manufacture of a medicament useful in treating diseases, disorders and conditions that may be responsive to the inhibition of $Na_v1.8$ sodium ion channel activity.

The present invention is also concerned with treatment or prevention of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

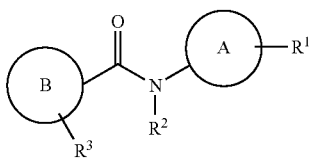

I or a pharmaceutically acceptable salt thereof, wherein
A is heteroaryl or heteroaryl fused to a saturated or unsaturated 5- or 6-membered ring containing 0-3 heteroatoms independently selected from O, S and $N(R^h)_q$, wherein each heteroaryl, 5-membered ring and 6-membered ring is unsubstituted or substituted with one to five substituents selected from $R^a$;
B is heteroaryl, wherein heteroaryl is unsubstituted or substituted with one to three substituents selected from $R^b$;
$R^1$ is selected from the group consisting of:

(1) hydrogen,
(2) —$SO_3H$,
(3) —$SO_2NH_2$,
(4) —$SO_2NR^eC_{1-6}$alkyl,
(5) —$SO_2NR^eC(O)C_{1-6}$alkyl,
(6) —$SO_2NR^eC_{2-6}$alkenyl,
(7) —$SO_2NR^eC_{3-6}$cycloalkyl,
(8) —$SO_2NR^eC(O)C_{3-6}$cycloalkyl,
(9) —$SO_2NR^eC_{2-6}$cycloheteroalkyl,
(10) —$SO_2NR^eC(O)C_{2-6}$cycloheteroalkyl,
(11) —$SO_2NR^e$-aryl,
(12) —$SO_2NR^e$-heteroaryl,
(13) —$SO_2C_{1-6}$alkyl,
(14) —$SO_2C_{1-6}$alkenyl,
(15) —$SO_2C_{3-6}$cycloalkyl,
(16) —$SO_2C_{2-6}$cycloheteroalkyl,
(17) —$SO_2$aryl,
(18) —$SO_2$heteroaryl,
(19) —$S(O)R^j$,
(20) —$SR^j$,
(21) —$C(O)NH_2$,
(22) —$C(O)NR^eR^j$,
(23) —$CO_2H$,
(24) —$CO_2R^j$,
(25) —$C(O)R^j$,
(26) —CN,
(27) $CF_3$,
(28) halogen,
(29) —OH,
(30) —$OC_{1-6}$alkyl,
(31) —$OC_{2-6}$alkenyl,
(32) —$OC_{3-6}$cycloalkyl,
(33) —$OC_{2-6}$cycloheteroalkyl,
(34) —O-aryl,
(35) —O-heteroaryl,
(36) —$OC(O)R^j$,
(37) —$OC(O)NR^eR^j$,
(38) —$OC(O)N(R^j)_2$,
(39) —$C_{1-6}$alkyl,
(40) —$C_{2-6}$alkenyl,
(41) —$C_{1-6}$cycloalkyl,
(42) —$C_{2-6}$cycloheteroalkyl,
(43) aryl,
(44) heteroaryl,
(45) —$(CH_2)_nNR^eC(O)R^j$,
(46) —$(CH_2)_nNR^eC(O)OR^j$,
(47) —$(CH_2)_nNR^eC(O)N(R^e)_2$,
(48) —$(CH_2)_nNR^eC(O)NR^eR^j$,
(49) —$(CH_2)_nNR^eC(O)N(R^j)_2$,
(50) —$(CH_2)_nNR^eS(O)_mR^j$,
(51) —$(CH_2)_nNR^eS(O)_mN(R^e)_2$,
(52) —$(CH_2)_nNR^eS(O)_mNR^eR^j$,
(53) —$(CH_2)_nNR^eS(O)_mN(R^j)_2$, and
(54) —$(CH_2)_nNR^eR^j$, wherein each $CH_2$, alkyl, alkenyl, cycloalkyl, cycloheteroalkyl, aryl and heteroaryl is unsubstituted or substituted with one to four substituents selected from $R^d$;
$R^2$ is selected from the group consisting of:
 1) hydrogen, and
 2) —$C_{1-6}$alkyl;
$R^3$ is selected from the group consisting of:
 1) a monocyclic, bicyclic or spirocyclic $C_{3-12}$cycloalkyl ring, and
 2) a monocyclic, bicyclic or spirocyclic $C_{2-12}$cycloheteroalkyl ring,
wherein the cycloheteroalkyl contains 1-4 heteroatoms independently selected from $N(R^m)_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to eight substituents selected from $R^e$;
each $R^a$ is selected from the group consisting of:
- (1) —$C_{1-6}$alkyl,
- (2) —$OC_{1-6}$alkyl,
- (3) halogen,
- (4) —OH,
- (5) oxo,
- (6) —CN,
- (7) —$C_{3-6}$cycloalkyl, and
- (8) —$C_{2-5}$cycloheteroalkyl, wherein each alkyl, cycloalkyl and cycloheteroalkyl is unsubstituted or substituted with one to six substituents selected from halogen, OH, $NH_2$, $NH(C_{1-6}alkyl)$ and $N(C_{1-6}alkyl)_2$;
each $R^b$ is independently selected from the group consisting of:
- (1) —$CF_3$,
- (2) —$CF_2CF_3$;
- (3) —$CHF_2$,
- (4) —$OCHF_2$,
- (5) —$OCH_2CF_3$,
- (6) —$OCF_3$,
- (7) CN,
- (8) halogen,
- (9) —$Si(C_{1-6}alkyl)_3$,
- (10) —$C_{1-6}$alkyl-O—$R^k$,
- (11) —$C_{1-6}$alkyl,
- (12) —$C_{2-6}$alkenyl,
- (13) —$C_{2-6}$alkynyl,
- (14) —$C_{3-6}$cycloalkyl,
- (15) —$C_{2-6}$cycloheteroalkyl,
- (16) aryl,
- (17) heteroaryl,
- (18) —$C_{1-6}$alkyl-$C_{3-6}$cycloalkyl,
- (19) —$C_{1-6}$alkyl-$C_{2-6}$cycloheteroalkyl,
- (20) —$C_{1-6}$alkyl-aryl,
- (21) —$C_{1-6}$alkyl-heteroaryl,
- (22) —$C_{2-6}$alkenyl-$C_{3-6}$cycloalkyl,
- (23) —$C_{2-6}$alkenyl-$C_{2-6}$cycloheteroalkyl,
- (24) —$C_{2-6}$alkenyl-aryl,
- (25) —$C_{2-6}$alkenyl-heteroaryl,
- (26) —$C_{2-6}$alkynyl-$C_{3-6}$cycloalkyl,
- (27) —$C_{2-6}$alkynyl cycloheteroalkyl,
- (28) —$C_{2-6}$alkynyl-aryl,
- (29) —$C_{2-6}$alkynyl-heteroaryl,
- (30) $NO_2$,
- (31) —OH,
- (32) —$(CH_2)_p$—$OC_{1-6}$alkyl,
- (33) —$(CH_2)_p$—$OC_{2-6}$alkenyl,
- (34) —$(CH_2)_p$—$OC_{2-6}$alkynyl,
- (35) —$(CH_2)_p$—$OC_{3-6}$cycloalkyl,
- (36) —$(CH_2)_p$—$OC_{2-6}$heterocycloalkyl,
- (37) —$(CH_2)_p$—O-aryl,
- (38) —$(CH_2)_p$—O-heteroaryl,
- (39) —$OC_{1-6}$alkyl-$C_{3-6}$cycloalkyl,
- (40) —$OC_{1-6}$alkyl-$C_{2-6}$heterocycloalkyl,
- (41) —$OC_{1-6}$alkyl-aryl,
- (42) —$OC_{1-6}$alkyl-heteroaryl,
- (55) —$S(O)_mR^k$,
- (43) —$C_{1-6}$alkyl-$S(O)_mR^k$,
- (44) —$C(O)R^k$,
- (45) —$N(R^j)_2$, and
- (46) —$NR^jR^k$, wherein each $R^b$ is unsubstituted or substituted with one to five substituents selected from $R^f$;
each $R^c$ is independently selected from the group consisting of:
- (1) —$CF_3$,
- (2) —$CH_2CF_3$,
- (3) —$CHF_2$,
- (4) —$OCHF_2$,
- (5) —$OCF_3$,
- (6) CN,
- (7) oxo,
- (8) —OH,
- (9) halogen,
- (10) —$C_{1-6}$alkyl,
- (11) —$C_{2-6}$alkenyl,
- (12) —$C_{2-6}$alkynyl,
- (13) —$C_{3-6}$cycloalkyl,
- (14) —$C_{2-6}$cycloheteroalkyl,
- (15) —$C_{1-6}$alkyl-$C_{3-6}$cycloalkyl,
- (16) —$C_{1-6}$alkyl-$C_{2-6}$cycloheteroalkyl,
- (17) —$C_{1-6}$alkyl-aryl,
- (18) —$C_{1-6}$alkyl-heteroaryl,
- (19) —$C_{1-6}$alkenyl-$C_{3-6}$cycloalkyl,
- (20) —$C_{1-6}$alkenyl-aryl,
- (21) —$C_{1-6}$alkenyl heteroaryl,
- (22) —$C_{1-6}$alkenyl-$C_{2-6}$cycloheteroalkyl,
- (23) —$C_{2-6}$alkynyl-$C_{3-6}$cycloalkyl,
- (24) —$C_{2-6}$alkynyl-$C_{2-6}$cycloheteroalkyl,
- (25) —$C_{2-6}$alkynyl-aryl,
- (26) —$C_{2-6}$alkynyl heteroaryl,
- (27) —$OC_{1-6}$alkyl,
- (28) —$OC_{2-6}$ alkenyl,
- (29) —$OC_{2-6}$ alkynyl,
- (30) —$OC_{3-6}$ cycloalkyl,
- (31) —$OC_{2-6}$heterocycloalkyl,
- (32) —O-aryl,
- (33) —O-heteroaryl,
- (34) —$OC_{1-6}$alkyl-cycloalkyl,
- (35) —$OC_{1-6}$alkyl-cycloheteroalkyl,
- (36) —$OC_{1-6}$alkyl-aryl,
- (37) —$OC_{1-6}$ alkyl-heteroaryl,
- (38) —$S(O)_mR^L$,
- (39) —$S(O)R^L$,
- (40) —S—$R^L$,
- (41) —$C_{1-6}$alkyl-$S(O)_mR^L$,
- (42) —$C(O)R^L$,
- (43) —$C(O)C_{1-6}$alkyl-$R^L$,
- (44) —$OC(O)R^L$,
- (45) —$CO_2R^L$,
- (46) aryl, and
- (47) heteroaryl, wherein each $R^c$ is unsubstituted or substituted with one to five substituents selected from $R^g$;
$R^d$ is independently selected from the group consisting of:
- (1) hydrogen,
- (2) halogen,
- (3) OH,
- (4) oxo,
- (5) —$C_{1-6}$alkyl,
- (6) —$OC_{1-6}$alkyl,
- (7) $NH_2$,
- (8) $NH(C_{1-6}alkyl)$, and
- (9) $N(C_{1-6}alkyl)_2$;

each $R^e$ is independently selected from the group consisting of:
  (1) hydrogen,
  (2) —$C_{1-6}$alkyl, and
  (3) $C_{2-6}$alkenyl;
each $R^f$ is selected from the group consisting of:
  (1) halogen, F
  (2) —$C_{1-6}$alkyl,
  (3) —OH,
  (4) —$OC_{1-6}$alkyl,
  (5) —$OC_{3-6}$cycloalkyl,
  (6) —$OC_{2-6}$cycloheteroalkyl,
  (7) CN,
  (8) —$NH_2$,
  (9) —NH($C_{1-6}$alkyl),
  (10) —NH($C_{3-6}$cycloalkyl),
  (11) —NH($C_{2-6}$cycloheteroalkyl),
  (12) —N($C_{1-6}$alkyl)$_2$,
  (13) —N($C_{3-6}$cycloalkyl)$_2$, and
  (14) —N($C_{2-6}$cycloheteroalkyl)$_2$,
wherein each alkyl, cycloalkyl, and cycloheteroalkyl is unsubstituted or substituted with one to three substituents independently selected from: —OH, halogen, cyano, and —$S(O)_2CH_3$;
each $R^g$ is selected from the group consisting of:
  (1) halogen,
  (2) $C_{1-6}$alkyl,
  (3) —OH,
  (4) —$OC_{1-6}$alkyl,
  (5) —$S(O)_m$—$C_{1-6}$alkyl,
  (6) —CN,
  (7) —$CF_3$,
  (8) —$OCHF_2$, and
  (9) —$OCF_3$,
wherein each alkyl is unsubstituted or substituted with one to three substituents independently selected from: —OH, halogen, cyano, and —$S(O)_2CH_3$;
each $R^h$ is independently selected from the group consisting of:
  (1) hydrogen, and
  (2) —$C_{1-6}$alkyl;
each $R^i$ is independently selected from the group consisting of:
  (1) hydrogen, and
  (2) —$C_{1-6}$alkyl;
each $R^j$ is selected from the group consisting of:
  (1) —$C_{1-6}$alkyl,
  (2) —$C_{2-6}$alkenyl,
  (3) —$C_{3-6}$cycloalkyl,
  (4) —$C_{2-6}$cycloheteroalkyl,
  (5) aryl, and
  (6) heteroaryl,
wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$;
each $R^k$ is selected from the group consisting of:
  (1) —$C_{1-6}$alkyl,
  (2) —$C_{2-6}$alkenyl,
  (3) —$C_{3-6}$cycloalkyl,
  (4) —$C_{3-6}$cycloalkyl,
  (5) —$C_{2-6}$cycloheteroalkyl,
  (6) aryl, and
  (7) heteroaryl,
wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$;
each $R^L$ is selected from the group consisting of:
  (1) —$C_{1-6}$alkyl,
  (2) —$C_{2-6}$alkenyl,
  (3) —$C_{3-6}$cycloalkyl,
  (4) —$C_{2-6}$cycloheteroalkyl,
  (5) aryl, and
  (6) heteroaryl,
wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$;
each $R^m$ is independently selected from the group consisting of:
  (1) hydrogen, and
  (2) —$C_{1-6}$alkyl;
each n is independently 0, 1, 2, 3 or 4;
each m is independently 0, 1 or 2;
each p is independently 0, 1, 2, 3 or 4;
each q is independently 0 or 1; and
each r is independently 0 or 1.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, A is heteroaryl or heteroaryl fused to a saturated or unsaturated 5- or 6-membered ring containing 0-3 heteroatoms independently selected from O, S and $N(R^h)_q$, wherein each heteroaryl, 5-membered ring and 6-membered ring is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment of the present invention, A is heteroaryl or heteroaryl fused to a saturated or unsaturated 5- or 6-membered ring containing 0-3 heteroatoms independently selected from O, S and $N(R^h)_q$, wherein each heteroaryl, 5-membered ring and 6-membered ring is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is heteroaryl, wherein heteroaryl is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is selected from the group consisting of: pyridine, pyrimidine, pyrazine, pyridazine, indazole, imidazo[1,2-a]pyridine, 1,3-dihydro-2H-imidazo[4,5-b]pyridin-2-one, 1H-[1,2,3]triazolo[4,5-b]pyridine, 1H-pyrazolo[4,3-b]pyridine, pyrrolo[3,2-c]pyridine, pyrrolo[2,3-b]pyridine, benzimidazole, imidazole, pyrazole, thiophene, furan, 1,2,4-oxadiazole, 1,3,4-oxadiazole, oxazole, isoxazole, isothiazole, thiazole, 1,2,4-thiadiazole, 1,3,4-thiadiazole, 4H-pyrido[2,3-e][1,2,4]thiadiazine 1,1-dioxide, 2H-pyrido[2,3-e][1,2]thiazine 1,1-dioxide, 2,3-dihydroisothiazolo[4,5-b]pyridine 1,1-dioxide, and 3,4-dihydro-2H-pyrido[2,3-e][1,2]thiazine 1,1-dioxide, wherein A is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is selected from the group consisting of: pyridine, pyrimidine, pyrazine, pyridazine, indazole, imidazo[1,2-a]pyridine, pyrrolo[3,2-c]pyridine, pyrrolo[2,3-b]pyridine, benzimidazole, imidazole, pyrazole, thiophene, furan, 1,2,4-oxadiazole, 1,3,4-oxadiazole, oxazole, isoxazole, isothiazole, thiazole, 1,2,4-thiadiazole, and 1,3,4-thiadiazole, wherein A is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is selected from the group consisting of: pyridine, pyrimidine, pyrazine, pyridazine, indazole, imidazo[1,2-a]pyridine, pyrrolo[3,2-c]pyridine, pyrrolo[2,3-b]pyridine, benzimidazole, imidazole, pyrazole, thiophene, 1,2,4-oxadiazole, 1,3,4-oxadiazole, oxazole, isothiazole, thiazole, 1,2,4-thiadiazole, and 1,3,4-thiadiazole, wherein A is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is selected from the group consisting of: pyridine, pyrimidine, pyrazine, indazole, imidazo[1,2-a]pyridine, pyrrolo[3,2-c]pyridine, pyrrolo[2,3-b]pyridine, pyrazole, thiophene, and 1,2,4-oxadiazole, wherein A is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is selected from the group consisting of: pyridine, pyrimidine, pyrazine, pyridazine, indazole, imidazo[1,2-a]pyridine, pyrrolo[3,2-c]pyridine, pyrrolo[2,3-b]pyridine, pyrazole, thiophene, and 1,2,4-oxadiazole, wherein A is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is selected from the group consisting of: pyridine, pyrimidine, and pyrazine, wherein A is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is pyridine, wherein pyridine is unsubstituted or substituted with one to three substituents selected from $R^a$. In a class of this embodiment, A is unsubstituted or substituted with one to two substituents selected from $R^a$. In another class of this embodiment, A is unsubstituted or substituted with one substituent selected from $R^a$. In another class of this embodiment, A is substituted with one substituent selected from $R^a$. In another class of this embodiment A is not substituted with a substituent selected from $R^a$. In another class of this embodiment A is unsubstituted.

In another embodiment, A is

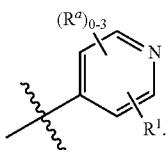

In another embodiment, A is

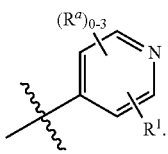

In another embodiment, A is

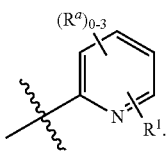

In another embodiment, A is

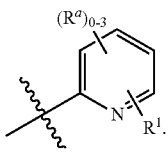

In another embodiment, A is:

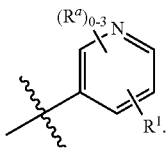

In another embodiment, A is:

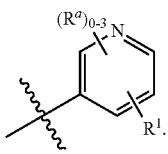

In another embodiment, B is heteroaryl, wherein heteroaryl is unsubstituted or substituted with one to three substituents selected from $R^b$. In a class of this embodiment, B is unsubstituted or substituted with one or two substituents selected from $R^b$. In another class of this embodiment, B is unsubstituted or substituted with one substituent selected from $R^b$. In another class of this embodiment, B is not substituted with a substituent selected from $R^b$. In another class of this embodiment B is unsubstituted.

In another embodiment of the present invention, B is selected from the group consisting of: pyrazine, pyridine, pyrimidine, and pyridazine, wherein each B is unsubstituted or substituted with one to three substituents selected from $R^b$. In a class of this embodiment, B is unsubstituted or substituted with one or two substituents selected from $R^b$. In another class of this embodiment, B is unsubstituted or substituted with one substituent selected from $R^b$. In another class of this embodiment, B is substituted with one substituent selected from $R^b$. In another class of this embodiment, B is not substituted with a substituent selected from $R^b$. In another class of this embodiment B is unsubstituted.

In another embodiment, B is pyrazine, wherein pyrazine is unsubstituted or substituted with one to three substituents selected from $R^b$. In another embodiment, B is pyrazine, wherein pyrazine is unsubstituted or substituted with one or two substituents selected from $R^b$. In another embodiment, B is pyrazine, wherein pyrazine is unsubstituted or substituted with one substituent selected from $R^b$. In another embodiment, B is pyrazine, wherein pyrazine is substituted with one substituent selected from $R^b$. In another class of this embodiment, pyrazine is not substituted with a substituent selected from $R^b$. In another class of this embodiment, pyrazine is unsubstituted.

In another embodiment, B is selected from the group consisting of pyridine, pyrimidine, and pyridazine, wherein each B is unsubstituted or substituted with one to three substituents selected from $R^b$. In a class of this embodiment, B is unsubstituted or substituted with one to two substituents selected from $R^b$. In another class of this embodiment, B is unsubstituted or substituted with one substituent selected from $R^b$. In another class of this embodiment, B is substituted with one substituent selected from $R^b$. In another class of this embodiment, B is not substituted with a substituent selected from $R^b$. In another class of this embodiment B is unsubstituted.

In another embodiment, B is pyridazine, wherein pyridazine is unsubstituted or substituted with one to three substituents selected from $R^b$. In another embodiment, B is pyridazine, wherein pyridazine is unsubstituted or substituted with one or two substituents selected from $R^b$. In another embodiment, B is pyridazine, wherein pyridazine is unsubstituted or substituted with one substituent selected from $R^b$. In another embodiment, B is pyridazine, wherein pyridazine is substituted with one substituent selected from $R^b$. In another class of this embodiment, pyridazine is not substituted with a substituent selected from $R^b$. In another class of this embodiment, pyridazine is unsubstituted.

In another embodiment, B is pyrimidine, wherein pyrimidine is unsubstituted or substituted with one to three substituents selected from $R^b$. In another embodiment, B is pyrimidine, wherein pyrimidine is unsubstituted or substituted with one or two substituents selected from $R^b$. In another embodiment, B is pyrimidine, wherein pyrimidine is unsubstituted or substituted with one substituent selected from $R^b$. In another embodiment, B is pyrimidine, wherein pyrimidine is substituted with one substituent selected from $R^b$. In another class of this embodiment, pyrimidine is not substituted with a substituent selected from $R^b$. In another class of this embodiment, pyrimidine is unsubstituted.

In another embodiment, B is pyridine, wherein pyridine is unsubstituted or substituted with one to three substituents selected from $R^b$. In another embodiment, B is pyridine, wherein pyridine is unsubstituted or substituted with one or two substituents selected from $R^b$. In another embodiment, B is pyridine, wherein pyridine is unsubstituted or substituted with one substituent selected from $R^b$. In another embodiment, B is pyridine, wherein pyridine is substituted with one substituent selected from $R^b$. In another class of this embodiment, pyridine is not substituted with a substituent selected from $R^b$. In another class of this embodiment, pyridine is unsubstituted.

In another embodiment of the present invention, $R^1$ is selected from the group consisting of: hydrogen, —$SO_3H$, —$SO_2NH_2$, —$SO_2NR^eC_{1-6}$alkyl, —$SO_2NR^eC(O)C_{1-6}$alkyl, —$SO_2NR^eC_{2-6}$alkenyl, —$SO_2NR^eC_{3-6}$cycloalkyl, —$SO_2NR^eC(O)C_{3-6}$cycloalkyl, —$SO_2NR^eC_{2-6}$cycloheteroalkyl, —$SO_2NR^eC(O)C_{2-6}$cycloheteroalkyl, —$SO_2NR^e$-aryl, —$SO_2NR^e$-heteroaryl, —$SO_2C_{1-6}$alkyl, —$SO_2C_{1-6}$alkenyl, —$SO_2C_{3-6}$cycloalkyl, —$SO_2C_{2-6}$cycloheteroalkyl, —$SO_2$aryl, —$SO_2$heteroaryl, —$S(O)R^j$, —$SR^j$, —$C(O)NH_2$, —$C(O)NR^eR^j$, —$CO_2H$, —$CO_2R^j$, —$C(O)R^j$, —CN, $CF_3$, halogen, —OH, —$OC_{1-6}$alkyl, —$OC_{2-6}$alkenyl, —$OC_{3-6}$cycloalkyl, —$OC_{2-6}$cycloheteroalkyl, —O-aryl, —O-heteroaryl, —$OC(O)R^j$, —$OC(O)NR^eR^j$, —$OC(O)N(R^j)_2$, —$C_{1-6}$alkyl, —$C_{2-6}$alkenyl, —$C_{1-6}$cycloalkyl, —$C_{2-6}$cycloheteroalkyl, aryl, heteroaryl, —$(CH_2)_nNR^eC(O)R^j$, —$(CH_2)_nNR^eC(O)OR^j$, —$(CH_2)_nNR^eC(O)N(R^e)_2$, —$(CH_2)_nNR^eC(O)NR^eR^j$, —$(CH_2)_nNR^eC(O)N(R^j)_2$, —$(CH_2)_nNR^eS(O)_mR^j$, —$(CH_2)_nNR^eS(O)_mN(R^e)_2$, —$(CH_2)_nNR^eS(O)_mNR^eR^j$, —$(CH_2)_nNR^eS(O)_mN(R^j)_2$, and —$(CH_2)_nNR^eR^j$, wherein each $CH_2$, alkyl, alkenyl, cycloalkyl, cycloheteroalkyl, aryl and heteroaryl is unsubstituted or substituted with one to four substituents selected from $R^d$;

In another embodiment of the present invention, $R^1$ is selected from the group consisting of: hydrogen, —$SO_3H$, —$SO_2NH_2$, —$SO_2NR^eC_{1-6}$alkyl, —$SO_2NR^eC_{2-6}$alkenyl, —$SO_2N(C_{2-6}$alkenyl$)_2$, —$SO_2NR^eC_{3-6}$cycloalkyl, —$SO_2NR^eC_{2-6}$cycloheteroalkyl, —$SO_2NR^e$-aryl, —$SO_2NR^e$-heteroaryl, —$SO_2C_{1-6}$alkyl, —$SO_2C_{1-6}$alkenyl, —$SO_2C_{3-6}$cycloalkyl, —$SO_2C_{2-6}$cycloheteroalkyl, —$SO_2$aryl, —$SO_2$heteroaryl, —$S(O)R^j$, —$SR^j$, —$C(O)NH_2$, —$C(O)NR^eR^j$, —$CO_2H$, —$CO_2R^j$, —$C(O)R^j$, —CN, —$CF_3$, halogen, —OH, —$OC_{1-6}$alkyl, —$OC_{2-6}$alkenyl, —$OC_{3-6}$cycloalkyl, —$OC_{2-6}$cycloheteroalkyl, —O-aryl, —O— heteroaryl, —$OC(O)R^j$, —$OC(O)NR^eR^j$, —$OC(O)N(R^j)_2$, —$C_{1-6}$alkyl, —$C_{2-6}$alkenyl, —$C_{1-6}$cycloalkyl, —$C_{2-6}$cycloheteroalkyl, aryl, heteroaryl, —$(CH_2)_nNR^eC(O)R^j$, —$(CH_2)_nNR^eC(O)OR^j$, —$(CH_2)_nNR^eC(O)N(R^e)_2$, —$(CH_2)_nNR^eC(O)NR^eR^j$, —$(CH_2)_nNR^eC(O)N(R^j)_2$, —$(CH_2)_nNR^eS(O)_mR^j$, —$(CH_2)_nNR^eS(O)_mN(R^e)_2$, —$(CH_2)_nNR^eS(O)_mNR^eR^j$, —$(CH_2)_nNR^eS(O)_mN(R^j)_2$, and —$(CH_2)_nNR^eR^j$, wherein each $CH_2$, alkyl, alkenyl, cycloalkyl, cycloheteroalkyl, aryl and heteroaryl is unsubstituted or substituted with one to four substituents selected from $R^d$. In a class of this embodiment, each alkyl, alkenyl, cycloalkyl, cycloheteroalkyl, aryl and heteroaryl is unsubstituted or substituted with one to three substituents selected from $R^d$. In another class of this embodiment, each alkyl, alkenyl, cycloalkyl, cycloheteroalkyl, aryl and heteroaryl is unsubstituted or substituted with one to two substituents selected from $R^d$.

In another embodiment of the present invention, $R^1$ is selected from the group consisting of: —$SO_3H$, —$SO_2NH_2$, —$SO_2NR^eC_{1-6}$alkyl, —$SO_2NR^eC_{2-6}$alkenyl, —$SO_2N(C_{2-6}$alkenyl$)_2$, —$SO_2NR^eC_{3-6}$cycloalkyl, —$SO_2NR^eC_{2-6}$cycloheteroalkyl, —$SO_2NR^e$-aryl, —$SO_2NR^e$-heteroaryl, —$SO_2C_{1-6}$alkyl, —$SO_2C_{1-6}$alkenyl, —$SO_2C_{3-6}$cycloalkyl, —$SO_2C_{2-6}$cycloheteroalkyl, —$SO_2$aryl, —$SO_2$heteroaryl, —$S(O)R^j$, —$SR^j$, —$C(O)NH_2$, —$C(O)NR^eR^j$, —$CO_2H$, —$CO_2R^j$, —$C(O)R^j$, —CN, —$CF_3$, halogen, —OH, —$OC_{1-6}$alkyl, —$OC_{2-6}$alkenyl, —$OC_{3-6}$cycloalkyl, —$OC_{2-6}$cycloheteroalkyl, —O-aryl, —O— heteroaryl, —$OC(O)R^j$, —$OC(O)NR^eR^j$, —$OC(O)N(R^j)_2$, —$C_{1-6}$alkyl, —$C_{2-6}$alkenyl, —$C_{1-6}$cycloalkyl, —$C_{2-6}$cycloheteroalkyl, aryl, heteroaryl, —$(CH_2)_nNR^eC(O)R^j$, —$(CH_2)_nNR^eC(O)OR^j$, —$(CH_2)_nNR^eC(O)N(R^e)_2$, —$(CH_2)_nNR^eC(O)NR^eR^j$, —$(CH_2)_nNR^eC(O)N(R^j)_2$, —$(CH_2)_nNR^eS(O)_mR^j$, —$(CH_2)_nNR^eS(O)_mN(R^e)_2$, —$(CH_2)_nNR^eS(O)_mNR^eR^j$, —$(CH_2)_nNR^eS(O)_mN(R^j)_2$, and —$(CH_2)_nNR^eR^j$, wherein each $CH_2$, alkyl, alkenyl, cycloalkyl, cycloheteroalkyl, aryl and heteroaryl is unsubstituted or substituted with one to four substituents selected from $R^d$. In a class of this embodiment, each alkyl, alkenyl, cycloalkyl, cycloheteroalkyl, aryl and heteroaryl is unsubstituted or substituted with one to three substituents selected from $R^d$. In another class of this embodiment, each alkyl, alkenyl, cycloalkyl, cycloheteroalkyl, aryl and heteroaryl is unsubstituted or substituted with one to two substituents selected from $R^d$.

In another embodiment of the present invention, $R^1$ is selected from the group consisting of: hydrogen, —$SO_3H$, —$SO_2NH_2$, —$SO_2C_{1-6}$alkyl-$NH_2$, —$SO_2NH$—$C_{1-6}$alkyl, —$SO_2N(C_{1-6}$alkyl$)_2$, —$SO_2C_{1-6}$alkyl, —$SO_2C_{3-6}$cycloalkyl, —$SO_2C_{3-6}$cycloheteroalkyl, —$C(O)NH_2$, —$CO_2H$, —$CO_2C_{1-6}$alkyl, —CN, halogen, —OH, —$OC_{1-6}$alkyl, —$C_{1-6}$alkyl, —$C_{2-6}$alkenyl, —$C_{1-6}$cycloalkyl, $CF_3$, —$SO_2NR^eC(O)C_{1-6}$alkyl, —$SO_2NR^eC(O)C_{3-6}$cycloalkyl, and —$SO_2NR^eC(O)C_{2-6}$cycloheteroalkyl, wherein each alkyl, alkenyl, cycloalkyl and cycloheteroalkyl is unsubstituted or substituted with one to four substituents selected from $R^d$.

In another embodiment of the present invention, $R^1$ is selected from the group consisting of: hydrogen, —$SO_3H$, —$SO_2NH_2$, —$SO_2C_{1-6}$alkyl-$NH_2$, —$SO_2NH$—$C_{1-6}$alkyl, —$SO_2N(C_{1-6}$alkyl$)_2$, —$SO_2C_{1-6}$alkyl, —$SO_2C_{3-6}$cycloalkyl, —$SO_2C_{3-6}$cycloheteroalkyl, —$C(O)NH_2$, —$CO_2H$, —$CO_2C_{1-6}$alkyl, —CN, halogen, —OH, —$OC_{1-6}$alkyl, —$C_{1-6}$alkyl, —$C_{2-6}$alkenyl, —$C_{1-6}$cycloalkyl, and $CF_3$, wherein each alkyl, alkenyl, cycloalkyl and cycloheteroalkyl is unsubstituted or substituted with one to four substituents selected from $R^d$.

In another embodiment of the present invention, $R^1$ is selected from the group consisting of: —$SO_3H$, —$SO_2NH_2$, —$SO_2C_{1-6}$alkyl, —$SO_2NH$—$C_{1-6}$alkyl, —$SO_2N(C_{1-6}$alkyl$)_2$, —$SO_2C_{3-6}$cycloalkyl, —$SO_2C_{3-6}$cycloheteroalkyl, —$C(O)NH_2$, —$CO_2H$, —$CO_2C_{1-6}$alkyl, —CN, halogen, —OH, —$OC_{1-6}$alkyl, —$C_{1-6}$alkyl, —$C_{2-6}$alkenyl, —$C_{1-6}$cycloalkyl, and $CF_3$, wherein each alkyl, alkenyl, cycloalkyl and cycloheteroalkyl is unsubstituted with one to four substituents selected from $R^d$.

In another embodiment of the present invention, $R^1$ is selected from the group consisting of: —$SO_3H$, —$SO_2NH_2$, —$SO_2C_{1-6}$alkyl-$NH_2$, —$SO_2NH$—$C_{1-6}$alkyl, —$SO_2N(C_{1-6}$alkyl$)_2$, —$SO_2C_{1-6}$alkyl, —$SO_2C_{3-6}$cycloalkyl, —$SO_2C_{3-6}$cycloheteroalkyl, —$C(O)NH_2$, —$CO_2H$, —$CO_2C_{1-6}$alkyl, —CN, halogen, —OH, —$OC_{1-6}$alkyl, —$C_{1-6}$alkyl, —$C_{2-6}$alkenyl, —$C_{1-6}$cycloalkyl, and $CF_3$, wherein each alkyl, alkenyl, cycloalkyl and cycloheteroalkyl is unsubstituted or substituted with one to four substituents selected from $R^d$.

In another embodiment, $R^1$ is hydrogen.

In another embodiment of the present invention, $R^1$ is selected from the group consisting of: —$SO_3H$, —$SO_2NH_2$, —$SO_2C_{1-6}$alkyl-$NH_2$, —$SO_2NH$—$C_{1-6}$alkyl, —$SO_2N(C_{1-6}$alkyl$)_2$, —$SO_2C_{1-6}$alkyl, —$SO_2C_{3-6}$cycloalkyl, —$SO_2C_{3-6}$cycloheteroalkyl, —$C(O)NH_2$, —$CO_2H$, —$CO_2C_{1-6}$alkyl, —CN, halogen, —OH, —$OC_{1-6}$alkyl, —$C_{1-6}$alkyl, —$C_{1-6}$alkyl-OH, —$C_{1-6}$alkyl-$NH_2$, —$C_{2-6}$alkenyl, —$C_{1-6}$cycloalkyl, and $CF_3$, wherein each alkyl, alkenyl, cycloalkyl and cycloheteroalkyl is unsubstituted or substituted with one to four substituents selected from $R^d$.

In another embodiment of the present invention, $R^1$ is selected from the group consisting of: hydrogen, —$SO_3H$, —$SO_2NH_2$, —$SO_2C_{1-6}$alkyl, —$SO_2NH$—$C_{1-6}$alkyl, —$SO_2C_{3-6}$cycloalkyl, —$C(O)NH_2$, —$CO_2H$, —CN, halogen, —OH, —$OC_{1-6}$alkyl, —$C_{1-6}$alkyl, —$C_{1-6}$cycloalkyl, and $CF_3$, wherein each alkyl and cycloalkyl is unsubstituted or substituted with one to three substituents selected from $R^d$.

In another embodiment of the present invention, $R^1$ is selected from the group consisting of: hydrogen, —$SO_3H$, —$SO_2NH_2$, —$SO_2C_{1-6}$alkyl-$NH_2$, —$SO_2NH$—$C_{1-6}$alkyl, —$SO_2C_{1-6}$alkyl, —$SO_2C_{3-6}$cycloalkyl, —$C(O)NH_2$, —$CO_2H$, —CN, halogen, —OH, —$OC_{1-6}$alkyl, —$C_{1-6}$alkyl, —$C_{1-6}$alkyl-OH, —$C_{1-6}$alkyl-$NH_2$, —$C_{1-6}$cycloalkyl-OH, —$C_{1-6}$cycloalkyl-$NH_2$, and $CF_3$, wherein each alkyl and cycloalkyl is unsubstituted or substituted with one to three substituents selected from $R^d$.

In another embodiment of the present invention, $R^1$ is selected from the group consisting of: —$SO_3H$, —$SO_2NH_2$, —$SO_2C_{1-6}$alkyl-$NH_2$, —$SO_2NH$—$C_{1-6}$alkyl, —$SO_2C_{1-6}$alkyl, —$SO_2C_{3-6}$cycloalkyl, —$C(O)NH_2$, —$CO_2H$, —CN, halogen, —OH, —$OC_{1-6}$alkyl, —$C_{1-6}$alkyl, —$C_{1-6}$alkyl-OH, —$C_{1-6}$alkyl-$NH_2$, —$C_{1-6}$cycloalkyl-OH, —$C_{1-6}$cycloalkyl-$NH_2$, and $CF_3$, wherein each alkyl and cycloalkyl is unsubstituted or substituted with one to three substituents selected from $R^d$.

In another embodiment of the present invention, $R^1$ is selected from the group consisting of: —$SO_3H$, —$SO_2NH_2$, —$SO_2C_{1-6}$alkyl-$NH_2$, —$SO_2NH$—$C_{1-6}$alkyl, —$SO_2C_{1-6}$alkyl, —$SO_2C_{3-6}$cycloalkyl, —$C(O)NH_2$, —$CO_2H$, —CN, halogen, —OH, —$OC_{1-6}$alkyl, —$C_{1-6}$alkyl, and $CF_3$, wherein each alkyl, and cycloalkyl is unsubstituted or substituted with one to three substituents selected from $R^d$. In a class of this embodiment, $R^1$ is selected from the group consisting of —$SO_3H$, —$SO_2NH_2$, —$SO_2(CH_2)_2$—$NH_2$, —$SO_2NH$—$C(CH_3)_3$, —$SO_2CH_3$, —$SO_2CH_2CH_3$, —$SO_2$-cyclopropyl, —$C(O)NH_2$, —$CO_2H$, —CN, F, Br, Cl, —OH, —$OCH_3$, —$CH_3$, —$CH_2OH$ and —$CF_3$, wherein each alkyl and cyclopropyl is unsubstituted or substituted with one to three substituents selected from $R^d$.

In another class of this embodiment, $R^1$ is selected from the group consisting of: —$SO_3H$, —$SO_2NH_2$, —$SO_2(CH_2)_2$—$NH_2$, —$SO_2NH$—$C(CH_3)_3$, —$SO_2CH_3$, —$SO_2CH_2CH_3$, —$SO_2$- cyclopropyl, —$C(O)NH_2$, —$CO_2H$, —CN, F, Br, —OH, —$OCH_3$, —$CH_3$, —$CH_2OH$, and —$CF_3$, wherein each alkyl and cyclopropyl is unsubstituted or substituted with one to three substituents selected from $R^d$.

In another embodiment of the present invention, $R^1$ is selected from the group consisting of: —$SO_2NR^eC(O)C_{1-6}$alkyl, —$SO_2NR^eC(O)C_{3-6}$cycloalkyl, and —$SO_2NR^eC(O)C_{2-6}$cycloheteroalkyl, wherein each alkyl, cycloalkyl and cycloheteroalkyl is unsubstituted or substituted with one to four substituents selected from $R^d$.

In another embodiment of the present invention, $R^1$ is selected from the group consisting of: —$SO_2NH_2$, —$SO_2C_{1-6}$alkyl, —$SO_2NH$—$C_{1-6}$alkyl, —$SO_2C_{3-6}$cycloalkyl, —$C(O)NH_2$, —$CO_2H$, —CN, halogen, —OH, —$OC_{1-6}$alkyl, —$C_{1-6}$alkyl, $CF_3$, —$SO_2NR^eC(O)C_{1-6}$alkyl, —$SO_2NR^eC(O)C_{3-6}$cycloalkyl, and —$SO_2NR^eC(O)C_{2-6}$cycloheteroalkyl, wherein each alkyl, and cycloalkyl is unsubstituted or substituted with one to three substituents selected from $R^d$.

In another embodiment of the present invention, $R^1$ is selected from the group consisting of: —$SO_2NH_2$, —$SO_2C_{1-6}$alkyl, —$SO_2NH$—$C_{1-6}$alkyl, —$SO_2C_{3-6}$cycloalkyl, —$C(O)NH_2$, —$CO_2H$, —CN, halogen, —OH, —$OC_{1-6}$alkyl, —$C_{1-6}$alkyl, and $CF_3$, wherein each alkyl, and cycloalkyl is unsubstituted or substituted with one to three substituents selected from $R^d$.

In another embodiment of the present invention, $R^1$ is selected from the group consisting of: —$SO_2NH_2$, —$C(O)NH_2$, and —OH. In another embodiment of the present invention, $R^1$ is selected from the group consisting of: —$SO_2NH_2$ and —$C(O)NH_2$. In another embodiment of the present invention, $R^1$ is —$SO_2NH_2$. In another embodiment of the present invention, $R^1$ is-$C(O)NH_2$. In another embodiment of the present invention, $R^1$ is —OH.

In another embodiment of the present invention, $R^2$ is selected from the group consisting of: hydrogen, and —$C_{1-6}$alkyl. In another embodiment, $R^2$ is —$C_{1-6}$alkyl. In another embodiment, $R^2$ is hydrogen.

In another embodiment of the present invention, $R^3$ is selected from the group consisting of: 1) a monocyclic, bicyclic or spirocyclic $C_{3-12}$cycloalkyl ring, and 2) a monocyclic, bicyclic or spirocyclic $C_{2-12}$cycloheteroalkyl ring, wherein the cycloheteroalkyl contains 1-4 heteroatoms independently selected from $N(R^m)_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to eight substitutents selected from $R^c$. In a class of this embodiment, $R^3$ is selected from the group consisting of: 1) a monocyclic, bicyclic or spirocyclic $C_{3-8}$cycloalkyl ring, and 2) a monocyclic, bicyclic or spirocyclic $C_{2-12}$cycloheteroalkyl ring, wherein the cycloheteroalkyl contains 1-4 heteroatoms independently selected from $N(R^m)_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to eight substitutents selected from $R^c$. In another class of this embodiment, $R^3$ is selected from the group consisting of: 1) a monocyclic, bicyclic or spirocyclic $C_{3-8}$cycloalkyl ring, and 2) a monocyclic, bicyclic or spirocyclic $C_{2-12}$cycloheteroalkyl ring, wherein the cycloheteroalkyl contains 1-4 heteroatoms independently selected from NH, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to eight substitutents selected from $R^c$. In another class of this embodiment, each cycloalkyl and cycloheteroalkyl may be fused to phenyl or thiene. In another class of this embodiment, each cycloalkyl and cycloheteroalkyl may be fused to phenyl. In another class of this embodiment, each cycloalkyl and cycloheteroalkyl ring may be fused to thiene. In another class of this embodiment and subclass of these classes, the cycloheteroalkyl contains nitrogen and is attached to the B ring via a bond to the nitrogen. In another class of this embodiment, $R^3$ is unsubstituted or substituted with one to six substituents selected from $R^c$. In another class of this embodiment, $R^3$ is unsubstituted or substituted with one to four substituents selected from $R^c$.

In another embodiment, $R^3$ is selected from the group consisting of: 1) a monocyclic, bicyclic or spirocyclic $C_{3-12}$cycloalkyl ring, and 2) a monocyclic, bicyclic or spirocyclic $C_{2-12}$cycloheteroalkyl ring, wherein the cycloheteroalkyl contains 1-4 heteroatoms independently selected from $N(R^m)_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to six substitutents selected from $R^c$. In a class of this embodiment, $R^3$ is selected from the group consisting of: 1) a monocyclic, bicyclic or spirocyclic $C_{3-8}$cycloalkyl ring, and 2) a monocyclic, bicyclic or spirocyclic $C_{2-12}$cycloheteroalkyl ring, wherein the cycloheteroalkyl contains 1-4 heteroatoms independently selected from $N(R''')_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to six substitutents selected from $R^c$. In another class of this embodiment, $R^3$ is selected from the group consisting of: 1) a monocyclic, bicyclic or spirocyclic $C_{3-8}$cycloalkyl ring, and 2) a monocyclic, bicyclic or spirocyclic $C_{2-12}$cycloheteroalkyl ring, wherein the cycloheteroalkyl contains 1-4 heteroatoms independently selected from NH, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to six substitutents selected from $R^c$. In another class of this embodiment, each cycloalkyl and cycloheteroalkyl may be fused to phenyl or thiene. In another class of this embodiment, each cycloalkyl and cycloheteroalkyl may be fused to phenyl.

In another class of this embodiment, each cycloalkyl and cycloheteroalkyl ring may be fused to thiene. In another class of this embodiment and subclass of these classes, the cycloheteroalkyl contains nitrogen and is attached to the B ring via a bond to the nitrogen. In another class of this embodiment, $R^3$ is unsubstituted or substituted with one to six substituents selected from $R^c$. In another class of this embodiment, $R^3$ is unsubstituted or substituted with one to four substitutents selected from $R^c$.

In another embodiment of the present invention, $R^3$ is selected from the group consisting of: 1) a monocyclic, bicyclic or spirocyclic $C_{3-12}$cycloalkyl ring, and 2) a monocyclic, bicyclic or spirocyclic $C_{2-12}$cycloheteroalkyl ring, wherein the cycloheteroalkyl contains 1-4 heteroatoms independently selected from $N(R''')_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to four substitutents selected from $R^c$. In a class of this embodiment, $R^3$ is selected from the group consisting of: 1) a monocyclic, bicyclic or spirocyclic $C_{3-8}$cycloalkyl ring, and 2) a monocyclic, bicyclic or spirocyclic $C_{2-12}$cycloheteroalkyl ring, wherein the cycloheteroalkyl contains 1-4 heteroatoms independently selected from $N(R''')_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to four substitutents selected from $R^c$. In another class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains 1-4 heteroatoms independently selected from NH, O, and S, wherein each cycloalkyl and cycloheteroalkyl may be fused to an aryl or heteroaryl, and wherein each cycloalkyl, cycloheteroalkyl, aryl and heteroaryl is unsubstituted or substituted with one to four substitutents selected from $R^c$. In another class of this embodiment, each cycloalkyl and cycloheteroalkyl may be fused to phenyl or thiene. In another class of this embodiment, each cycloalkyl and cycloheteroalkyl may be fused to phenyl.

In another class of this embodiment, each cycloalkyl and cycloheteroalkyl ring may be fused to thiene. In another class of this embodiment and subclass of these classes, the cycloheteroalkyl contains nitrogen and is attached to the B ring via a bond to the nitrogen.

In another embodiment of the present invention, $R^3$ is a monocyclic, bicyclic or spirocyclic $C_{3-12}$cycloalkyl ring, wherein each cycloalkyl may be fused to an aryl or heteroaryl, and wherein each cycloalkyl, aryl and heteroaryl is unsubstituted or substituted with one to eight substitutents selected from $R^c$. In a class of this embodiment, $R^3$ is a monocyclic, bicyclic or spirocyclic $C_{3-8}$cycloalkyl ring, wherein each cycloalkyl may be fused to an aryl or heteroaryl, and wherein each cycloalkyl, aryl and heteroaryl is unsubstituted or substituted with one to eight substitutents selected from $R^c$. In another class of this embodiment, each cycloalkyl may be fused to phenyl or thiene. In another class of this embodiment, each cycloalkyl may be fused to phenyl. In another class of this embodiment, each cycloalkyl may be fused to thiene. In another class of this embodiment, $R^3$ is unsubstituted or substituted with one to six substituents selected from $R^c$. In another class of this embodiment, $R^3$ is unsubstituted or substituted with one to four substituents selected from $R^c$.

In another embodiment of the present invention, $R^3$ is a monocyclic, bicyclic or spirocyclic $C_{2-12}$cycloheteroalkyl ring, wherein the cycloheteroalkyl contains 1-4 heteroatoms independently selected from $N(R''')_r$, O, and S, wherein each cycloheteroalkyl may be fused to an aryl or heteroaryl, and wherein each cycloheteroalkyl, aryl and heteroaryl is unsubstituted or substituted with one to eight substitutents selected from $R^c$. In a class of this embodiment, $R^3$ is a monocyclic, bicyclic or spirocyclic $C_{2-10}$cycloheteroalkyl ring, wherein the cycloheteroalkyl contains 1-4 heteroatoms independently selected from $N(R''')_r$, O, and S, wherein each cycloheteroalkyl may be fused to an aryl or heteroaryl, and wherein each cycloheteroalkyl, aryl and heteroaryl is unsubstituted or substituted with one to eight substitutents selected from $R^c$. In another class of this embodiment, $R^3$ is a monocyclic, bicyclic or spirocyclic $C_{2-12}$cycloheteroalkyl ring, wherein the cycloheteroalkyl contains 1-4 heteroatoms independently selected from NH, O, and S, wherein each cycloheteroalkyl may be fused to an aryl or heteroaryl, and wherein each cycloheteroalkyl, aryl and heteroaryl is unsubstituted or substituted with one to eight substitutents selected from $R^c$. In another class of this embodiment, each cycloheteroalkyl may be fused to phenyl or thiene. In another class of this embodiment, each cycloheteroalkyl may be fused to phenyl. In another class of this embodiment, each cycloheteroalkyl ring may be fused to thiene. In another class of this embodiment and subclass of these classes, the cycloheteroalkyl contains nitrogen and is attached to the B ring via a bond to the nitrogen. In another class of this embodiment, $R^3$ is unsubstituted or substituted with one to six substituents selected from $R^c$. In another class of this embodiment, $R^3$ is unsubstituted or substituted with one to four substitutents selected from $R^c$.

In another embodiment of the present invention, $R^3$ is selected from the group consisting of: a monocyclic, bicyclic or spirocyclic $C_{3-12}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from $N(R''')_r$, O, and S, wherein each cycloalkyl and cycloheteroalkyl may be fused to an aryl or heteroaryl, and wherein each cycloalkyl, cycloheteroalkyl, aryl and heteroaryl is unsubstituted or substituted with one to six substitutents selected from $R^c$. In a class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, wherein each cycloalkyl and cycloheteroalkyl may be fused to an aryl or heteroaryl, and wherein each cycloalkyl, cycloheteroalkyl, aryl and heteroaryl is unsubstituted or substituted with one to six substitutents selected from $R^c$. In another class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from NH, O, and S, wherein each cycloalkyl and cycloheteroalkyl may be fused to an aryl or heteroaryl, and wherein each cycloalkyl, cycloheteroalkyl, aryl and heteroaryl is unsubstituted or substituted with one to six substitutents selected from $R^c$. In another class of this embodiment, each cycloalkyl and cycloheteroalkyl may be fused to phenyl or thiene. In another class of this embodiment, each cycloalkyl and cycloheteroalkyl may be fused to phenyl.

In another class of this embodiment, each cycloalkyl and cycloheteroalkyl ring may be fused to thiene. In another class of this embodiment and subclass of these classes, the cycloheteroalkyl is attached to the B ring via a bond to the $R^3$ nitrogen. In another class of this embodiment, $R^3$ is unsubstituted or substituted with one to four substituents selected from $R^c$.

In another embodiment of the present invention, $R^3$ is a monocyclic, bicyclic or spirocyclic $C_{3-12}$cycloalkyl ring, wherein each cycloalkyl may be fused to an aryl or heteroaryl, and wherein each cycloalkyl, aryl and heteroaryl is unsubstituted or substituted with one to six substitutents selected from $R^c$. In a class of this embodiment, $R^3$ is a monocyclic, bicyclic or spirocyclic $C_{3-8}$cycloalkyl ring, wherein each cycloalkyl may be fused to an aryl or heteroaryl, and wherein each cycloalkyl, aryl and heteroaryl is unsubstituted or substituted with one to six substitutents selected from $R^c$. In another class of this embodiment, each cycloalkyl may be fused to phenyl or thiene. In another class of this embodiment, each cycloalkyl may be fused to phenyl. In another class of this embodiment, each cycloalkyl may be fused to thiene. In another class of this embodiment, $R^3$ is unsubstituted or substituted with one to six substitutents selected from $R^c$. In another class of this embodiment, $R^3$ is unsubstituted or substituted with one to four substitutents selected from $R^c$.

In another embodiment of the present invention, $R^3$ is a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, wherein each cycloheteroalkyl may be fused to an aryl or heteroaryl, and wherein each cycloheteroalkyl, aryl and heteroaryl is unsubstituted or substituted with one to six substitutents selected from $R^c$. In a class of this embodiment, $R^3$ is a monocyclic, bicyclic or spirocyclic $C_{2-10}$cycloheteroalkyl ring, wherein the cycloheteroalkyl contains a nitrogen and 0-3 heteroatoms independently selected from $N(R^m)_r$, O, and S, wherein each cycloheteroalkyl may be fused to an aryl or heteroaryl, and wherein each cycloheteroalkyl, aryl and heteroaryl is unsubstituted or substituted with one to six substitutents selected from $R^c$. In another class of this embodiment, $R^3$ is a monocyclic, bicyclic or spirocyclic $C_{2-12}$cycloheteroalkyl ring, wherein the cycloheteroalkyl contains a nitrogen and 0-3 heteroatoms independently selected from NH, O, and S, wherein each cycloheteroalkyl may be fused to an aryl or heteroaryl, and wherein each cycloheteroalkyl, aryl and heteroaryl is unsubstituted or substituted with one to six substitutents selected from $R^c$. In another class of this embodiment, the cycloheteroalkyl contains a nitrogen and 0-2 heteroatoms independently selected from N, O, and S. In another class of this embodiment, each cycloheteroalkyl may be fused to phenyl or thiene. In another class of this embodiment, each cycloheteroalkyl may be fused to phenyl. In another class of this embodiment, each cycloheteroalkyl ring may be fused to thiene. In another class of this embodiment and subclass of these classes, the cycloheteroalkyl is attached to the B ring via a bond to the $R^3$ nitrogen. In another class of this embodiment, $R^3$ is unsubstituted or substituted with one to four substituents selected from $R^c$.

In another embodiment of the present invention, $R^3$ is selected from the group consisting of: a monocyclic, bicyclic or spirocyclic $C_{3-12}$cycloalkyl ring, and a monocyclic, bicyclic or spirocyclic $C_{2-12}$cycloheteroalkyl ring, wherein the cycloheteroalkyl contains 1-4 heteroatoms independently selected from $N(R^m)_r$, O, and S, and wherein each cycloalkyl and cycloheteroalkyl is unsubstituted or substituted with one to eight substitutents selected from $R^c$. In a class of this embodiment, $R^3$ is selected from the group consisting of a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains 1-4 heteroatoms independently selected from $N(R^m)_r$, O, and S, and wherein each cycloalkyl and cycloheteroalkyl is unsubstituted or substituted with one to eight substitutents selected from $R^c$. In another class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains 1-4 heteroatoms independently selected from NH, O, and S, and wherein each cycloalkyl and cycloheteroalkyl is unsubstituted or substituted with one to eight substitutents selected from $R^c$.

In another class of this embodiment, the cycloheteroalkyl contains nitrogen and is attached to the B ring via a bond to the $R^3$ nitrogen. In another class of this embodiment, $R^3$ is unsubstituted or substituted with one to six substitutents selected from $R^c$. In another class of this embodiment, $R^3$ is unsubstituted or substituted with one to four substitutents selected from $R^c$.

In another embodiment of the present invention, $R^3$ is a monocyclic, bicyclic or spirocyclic $C_{3-12}$cycloalkyl ring, wherein each cycloalkyl is unsubstituted or substituted with one to eight substitutents selected from $R^c$. In a class of this embodiment, $R^3$ is a monocyclic, bicyclic or spirocyclic $C_{3-8}$cycloalkyl ring, wherein each cycloalkyl is unsubstituted or substituted with one to eight substitutents selected from $R^c$. In another class of this embodiment, $R^3$ is unsubstituted or substituted with one to six substitutents selected from $R^c$. In another class of this embodiment, $R^3$ is unsubstituted or substituted with one to four substitutents selected from $R^c$.

In another embodiment of the present invention, $R^3$ is a monocyclic, bicyclic or spirocyclic $C_{2-12}$cycloheteroalkyl ring, wherein the cycloheteroalkyl contains 1-4 heteroatoms independently selected from $N(R^m)_r$, O, and S, and wherein each cycloheteroalkyl is unsubstituted or substituted with one to eight substitutents selected from $R^c$. In a class of this embodiment of the present invention, $R^3$ is a monocyclic, bicyclic or spirocyclic $C_{2-10}$cycloheteroalkyl ring, wherein the cycloheteroalkyl contains 1-4 heteroatoms independently selected from $N(R^m)_r$, O, and S, and wherein each cycloheteroalkyl is unsubstituted or substituted with one to eight substituents selected from $R^c$. In another class of this embodiment, $R^3$ is a monocyclic, bicyclic or spirocyclic $C_{2-12}$cycloheteroalkyl ring, wherein the cycloheteroalkyl contains 1-4 heteroatoms independently selected from NH, O, and S, and wherein each cycloheteroalkyl is unsubstituted or substituted with one to eight substituents selected from $R^c$.

In another class of this embodiment, the cycloheteroalkyl contains nitrogen and is attached to the B ring via a bond to the $R^3$ nitrogen. In another class of this embodiment, $R^3$ is unsubstituted or substituted with one to six substituents selected from $R^c$. In another class of this embodiment, $R^3$ is unsubstituted or substituted with one to four substituents selected from $R^c$.

In another embodiment of the present invention, $R^3$ is selected from the group consisting of: a monocyclic, bicyclic or spirocyclic $C_{3-12}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, and wherein each cycloalkyl and cycloheteroalkyl is unsubstituted or substituted with one to six substituents selected from $R^c$. In a class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, and wherein each cycloalkyl and cycloheteroalkyl is unsubstituted or substituted with one to six substituents selected from $R^c$. In another class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from NH, O, and S, and wherein each cycloalkyl and cycloheteroalkyl is unsubstituted or substituted with one to six substituents selected from $R^c$. In another class of this embodiment, the cycloheteroalkyl contains a nitrogen and 0-2 heteroatoms independently selected from $N(R^m)_r$, O, and S. In another class of this embodiment, the cycloheteroalkyl contains a nitrogen and 0-2 heteroatoms independently selected from NH, O, and S. In another class of this embodiment and a subclass of this class, the cycloheteroalkyl is attached to the B ring via a bond to the $R^3$ nitrogen. In another class of this embodiment, $R^3$ is unsubstituted or substituted with one to four substituents selected from $R^c$.

In another embodiment of the present invention, $R^3$ is a monocyclic, bicyclic or spirocyclic $C_{3-12}$cycloalkyl ring, and wherein each cycloalkyl is unsubstituted or substituted with one to four substituents selected from $R^c$. In a class of this embodiment, $R^3$ is a monocyclic, bicyclic or spirocyclic $C_{3-8}$cycloalkyl ring, and wherein each cycloalkyl is unsubstituted or substituted with one to four substituents selected from $R^c$.

In another embodiment of the present invention, $R^3$ is a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, and wherein each cycloheteroalkyl is unsubstituted or substituted with one to four substituents selected from $R^c$. In a class of this embodiment, $R^3$ is a monocyclic, bicyclic or spirocyclic $C_{2-12}$cycloheteroalkyl ring, wherein the cycloheteroalkyl contains a nitrogen and 0-3 heteroatoms independently selected from NH, O, and S, and wherein each cycloheteroalkyl is unsubstituted or substituted with one to four substituents selected from $R^c$. In another class of this embodiment, $R^3$ is a monocyclic, bicyclic or spirocyclic $C_{2-10}$cycloheteroalkyl ring, wherein the cycloheteroalkyl contains a nitrogen and 0-3 heteroatoms independently selected from $N(R^m)_r$, O, and S, and wherein each cycloheteroalkyl is unsubstituted or substituted with one to four substituents selected from $R^c$. In another class of this embodiment, the cycloheteroalkyl contains a nitrogen and 0-2 heteroatoms independently selected from $N(R^m)_r$, O, and S. In another class of this embodiment, the cycloheteroalkyl contains a nitrogen and 0-2 heteroatoms independently selected from NH, O, and S. In another class of this embodiment and a subclass of this class, the cycloheteroalkyl is attached to the B ring via a bond to the $R^3$ nitrogen.

In another embodiment of the present invention, $R^3$ is selected from the group consisting of: cyclohexane, cycloheptane, pyrrolidine, azetidine, piperidine, piperazine, azepane, morpholine, thiomorpholine, oxazepane, isoindoline, dihydroisoquinoline, azabicyclo[2.2.1]heptane, azabicyclo[3.1.1]heptane, azabicyclo[4.1.0]heptane, azabicyclo[3.2.0]heptane, azabicyclo[3.2.1]octane, azabicyclo[3.2.0]heptane, azaspiro[2.5] octane, dihydrothieno[3,2-c]pyridine, dihydroimidazo[1,2-a]pyrazine, and hexahydrofuro[3,2-b]pyrrole, wherein $R^3$ is unsubstituted or substituted with one to eight substituents selected from $R^c$. In a class of this embodiment, $R^3$ is attached to the B ring via a bond to the $R^3$ nitrogen. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$.

In another embodiment of the present invention, $R^3$ is selected from the group consisting of: cyclohexane, and cycloheptane, wherein $R^3$ is unsubstituted or substituted with one to eight substituents selected from $R^c$. In a class of this embodiment, $R^3$ is attached to the B ring via a bond to the $R^3$ nitrogen. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$.

In another embodiment, $R^3$ is selected from the group consisting of: pyrrolidine, azetidine, piperidine, piperazine, azepane, azocane, morpholine, thiomorpholine, thiomorpholine dione, oxazepane, 1,4-thiazepane, isoindoline, dihydroisoquinoline, tetrahydroisoquinoline, octahydro-isoindole, azabicyclo[2.2.1]heptane, oxa-azabicyclo[2.2.1]heptane, azabicyclo[3.1.1]heptane, azabicyclo[4.1.0]heptane, azabicyclo[3.2.1]octane, diazabicyclo[3.2.1]octane, oxa-azabicyclo-[3.2.1]octane, azabicyclo[3.2.0]heptane, oxa-azabicyclo[3.2.0]heptane, azaspiro[2.5]octane, azaspiro[2.6]nonane, azaspiro[3.5]nonane, oxa-azaspiro

[3.5]nonane, oxa-azaspiro[4.5]decane, dihydrothieno[3,2-c]pyridine, dihydrothiazolo[4,5-c]pyridine, dihydrooxazolo[4,5-c]pyridine, dihydroimidazo[1,2-a]pyrazine, hexahydrofuro[3,2-b]pyrrole, hexahydrocyclopenta[c]pyrrole, octahydrocyclpenta[c]pyrrole, and azatricyclo[4.3.1.13,8]undecane, wherein $R^3$ is unsubstituted or substituted with one to eight substituents selected from $R^c$. In a class of this embodiment, $R^3$ is attached to the B ring via a bond to the $R^3$ nitrogen. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$.

In another embodiment, $R^3$ is selected from the group consisting of: pyrrolidine, azetidine, piperidine, piperazine, azepane, azocane, morpholine, thiomorpholine, oxazepane, 1,4-thiazepane, isoindoline, dihydroisoquinoline, octahydroisoindole, azabicyclo[2.2.1]heptane, oxa-azabicyclo[2.2.1]heptane, azabicyclo[3.1.1]heptane, azabicyclo[4.1.0]heptane, azabicyclo[3.2.1]-octane, diazabicyclo[3.2.1]octane, oxa-azabicyclo[3.2.1]octane, azabicyclo[3.2.0]heptane, azaspiro[2.5]octane, azaspiro[2.6]nonane, azaspiro[3.5]nonane, oxa-azaspiro[3.5]nonane, oxa-azaspiro[4.5]decane, dihydrothieno[3,2-c]pyridine, dihydrothiazolo[4,5-c]pyridine, dihydrooxazolo[4,5-c]pyridine, dihydroimidazo[1,2-a]pyrazine, hexahydrofuro[3,2-b]pyrrole, hexahydrocyclopenta[c]pyrrole, and azatricyclo[4.3.1.13,8]undecane, wherein $R^3$ is unsubstituted or substituted with one to eight substituents selected from $R^c$. In a class of this embodiment, $R^3$ is attached to the B ring via a bond to the $R^3$ nitrogen. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$.

In another embodiment of the present invention, $R^3$ is selected from the group consisting of: pyrrolidine, azetidine, piperidine, piperazine, azepane, azocane, morpholine, thiomorpholine, oxazepane, isoindoline, dihydroisoquinoline, octahydroisoindole, azabicyclo[2.2.1]heptane, azabicyclo[3.1.1]heptane, azabicyclo[4.1.0]heptane, azabicyclo[3.2.1]octane, diazabicyclo-[3.2.1]octane, azabicyclo[3.2.0]heptane, oxa-azabicyclo[3.2.1]octane, azaspiro[2.5]octane, azaspiro[2.6]nonane, azaspiro[3.5]nonane, oxa-azaspiro[3.5}nonane, oxa-oazaspiro[4.5]decane, dihydrothieno[3,2-c]pyridine, dihydrothiazolo[4,5-c]pyridine, dihydrooxazolo[4,5-c]pyridine, dihydroimidazo[1,2-a]pyrazine, hexahydrofuro[3,2-b]pyrrole, hexahydrocyclopenta[c]pyrrole, and azatricyclo[4.3.1.13,8]undecane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$. In another class of this embodiment and a subclass of these classes, $R^3$ is attached to the B ring via a bond to the $R^3$ nitrogen.

In another embodiment of the present invention, $R^3$ is selected from the group consisting of: pyrrolidine, azetidine, piperidine, piperazine, azepane, morpholine, thiomorpholine, oxazepane, isoindoline, dihydroisoquinoline, azabicyclo[2.2.1]heptane, azabicyclo[3.1.1]-heptane, azabicyclo[4.1.0]heptane, azabicyclo[3.2.1]octane, azabicyclo[3.2.0]heptane, azaspiro[2.5]octane, dihydrothieno[3,2-c]pyridine, dihydroimidazo[1,2-a]pyrazine, and hexahydrofuro[3,2-b]pyrrole, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$. In another class of this embodiment and a subclass of these classes, $R^3$ is attached to the B ring via a bond to the $R^3$ nitrogen.

In another embodiment of the present invention, $R^3$ is selected from the group consisting of: pyrrolidine, azetidine, piperidine, piperazine, azepane, morpholine, thiomorpholine, 1,4-oxazepane, isoindoline, 3,4-dihydroisoqinoline, 2-azabicyclo[2.2.1]heptane, 3-azabicyclo-[3.1.1]heptane, 3-azabicyclo[4.1.0]heptane, 3-azabicyclo[3.2.1]octane, 3-azabicyclo[3.2.0]-heptane, 6-azaspiro[2.5]octane, 5-azaspiro[2.5]octane, 6,7-dihydrothieno[3,2-c]pyridine, 6,8-dihydroimidazo[1,2-a]pyrazine, and 2,3,3a,5,6,6a-hexahydrofuro[3,2-b]pyrrole, wherein $R^3$ is unsubstituted or substituted with one to eight substituents selected from $R^c$ In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$. In another class of this embodiment and a subclass of these classes, $R^3$ is attached to the B ring via a bond to the $R^3$ nitrogen.

In another embodiment of the present invention, $R^3$ is selected from the group consisting of: piperidine, azepane, morpholine, and azaspiro[2.5]octane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$. In another class of this embodiment and a subclass of these classes, $R^3$ is attached to the B ring via a bond to the $R^3$ nitrogen.

In another embodiment of the present invention, $R^3$ is selected from the group consisting of: piperidine, azepane, morpholine, and 6-azaspiro[2.5]octane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$. In another class of this embodiment and a subclass of these classes, $R^3$ is attached to the B ring via a bond to the $R^3$ nitrogen.

In another embodiment of the present invention, $R^3$ is selected from the group consisting of: piperidine, azepane, and morpholine, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$. In another class of this embodiment and a subclass of these classes, $R^3$ is attached to the B ring via a bond to the $R^3$ nitrogen.

In another embodiment of the present invention, $R^3$ is selected from the group consisting of: piperidine, and azepane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, $R^3$ is unsubstituted or substituted with one substituent selected from $R^c$. In another class of this embodiment and a subclass of these classes, $R^3$ is attached to the B ring via a bond to the $R^3$ nitrogen. In another class of this embodiment and a subclass of these classes, piperidine and azepane are each individually attached to the B ring via a bond to the piperidine or azepane nitrogen.

In another embodiment of the present invention, $R^3$ is piperidine, wherein piperidine is unsubstituted or substituted with one to eight substituents selected from $R^c$. In a class of this embodiment, piperidine is unsubstituted or substituted with one to six substituents selected from $R^c$. In another class of this embodiment, piperidine is unsubstituted or substituted with one to four substituents selected from $R^c$. In another class of this embodiment, piperidine is unsubstituted or substituted with one to three substituents selected from $R^c$. In another class of this embodiment, piperidine is unsubstituted or substituted with one to two substituents selected from $R^c$. In another class of this embodiment, piperidine is unsubstituted or substituted with one substituent selected from $R^c$. In another class of this embodiment and a subclass of these classes, piperidine is attached to the B ring via a bond to the $R^3$ nitrogen. In another class of this embodiment and a subclass of these classes, piperidine is attached to the B ring via a bond to the piperidine nitrogen.

In another embodiment of the present invention, $R^3$ is azepane, wherein azepane is unsubstituted or substituted with one to eight substituents selected from $R^c$. In a class of this embodiment, azepane is unsubstituted or substituted with one to six substituents selected from $R^c$. In another class of this embodiment, azepane is unsubstituted or substituted with one to four substituents selected from $R^c$. In another class of this embodiment, azepane is unsubstituted or substituted with one to three substituents selected from $R^c$. In another class of this embodiment, azepane is unsubstituted or substituted with one to two substituents selected from $R^c$. In another class of this embodiment, azepane is unsubstituted or substituted with one substituent selected from $R^c$. In another class of this embodiment and a subclass of these classes, azepane is attached to the B ring via a bond to the $R^3$ nitrogen. In another class of this embodiment and a subclass of these classes, azepane is attached to the B ring via a bond to the azepane nitrogen.

In another embodiment of the present invention, $R^3$ is morpholine, wherein morpholine is unsubstituted or substituted with one to eight substituents selected from $R^c$. In a class of this embodiment, morpholine is unsubstituted or substituted with one to six substituents selected from $R^c$. In another class of this embodiment, morpholine is unsubstituted or substituted with one to four substituents selected from $R^c$. In another class of this embodiment, morpholine is unsubstituted or substituted with one to three substituents selected from $R^c$. In another class of this embodiment, morpholine is unsubstituted or substituted with one to two substituents selected from $R^c$. In another class of this embodiment, morpholine is unsubstituted or substituted with one substituent selected from $R^c$. In another class of this embodiment and a subclass of these classes, morpholine is attached to the B ring via a bond to the $R^3$ nitrogen. In another class of this embodiment and a subclass of these classes, morpholine is attached to the B ring via a bond to the morpholine nitrogen.

In another embodiment of the present invention, each $R^a$ is selected from the group consisting of —$C_{1-6}$alkyl, —$OC_{1-6}$alkyl, halogen, —OH, oxo, —CN, —$C_{3-6}$cycloalkyl, and —$C_{2-5}$cycloheteroalkyl, wherein each alkyl, cycloalkyl and cycloheteroalkyl is unsubstituted or substituted with one to six substituents selected from halogen, OH, $NH_2$, $NH(C_{1-6}alkyl)$ and $N(C_{1-6}alkyl)_2$; In a class of this embodiment, $R^a$ is substituted with a halogen selected from: F, Br, and Cl. In a subclass of this class, the halogen is F or Cl. In another subclass of this class, the halogen is Cl. In another subclass of this class, the halogen is F.

In another embodiment, each $R^a$ is selected from the group consisting of —$C_{1-6}$alkyl, —$OC_{1-6}$alkyl, halogen, —OH, oxo, —CN, and —$C_{3-6}$cycloalkyl, wherein each alkyl and cycloalkyl is unsubstituted or substituted with one to six substituents selected from halogen, OH, $NH_2$, $NH(C_{1-6}alkyl)$ and $N(C_{1-6}alkyl)_2$. In a class of this embodiment, $R^a$ is substituted with a halogen selected from: F, Br, and Cl. In a subclass of this class, the halogen is F or Cl. In another subclass of this class, the halogen is CL. In another subclass of this class, the halogen is F.

In another embodiment, each $R^a$ is selected from the group consisting of: —$C_{1-6}$ alkyl, —$OC_{1-6}$alkyl, halogen, —OH, oxo, and CN, wherein each alkyl is unsubstituted or substituted with one to six substituents selected from halogen, OH, NH$_2$, NH(C$_{1-6}$alkyl) and N(C$_{1-6}$alkyl)$_2$. In a class of this embodiment, R$^a$ is substituted with a halogen selected from: F, Br, and CL. In a subclass of this class, the halogen is F or CL. In another subclass of this class, the halogen is CL. In another subclass of this class, the halogen is F.

In another embodiment, each R$^a$ is selected from the group consisting of: —C$_{1-6}$ alkyl, halogen, —OH, oxo, and CN, wherein each alkyl is unsubstituted or substituted with one to six substituents selected from halogen, OH, NH$_2$, NH(C$_{1-6}$alkyl) and N(C$_{1-6}$alkyl)$_2$. In a class of this embodiment, R$^a$ is substituted with a halogen selected from: F, Br, and CL. In a subclass of this class, the halogen is F or CL. In another subclass of this class, the halogen is CL. In another subclass of this class, the halogen is F.

In another embodiment, each R$^a$ is selected from the group consisting of —C$_{1-6}$alkyl, halogen, —OH, and oxo, wherein each alkyl is unsubstituted or substituted with one to six substituents selected from halogen, OH, NH$_2$, NH(C$_{1-6}$alkyl) and N(C$_{1-6}$alkyl)$_2$. In a class of this embodiment, R$^a$ is substituted with a halogen selected from: F, Br, and Cl. In a subclass of this class, the halogen is F or Cl. In another subclass of this class, the halogen is Cl. In another subclass of this class, the halogen is F.

In another embodiment, each R$^a$ is selected from the group consisting of: —C$_{1-6}$alkyl, halogen, —OH, and oxo. In a class of this embodiment, each R$^a$ is selected from the group consisting of: CH$_3$, halogen, —OH, and oxo.

In another embodiment, each R$^a$ is selected from the group consisting of: —C$_{1-6}$alkyl and halogen. In another embodiment, each R$^a$ is selected from the group consisting of: CH$_3$ and halogen.

In another embodiment, each R$^a$ is halogen.

In another embodiment, R$^a$ is —C$_{1-6}$alkyl, wherein alkyl is substituted with a halogen selected from: F, Br, and Cl. In a subclass of this class, the halogen is F or Cl. In another subclass of this class, the halogen is Cl. In another subclass of this class, the halogen is F.

In another embodiment, R$^a$ is —C$_{1-6}$alkyl. In a class of this embodiment, R$^a$ is CH$_3$.

In another embodiment of the present invention, each R$^b$ is independently selected from the group consisting of: —CF$_3$, —CF$_2$CF$_3$; —CHF$_2$, —OCHF$_2$, —OCH$_2$CF$_3$, —OCF$_3$, CN, halogen, —Si(C$_{1-6}$alkyl)$_3$, —C$_{1-6}$alkyl-O—R$^k$, —C$_{1-6}$alkyl, —C$_{2-6}$alkenyl, —C$_{2-6}$alkynyl, —C$_{3-6}$cycloalkyl, —C$_{2-6}$cycloheteroalkyl, aryl, heteroaryl, —C$_{1-6}$alkyl-C$_{3-6}$cycloalkyl, —C$_{1-6}$alkyl-C$_{2-6}$cycloheteroalkyl, —C$_{1-6}$alkyl-aryl, —C$_{1-6}$alkyl-heteroaryl, —C$_{2-6}$alkenyl-C$_{3-6}$cycloalkyl, —C$_{2-6}$alkenyl-C$_{2-6}$cycloheteroalkyl, —C$_{2-6}$alkenyl-aryl, —C$_{2-6}$alkenyl-heteroaryl, —C$_{2-6}$alkynyl-C$_{3-6}$cycloalkyl, —C$_{2-6}$alkynyl cycloheteroalkyl, —C$_{2-6}$alkynyl-aryl, —C$_{2-6}$alkynyl-heteroaryl, NO$_2$, —OH, —(CH$_2$)$_p$—OC$_{1-6}$alkyl, —(CH$_2$)$_p$—OC$_{2-6}$alkenyl, —(CH$_2$)$_p$—OC$_{2-6}$alkynyl, —(CH$_2$)$_p$—OC$_{3-6}$cycloalkyl, —(CH$_2$)$_p$—OC$_{2-6}$heterocycloalkyl, —(CH$_2$)$_p$—O-aryl, —(CH$_2$)$_p$—O-heteroaryl, —OC$_{1-6}$alkyl-C$_{3-6}$cycloalkyl, —OC$_{1-6}$alkyl-C$_{2-6}$heterocycloalkyl, —OC$_{1-6}$alkyl-aryl, —OC$_{1-6}$alkyl-heteroaryl, —S(O)$_m$R$^k$, —C$_{1-6}$alkyl-S(O)$_m$R$^k$, —C(O)R$^k$, —N(R$^i$)$_2$, and —NR$^i$R$^k$, wherein each R$^b$ is unsubstituted or substituted with one to five substituents selected from R$^f$.

In another embodiment, each R$^b$ is independently selected from the group consisting of: —CF$_3$, —CHF$_2$, —OCHF$_2$, —OCH$_2$CF$_3$, —OCF$_3$, CN, halogen, —Si(C$_{1-6}$alkyl)$_3$, —C$_{1-6}$alkyl, —OC$_{1-6}$alkyl, —C$_{3-6}$cycloalkyl, —C$_{2-6}$cycloheteroalkyl, —C$_{2-6}$alkyl-C$_{3-6}$cycloalkyl, —C$_{2-6}$alkynyl-C$_{3-6}$cycloalkyl, and heteroaryl, wherein each R$^b$ is unsubstituted or substituted with one to five substituents selected from R$^f$. In a class of this embodiment, each R$^b$ is independently selected from the group consisting of: —CF$_3$, —CHF$_2$, —OCHF$_2$, —OCH$_2$CF$_3$, —OCF$_3$, CN, F, Cl, Br, —Si(CH$_3$)$_3$, —CH$_3$, —C(CH$_3$)$_3$, —OCH$_3$, cyclopropyl, cyclobutyl, piperidine, —CH$_2$-cyclopropyl, —C$_2$alkynyl-cyclopropyl, and pyrazole, wherein each R$^b$ is unsubstituted or substituted with one to five substituents selected from R$^f$.

In another embodiment, each R$^b$ is independently selected from the group consisting of: —CF$_3$, —CHF$_2$, —OCHF$_2$, —OCH$_2$CF$_3$, —OCF$_3$, CN, halogen, —C$_{1-6}$alkyl, —OC$_{1-6}$alkyl, —C$_{3-6}$cycloalkyl, —C$_{2-6}$cycloheteroalkyl, —C$_{2-6}$alkyl-C$_{3-6}$cycloalkyl, —C$_{2-6}$alkynyl-C$_{3-6}$cycloalkyl, and heteroaryl, wherein each R$^b$ is unsubstituted or substituted with one to five substituents selected from R$^f$. In a class of this embodiment, each R$^b$ is independently selected from the group consisting of: —CF$_3$, —CHF$_2$, —OCHF$_2$, —OCH$_2$CF$_3$, —OCF$_3$, CN, F, Cl, Br, —CH$_3$, —C(CH$_3$)$_3$, —OCH$_3$, cyclopropyl, cyclobutyl, piperidine, —CH$_2$-cyclopropyl, —C$_2$alkynyl-cyclopropyl, and pyrazole, wherein each R$^b$ is unsubstituted or substituted with one to five substituents selected from R$^f$.

In another embodiment, each R$^b$ is independently selected from the group consisting of: —CF$_3$, —CHF$_2$, —OCHF$_2$, CN, halogen, —C$_{1-6}$alkyl, —C$_{3-6}$cycloalkyl, and —C$_{2-6}$alkyl-C$_{3-6}$cycloalkyl, wherein each R$^b$ is unsubstituted or substituted with one to five substituents selected from R$^f$. In a class of this embodiment, each R$^b$ is independently selected from the group consisting of: —CF$_3$, —CHF$_2$, —OCHF$_2$, CN, F, Cl, Br, —CH$_3$, —C(CH$_3$)$_3$, cyclopropyl, cyclobutyl, and —CH$_2$-cyclopropyl, wherein each R$^b$ is unsubstituted or substituted with one to five substituents selected from R$^f$.

In another embodiment, each R$^b$ is independently selected from the group consisting of: —CF$_3$, —CHF$_2$, halogen, —C$_{1-6}$alkyl, and —C$_{3-6}$cycloalkyl, wherein each R$^b$ is unsubstituted or substituted with one to five substituents selected from R$^f$. In a class of this embodiment, each R$^b$ is independently selected from the group consisting of: —CF$_3$, —CHF$_2$, F, Cl, Br, —CH$_3$, —C(CH$_3$)$_3$, cyclopropyl, and cyclobutyl, wherein each R$^b$ is unsubstituted or substituted with one to five substituents selected from R$^f$. In another class of this embodiment, each R$^b$ is independently selected from the group consisting of: —CF$_3$, —CHF$_2$, F, Cl, —CH$_3$, cyclopropyl and cyclobutyl, wherein each R$^b$ is unsubstituted or substituted with one to five substituents selected from R$^f$.

In another embodiment, each R$^b$ is independently selected from the group consisting of: —CF$_3$, and —C$_{1-6}$alkyl, wherein each R$^b$ is unsubstituted or substituted with one to five substituents selected from R$^f$. In a class of this embodiment, each R$^b$ is independently selected from the group consisting of: —CF$_3$, and —C$_{1-6}$alkyl. In another class of this embodiment, each R$^b$ is independently selected from the group consisting of: —CF$_3$, and —CH$_3$, wherein —CH$_3$ is unsubstituted or substituted with one to five substituents selected from R$^f$. In a class of this embodiment, each R$^b$ is independently selected from the group consisting of: —CF$_3$, and —CH$_3$. In another class of this embodiment, each R$^b$ is —CH$_3$. In another class of this embodiment, each R$^b$ is CF$_3$.

In another embodiment of the present invention, each R$^c$ is independently selected from the group consisting of: —CF$_3$, —CH$_2$CF$_3$, —CHF$_2$, —OCHF$_2$, —OCF$_3$, CN, oxo, —OH, halogen, —C$_{1-6}$alkyl, —C$_{2-6}$alkenyl, —C$_{2-6}$alkynyl, —C$_{3-6}$cycloalkyl, —C$_{2-6}$cycloheteroalkyl, —C$_{1-6}$alkyl-C$_{3-6}$cycloalkyl, —C$_{1-6}$alkyl-C$_{2-6}$cycloheteroalkyl, —C$_{1-6}$alkyl-aryl, —C$_{1-6}$alkyl-heteroaryl, —C$_{1-6}$alkenyl-C$_{3-6}$cycloalkyl, —C$_{1-6}$alkenyl-aryl, —C$_{1-6}$alkenyl heteroaryl, —C$_{1-6}$alkenyl-C$_{2-6}$cycloheteroalkyl, —C$_{2-6}$alkynyl-C$_{3-6}$cycloalkyl, —C$_{2-6}$alkynyl-C$_{2-6}$cycloheteroalkyl, —C$_{2-6}$alkynyl-aryl, —C$_{2-6}$alkynyl heteroaryl, —OC$_{1-6}$alkyl, —OC$_{2-6}$alkenyl, —OC$_{2-6}$ alkynyl, —OC$_{3-6}$ cycloalkyl, —OC$_{2-6}$ heterocycloalkyl, —O-aryl, —O-heteroaryl, —OC$_{1-6}$alkyl-cycloalkyl, —OC$_{1-6}$alkyl-cycloheteroalkyl, —OC$_{1-6}$alkyl-aryl, —OC$_{1-6}$ alkyl-heteroaryl, —S(O)$_m$R$^L$, —S(O)R$^L$, —S—R$^L$, —C$_{1-6}$alkyl-S(O)$_m$R$^L$, —C(O)R$^L$, —C(O)C$_{1-6}$alkyl-R$^L$, —OC(O)R$^L$, —CO$_2$R$^L$, aryl, and heteroaryl, wherein each R$^c$ is unsubstituted or substituted with one to five substituents selected from R$^g$.

In another embodiment, each R$^c$ is independently selected from the group consisting of: —CF$_3$, —CH$_2$CF$_3$, —CHF$_2$, —OCF$_3$, CN, halogen, —C$_{1-6}$alkyl, oxo, —OH, —C$_{1-6}$alkyl-OH, —O-aryl, —O-heteroaryl, aryl, heteroaryl, —C$_{1-6}$alkyl-aryl, and —C$_{1-6}$alkyl-heteroaryl, wherein each R$^c$ is unsubstituted or substituted with one to five substituents selected from R$^g$. In a class of this embodiment, each R$^c$ is independently selected from the group consisting of: —CF$_3$, —CH$_2$CF$_3$, —CHF$_2$, —OCF$_3$, CN, F, Cl, —CH$_3$, —CH$_2$CH$_3$, oxo, —OH, —CH$_2$OH, —O-phenyl, phenyl, pyrazole, and —CH$_2$-phenyl, wherein each R$^c$ is unsubstituted or substituted with one to five substituents selected from R$^g$.

In another embodiment, each R$^c$ is independently selected from the group consisting of: —CF$_3$, —CH$_2$CF$_3$, —CHF$_2$, —OCF$_3$, CN, halogen, —C$_{1-6}$alkyl, oxo, —OH, —C$_{1-6}$alkyl-OH, —O-aryl, aryl, heteroaryl, and —C$_{1-6}$alkyl-aryl, wherein each R$^c$ is unsubstituted or substituted with one to five substituents selected from R$^g$. In a class of this embodiment, each R$^c$ is independently selected from the group consisting of: —CF$_3$, —CH$_2$CF$_3$, —CHF$_2$, —OCF$_3$, CN, F, Cl, —CH$_3$, —CH$_2$CH$_3$, oxo, —OH, —CH$_2$OH, —O-phenyl, phenyl, pyrazole, and —CH$_2$-phenyl, wherein each R$^c$ is unsubstituted or substituted with one to five substituents selected from R$^g$.

In another embodiment, each R$^c$ is independently selected from the group consisting of: —CF$_3$, halogen, and —C$_{1-6}$alkyl, wherein each R$^c$ is unsubstituted or substituted with one to five substituents selected from R$^g$. In a class of this embodiment, each R$^c$ is independently selected from the group consisting of: —CF$_3$, F, Cl, —CH$_3$ and —CH$_2$CH$_3$. In another class of this embodiment, each R$^c$ is independently selected from the group consisting of —CF$_3$, F, and —CH$_3$.

In another embodiment, each R$^c$ is independently selected from the group consisting of: halogen and —C$_{1-6}$alkyl, wherein each alkyl is unsubstituted or substituted with one to five substituents selected from R$^g$. In a class of this embodiment, each R$^c$ is independently selected from the group consisting of: halogen and —C$_{1-6}$alkyl, wherein each alkyl is unsubstituted or substituted with one to three substituents selected from R$^g$. In another class of this embodiment, each R$^c$ is independently selected from the group consisting of halogen and —C$_{1-6}$alkyl. In another class of this embodiment, each R$^c$ is independently selected from the group consisting of: F and —CH$_3$.

In another embodiment, each R$^c$ is —C$_{1-6}$alkyl, wherein each alkyl is unsubstituted or substituted with one to five substituents selected from R$^g$. In a class of this embodiment, each R$^c$ is —C$_{1-6}$alkyl, wherein each alkyl is unsubstituted or substituted with one to three substituents selected from R$^g$. In another class of this embodiment, each R$^c$ is —C$_{1-6}$alkyl. In another class of this embodiment, each R$^c$ is —CH$_3$.

In another embodiment, each R$^c$ is halogen. In a class of this embodiment, each R$^c$ is F.

In another embodiment of the present invention, R$^d$ is independently selected from the group consisting of: hydrogen, halogen, OH, oxo, —C$_{1-6}$alkyl, —OC$_{1-6}$alkyl, NH$_2$, NH(C$_{1-6}$alkyl), and N(C$_{1-6}$alkyl)$_2$. In another embodiment of the present invention, R$^d$ is independently selected from the group consisting of: halogen, OH, oxo, —C$_{1-6}$alkyl, —OC$_{1-6}$alkyl, NH$_2$, NH(C$_{1-6}$alkyl), and N(C$_{1-6}$alkyl)$_2$.

In another embodiment of the present invention, R$^d$ is independently selected from the group consisting of: hydrogen, halogen, OH, oxo, —C$_{1-6}$alkyl, —OC$_{1-6}$alkyl, and NH$_2$. In another embodiment of the present invention, R$^d$ is independently selected from the group consisting of: halogen, OH, oxo, —C$_{1-6}$alkyl, —OC$_{1-6}$alkyl, and NH$_2$.

In another embodiment, R$^d$ is independently selected from the group consisting of: hydrogen, halogen, —OH, N(R$^9$)$_2$, and C$_{1-6}$alkyl. In a class of this embodiment, R$^d$ is independently selected from the group consisting of: hydrogen, F, —OH, NH$_2$, and CH$_3$.

In another embodiment, R$^d$ is independently selected from the group consisting of: hydrogen, halogen, —OH, oxo, N(R$^9$)$_2$, and C$_{1-6}$alkyl. In a class of this embodiment, R$^d$ is independently selected from the group consisting of: hydrogen, F, —OH, NH$_2$, and CH$_3$. In another embodiment, R$^d$ is independently selected from the group consisting of: halogen, —OH, oxo, N(R$^g$)$_2$, and C$_{1-6}$alkyl. In a class of this embodiment, R$^d$ is independently selected from the group consisting of: F, —OH, NH$_2$, and CH$_3$.

In another embodiment, R$^d$ is independently selected from the group consisting of: halogen, —OH, N(R$^9$)$_2$, and C$_{1-6}$alkyl. In a class of this embodiment, R$^d$ is independently selected from the group consisting of F, —OH, NH$_2$, and CH$_3$.

In another embodiment, R$^d$ is independently selected from the group consisting of: hydrogen, halogen, and C$_{1-6}$alkyl. In a class of this embodiment, R$^d$ is independently selected from the group consisting of: hydrogen, F and CH$_3$. In another embodiment, R$^d$ is independently selected from the group consisting of: halogen, and C$_{1-6}$alkyl. In a class of this embodiment, R$^d$ is independently selected from the group consisting of: F and CH$_3$.

In another embodiment of the present invention, each R$^e$ is independently selected from the group consisting of: hydrogen, —C$_{1-6}$alkyl, and —C$_{2-6}$alkenyl. In another embodiment, R$^d$ is independently selected from the group consisting of —OH, and N(R$^9$)$_2$. In a class of this embodiment, R$^d$ is independently selected from the group consisting of: —OH, and NH$_2$. In another class of this embodiment, R$^d$ is —OH. In another class of this embodiment, R$^d$ is NH$_2$.

In another embodiment of the present invention, each R$^e$ is independently selected from the group consisting of: hydrogen, and —C$_{1-6}$alkyl. In a class of this embodiment, R$^e$ is hydrogen. In another class of this embodiment, R$^e$ is —C$_{1-6}$alkyl.

In another embodiment of the present invention, each R$^f$ is selected from the group consisting of: halogen, —C$_{1-6}$alkyl, —OH, —OC$_{1-6}$alkyl, —OC$_{3-6}$cycloalkyl, —OC$_{2-6}$cycloheteroalkyl, CN, —NH$_2$, —NH(C$_{1-6}$alkyl), —NH(C$_{3-6}$cycloalkyl), —NH(C$_{2-6}$cycloheteroalkyl), —N(C$_{1-6}$alkyl)$_2$, —N(C$_{3-6}$cycloalkyl)$_2$, and —N(C$_{2-6}$cycloheteroalkyl)$_2$, wherein each alkyl, cycloalkyl, and cycloheteroalkyl is unsubstituted or substituted with one to three substituents independently selected from: —OH, halogen, cyano, and —S(O)$_2$CH$_3$.

In another embodiment of the present invention, each R$^f$ is selected from the group consisting of: halogen, —C$_{1-6}$alkyl, —OH, —OC$_{1-6}$alkyl, —OC$_{3-6}$cycloalkyl, —OC$_{2-6}$cycloheteroalkyl, CN, —NH$_2$, —NH(C$_{1-6}$alkyl), and —N($C_{1-6}$alkyl)$_2$, wherein each alkyl, cycloalkyl, and cycloheteroalkyl is unsubstituted or substituted with one to three substituents independently selected from: —OH, halogen, cyano, and —S(O)$_2$CH$_3$.

In another embodiment of the present invention, each $R^f$ is selected from the group consisting of: halogen, —$C_{1-6}$alkyl, —OH, —O$C_{1-6}$alkyl, CN, —NH$_2$, —NH($C_{1-6}$alkyl), and —N($C_{1-6}$alkyl)$_2$, wherein each alkyl is unsubstituted or substituted with one to three substituents independently selected from: —OH, halogen, cyano, and —S(O)$_2$CH$_3$.

In another embodiment of the present invention, each $R^f$ is selected from the group consisting of: halogen, —$C_{1-6}$alkyl, —OH, —O$C_{1-6}$alkyl, and CN, wherein each alkyl is unsubstituted or substituted with one to three substituents independently selected from: —OH, halogen, cyano, and —S(O)$_2$CH$_3$.

In another embodiment of the present invention, each $R^f$ is selected from the group consisting of: halogen, —$C_{1-6}$alkyl, and —OH, wherein each alkyl is unsubstituted or substituted with one to three substituents independently selected from: —OH, halogen, cyano, and —S(O)$_2$CH$_3$. In a class of this embodiment, each $R^f$ is selected from the group consisting of: F, —CH$_3$, and —OH.

In another embodiment of the present invention, each $R^f$ is halogen. In a class of this embodiment, $R^f$ is F.

In another embodiment of the present invention, each $R^f$ is —$C_{1-6}$alkyl, wherein each alkyl is unsubstituted or substituted with one to three substituents independently selected from: —OH, halogen, cyano, and —S(O)$_2$CH$_3$. In a class of this embodiment, each $R^f$ is —$C_{1-6}$alkyl. In a subclass of this class, $R^f$ is —CH$_3$.

In another embodiment of the present invention, each $R^f$ is —OH.

In another embodiment of the present invention, each $R^g$ is selected from the group consisting of: halogen, $C_{1-6}$alkyl, —OH, —O$C_{1-6}$alkyl, —S(O)$_m$—$C_{1-6}$alkyl, —CN, —CF$_3$, —OCHF$_2$, and —OCF$_3$, wherein each alkyl is unsubstituted or substituted with one to three substituents independently selected from: —OH, halogen, cyano, and —S(O)$_2$CH$_3$.

In another embodiment of the present invention, each $R^g$ is selected from the group consisting of: halogen, $C_{1-6}$alkyl, —OH, —O$C_{1-6}$alkyl, —CN, —CF$_3$, —OCHF$_2$, and —OCF$_3$, wherein each alkyl is unsubstituted or substituted with one to three substituents independently selected from: —OH, halogen, cyano, and —S(O)$_2$CH$_3$.

In another embodiment of the present invention, each $R^g$ is selected from the group consisting of: halogen, $C_{1-6}$alkyl, —OH, —CN, —CF$_3$, wherein each alkyl is unsubstituted or substituted with one to three substituents independently selected from: —OH, halogen, cyano, and —S(O)$_2$CH$_3$.

In another embodiment of the present invention, each $R^g$ is selected from the group consisting of: halogen, —OH, —CN, and —CF$_3$. In a class of this embodiment, each $R^g$ is selected from the group consisting of: F, —OH, —CN, and —CF$_3$.

In another embodiment of the present invention, each $R^h$ is independently selected from the group consisting of: hydrogen, and —$C_{1-6}$alkyl. In a class of this embodiment, $R^h$ is hydrogen. In another class of this embodiment, $R^h$ is —$C_{1-6}$alkyl.

In another embodiment of the present invention, each $R^i$ is independently selected from the group consisting of: hydrogen, and —$C_{1-6}$alkyl. In a class of this embodiment, $R^i$ is hydrogen. In another class of this embodiment, $R^i$ is —$C_{1-6}$alkyl.

In another embodiment of the present invention, each $R^g$ halogen. In a class of this embodiment, each $R^g$ is F.

In another embodiment of the present invention, each $R^j$ is selected from the group consisting of: —$C_{1-6}$alkyl, —$C_{2-6}$alkenyl, —$C_{3-6}$cycloalkyl, —$C_{2-6}$cycloheteroalkyl, aryl, and heteroaryl, wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —O$C_{1-6}$alkyl, —O$C_{3-6}$cycloalkyl, halogen, cyano, and —S(O)$_2$CH$_3$.

In another embodiment of the present invention, each $R^j$ is selected from the group consisting of: —$C_{1-6}$alkyl, —$C_{2-6}$alkenyl, —$C_{3-6}$cycloalkyl, and —$C_{2-6}$cycloheteroalkyl, wherein each alkyl, alkenyl, cycloalkyl, and cycloheteroalkyl is unsubstituted or substituted with one to three substituents independently selected from: —$C_{1-6}$alkyl, —$C_{3-6}$cycloalkyl, —OH, —O$C_{1-6}$alkyl, —O$C_{3-6}$cycloalkyl, halogen, cyano, and —S(O)$_2$CH$_3$.

In another embodiment of the present invention, each $R^j$ is selected from the group consisting of —$C_{1-6}$alkyl, —$C_{3-6}$cycloalkyl, and —$C_{2-6}$cycloheteroalkyl, wherein each alkyl, cycloalkyl, and cycloheteroalkyl is unsubstituted or substituted with one to three substituents independently selected from: —$C_{1-6}$alkyl, —$C_{3-6}$cycloalkyl, —OH, —O$C_{1-6}$alkyl, —O$C_{3-6}$cycloalkyl, halogen, cyano, and —S(O)$_2$CH$_3$. In another embodiment of the present invention, each $R^j$ is selected from the group consisting of: —$C_{1-6}$alkyl, —$C_{3-6}$cycloalkyl, and —$C_{2-6}$cycloheteroalkyl, wherein each alkyl, cycloalkyl, and cycloheteroalkyl.

In another embodiment of the present invention, each $R^j$ is —$C_{1-6}$alkyl, wherein each alkyl, is unsubstituted or substituted with one to three substituents independently selected from: —$C_{1-6}$alkyl, —$C_{3-6}$cycloalkyl, —OH, —O$C_{1-6}$alkyl, —O$C_{3-6}$cycloalkyl, halogen, cyano, and —S(O)$_2$CH$_3$. In a class of this embodiment, each $R^j$ is —$C_{1-6}$alkyl.

In another embodiment of the present invention, each $R^k$ is selected from the group consisting of —$C_{1-6}$alkyl, —$C_{2-6}$alkenyl, —$C_{3-6}$cycloalkyl, —$C_{3-6}$cycloalkyl, —$C_{2-6}$cycloheteroalkyl, aryl, and heteroaryl, wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —O$C_{1-6}$alkyl, —O$C_{3-6}$cycloalkyl, halogen, cyano, and —S(O)$_2$CH$_3$.

In another embodiment of the present invention, each $R^k$ is selected from the group consisting of —$C_{1-6}$alkyl, —$C_{2-6}$alkenyl, —$C_{3-6}$cycloalkyl, and —$C_{2-6}$cycloheteroalkyl, wherein each alkyl, alkenyl, cycloalkyl, and cycloheteroalkyl is unsubstituted or substituted with one to three substituents independently selected from: —$C_{1-6}$alkyl, —$C_{3-6}$cycloalkyl, —OH, —O$C_{1-6}$alkyl, —O$C_{3-6}$cycloalkyl, halogen, cyano, and —S(O)$_2$CH$_3$.

In another embodiment of the present invention, each $R^k$ is selected from the group consisting of —$C_{1-6}$alkyl, —$C_{3-6}$cycloalkyl, and —$C_{2-6}$cycloheteroalkyl, wherein each alkyl, cycloalkyl, and cycloheteroalkyl is unsubstituted or substituted with one to three substituents independently selected from: —$C_{1-6}$alkyl, —$C_{3-6}$cycloalkyl, —OH, —O$C_{1-6}$alkyl, —O$C_{3-6}$cycloalkyl, halogen, cyano, and —S(O)$_2$CH$_3$.

In another embodiment of the present invention, each $R^k$ is —$C_{1-6}$alkyl, wherein each alkyl, is unsubstituted or substituted with one to three substituents independently selected from: —$C_{1-6}$alkyl, —$C_{3-6}$cycloalkyl, —OH, —O$C_{1-6}$alkyl, —O$C_{3-6}$cycloalkyl, halogen, cyano, and —S(O)$_2$CH$_3$. In a class of this embodiment, each $R^k$ is —$C_{1-6}$alkyl.

In another embodiment of the present invention, each $R^L$ is selected from the group consisting of: —$C_{1-6}$alkyl, —$C_{2-6}$alkenyl, —$C_{3-6}$cycloalkyl, —$C_{2-6}$cycloheteroalkyl, aryl, and heteroaryl, wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$.

In another embodiment of the present invention, each $R^L$ is selected from the group consisting of: —$C_{1-6}$alkyl, —$C_{2-6}$alkenyl, —$C_{3-6}$cycloalkyl, and —$C_{2-6}$cycloheteroalkyl, wherein each alkyl, alkenyl, cycloalkyl, and cycloheteroalkyl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$.

In another embodiment of the present invention, each $R^L$ is selected from the group consisting of: —$C_{1-6}$alkyl, —$C_{3-6}$cycloalkyl, and —$C_{2-6}$cycloheteroalkyl, wherein each alkyl, cycloalkyl, and cycloheteroalkyl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$.

In another embodiment of the present invention, each $R^L$ is —$C_{1-6}$alkyl, wherein each alkyl, is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$. In a class of this embodiment, each $R^L$ is —$C_{1-6}$alkyl.

In another embodiment of the present invention, each $R^m$ is independently selected from the group consisting of: hydrogen, and —$C_{1-6}$alkyl. In a class of this embodiment, $R^m$ is hydrogen. In another class of this embodiment, $R^m$ is —$C_{1-6}$alkyl.

In another embodiment of the present invention, n is 0, 1, 2, 3 or 4. In a class of this embodiment, n is 0, 1, 2 or 3. In another class of this embodiment, n is 0, 1 or 2. In a class of this embodiment, n is 0 or 1. In a class of this embodiment, n is 1, 2, 3 or 4. In another class of this embodiment, n is 1, 2 or 3. In another class of this embodiment, n is 1 or 2. In another class of this embodiment, n is 0. In another class of this embodiment, n is 1. In another class of this embodiment, n is 2. In another class of this embodiment, n is 3. In another class of this embodiment, n is 4.

In another embodiment of the present invention, m is 0, 1 or 2. In a class of this embodiment, m is 0 or 1. In another class of this embodiment, m is 1 or 2. In another class of this embodiment, m is 0. In another class of this embodiment, m is 1. In another class of this embodiment, m is 2.

In another embodiment of the present invention, p is 0, 1, 2, 3 or 4. In a class of this embodiment, p is 0, 1, 2 or 3. In another class of this embodiment, p is 0, 1 or 2. In a class of this embodiment, p is 0 or 1. In a class of this embodiment, p is 1, 2, 3 or 4. In another class of this embodiment, p is 1, 2 or 3. In another class of this embodiment, p is 1 or 2. In another class of this embodiment, p is 0. In another class of this embodiment, p is 1. In another class of this embodiment, p is 2. In another class of this embodiment, p is 3. In another class of this embodiment, p is 4.

In another embodiment of the present invention, q is 0 or 1. In another class of this embodiment, q is 0. In another class of this embodiment, q is 1.

In another embodiment of the present invention, r is 0 or 1. In another class of this embodiment, r is 0. In another class of this embodiment, r is 1.

In another embodiment of the present invention, the invention relates to compounds of structural formula Ia:

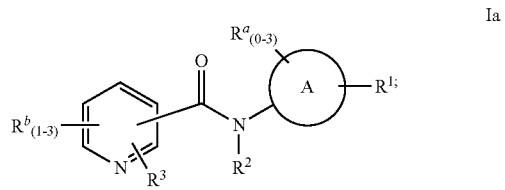

or a pharmaceutically acceptable salt thereof. In a class of this embodiment, A is pyridine. In another class of this embodiment, A is

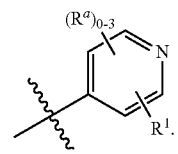

In another class of this embodiment, A is

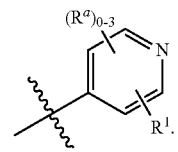

In another class of this embodiment, A is

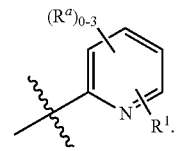

In another class of this embodiment, A is

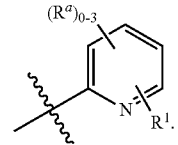

In another class of this embodiment, A is:

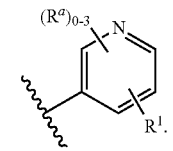

In another class of this embodiment, A is:

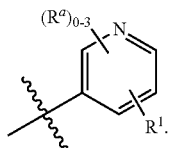

In another embodiment of the present invention, the invention relates to compounds of structural formula Ib:

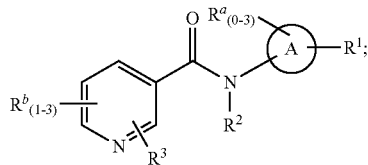

Ib or a pharmaceutically acceptable salt thereof. In a class of this embodiment, A is pyridine. In another class of this embodiment, A is

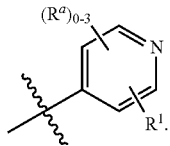

In another class of this embodiment, A is

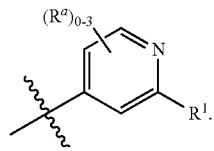

In another class of this embodiment, A is

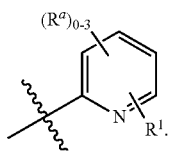

In another class of this embodiment, A is

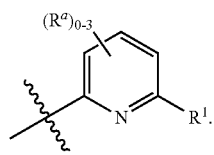

In another class of this embodiment, A is

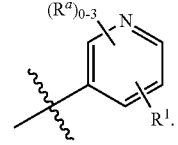

In another class of this embodiment, A is:

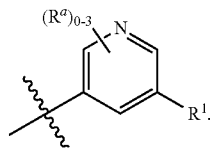

In another embodiment of the present invention, the invention relates to compounds of structural formula Ic:

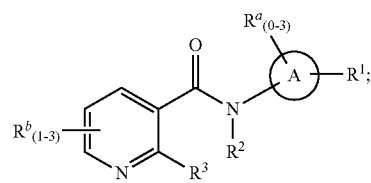

Ic or a pharmaceutically acceptable salt thereof. In a class of this embodiment, A is pyridine.

In another class of this embodiment, A is

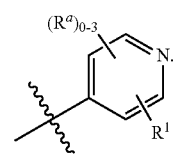

In another class of this embodiment, A is

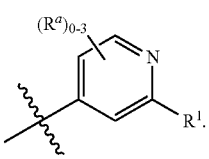

In another class of this embodiment, A is

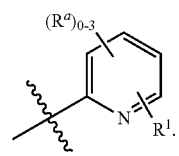

In another class of this embodiment, A is

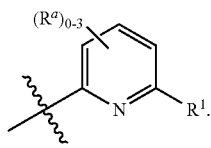

In another class of this embodiment, A is:

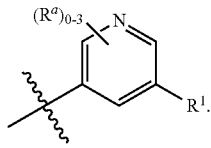

In another class of this embodiment, A is

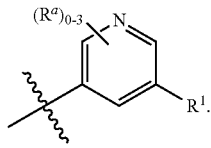

The compound of structural formula I, includes the compounds of structural formulas Ia, Ib, and 1c, and pharmaceutically acceptable salts, hydrates and solvates thereof.

Another embodiment of the present invention relates to compounds of structural formula I wherein:
A is selected from the group consisting of
(1) pyridine,
(2) pyrimidine,
(3) pyrazine,
(4) indazole,
(5) imidazo[1,2-a]pyridine,
(6) pyrrolo[3,2-c]pyridine,
(7) pyrrolo[2,3-b]pyridine,
(8) pyrazole,
(9) thiophene, and
(10) 1,2,4-oxadiazole,
wherein A is unsubstituted or substituted with one to five substituents selected from $R^a$;
B is selected from the group consisting of:
(1) pyrazine,
(2) pyridine,
(3) pyrimidine, and
(4) pyridazine,
wherein each B is unsubstituted or substituted with one to three substituents selected from $R^b$;
$R^1$ is selected from the group consisting of:
(1) —$SO_3H$,
(2) —$SO_2NH_2$,
(3) —$SO_2C_{1-6}$alkyl-$NH_2$,
(4) —$SO_2NH$—$C_{1-6}$alkyl,
(5) —$SO_2C_{1-6}$alkyl,
(6) —$SO_2C_{3-6}$cycloalkyl,
(7) —$C(O)NH_2$,
(8) —$CO_2H$,
(9) —CN,
(10) halogen,
(11) —OH,
(12) —$OC_{1-6}$alkyl,
(13) —$C_{1-6}$alkyl,
(14) —$C_{1-6}$alkyl-OH, and
(15) $CF_3$,
wherein each alkyl, and cycloalkyl is unsubstituted or substituted with one to three substituents selected from $R^d$;
$R^2$ is hydrogen;
$R^3$ is selected from the group consisting of:
(1) cyclohexane,
(2) cycloheptane,
(3) pyrrolidine,
(4) azetidine,
(5) piperidine,
(6) piperazine,
(7) azepane,
(8) morpholine,
(9) thiomorpholine,
(10) oxazepane,
(11) isoindoline,
(12) dihydroisoquinoline,
(13) azabicyclo[2.2.1]heptane,
(14) azabicyclo[3.1.1]heptane,
(15) azabicyclo[4.1.0]heptane,
(16) azabicyclo[3.2.1]octane,
(17) azabicyclo[3.2.0]heptane,
(18) azaspiro[2.5]octane,
(19) dihydrothieno[3,2-c]pyridine,
(20) dihydroimidazo[1,2-a]pyrazine, and
(21) hexahydrofuro[3,2-b]pyrrole,
wherein $R^3$ is unsubstituted or substituted with one to eight substituents selected from $R^c$; or a pharmaceutically acceptable salt thereof.

Another embodiment of the present invention relates to compounds of structural formula I wherein:
A is selected from the group consisting of:
(1) pyridine,
(2) pyrimidine,
(3) pyrazine,
(4) indazole,
(5) imidazo[1,2-a]pyridine,
(6) pyrrolo[3,2-c]pyridine,
(7) pyrrolo[2,3-b]pyridine,
(8) pyrazole,
(9) thiophene, and
(10) 1,2,4-oxadiazole,
wherein A is unsubstituted or substituted with one to five substituents selected from $R^a$;
B is selected from the group consisting of:
(1) pyridine,
(2) pyrimidine, and
(3) pyridazine,
wherein each B is unsubstituted or substituted with one to three substituents selected from $R^b$;
$R^1$ is selected from the group consisting of:
(1) —$SO_3H$,
(2) —$SO_2NH_2$,
(3) —$SO_2C_{1-6}$alkyl-$NH_2$,
(4) —$SO_2NH$—$C_{1-6}$alkyl,
(5) —$SO_2C_{1-6}$alkyl,
(6) —$SO_2C_{3-6}$cycloalkyl,
(7) —$C(O)NH_2$,
(8) —$CO_2H$,
(9) —CN,
(10) halogen,
(11) —OH,
(12) —$OC_{1-6}$alkyl,
(13) —$C_{1-6}$alkyl,
(14) —$C_{1-6}$alkyl-OH, and
(15) $CF_3$, wherein each alkyl, and cycloalkyl is unsubstituted or substituted with one to three substituents selected from $R^d$;
$R^2$ is hydrogen;
$R^3$ is selected from the group consisting of
(1) pyrrolidine,
(2) azetidine,
(3) piperidine,
(4) piperazine,
(5) azepane,
(6) morpholine,
(7) thiomorpholine,
(8) oxazepane,
(9) isoindoline,
(10) dihydroisoquinoline,
(11) azabicyclo[2.2.1]heptane,
(12) azabicyclo[3.1.1]heptane,
(13) azabicyclo[4.1.0]heptane,
(14) azabicyclo[3.2.1]octane,
(15) azabicyclo[3.2.0]heptane,
(16) azaspiro[2.5]octane,
(17) dihydrothieno[3,2-c]pyridine,
(18) dihydroimidazo[1,2-a]pyrazine, and
(19) hexahydrofuro[3,2-b]pyrrole,
wherein $R^3$ is unsubstituted or substituted with one to eight substituents selected from $R^c$;
or a pharmaceutically acceptable salt thereof.

Another embodiment of the present invention relates to compounds of structural formula I wherein:
A is pyridine, wherein pyridine is unsubstituted or substituted with one to three substituents selected from $R^a$;
B is pyridine, wherein pyridine is unsubstituted or substituted with one to three substituents selected from $R^b$;
$R^1$ is selected from the group consisting of:
(1) —SO$_2$NH$_2$,
(2) —C(O)NH$_2$, and
(3) —OH;
$R^2$ is hydrogen;
$R^3$ is selected from the group consisting of
(1) piperidine,
(2) azepane, and
(3) morpholine,
wherein $R^3$ is unsubstituted or substituted with one to eight substituents selected from $R^c$; or a pharmaceutically acceptable salt thereof.

Illustrative, but non-limiting, examples of the compounds of the present invention that are useful as inhibitors of Na$_v$1.8 channel activity are the following compounds:
1) 2-(4,4-difluoropiperidin-1-yl)-N-(6-sulfamoylpyrazin-2-yl)-5-(trifluoromethyl)-nicotinamide;
2) 2-(4,4-difluoropiperidin-1-yl)-N-(4-hydroxypyrimidin-2-yl)-5-(trifluoromethyl)-nicotinamide;
3) 5-(2-(4,4-difluoropiperidin-1-yl)-5-(trifluoromethyl) nicotinamido)picolinic acid;
4) 4-(2-(4,4-difluoropiperidin-1-yl)-5-(trifluoromethyl) nicotinamido)picolinic acid;
5) N-(6-cyanopyridin-3-yl)-2-(4,4-difluoropiperidin-1-yl)-5-(trifluoromethyl)nicotinamide;
6) 2-(azepan-1-yl)-N-(5-(methylsulfonyl)pyridin-3-yl)-5-(trifluoromethyl)nicotinamide;
7) 2-(3-(hydroxymethyl)piperidin-1-yl)-N-(2-sulfamoylpyridin-4-yl)-5-(trifluoromethyl)-nicotinamide;
8) 2-(azepan-1-yl)-N-(5-carbamoylpyridin-3-yl)-5-(trifluoromethyl)nicotinamide;
9) 2-(4,4-difluoro-1-piperidyl)-6-methyl-N-(5-sulfamoyl-3-pyridyl)pyridine-3-carboxamide;
10) 5-chloro-2-(4,4-difluoro-1-piperidyl)-N-(5-sulfamoyl-3-pyridyl)pyridine-3-carboxamide;
11) 6-chloro-2-(4,4-difluoropiperidin-1-yl)-4-methyl-N-(5-sulfamoylpyridin-3-yl)nicotinamide;
12) 5,6-dicyclopropyl-2-(4,4-difluoropiperidin-1-yl)-N-(2-sulfamoylpyridin-4-yl)nicotinamide;
13) 2-(4,4-difluoroazepan-1-yl)-N-(2-sulfamoylpyridin-4-yl)-5-(trifluoromethyl)nicotinamide;
14) 5-cyclopropyl-2-(4,4-difluoropiperidin-1-yl)-6-methyl-N-(2-sulfamoylpyridin-4-yl)nicotinamide;
15) 5-cyclobutyl-2-(4,4-difluoropiperidin-1-yl)-6-methyl-N-(2-sulfamoylpyridin-4-yl)nicotinamide;
16) 5-(cyclopropylethynyl)-2-(4,4-difluoropiperidin-1-yl)-6-methyl-N-(2-sulfamoylpyridin-4-yl)nicotinamide;
17) 2-(4,4-difluoroazepan-1-yl)-6-methyl-N-(2-sulfamoylpyridin-4-yl)nicotinamide;
18) 6-(cyclopropylmethyl)-2-(4,4-difluoroazepan-1-yl)-N-(2-sulfamoylpyridin-4-yl)nicotinamide;
19) 2-(4,4-difluoroazepan-1-yl)-5,6-dimethyl-N-(2-sulfamoylpyridin-4-yl)nicotinamide;
20) 5-cyclopropyl-2-(4,4-difluoropiperidin-1-yl)-N-(2-sulfamoylpyridin-4-yl)-6-(2,2,2-trifluoroethoxy)nicotinamide;
21) 5-chloro-6-cyclopropyl-2-(4,4-difluoroazepan-1-yl)-N-(2-sulfamoylpyridin-4-yl)-nicotinamide;
22) 6-cyclopropyl-2-(4,4-difluoroazepan-1-yl)-N-(2-sulfamoylpyridin-4-yl)nicotinamide;
23) 5-chloro-6-cyclobutyl-2-(4,4-difluoroazepan-1-yl)-N-(2-sulfamoylpyridin-4-yl)-nicotinamide;
24) 6-cyclobutyl-2-(4,4-difluoroazepan-1-yl)-N-(2-sulfamoylpyridin-4-yl)nicotinamide;
25) 2-(5,5-Difluoro-2-oxoazepan-1-yl)-N-(2-sulfamoylpyridin-4-yl)-5-(trifluoromethyl)-nicotinamide;
26) 2-(4,4-difluoropiperidin-1-yl)-N-(2-sulfamoylpyridin-4-yl)nicotinamide;
27) 5-chloro-6-cyclopropyl-2-(4,4-difluoroazepan-1-yl)-N-(2-oxo-1,2-dihydropyridin-4-yl)-nicotinamide;
28) 2-(5,5-Difluoro-2-oxoazepan-1-yl)-N-(2-sulfamoylpyridin-4-yl)-5-(trifluoromethyl)-nicotinamide;
29) 2-(4,4-Dichloropiperidin-1-yl)-N-(2-sulfamoylpyridin-4-yl)-5-(trifluoromethyl)-nicotinamide;
30) 2-(4,4-difluoroazepan-1-yl)-N-[1-(methylsulfonyl)-1H-pyrrolo[2,3-b]pyridin-3-yl]-5-(trifluoromethyl)pyridine-3-carboxamide;
31) 5-chloro-2-(4,4-difluoroazepan-1-yl)-6-methyl-N-[1-(methylsulfonyl)-1H-pyrazol-4-yl]pyridine-3-carboxamide;
32) 5-chloro-2-(4,4-difluoroazepan-1-yl)-4,6-dimethyl-N-[1-(methylsulfonyl)-1H-pyrazol-4-yl]pyridine-3-carboxamide;
33) N-{1-[(2-aminoethyl)sulfonyl]-1H-pyrazol-4-yl}-5-chloro-2-(4,4-difluoroazepan-1-yl)-6-methylpyridine-3-carboxamide;
34) 2-(4,4-difluoroazepan-1-yl)-N-[1-(methylsulfonyl)-1H-indazol-3-yl]-5-(trifluoromethyl)-pyridine-3-carboxamide;
35) 2-(4,4-difluoroazepan-1-yl)-N-[1-(methylsulfonyl)-1H-pyrrolo[3,2-c]pyridin-3-yl]-5-(trifluoromethyl)pyridine-3-carboxamide;
36) N-[1-(cyclopropylsulfonyl)-1H-pyrazol-4-yl]-2-(4,4-difluoroazepan-1-yl)-5-(trifluoro-methyl)pyridine-3-carboxamide;
37) N-[5-cyclopropyl-1-(methylsulfonyl)-1H-pyrazol-4-yl]-2-(4,4-difluoroazepan-1-yl)-5-(trifluoromethyl)pyridine-3-carboxamide;
38) 2-cyclopropyl-4-(4,4-difluoroazepan-1-yl)-N-(2-sulfamoylpyridin-4-yl)pyrimidine-5-carboxamide;
39) 6-cyclopropyl-3-(4,4-difluoroazepan-1-yl)-N-(2-sulfamoylpyridin-4-yl)pyridazine-4-carboxamide;

40) 6-methyl-N-(2-sulfamoylpyridin-4-yl)-2-(3,4,4-trifluoroazepan-1-yl)nicotinamide;
41) 5-chloro-2-(4,4-difluoroazepan-1-yl)-6-methoxy-N-(2-sulfamoylpyridin-4-yl)pyridine-3-carboxamide;
42) N-[2-(tert-butylsulfamoyl)pyridin-4-yl]-5-chloro-2-(4,4-difluoroazepan-1-yl)-6-methoxy-pyridine-3-carboxamide;
43) 5-cyano-2-(4,4-difluoropiperidin-1-yl)-N-(2-sulfamoylpyridin-4-yl)-6-(trifluoromethyl)-nicotinamide;
44) 5-(cyclopropylethynyl)-2-(4,4-difluoropiperidin-1-yl)-N-(2-sulfamoylpyridin-4-yl)-6-(trifluoromethyl)nicotinamide;
45) 2-(azepan-1-yl)-N-(3-cyano-1,2,4-oxadiazol-5-yl)-5-(trifluoromethyl)pyridine-3-carboxamide;
46) 5-(cyclopropylmethyl)-2-(4,4-difluoroazepan-1-yl)-N-(2-sulfamoylpyridin-4-yl)nicotinamide;
47) (S)-2-(4,4-difluoro-3-methylpiperidin-1-yl)-N-(2-sulfamoylpyridin-4-yl)-5-(trifluoro-methyl)nicotinamide;
48) (R)-2-(4,4-difluoro-3-methylpiperidin-1-yl)-N-(2-sulfamoylpyridin-4-yl)-5-(trifluoro-methyl)-nicotinamide;
49) (R)-2-(4,4-dichloro-3-methylpiperidin-1-yl)-N-(2-sulfamoylpyridin-4-yl)-5-(trifluoro-methyl)nicotinamide;
50) (S)-2-(4,4-dichloro-3-methylpiperidin-1-yl)-N-(2-sulfamoylpyridin-4-yl)-5-(trifluoro-methyl)nicotinamide;
51) 2-(4,4-Dichloroazepan-1-yl)-N-(2-sulfamoylpyridin-4-yl)-5-(trifluoromethyl)nicotinamide;
52) 2-[(3S,5R)-4,4-difluoro-3,5-dimethyl-1-piperidyl]-N-(2-sulfamoyl-4-pyridyl)-5-(trifluoromethyl)pyridine-3-carboxamide;
53) 5-chloro-2-[(3S,5R)-4,4-difluoro-3,5-dimethyl-1-piperidyl]-6-methyl-N-(2-sulfamoyl-4-pyridyl)pyridine-3-carboxamide;
54) (S)-5-chloro-2-(4,4-difluoro-3-methylpiperidin-1-yl)-6-methyl-N-(2-sulfamoylpyridin-4-yl)nicotinamide;
55) (R)-5-chloro-2-(4,4-difluoro-3-methylpiperidin-1-yl)-6-methyl-N-(2-sulfamoylpyridin-4-yl)nicotinamide;
56) (S)-2-(3-methylpiperidin-1-yl)-N-(2-sulfamoylpyridin-4-yl)-5-(trifluoromethyl)-nicotinamide;
57) (R)-2-(3-methylpiperidin-1-yl)-N-(2-sulfamoylpyridin-4-yl)-5-(trifluoromethyl)-nicotinamide;
58) N-(2-sulfamoyl-4-pyridyl)-5-(trifluoromethyl)-2-[(1S,5S)-1-(trifluoromethyl)-3-azabicyclo[3.2.0]heptan-3-yl]pyridine-3-carboxamide;
59) N-(2-sulfamoyl-4-pyridyl)-5-(trifluoromethyl)-2-[(1R,5R)-1-(trifluoromethyl)-3-azabicyclo[3.2.0]heptan-3-yl]pyridine-3-carboxamide;
60) N-(2-sulfamoylpyridin-4-yl)-2-((1R,5S)-6,6,7,7-tetrafluoro-3-azabicyclo[3.2.0]heptan-3-yl)-5-(trifluoromethyl)nicotinamide;
61) 2-[(1S,6S)-7,7-difluoro-6-methyl-3-azabicyclo[4.1.0]heptan-3-yl]-N-(2-sulfamoyl-4-pyridyl)-5-(trifluoromethyl)pyridine-3-carboxamide;
62) 2-[(1R,6R)-7,7-difluoro-6-methyl-3-azabicyclo[4.1.0]heptan-3-yl]-N-(2-sulfamoyl-4-pyridyl)-5-(trifluoromethyl)pyridine-3-carboxamide;
63) 2-((1R,5S)-8,8-difluoro-3-azabicyclo[3.2.1]octan-3-yl)-N-(2-sulfamoylpyridin-4-yl)-5-(trifluoromethyl)nicotinamide;
64) 2-((1R,5S)-6,6-difluoro-3-azabicyclo[3.2.0]heptan-3-yl)-N-(2-sulfamoylpyridin-4-yl)-5-(trifluoromethyl)nicotinamide;
65) 2-((1S,5R)-6,6-difluoro-3-azabicyclo[3.2.0]heptan-3-yl)-N-(2-sulfamoylpyridin-4-yl)-5-(trifluoromethyl)nicotinamide;
66) (R)-2-(1,1-difluoro-5-azaspiro[2.5]octan-5-yl)-N-(2-sulfamoylpyridin-4-yl)-5-(trifluoromethyl)nicotinamide;
67) (S)-2-(1,1-difluoro-5-azaspiro[2.5]octan-5-yl)-N-(2-sulfamoylpyridin-4-yl)-5-(trifluoromethyl)nicotinamide;
68) 2-((1R,5S)-3-azabicyclo[3.2.0]heptan-3-yl)-N-(2-sulfamoylpyridin-4-yl)-5-(trifluoromethyl)nicotinamide;
69) 2-((1S,6S)-7,7-difluoro-3-azabicyclo[4.1.0]heptan-3-yl)-N-(2-sulfamoylpyridin-4-yl)-5-(trifluoromethyl)nicotinamide;
70) 2-((1R,6R)-7,7-difluoro-3-azabicyclo[4.1.0]heptan-3-yl)-N-(2-sulfamoylpyridin-4-yl)-5-(trifluoromethyl)nicotinamide;
71) 2-[(1R,4R)-5,5-difluoro-2-azabicyclo[2.2.1]heptan-2-yl]-N-(2-sulfamoyl-4-pyridyl)-5-(trifluoromethyl)pyridine-3-carboxamide;
72) 2-[(1S,4S)-5,5-difluoro-2-azabicyclo[2.2.1]heptan-2-yl]-N-(2-sulfamoyl-4-pyridyl)-5-(trifluoromethyl)pyridine-3-carboxamide;
73) (R)-2-(4,4-difluoro-2-methylpiperidin-1-yl)-N-(2-sulfamoylpyridin-4-yl)-5-(trifluoromethyl)nicotinamide;
74) (S)-2-(4,4-difluoro-2-methylpiperidin-1-yl)-N-(2-sulfamoylpyridin-4-yl)-5-(trifluoromethyl)nicotinamide;
75) 2-((3R,4s,5S)-4-hydroxy-3,4,5-trimethylpiperidin-1-yl)-N-(2-sulfamoylpyridin-4-yl)-5-(trifluoromethyl)nicotinamide;
76) 2-((1R,5S)-6,6-difluoro-3-azabicyclo[3.1.1]heptan-3-yl)-N-(2-sulfamoylpyridin-4-yl)-5-(trifluoromethyl)nicotinamide;
77) 2-[(3S,4S)-4-hydroxy-3-methyl-1-piperidyl]-N-(2-sulfamoyl-4-pyridyl)-5-(trifluoromethyl)-pyridine-3-carboxamide;
78) 2-[(3S,4r,5R)-4-hydroxy-3,5-dimethyl-1-piperidyl]-N-(2-sulfamoyl-4-pyridyl)-5-(trifluoro-methyl)pyridine-3-carboxamide;
79) 2-(6,7-dihydro-4H-thieno[3,2-c]pyridin-5-yl)-N-(2-sulfamoyl-4-pyridyl)-5-(trifluoro-methyl)pyridine-3-carboxamide;
80) N-(2-sulfamoyl-4-pyridyl)-5-(trifluoromethyl)-2-[3-(trifluoromethyl)-1-piperidyl]pyridine-3-carboxamide;
81) 2-[3-(3,5-difluorophenyl)-1-piperidyl]-N-(2-sulfamoyl-4-pyridyl)-5-(trifluoromethyl)-pyridine-3-carboxamide;
82) N-(2-sulfamoyl-4-pyridyl)-5-(trifluoromethyl)-2-[4-(trifluoromethyl)-1-piperidyl]pyridine-3-carboxamide;
83) N-(2-sulfamoyl-4-pyridyl)-5-(trifluoromethyl)-2-[3-[[4-(trifluoromethyl)phenyl]methyl]-1-piperidyl]pyridine-3-carboxamide;
84) N-(2-sulfamoyl-4-pyridyl)-2-thiomorpholino-5-(trifluoromethyl)pyridine-3-carboxamide;
85) N-(2-sulfamoyl-4-pyridyl)-5-(trifluoromethyl)-2-[3-[4-(trifluoromethyl)phenyl]pyrrolidin-1-yl]pyridine-3-carboxamide;
86) 2-(3-benzyl-6,8-dihydro-5H-imidazo[1,2-a]pyrazin-7-yl)-N-(2-sulfamoyl-4-pyridyl)-5-(trifluoromethyl)pyridine-3-carboxamide;
87) 2-[3,3-dimethyl-4-(2,2,2-trifluoroethyl)piperazin-1-yl]-N-(2-sulfamoyl-4-pyridyl)-5-(trifluoromethyl)pyridine-3-carboxamide;
88) 2-(2,2-dimethylmorpholin-4-yl)-N-(2-sulfamoyl-4-pyridyl)-5-(trifluoromethyl)pyridine-3-carboxamide;
89) N-(2-sulfamoyl-4-pyridyl)-5-(trifluoromethyl)-2-[8-(trifluoromethyl)-3,4-dihydro-1H-isoquinolin-2-yl]pyridine-3-carboxamide;
90) N-(2-sulfamoyl-4-pyridyl)-2-[4-(trifluoromethoxy)isoindolin-2-yl]-5-(trifluoromethyl)-pyridine-3-carboxamide;
91) N-(2-sulfamoyl-4-pyridyl)-5-(trifluoromethyl)-2-[2-[4-(trifluoromethyl)phenyl]morpholin-4-yl]pyridine-3-carboxamide;

92) N-(2-sulfamoyl-4-pyridyl)-2-(3,3,4,4-tetrafluoropyrrolidin-1-yl)-5-(trifluoromethyl)-pyridine-3-carboxamide;
93) N-(2-sulfamoyl-4-pyridyl)-5-(trifluoromethyl)-2-[3-(trifluoromethyl)azetidin-1-yl]pyridine-3-carboxamide;
94) 2-(3-pyrazol-1-ylpyrrolidin-1-yl)-N-(2-sulfamoyl-4-pyridyl)-5-(trifluoromethyl)pyridine-3-carboxamide;
95) 2-[2-(4-fluorophenyl)-1-piperidyl]-N-(2-sulfamoyl-4-pyridyl)-5-(trifluoromethyl)pyridine-3-carboxamide;
96) 2-(2,3,3a,5,6,6a-hexahydrofuro[3,2-b]pyrrol-4-yl)-N-(2-sulfamoyl-4-pyridyl)-5-(trifluoro-methyl)pyridine-3-carboxamide;
97) N-(2-sulfamoyl-4-pyridyl)-5-(trifluoromethyl)-2-[3-[4-(trifluoromethyl)phenoxy]azetidin-1-yl]pyridine-3-carboxamide;
98) N-(2-sulfamoyl-4-pyridyl)-5-(trifluoromethyl)-2-[4-[3-(trifluoromethyl)phenoxy]-1-piperidyl]pyridine-3-carboxamide;
99) 2-[4-(cyclopropylmethyl)-3-oxo-piperazin-1-yl]-N-(2-sulfamoyl-4-pyridyl)-5-(trifluoro-methyl)pyridine-3-carboxamide;
100) N-(2-sulfamoyl-4-pyridyl)-2-[4-(2,2,2-trifluoroethyl)piperazin-1-yl]-5-(trifluoromethyl)-pyridine-3-carboxamide;
101) 5-chloro-2-(4,4-difluoroazepan-1-yl)-N-(2-sulfamoyl-4-pyridyl)pyridine-3-carboxamide;
102) 2-((2R,6S)-2-methyl-6-(trifluoromethyl)morpholino)-N-(2-sulfamoylpyridin-4-yl)-5-(trifluoromethyl)nicotinamide;
103) 2-((2S,6R)-2-methyl-6-(trifluoromethyl)morpholino)-N-(2-sulfamoylpyridin-4-yl)-5-(trifluoromethyl)nicotinamide;
104) (S)—N-(2-sulfamoylpyridin-4-yl)-5-(trifluoromethyl)-2-(2-(trifluoromethyl)-1,4-oxazepan-4-yl)nicotinamide;
105) (R)—N-(2-sulfamoylpyridin-4-yl)-5-(trifluoromethyl)-2-(2-(trifluoromethyl)-1,4-oxazepan-4-yl)nicotinamide;
106) 2-[(2R)-6,6-dimethyl-2-(trifluoromethyl)-1,4-oxazepan-4-yl]-N-(2-sulfamoyl-4-pyridyl)-5-(trifluoromethyl)pyridine-3-carboxamide;
107) 2-(2,2-dimethyl-1,4-oxazepan-4-yl)-N-(2-sulfamoyl-4-pyridyl)-5-(trifluoromethyl)pyridine-3-carboxamide;
108) 2-[(7S)-7-methyl-1,4-oxazepan-4-yl]-N-(2-sulfamoyl-4-pyridyl)-5-(trifluoromethyl)-pyridine-3-carboxamide;
109) N-[2-(tert-butylsulfamoyl)-4-pyridyl]-5-chloro-2-(4,4-difluoroazepan-1-yl)pyridine-3-carboxamide;
110) 2-[(2S)-2-methylmorpholin-4-yl]-N-(2-sulfamoyl-4-pyridyl)-5-(trifluoromethyl)pyridine-3-carboxamide;
111) 2-[(2R)-2-methyl-1,4-oxazepan-4-yl]-N-(2-sulfamoyl-4-pyridyl)-5-(trifluoromethyl)-pyridine-3-carboxamide;
112) 2-(3-hydroxy-3-methyl-1-piperidyl)-N-(2-sulfamoyl-4-pyridyl)-5-(trifluoromethyl)pyridine-3-carboxamide;
113) 2-(6-fluoro-1,1-dimethyl-isoindolin-2-yl)-N-(2-sulfamoyl-4-pyridyl)-5-(trifluoromethyl)-pyridine-3-carboxamide;
114) 2-(azepan-1-yl)-N-(2-methyl-5-sulfamoylthiophen-3-yl)-5-(trifluoromethyl)pyridine-3-carboxamide;
115) 2-(4,4-difluoro-5-methylazepan-1-yl)-N-(2-sulfamoylpyridin-4-yl)-5-(trifluoromethyl)-pyridine-3-carboxamide;
116) 5-chloro-2-[(7R)-7-(difluoromethyl)-1,4-oxazepan-4-yl]-6-methyl-N-(2-sulfamoylpyridin-4-yl)pyridine-3-carboxamide;
117) 5-chloro-2-[(7S)-7-(difluoromethyl)-1,4-oxazepan-4-yl]-6-methyl-N-(2-sulfamoylpyridin-4-yl)pyridine-3-carboxamide;
118) (R)—N-(2-sulfamoylpyridin-4-yl)-5-(trifluoromethyl)-2-(7-(trifluoromethyl)-1,4-oxazepan-4-yl)nicotinamide;
119) (S)—N-(2-sulfamoylpyridin-4-yl)-5-(trifluoromethyl)-2-(7-(trifluoromethyl)-1,4-oxazepan-4-yl)nicotinamide;
120) 2-[(2S,7R)-2-methyl-7-(trifluoromethyl)-1,4-oxazepan-4-yl]-N-(2-sulfamoylpyridin-4-yl)-5-(trifluoromethyl)pyridine-3-carboxamide;
121) 2-((2R,7S)-2-methyl-7-(trifluoromethyl)-1,4-oxazepan-4-yl)-N-(2-sulfamoylpyridin-4-yl)-5-(trifluoromethyl)nicotinamide;
122) 2-((2R,7R)-2-methyl-7-(trifluoromethyl)-1,4-oxazepan-4-yl)-N-(2-sulfamoylpyridin-4-yl)-5-(trifluoromethyl)nicotinamide;
123) 2-((2S,7S)-2-methyl-7-(trifluoromethyl)-1,4-oxazepan-4-yl)-N-(2-sulfamoylpyridin-4-yl)-5-(trifluoromethyl)nicotinamide;
124) (S)-5-chloro-2-(2-(difluoromethyl)morpholino)-6-methyl-N-(2-sulfamoylpyridin-4-yl)-nicotinamide;
125) (R)-5-chloro-2-(2-(difluoromethyl)morpholino)-6-methyl-N-(2-sulfamoylpyridin-4-yl)-nicotinamide;
126) N-(2-sulfamoylpyridin-4-yl)-5-(trifluoromethyl)-2-[(2S)-2-(trifluoromethyl)pyrrolidin-1-yl]pyridine-3-carboxamide;
127) (R)—N-(2-sulfamoylpyridin-4-yl)-5-(trifluoromethyl)-2-(2-(trifluoromethyl)pyrrolidin-1-yl)nicotinamide;
128) N-(2-sulfamoylpyridin-4-yl)-5-(trifluoromethyl)-2-[3-(trifluoromethyl)pyrrolidin-1-yl]pyridine-3-carboxamide;
129) (S)-2-(3-cyanopyrrolidin-1-yl)-N-(2-sulfamoylpyridin-4-yl)-5-(trifluoromethyl)-nicotinamide;
130) (R)-2-(3-cyanopyrrolidin-1-yl)-N-(2-sulfamoylpyridin-4-yl)-5-(trifluoromethyl-)nicotinamide;
131) 2-(4,4-difluoro-3-methylazepan-1-yl)-N-(2-sulfamoylpyridin-4-yl)-5-(trifluoromethyl)-nicotinamide;
132) 2-(4,4-difluoroazepan-1-yl)-N-(2-sulfamoylpyridin-4-yl)-6-(trifluoromethyl)nicotinamide;
133) 2-((2R,6S)-2-ethyl-6-(trifluoromethyl)morpholino)-N-(2-sulfamoylpyridin-4-yl)-5-(trifluoromethyl)nicotinamide;
134) 2-((2S,6R)-2-ethyl-6-(trifluoromethyl)-morpholino)-N-(2-sulfamoylpyridin-4-yl)-5-(trifluoromethyl)nicotinamide;
135) (R)-2-(2,2-dimethyl-6-(trifluoromethyl)-morpholino)-N-(2-sulfamoylpyridin-4-yl)-5-(trifluoromethyl)nicotinamide;
136) (S)-2-(2,2-dimethyl-6-(trifluoromethyl)-morpholino)-N-(2-sulfamoylpyridin-4-yl)-5-(trifluoromethyl)nicotinamide;
137) 4-(2-(4,4-difluoroazepan-1-yl)-5-(trifluoromethyl)nicotinamido)picolinamide;
138) 6-chloro-2-(4,4-difluoroazepan-1-yl)-N-(2-sulfamoyl-4-pyridyl)pyridine-3-carboxamide;
139) 2-(azepan-1-yl)-N-(2-sulfamoyl-4-pyridyl)-5-(trifluoromethyl)pyridine-3-carboxamide;
140) 2-(azepan-1-yl)-N-(2-methylsulfonyl-4-pyridyl)-5-(trifluoromethyl)pyridine-3-carboxamide;
141) 2-(azepan-1-yl)-N-(6-sulfamoyl-2-pyridyl)-5-(trifluoromethyl)pyridine-3-carboxamide;
142) 2-(4,4-difluoroazepan-1-yl)-6-methoxy-N-(2-sulfamoylpyridin-4-yl)nicotinamide;
143) N-(2-methoxypyridin-4-yl)-2-(6-azaspiro[2.5]octan-6-yl)-5-(trifluoromethyl)nicotinamide;
144) 2-(4,4-difluoroazepan-1-yl)-N-(5-sulfamoyl-3-pyridyl)-5-(trifluoromethyl)pyridine-3-carboxamide;
145) 2-(azepan-1-yl)-N-(5-sulfamoyl-3-pyridyl)-5-(trifluoromethyl)pyridine-3-carboxamide;
146) 2-(4,4-difluoroazepan-1-yl)-N-(2-methoxy-4-pyridyl)-5-(trifluoromethyl)pyridine-3-carboxamide;

147) 2-((3S,5R)-4,4-difluoro-3,5-dimethylpiperidin-1-yl)-N-(2-(methylsulfonyl)pyridin-4-yl)-5-(trifluoromethyl)nicotinamide;
148) 2-[(3R)-4,4-difluoro-3-methyl-1-piperidyl]-N-(2-methylsulfonyl-4-pyridyl)-5-(trifluoro-methyl)-pyridine-3-carboxamide;
149) 2-[(3S)-4,4-difluoro-3-methyl-1-piperidyl]-N-(2-methylsulfonyl-4-pyridyl)-5-(trifluoro-methyl)-pyridine-3-carboxamide;
150) N-(2-cyano-4-pyridyl)-2-[(3S,5R)-4,4-difluoro-3,5-dimethyl-1-piperidyl]-5-(trifluoro-methyl)-pyridine-3-carboxamide;
151) N-(2-methylsulfonyl-4-pyridyl)-2-[(1R,5S)-6,6,7,7-tetrafluoro-3-azabicyclo[3.2.0]heptan-3-yl]-5-(trifluoromethyl)pyridine-3-carboxamide;
152) 2-[(1R,5S)-3-azabicyclo[3.2.0]heptan-3-yl]-N-(2-methylsulfonyl-4-pyridyl)-5-(trifluoromethyl)pyridine-3-carboxamide;
153) 2-[(1R,5S)-3-azabicyclo[3.2.0]heptan-3-yl]-N-(2-cyano-4-pyridyl)-5-(trifluoromethyl)pyridine-3-carboxamide;
154) (R)—N-(2-cyanopyridin-4-yl)-2-(4,4-difluoro-3-methylpiperidin-1-yl)-5-(trifluoromethyl)-nicotinamide;
155) (S)—N-(2-cyanopyridin-4-yl)-2-(4,4-difluoro-3-methylpiperidin-1-yl)-5-(trifluoromethyl)-nicotinamide;
156) 4-(2-((3S,5R)-4,4-difluoro-3,5-dimethylpiperidin-1-yl)-5-(trifluoromethyl)nicotinamido)-picolinamide;
157) N-(2-carbamoyl-4-pyridyl)-2-[(3S)-4,4-difluoro-3-methyl-1-piperidyl]-5-(trifluoromethyl)-pyridine-3-carboxamide;
158) N-(2-carbamoyl-4-pyridyl)-2-[(3R)-4,4-difluoro-3-methyl-1-piperidyl]-5-(trifluoromethyl)-pyridine-3-carboxamide;
159) 2-(4,4-difluoropiperidin-1-yl)-4-methoxy-N-(2-sulfamoylpyridin-4-yl)nicotinamide;
160) 5-chloro-6-cyclobutyl-2-((2R,6S)-2-methyl-6-(trifluoromethyl)morpholino)-N-(2-sulfamoylpyridin-4-yl)nicotinamide;
161) 5-chloro-6-cyclobutyl-2-((2S,6R)-2-methyl-6-(trifluoromethyl)morpholino)-N-(2-sulfamoylpyridin-4-yl)nicotinamide;
162) (R)-2-(4,4-difluoro-3-methylpiperidin-1-yl)-N-(2-sulfamoylpyridin-4-yl)-6-(trifluoro-methyl)nicotinamide;
163) (S)-2-(4,4-difluoro-3-methylpiperidin-1-yl)-N-(2-sulfamoylpyridin-4-yl)-6-(trifluoro-methyl)nicotinamide;
164) (S)-5-chloro-2-(4,4-difluoro-3-methylpiperidin-1-yl)-N-(2-sulfamoylpyridin-4-yl)-6-(trifluoromethyl)nicotinamide;
165) (R)-5-chloro-2-(4,4-difluoro-3-methylpiperidin-1-yl)-N-(2-sulfamoylpyridin-4-yl)-6-(trifluoromethyl)nicotinamide;
166) 6-cyclobutyl-2-((3S,5R)-4,4-difluoro-3,5-dimethylpiperidin-1-yl)-N-(2-sulfamoylpyridin-4-yl)nicotinamide;
167) 6-cyclobutyl-2-((2R,6S)-2-methyl-6-(trifluoromethyl)morpholino)-N-(2-sulfamoylpyridin-4-yl)nicotinamide;
168) 6-cyclobutyl-2-((2S,6R)-2-methyl-6-(trifluoromethyl)morpholino)-N-(2-sulfamoylpyridin-4-yl)nicotinamide;
169) 5-chloro-6-cyclobutyl-2-((3S,5R)-4,4-difluoro-3,5-dimethylpiperidin-1-yl)-N-(2-sulfamoyl-pyridin-4-yl)nicotinamide;
170) 6-chloro-2-(4,4-difluoropiperidin-1-yl)-4-methyl-N-(2-sulfamoylpyridin-4-yl)nicotinamide;
171) 2-(4,4-difluoroazepan-1-yl)-5-(difluoromethoxy)-N-(2-sulfamoylpyridin-4-yl)nicotinamide;
172) 5-chloro-2-(4,4-difluoroazepan-1-yl)-6-methyl-N-(2-sulfamoylpyridin-4-yl)nicotinamide;
173) 4-(4,4-difluoroazepan-1-yl)-2-methyl-N-(2-sulfamoylpyridin-4-yl)pyrimidine-5-carboxamide;
174) 2-(4,4-difluoroazepan-1-yl)-6-(difluoromethyl)-N-(2-sulfamoylpyridin-4-yl)nicotinamide;
175) 2-(4,4-difluoropiperidin-1-yl)-N-(2-sulfamoylpyridin-4-yl)-5-(trifluoromethyl) nicotinamide;
176) 4-(2-(4,4-difluoropiperidin-1-yl)-5-(trifluoromethyl)nicotinamido)pyridine-2-sulfonic acid;
177) 2-(4,4-difluoroazepan-1-yl)-N-(2-sulfamoylpyridin-4-yl)-5-(trifluoromethoxy)nicotinamide
178) 2-(4,4-difluoropiperidin-1-yl)-5-fluoro-6-methyl-N-(2-sulfamoylpyridin-4-yl)nicotinamide;
179) 3-(4,4-difluoroazepan-1-yl)-N-(2-sulfamoylpyridin-4-yl)-6-(trifluoromethyl)pyridazine-4-carboxamide;
180) 5-(tert-butyl)-2-(4,4-difluoropiperidin-1-yl)-6-methyl-N-(2-sulfamoylpyridin-4-yl)-nicotinamide;
181) 5-cyclopropyl-2-(4,4-difluoropiperidin-1-yl)-N-(2-sulfamoylpyridin-4-yl)-6-(trifluoro-methyl)-nicotinamide;
182) 5-cyclopropyl-2-(4,4-difluoropiperidin-1-yl)-N-(2-sulfamoylpyridin-4-yl)-6-(trifluoro-methoxy)-nicotinamide;
183) 2-(4,4-difluoropiperidin-1-yl)-6-methyl-N-(2-sulfamoylpyridin-4-yl)-5-(2,2,2-trifluoro-ethoxy)-nicotinamide;
184) 2-(4,4-difluoroazepan-1-yl)-6-methyl-N-(2-sulfamoylpyridin-4-yl)-5-(trifluoromethyl)-nicotinamide;
185) 6-cyclopropyl-2-(4,4-difluoroazepan-1-yl)-N-(2-sulfamoylpyridin-4-yl)-5-(trifluoro-methyl)nicotinamide;
186) 2-(azepan-1-yl)-N-(5-fluoropyridin-3-yl)-5-(trifluoromethyl)nicotinamide;
187) 2-(azepan-1-yl)-5-chloro-N-(2-methoxy-4-pyridyl)-4,6-dimethyl-pyridine-3-carboxamide;
188) 2-(azepan-1-yl)-5-chloro-4,6-dimethyl-N-(5-sulfamoyl-3-pyridyl)pyridine-3-carboxamide;
189) 5-chloro-2-(4,4-difluoro-1-piperidyl)-4,6-dimethyl-N-(5-sulfamoyl-3-pyridyl)pyridine-3-carboxamide;
190) 2-(6-azaspiro[2.5]octan-6-yl)-5-chloro-4,6-dimethyl-N-(5-sulfamoyl-3-pyridyl)pyridine-3-carboxamide;
191) 5-chloro-4,6-dimethyl-2-(1-piperidyl)-N-(5-sulfamoyl-3-pyridyl)pyridine-3-carboxamide;
192) 2-(4,4-difluoroazepan-1-yl)-6-methoxy-N-(5-sulfamoyl-3-pyridyl)pyridine-3-carboxamide;
193) 2-(azepan-1-yl)-N-(5-cyano-3-pyridyl)-5-(trifluoromethyl)pyridine-3-carboxamide;
194) 2-(azepan-1-yl)-N-(5-methoxy-3-pyridyl)-5-(trifluoromethyl)pyridine-3-carboxamide;
195) 2-(azepan-1-yl)-N-(5-methyl-3-pyridyl)-5-(trifluoromethyl)pyridine-3-carboxamide;
196) 2-(azepan-1-yl)-N-[5-(hydroxymethyl)-3-pyridyl]-5-(trifluoromethyl)pyridine-3-carboxamide;
197) 2-(azepan-1-yl)-N-(2-cyano-4-pyridyl)-5-(trifluoromethyl)pyridine-3-carboxamide;
198) 2-(azepan-1-yl)-N-(2-ethylsulfonyl-4-pyridyl)-5-(trifluoromethyl)pyridine-3-carboxamide;
199) 2-(azepan-1-yl)-N-(3-bromoimidazo[1,2-a]pyridin-6-yl)-5-(trifluoromethyl)pyridine-3-carboxamide;
200) 2-(azepan-1-yl)-5-(trifluoromethyl)-N-[5-(trifluoromethyl)-3-pyridyl]pyridine-3-carboxamide;
201) 2-(azepan-1-yl)-5-chloro-4,6-dimethyl-N-(2-sulfamoylpyridin-4-yl)nicotinamide;
202) 5-chloro-4,6-dimethyl-2-(6-azaspiro[2.5]octan-6-yl)-N-(2-sulfamoylpyridin-4-yl)nicotinamide;
203) 4-(2-(azepan-1-yl)-5-(trifluoromethyl)nicotinamido)picolinamide;
204) 5-bromo-2-(4,4-difluoropiperidin-1-yl)-N-(2-sulfamoylpyridin-4-yl)nicotinamide;
205) 2-(4,4-difluoropiperidin-1-yl)-5-phenyl-N-(2-sulfamoylpyridin-4-yl)nicotinamide;

206) 2-(4,4-difluoropiperidin-1-yl)-5-(piperidin-1-yl)-N-(2-sulfamoylpyridin-4-yl)nicotinamide;
207) 2-(4,4-difluoropiperidin-1-yl)-5-(1H-pyrazol-1-yl)-N-(2-sulfamoylpyridin-4-yl)-nicotinamide;
208) N-(2-oxo-1,2-dihydropyridin-4-yl)-2-(6-azaspiro[2.5]octan-6-yl)-5-(trifluoromethyl)-nicotinamide;
209) 5-chloro-4,6-dimethyl-N-(2-oxo-1,2-dihydropyridin-4-yl)-2-(6-azaspiro[2.5]octan-6-yl)nicotinamide;
210) 2-(4,4-difluoroazepan-1-yl)-N-(2-oxo-1,2-dihydropyridin-4-yl)-5-(trifluoromethyl)-nicotinamide;
211) 5-chloro-4,6-dimethyl-N-(2-oxo-1,2-dihydropyridin-4-yl)-2-(piperidin-1-yl)nicotinamide;
212) 2-(azepan-1-yl)-N-(2-oxo-1,2-dihydropyridin-4-yl)-5-(trifluoromethyl)nicotinamide; and
213) 2-(azepan-1-yl)-5-chloro-4,6-dimethyl-N-(2-oxo-1,2-dihydropyridin-4-yl)nicotinamide;
214) 5-chloro-2-(4,4-difluorocyclohexyl)-4,6-dimethyl-N-(2-sulfamoylpyridin-4-yl)nicotinamide;
215) 5-chloro-2-cycloheptyl-4,6-dimethyl-N-(2-sulfamoylpyridin-4-yl)nicotinamide
216) 5-chloro-3-(4,4-difluoroazepan-1-yl)-N-(2-sulfamoylpyridin-4-yl)pyrazine-2-carboxamide;
217) 5-chloro-4,6-dimethyl-2-(4-methylcyclohexyl)-N-(2-sulfamoylpyridin-4-yl)nicotinamide; and 218) 5-chloro-2-(4,4-difluoroazepan-1-yl)-N,4,6-trimethyl-N-(2-sulfamoylpyridin-4-yl)nicotinamide;

or a pharmaceutically acceptable salt thereof.

Although the specific stereochemistries described above are preferred, other stereoisomers, including diastereoisomers, enantiomers, epimers, and mixtures of these may also have utility in treating $Na_v1.8$ mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated monocyclic, bicyclic, spirocyclic or bridged carbocyclic ring, having a specified number of carbon atoms. Examples of cycloalkyl include cyclopropyl, cyclobutyl, cyclopentyl, cyclohexyl, cycloheptyl, and the like. In one embodiment of the present invention, cycloalkyl is selected from: cyclopropane, cyclobutane and cyclohexane. In another embodiment, cycloalkyl is cyclopropane, cyclobutane or cyclopentane. In another embodiment, cycloalkyl is cyclopropane or cyclobutane. In another embodiment, cycloalkyl is cyclopropane.

In another embodiment, cycloalkyl is cyclobutane. In another embodiment, cycloalkyl is cyclopentane. In another embodiment, cycloalkyl is cyclohexane. In another embodiment, cycloalkyl is cycloheptane.

"Cycloheteroalkyl" means a saturated or partly unsaturated non-aromatic monocyclic, bicyclic, spirocyclic or bridged ring or ring system having a specified number of carbon atoms and containing at least one ring heteroatom selected from N, NH, S (including SO and $SO_2$) and O. The cycloheteroalkyl ring may be substituted on the ring carbons and/or the ring nitrogen or sulfur. Examples of cycloheteroalkyl include tetrahydrofuran, pyrrolidine, tetrahydrothiophene, azetidine, piperazine, piperidine, morpholine, oxetane and tetrahydropyran. In one embodiment of the present invention, cycloheteroalkyl is selected from: pyrrolidine, azetidine, piperidine, piperazine, azepane, azocane, morpholine, thiomorpholine, thiomorpholine dione, oxazepane, 1,4-thiazepane, isoindoline, dihydroisoquinoline, tetra-hydroisoquinoline, octahydro-isoindole, azabicyclo[2.2.1]heptane, oxa-azabicyclo[2.2.1]-heptane, azabicyclo[3.1.1]heptane, azabicyclo[4.1.0]heptane, azabicyclo[3.2.1]octane, diazabicyclo[3.2.1]octane, oxa-azabicyclo-[3.2.1]octane, azabicyclo[3.2.0]heptane, oxa-azabicyclo[3.2.0]heptane, azaspiro[2.5]octane, azaspiro[2.6]nonane, azaspiro[3.5]nonane, oxa-azaspiro[3.5]nonane, oxa-azaspiro[4.5]decane, dihydrothieno[3,2-c]pyridine, dihydro-thiazolo[4,5-c]pyridine, dihydrooxazolo[4,5-c]pyridine, dihydroimidazo[1,2-a]pyrazine, hexahydrofuro[3,2-b]pyrrole, hexahydrocyclopenta[c]pyrrole, octahydrocyclpenta[c]pyrrole, and azatricyclo[4.3.1.13,8]undecane. In another embodiment, cycloheteroalkyl is selected from: pyrrolidine, azetidine, piperidine, piperazine, azepane, morpholine, thiomorpholine, oxazepane, isoindoline, dihydroisoquinoline, azabicyclo[2.2.1]heptane, azabicyclo[3.1.1]-heptane, azabicyclo[4.1.0]heptane, azabicyclo[3.2.1]octane, azabicyclo[3.2.0]heptane, azaspiro[2.5]octane, dihydrothieno[3,2-c]pyridine, dihydroimidazo[1,2-a]pyrazine, and hexahydrofuro[3,2-b]pyrrole. In another embodiment, cycloheteroalkyl is selected from: azepane, morpholine and piperidine. In another embodiment, cycloheteroalkyl is azepane. In another embodiment, cycloheteroalkyl is morpholine. In another embodiment, cycloheteroalkyl is piperidine.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment of the present invention, aryl is phenyl.

"Heteroaryl" means a monocyclic, bicyclic or tricyclic ring or ring system containing 5-14 ring atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl, quinolyl, indolyl, isoquinolyl, quinazolinyl, dibenzofuranyl, and the like. In one embodiment of the present invention, heteroaryl is a 5 or 6 membered heteroaryl ring. In another embodiment, heteroaryl is selected from: pyrazole, pyridyl, isoxazole and thiazole. In another embodiment of the present invention, heteroaryl is selected from: pyridine, pyrimidine, pyrazine, pyridazine, indazole, imidazo[1,2-a]pyridine, 1,3-dihydro-2H-imidazo[4,5-b]pyridin-2-one, 1H-[1,2,3]triazolo[4,5-b]pyridine, 1H-pyrazolo[4,3-b]pyridine, pyrrolo[3,2-c]pyridine, pyrrolo[2,3-b]pyridine, benzimidazole, imidazole, pyrazole, thiophene, furan, 1,2,4-oxadiazole, 1,3,4-oxadiazole, oxazole, isoxazole, isothiazole, thiazole, 1,2,4-thiadiazole, 1,3,4-thiadiazole; 4H-pyrido[2,3-e][1,2,4]thiadiazine 1,1-dioxide, 2H-pyrido[2,3-e][1,2]thiazine 1,1-dioxide, 2,3-dihydroisothiazolo[4,5-b]pyridine 1,1-dioxide, and 3,4-dihydro-2H-pyrido[2,3-e][1,2]thiazine 1,1-dioxide. In another embodiment of the present invention, heteroaryl is selected from: pyridine, pyrimidine, and pyridazine. In another embodiment of the present invention, heteroaryl is pyridine.

"Halogen" includes fluorine, chlorine, bromine and iodine. In one embodiment, halogen is fluorine, chorine or bromine. In another embodiment, halogen is fluorine or chlorine. In another embodiment, halogen is fluorine or bromine. In another embodiment, halogen is fluorine. In another embodiment, halogen is chlorine. In another embodiment, halogen is bromine.

"Me" represents methyl.

"Oxo" represents =O.

"Saturated" means containing only single bonds.

"Unsaturated" means containing at least one double or triple bond. In one embodiment, unsaturated means containing at least one double bond. In another embodiment, unsaturated means containing at least one triple bond.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

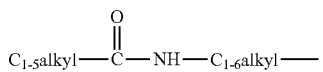

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration or sufficient heavy atoms to make an absolute assignment.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I. For example, the compounds of formula I include the following tautomers:

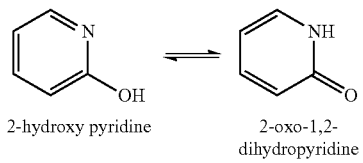

2-hydroxy pyridine     2-oxo-1,2-dihydropyridine

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

The term "prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. The scope of this invention includes prodrugs of the novel compounds of this invention.

Solvates, and in particular, the hydrates of the compounds of the present invention are included in the present invention as well.

Utilities

The compound of the present invention are selective inhibitors of $Na_v1.8$ sodium ion channel activity or have selective activity as $Na_v1.8$ sodium ion channel blockers. In one embodiment, the compounds of the present invention exhibit at least 10-fold selectivity for $Na_v1.8$ sodium channels over $Na_v1.5$ sodium channels, and in some embodiments exhibit at least 100-fold selectivity for $Na_v1.8$ sodium channels over $Na_v1.5$ sodium channels based on functional potency ($IC_{50}$ values) for each channel in Qube® assay system.

The compounds of the present invention are potent inhibitors of $Na_v1.8$ channel activity. The compounds, and pharmaceutically acceptable salts thereof, may be efficacious in the treatment of diseases, disorders and conditions that are mediated by the inhibition of $Na_v1.8$ sodium ion channel activity and/or $Na_v1.8$ receptors.

Diseases, disorders or conditions mediated by $Na_v1.8$ sodium ion channel activity and/or $Na_v1.8$ receptors, include but are not limited to nociception, osteoarthritis, peripheral neuropathy, inherited erythromelalgia, multiple sclerosis, asthma, pruritus, acute itch, chronic itch, migraine, neurodegeneration following ischemia, epilepsy, inflammatory pain, spontaneous pain, acute pain, peri-operative pain, post-operative pain, neuropathic pain, postherpetic neuralgia, trigeminal neuralgia, diabetic neuropathy, chronic lower back pain, phantom limb pain, pain resulting from cancer and chemotherapy, chronic pelvic pain, pain syndromes, and complex regional pain syndromes.

One or more of these conditions or diseases may be treated, managed, prevented, reduced, alleviated, ameliorated or controlled by the administration of a therapeutically effective amount of a compound of the present invention, or a pharmaceutically acceptable salt thereof, to a patient in need of treatment. Also, the compounds of the present invention may be used for the manufacture of a medicament which may be useful for treating, preventing, managing, alleviating, ameliorating or controlling one or more of these conditions, diseases or disorders: nociception, osteoarthritis, peripheral neuropathy, inherited erythromelalgia, multiple sclerosis, asthma, pruritus, acute itch, chronic itch, migraine, neurodegeneration following ischemia, epilepsy, inflammatory pain, spontaneous pain, acute pain, peri-operative pain, post-operative pain, neuropathic pain, postherpetic neuralgia, trigeminal neuralgia, diabetic neuropathy, chronic lower back pain, phantom limb pain, pain resulting from cancer and chemotherapy, chronic pelvic pain, pain syndromes, and complex regional pain syndromes.

Preferred uses of the compounds may be for the treatment of one or more of the following diseases by administering a therapeutically effective amount to a patient in need of treatment. The compounds may be used for manufacturing a medicament for the treatment of one or more of these diseases:

1) pain conditions,
2) pruritic conditions, and
3) cough conditions.

In one embodiment of the present invention, the pain condition is an acute pain or chronic pain disorder. In another embodiment of the present invention, the pain condition is an acute pain disorder.

The compounds of the present invention may be effective in treating nociception. Nociception or pain is essential for survival and often serves a protective function. However, the pain associated with surgical procedures and current therapies to relieve that pain, can delay recovery after surgery and increase the length of hospital stays. As many as 80% of surgical patients experience post-operative pain due to tissue damage, and damage to peripheral nerves and subsequent inflammation. Approximately 10-50% of surgical patients will develop chronic pain after surgery often because the nerve damage results in lasting neuropathic pain once the wound has healed.

The compounds of the present invention may be effective in treating osteoarthritis. Osteoarthritis is type of arthritis caused by inflammation, breakdown, and eventual loss of cartilage in the joints. The standards of care for pain associated with osteoarthritis are non-steroidal anti-inflammatory drugs (NSAIDs), for example celecoxib and diclofenac (reviewed in Zeng et al., 2018). Patients that do not respond to NSAID therapies are typically treated with low dose opiates, such as hydrocodone. Patients that are refractory to the above therapies will usually opt for total joint replacement.

The compounds of the present invention may be effective in treating peripheral neuropathy. Peripheral neuropathy is nerve damage caused by chronically high blood sugar and diabetes. It leads to numbness, loss of sensation, and sometimes pain in distal limbs such as feet, legs, or hands. It is the most common complication of diabetes. The standards of care for the treatment of painful diabetic neuropathy are gabapentinoids, for example gabapentin and pregabalin. Some patients will respond well to tricyclic antidepressants such as amitriptyline, while other patients get significant relief using SRI/NRI drugs such as duloxetine (Schreiber et al., World J Diabetes. 2015 Apr. 15; 6(3):432-44). Many options are available, however side-effects are common (e.g. dizziness, nausea) which limit their full potential.

The compounds of the present invention may be effective in treating inherited erythromelalgia. Inherited erythromelalgia (IEM) is a chronic pain syndrome which has been linked to mutations in several voltage-gated sodium channels, including Nav1.8 (Kist et al., PLoS One. 2016 Sep. 6; 11(9):e0161789). Patients present with the classic "gloves and stocking" flare pattern on distal regions such as hands and feet, typically brought on with warm temperatures and exercise. Some patients find relief from the burning pain associated with flares by cold water immersion. Although medications that affect voltage-gated sodium channels (eg, lidocaine and mexiletine) show promise, there is no current standard of care to treat IEM.

The compounds of the present invention may be effective in treating neuropathic pain. Neuropathic pain is pain caused by damage or disease affecting the somatosensory nervous system. It has been demonstrated in human patients, as well as in animal models of neuropathic pain, that damage to primary afferent sensory neurons can lead to neuroma formation and spontaneous activity, as well as evoked activity in response to normally innocuous stimuli. (Colloca et al., Nat Rev Dis Primers. 2017 Feb. 16; 3:17002; Coward et al., Pain. 2000 March; 85(1-2):41-50; Yiangou et al., FEBS Lett. 2000 Feb. 11; 467(2-3):249-52; Carter et al., Phys Med Rehabil Clin N Am. 2001 May; 12(2):447-59). Some nerve injuries result in an increase in Nav1.8 expression, which is believed to be an underlying mechanism for pathological pain. (Black et al., Ann Neurol. 2008 December; 64(6):644-53; Bird et al., Br J Pharmacol. 2015 May; 172(10):2654-70). Injuries of the peripheral nervous system often result in neuropathic pain persisting long after an initial injury resolves. Examples of neuropathic pain include, but are not limited to, post herpetic neuralgia, trigeminal neuralgia, diabetic neuropathy, chronic lower back pain, lumbar radiculopathy, phantom limb pain, pain resulting from cancer and chemotherapy, chronic pelvic pain, complex regional pain syndrome and related neuralgias, and painful conditions that arise due to gain-of-function mutations in Nav1.8 (Huang et al., J Neurosci. 2013 Aug. 28; 33(35): 14087-97; Kist et al., PLoS One. 2016 Sep. 6; 11(9): e0161789; Emery et al., J Neurosci. 2015 May 20; 35(20): 7674-81; and Schreiber et al., World J Diabetes. 2015 Apr. 15; 6(3):432-44.

The ectopic activity of normally silent sensory neurons is thought to contribute to the generation and maintenance of neuropathic pain, which is generally assumed to be associated with an increase in sodium channel activity in the injured nerve. (Wood et al., Curr Opin Pharmacol. 2001 February; 1(1):17-21; Baker et al., TRENDS in Pharmacological Sciences, 2001, 22(1): 27-31). Standards of care for neuropathic pain vary considerably depending on the particular condition, but first line therapies are typically pregabalin, gabapentin, tricyclic antidepressants (e.g. amitriptyline), and SRI/NRI drugs (e.g. duloxetine). Patients refractory to these therapies are usually prescribed low dose opiates (e.g. hydrocodone).

The compounds of the present invention may be effective in treating multiple sclerosis. Recent evidence points to a potential role for Nav1.8 in multiple sclerosis. Nav1.8 expression in cerebellum has been identified in tissues taken from animal models of multiple sclerosis (EAE model) and in postmortem brains from patients suffering from multiple sclerosis (MS) (Shields et al., Ann Neurol. 2012 February; 71(2):186-94; Black et al., Proc Natl Acad Sci USA. 2000 Oct. 10; 97(21):11598-602). Also, two SCN10A polymorphisms showed significant association with MS (Roostaei et al., Neurology. 2016 Feb. 2; 86 (5):410-7). When Nav1.8 is overexpressed in cerebellum, mice develop ataxic-related motor deficits which are ameliorated with oral delivery of a selective small molecule Nav1.8 antagonist (Shields et al., PLoS One. 2015 Mar. 6; 10(3)). These studies suggest that a Nav1.8 antagonist may be a useful therapy to treat symptoms related to multiple sclerosis.

The compounds of the present invention may be effective in treating asthma. Asthma is caused by airway inflammation in which a person's airways become hyper-responsive, narrow and swollen, which makes it difficult to breathe. These symptoms are typically triggered through an allergic reaction (Nair P et al., J Allergy Clin Immunol Pract. 2017 May-June; 5(3):649-659). In a preclinical model of asthma, deletion of Nav1.8-containing neurons, or inhibition of nerve fibers via small molecules reduces airway inflammation and immune cell infiltration (Talbot et al., Neuron. 2015 Jul. 15; 87(2):341-54). Selective Nav1.8 antagonists may be a useful therapy to prevent airway hypersensitivity caused by immune cell infiltration.

The compounds of the present invention may be effective in treating pruritus. Pruritus, also commonly known as itch, affects approximately 4% of the global population is an unpleasant sensation that elicits the desire or reflex to scratch, and is regarded as closely related to pain (Luo et al., Cell Mol Life Sci. 2015 September; 72 (17): 3201-23). Theories on the origin of itch implicate the subtle, low-frequency activation of nociceptors (pain-sensing neurons); however, it has been described that some afferents preferentially respond to histamine, which induces itch (Schmelz et al., J Neurosci. 1997 Oct. 15; 17(20):8003-8). At the same time, it has been found that histamine-responding neurons also respond to capsaicin which produces pain (McMahon et al., Trends in Neuroscience 1992, 15:497-501). Members of the transient receptor potential (TRP) family, and nerve growth factor (NGF) are both known to play a role in itch and pain, and clinically, both maladies are treated with therapeutic agents such as gabapentin and antidepressants. Therefore, it continues to be accepted that the underlying mechanisms of pain and itch are highly interwoven and complex, and distinguishing pan-selective or itch-selective pathways remains ambiguous (Ikoma et al., Nat Rev Neurosci. 2006 July; 7(7):535-47). A role for Nav1.8 in pruritis was studied using a mouse transgenically expressing a constitutively active form of the serine/threonine kinase BRAF was expressed in Nav1.8-expressing neurons. This resulted in enhanced pruriceptor excitability, and heightened evoked and spontaneous scratching behavior (Zhao et al., 2013). In skin, pruritogens are released from keratinocytes, lymphocytes, mast cells, and eosinophils during inflammation. These molecules act directly on free nerve endings which express Nav1.8 to induce itch (Riol-Blanco et al., Nature. 2014 Jun. 5; 510 (7503):157-61). Chronic and acute itch can arise from many different insults, diseases and disorders, and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. Medicines such as opioids and chloroquine can also trigger itch (Ikoma et al., Nat Rev Neurosci. 2006 July; 7(7):535-47). Itching following burn is also an extremely serious clinical problem as it hampers the healing process, resulting in permanent scaring, and negatively impacting quality of life (Van Loey et al., Br J Dermatol. 2008 January; 158(1):95-100).

The invention also includes pharmaceutically acceptable salts of the compounds, and pharmaceutical compositions comprising the compounds and a pharmaceutically acceptable carrier.

The compounds, or pharmaceutically acceptable salts thereof, may be useful in treating pain conditions, pruritic conditions, and cough conditions.

A compound of the present invention, or a pharmaceutically acceptable salt thereof, may be used in the manufacture of a medicament for the treatment of pain conditions, pruritic conditions, and cough conditions in a human or other mammalian patient.

A method of treating a pain conditions comprises the administration of a therapeutically effective amount of a compound of the present invention, or a pharmaceutically acceptable salt thereof, or a pharmaceutical composition comprising the compound, to a patient in need of treatment. A method of treating a pruritic condition comprises the administration of a therapeutically effective amount of a compound of the present invention, or a pharmaceutically acceptable salt thereof, or a pharmaceutical composition comprising the compound, to a patient in need of treatment. A method of treating a cough condition comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The term "pain condition" as used herein includes, but are not limited to, acute pain, pen-operative pain, pre-operative pain, post-operative pain, neuropathic pain, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, The term "pruritic condition" or "pruritic disorder" as used herein includes, but is not limited to, conditions with an unpleasant sensation that provokes the desire to scratch, such as chronic itch.

The term "cough condition" or "cough disorder" as used herein includes, but is not limited to, chronic cough, neuropathic cough or cough due to neurological conditions.

Treatment of a disease, disorder or condition mediated by $Na_v1.8$ sodium ion channel activity or $Na_v1.8$ receptors refers to the administration of the compounds of the present invention to a subject with the disease, disorder or condition. One outcome of treatment may be reducing the disease, disorder or condition mediated by $Na_v1.8$ sodium ion channel activity or $Na_v1.8$ receptors. Another outcome of treatment may be alleviating the disease, disorder or condition mediated by $Na_v1.8$ sodium ion channel activity or $Na_v1.8$ receptors. Another outcome of treatment may be ameliorating the disease, disorder or condition mediated by $Na_v1.8$ sodium ion channel activity or $Na_v1.8$ receptors. Another outcome of treatment may be suppressing the disease, disorder or condition mediated by $Na_v1.8$ sodium ion channel activity or $Na_v1.8$ receptors. Another outcome of treatment may be managing the disease, disorder or condition mediated by $Na_v1.8$ sodium ion channel activity or $Na_v1.8$ receptors.

Another outcome of treatment may be preventing the disease, disorder or condition mediated by $Na_v1.8$ sodium ion channel activity or $Na_v1.8$ receptors.

Prevention of the disease, disorder or condition mediated by $Na_v1.8$ sodium ion channel activity or $Na_v1.8$ receptors refers to the administration of the compounds of the present invention to a subject at risk of the disease, disorder or condition. One outcome of prevention may be reducing the disease, disorder or condition mediated by $Na_v1.8$ sodium ion channel activity or $Na_v1.8$ receptors in a subject at risk of the disease, disorder or condition. Another outcome of prevention may be suppressing the disease, disorder or condition mediated by $Na_v1.8$ sodium ion channel activity or $Na_v1.8$ receptors in a subject at risk of the disease, disorder or condition. Another outcome of prevention may be ameliorating the disease, disorder or condition mediated by $Na_v1.8$ sodium ion channel activity or $Na_v1.8$ receptors in a subject at risk of the disease, disorder or condition. Another outcome of prevention may be alleviating the disease, disorder or condition mediated by $Na_v1.8$ sodium ion channel activity or $Na_v1.8$ receptors in a subject at risk of the disease, disorder or condition. Another outcome of prevention may be managing the disease, disorder or condition mediated by $Na_v1.8$ sodium ion channel activity or $Na_v1.8$ receptors in a subject at risk of the disease, disorder or condition.

One outcome of treatment may be reducing the amount of pain experienced by a subject relative to that subject's pain immediately before the administration of the compounds of the present invention. Another outcome of treatment may be alleviating the amount of pain experienced by a subject relative to that subject's pain immediately before the administration of the compounds of the present invention. Another outcome of treatment may be ameliorating the amount of pain experienced by a subject relative to that subject's pain immediately before the administration of the compounds of the present invention. Another outcome of treatment may be suppressing the amount of pain experienced by a subject relative to that subject's pain immediately before the administration of the compounds of the present invention. Another outcome of treatment may be managing the amount of pain experienced by a subject relative to that subject's pain immediately before the administration of the compounds of the present invention. Another outcome of treatment may be ameliorating the amount of pain experienced by a subject relative to that subject's pain immediately before the administration of the compounds of the present invention.

Another outcome of treatment may be preventing further pain experienced by a subject after the administration of the compounds of the present invention.

Prevention of pain refers to the administration of the compounds of the present invention to reduce the pain of a subject at risk of pain. Prevention includes, but is not limited to, the administration to a subject prior to surgery or other expected painful event. One outcome of prevention may be reducing pain in a subject at risk of pain. Another outcome of prevention may be suppressing pain in a subject at risk of pain. Another outcome of prevention may be ameliorating pain in a subject at risk of pain. Another outcome of prevention may be alleviating pain in a subject at risk of pain. Another outcome of prevention may be managing pain in a subject at risk of pain.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, intravenous, infusion, subcutaneous, transcutaneous, intramuscular, intradermal, transmucosal, intramucosal, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of disorders, diseases and/or conditions which require inhibition of $Na_v1.8$ sodium ion channel activity, a suitable dosage level will generally be about 0.0001 to 500 mg per kg patient body weight per day which can be administered in single or multiple doses. In one embodiment, a suitable dosage level may be about 0.001 to 500 mg per kg patient body weight per day. In another embodiment, a suitable dosage level may be about 0.001 to about 250 mg/kg per day. In another embodiment, a suitable dosage level may be about 0.01 to about 250 mg/kg per day. In another embodiment, a suitable dosage level may be about 0.1 to about 100 mg/kg per day. In another embodiment, a suitable dosage level may be about 0.05 to 100 mg/kg per day. In another embodiment, a suitable dosage level may be about 0.1 to 50 mg/kg per day. In another embodiment, a suitable dosage level may be about 0.05 to 0.5 mg/kg per day. In another embodiment, a suitable dosage level may be about 0.5 to 5 mg/kg per day. In another embodiment, a suitable dosage level may be about 5 to 50 mg/kg per day. For oral administration, the compositions are preferably provided in the form of tablets containing 0.01 to 1000 mg of the active ingredient, particularly 0.01, 0.025, 0.05, 0.075, 0.1, 0.25, 0.5, 0.75, 1.0, 2.5, 5.0, 7.5, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 8 times per day; preferably, 1 to 4 times a day; more preferably once or twice per day. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

Accordingly, the pharmaceutical compositions of the present invention encompass any composition made by admixing a compound of the present invention and a pharmaceutically acceptable carrier.

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have pain conditions, pruritic conditions and cough conditions, more than one drug is commonly administered. The compounds of this invention may generally be administered to a patient who is already taking one or more other drugs for these conditions. Often the compounds will be administered to a patient who is already being treated with one or more anti-pain compounds when the patient's pain is not adequately responding to treatment.

The combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients that may be administered in combination with a compound of the present invention, and either administered separately or in the same pharmaceutical composition, include but are not limited to:
    (i) an opioid agonist;
    (ii) an opioid antagonist;
    (iii) a calcium channel antagonist;
    (iv) a NMDA receptor agonist;
    (v) a NMDA receptor antagonist;
    (vi) a COX-2 selective inhibitor;
    (vii) a NSAID (non-steroidal anti-inflammatory drug); and
    (viii) an analgesic;
    (ix) a sodium channel inhibitor;
    (x) an anti-NGF antibody;
    (xi) a $Na_v1.7$ inhibitor;
    (xii) a HCN inhibitor;
    (xiii) a TRPV1 antagonist;
    (xiv) a $Na_v1.7$ biological; and
    (xv) a $Na_v1.8$ biological; and
pharmaceutically acceptable salts thereof.

In another embodiment of the present invention, the pharmaceutical composition comprises:
    (1) a compound of Claim 1 or a pharmaceutically acceptable salt thereof;
    (2) one or more compounds, or pharmaceutically acceptable salts thereof, selected from the group consisting of:
        (i) an opioid agonist;
        (ii) an opioid antagonist;
        (iii) a calcium channel antagonist;
        (iv) a NMDA receptor agonist;
        (v) a NMDA receptor antagonist;
        (vi) a COX-2 selective inhibitor;
        (vii) a NSAID (non-steroidal anti-inflammatory drug); and
        (viii) an analgesic;
        (ix) a sodium channel inhibitor;
        (x) an anti-NGF antibody;
        (xi) a $Na_v1.7$ inhibitor;
        (xii) a HCN inhibitor;
        (xiii) a TRPV1 antagonist;
        (xiv) a $Na_v1.7$ biological; and
        (xv) a $Na_v1.8$ biological; and
pharmaceutically acceptable salts thereof; and
    (3) a pharmaceutically acceptable carrier.

A Nav 1.7 biological means a protein, including, but not limited to, antibodies, nanobodies and peptides, that inhibits the function of the Nav1.7 channel. A Nav 1.8 biological means a protein, including, but not limited to, antibodies, nanobodies and peptides, that inhibits the function of the Nav1.8 channel.

Specific compounds of use in combination with a compound of the present invention include: sodium channel inhibitors, including but not limited to, lidocaine including the lidocaine patch; tricyclic antidepressants including, but not limited to, amitriptyline; and SRI/NRI drugs, including but not limited to, duloxetine.

Suitable opioid agonists include, but are not limited to, codeine, fentanyl, hydrocodone, hydromorphone, levorphanol, meperidine, methadone, morphine, oxycodone, oxymorphone, buprenorphine, butorphanol, dezocine, nalbuphine, pentazocine, and tramadol.

Suitable opioid antagonists include, but are not limited to, naltrexone and naloxone.

Suitable calcium channel antagonists include, but are not limited to, Amlodipine, Diltiazem, Felodipine, gabapentin, Isradipine, Nicardipine, Nifedipine, Nisoldipine, pregabalin, Veraparnil, and ziconitide.

Suitable NMDA receptor antagonists include, but are not limited to, ketarnine, methadone, memantine, amantadine, and dextromethorphan.

Suitable COX-2 inhibitors include, but are not limited to, celecoxib, eioricoxib and parecoxib.

Suitable NSAIDs or non-steroidal anti-inflammatory drugs include, but are not limited to, aspirin, diclofenac, diflunisal, etodolac, fenoprofin, flurbiprofen, ibuprofen, indomethacin, ketoprofen, meclofenamic acid, mefenamic acid, meloxicam, naproxen, naproxen sodium, oxaprozin, piroxicam, sulindac, and tolmetin.

Suitable analgesics include, but are not limited to, acetaminophen and duloxetine.

The above combinations include combinations of a compound of the present invention not only with one other active compound, but also with two or more other active compounds.

Non-limiting examples include combinations of compounds with two or more active compounds selected from: opioid agonists; opioid antagonists; calcium channel antagonists; NMDA receptor agonists; NMDA receptor antagonists; COX-2 selective inhibitors; NSAIDs (non-steroidal anti-inflammatory drugs); and an analgesic.

The compounds of the present invention, or a pharmaceutically acceptable salt thereof, may also be used in combination with spinal cord stimulation therapy and cutaneous stimulation therapy.

The present invention also provides a method for the treatment or prevention of a $Na_v1.8$ sodium ion channel activity mediated disease, disorder or condition, which method comprises administration to a patient in need of such treatment or at risk of developing a $Na_v1.8$ sodium ion channel activity mediated disease with a therapeutically effective amount of a $Na_v1.8$ sodium ion channel activity inhibitor and an amount of one or more active ingredients, such that together they give effective relief.

In a further aspect of the present invention, there is provided a pharmaceutical composition comprising a $Na_v1.8$ sodium ion channel activity inhibitor and one or more active ingredients, together with at least one pharmaceutically acceptable carrier or excipient.

Thus, according to a further aspect of the present invention there is provided the use of a $Na_v1.8$ sodium ion channel activity inhibitor and one or more active ingredients for the manufacture of a medicament for the treatment or prevention of a $Na_v1.8$ sodium ion channel activity mediated disease, disorder or condition. In a further or alternative aspect of the present invention, there is therefore provided a product comprising a $Na_v1.8$ sodium ion channel activity inhibitor and one or more active ingredients as a combined preparation for simultaneous, separate or sequential use in the treatment or prevention of a $Na_v1.8$ sodium ion channel activity mediated disease, disorder or condition. Such a combined preparation may be, for example, in the form of a twin pack.

It will be appreciated that for the treatment or prevention of pain conditions, pruritic conditions and cough conditions, a compound of the present invention may be used in conjunction with another pharmaceutical agent effective to treat that disease, disorder or condition.

The present invention also provides a method for the treatment or prevention of pain conditions, pruritic conditions and cough conditions, which method comprises administration to a patient in need of such treatment an amount of a compound of the present invention and an amount of another pharmaceutical agent effective to threat that disorder, disease or condition, such that together they give effective relief.

The present invention also provides a method for the treatment or prevention of pain conditions, pruritic conditions and cough conditions, which method comprises administration to a patient in need of such treatment an amount of a compound of the present invention and an amount of another pharmaceutical agent useful in treating that particular condition, disorder or disease, such that together they give effective relief.

The term "therapeutically effective amount" means the amount the compound of structural formula I that will elicit the biological or medical response of a cell, tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a COX-2 inhibitor the weight ratio of the compound of the Formula I to the COX-2 inhibitor will generally range from about 1000:1 to about 1:1000, preferably about 200:1 to about 1:200.

Combinations of a compound of the Formula I and other active ingredients will generally also be within the aforementioned range, but in each case, an effective dose of each active ingredient should be used.

Methods of Synthesis

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

Instrumentation

Reverse phase chromatography was carried out on a Gilson GX-281 equipped with a column selected from the following: Phenomenexd Synergi C18 (150 mm×30 mm×4 micron), YMC-Actus Pro C18 (150 mm×30 mm×5 micron), Xtimate C18 (150 mm×25 mm×5 micron), Boston Green ODS (150 mm×30 mm×5 micron), XSELECT C18 (150 mm×30 mm×5 micron), and Waters XSELECT C18 (150 mm×30 mm×5 micron). Conditions included either high pH (0-100% acetonitrile/water eluent comprising 0.1% v/v 10 mM $NH_4CO_3$ or 0.05% $NH_4OH$) or low pH (0-95% acetonitrile/water eluent comprising 0.1% v/v TFA) and are noted for some examples.

SFC chiral resolution was carried out on a Sepiate Prep SFC 100, Multigram II (MG II), THAR80 prep SFC, or a Waters SFC (80, 200, or 350) using the following conditions: Chiral Method A: AD-H column, 15% ethanol/$CO_2$; Chiral Method B: AD-H column, 20% IPA/$CO_2$; Chiral Method C: AS-H column, 20% MeOH/$CO_2$; Chiral Method D: AD-H column, 20% ethanol/$CO_2$; Chiral Method E: Lux Cellulose-4 column, 30% ethanol/$CO_2$; Chiral Method F: IA column, 15% ethanol/$CO_2$; Chiral Method G: IA column, 40% methanol/$CO_2$; Chiral Method H: AD-H column, 10% methanol/$CO_2$; Chiral Method I: AD-H column, 30% ethanol/$CO_2$; Chiral Method J: AD-H column, 40% ethanol/$CO_2$; and Chiral Method K: IG column, 12% methanol/$CO_2$.

LC/MS determinations were carried out on a Waters Classing Aquity system equipped with TUV and MS detectors and a Waters SQD mass spectrometer, a Shimadzu 20 UV 254 and 220 nM with Shimadzu 2010 or 2020 mass spectrometer, or an Agilent 1200 HPLC quipped with DAD/ELSD and G6110 MSD using one of the following conditions: 1) Ascentis Express C18 (3×50 mm) 2.7 μm column using mobile phase containing A: 0.05% Trifluoroacetic acid in water and B: 0.05% Trifluoroacetic acid in acetonitrile with a gradient from 90:10 (A:B) to 5:95 (A:B) over 6 min at a flow rate of 1.8 mL/min, UV detection at 210 nm; 2) Aquity BEH C18, (1.0×50 mm) 1.7 μm column using mobile phase containing A: 0.05% Trifluoroacetic acid in water and B: 0.05% Trifluoroacetic acid in acetonitrile with a gradient from 90:10 (A:B) to 5:95 (A:B) over 2 min at a flow rate of 0.3 mL/min, UV detection at 215 nm; 3) Agilent YMC J'Sphere H-80 (3×50 mm) 5 μm column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer; 4) an Agilent TC-C18 (2.1×50 mm) 5 μm column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

Proton or $^1H$ NMR was acquired using a Varian Unity-Inova 400 MHz NMR spectrometer equipped with a Varian 400 ATB PFG 5 mm, Nalorac DBG 400-5 or a Nalorac IDG 400-5 probe, a Varian-400 MHz MR spectrometer equipped with an Auto X ID PFG Probe 5 mm, a Varian 400 MHz VNMRS spectrometer equipped with a PFG 4Nuc Probe 5 mm, or a Bruker AvanceIII 500 MHz spectrometer equipped with a PABBO Probe 5 mm in accordance with standard analytical techniques, unless specified otherwise, and results of spectral analysis are reported.

Abbreviations

Throughout the Examples section, the following abbreviations are used to indicate various reagents, substituents and solvents: AcCN is acetonitrile; ACE-Cl is 1-chloroethyl chloroformate; AcOH is acetic acid; BAST is bis(2-methoxyethyl)aminosulfur trifluoride; Boc is tert-butoxycarbonyl; $Boc_2O$ is di-tert-butyl carbonate; Brettphos-Pd-G3 is [(2-di-cyclo-hexylphosphino-3,6-dimethoxy-2',4',6'-triisopropyl-1,1'-biphenyl)-2-(2'-amino-1,1'-biphenyl)]palladium (II) methanesulfonate; Calc'd is calculated; $Cu(OTf)_2$ is copper(II) trifluoromethanesulfonate; DBU is 1,8-diazabicyclo-[5.4.0]-undec-7-ene; DCE is dichloroethane; DCM is dichloromethane; DIPEA is diisopropylamine; DMA is dimethylacetamide; DMAP is 4-dimethylaminopyridine; DMB is 2,4-dimethoxybenzyl-; DMF is dimethylformamide; DMSO is dimethylsulfoxide; dppf is 1,1'-bis(diphenylphosphino)ferrocene; DTBPF-Pd-G3 is methanesulfonato(1,1-bis(di-t-butylphosphino)ferrocene)(2'-amino-1,1'-biphenyl-2-yl)palladium(II); EDC is 1-ethyl-3-(3-dimethylaminopropyl)carbodiimide; $Et_2O$ is diethyl ether; EtOAc is ethyl acetate; EtOH is ethanol; g is grams; HATU is 1-[bis(dimethylamino)-methylene]-1H-1,2,3-triazolo[4,5-b]pyridinium-3-oxide-hexafluorophosphate; Hex is hexanes; h or hr(s) is hour(s); HPLC is high-performance liquid chromatography; IPA is isopropyl alcohol; L is liter; LAH is lithium aluminum hydride; LC/MS is liquid chromatography/mass spectrometry; LRMS is low resolution mass spectrometry; Me is methyl; MeCN is acetonitrile; MeOH is methanol; MTBE is methyl tert-butyl ether; mg is milligrams; mL is milliliter; mmol is millimolar; M is molar; NBS is N-bromosuccinimide; NCS is N-chlorosuccinimide; NIS is N-iodosuccinimide; NMP is N-methylpyrrolidone; Pd/C is palladium on carbon; $Pd_2(dba)_3$ is tris(dibenzylidene-acetone)-dipalladium(O); $Pd(PPh_3)_4$ is tetrakis(triphenylphosphine)-palladium(O); $Pd(dppf)Cl_2$ is [1,1'-bis(diphenylphosphino)-ferrocene]dichloropalladium(II); $Pd(tBu_3P)_2$ is bis(tri-tert-butyl-phosphine)palladium(O); PE is petroleum ether; PG is protecting group; $POCl_3$ is phosphorus(V)oxychloride; $P(tBu)_3$-Pd-G2 is chloro[(tri-tert-butylphosphine)-2-(2-amino-biphenyl)] palladium(II); prep is preparative; PyBOP is benzotriazol-1-yl-oxytri-pyrrolidino-phosphonium hexafluorophosphate; RuPhos-Pd-G2 is chloro(2-dicyclohexyl-phosphino-2',6'-diisopropoxy-1,1'-biphenyl)[2-(2'-amino-1,1'-biphenyl)]-palladium(II); Ruphos Pd G3 or Ruphos-Pd-G3 is (2-Dicyclohexyl-phosphino-2',6'-diisopropoxy-1,1'-biphenyl)[2-(2'-amino-1,1'-biphenyl)]-palladium(II) methanesulfonate; r.t. or rt or RT is room temperature; SFC is Supercritical Fluid Chromatography; TEA is triethylamine; t-BuONa is sodium tert-butoxide; THF is tetrahydrofuran; TFA is trifluoroacetic acid; TMSCl is trimethylsilyl chloride; UV is ultraviolet; XantPhos Pd G2 or XantPhos-Pd-G2 is chloro[(4,5-bis(diphenylphosphino)-9,9-dimethyl-xanthene)-2-(2'-amino-1,1'-biphenyl)]-palladium(II); Xantphos G3 or XantPhos-Pd-G3 is [(4,5-Bis-(diphenyl-phosphino)-9,9-dimethylxanthene)-2-(2'-amino-1,1'-biphenyl)]-palladium(II) methane-sulfonate; XantPhos is 4,5-Bis(diphenylphosphino)-9,9-dimethyl-xanthene; t-BuXPhos Pd G3, tBu Xphos Pd G3, t-Bu Xphos-Pd-G3 or tBuXphos-Pd-G3 is [(2-di-tert-butylphosphino-2',4',6'-triisopropyl-1,1'-biphenyl)-2-(2'-amino-1,1'-biphenyl)] palladium(II) methanesulfonate; tBuXPhos is 2-Di-tert-butylphosphino-2',4',6'-triisopropylbiphenyl; and Xphos-Pd-G2 is chloro-(2-di-cyclohexylphosphino-2',4',6'-triisopropyl-1,1'-biphenyl)[2-(2'-amino-1,1'-biphenyl)]-palladium(II).

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention.

As illustrated in Scheme A, in general, compounds of the invention can be prepared by nucleophilic aromatic substitution between an appropriately functionalized carboxylic acid A-1 and an amine A-2, under basic conditions using a base such as DIPEA, to afford intermediate A-3. Intermediate A-3 can then be transformed into a primary carboxamide A-4 which can be coupled to an appropriately functionalized heteroaryl halide A-5 to provide compounds of Formula A-5. In some embodiments a protecting group such as 2,4-dimethoxybenzyl (DMB), tert-butyl or Boc may need to be removed after the C—N coupling to afford the compound of Formula A-6. Amines of type A-2 and heteroaryl halides of type A-5 are commercially available or may be synthesized from appropriate intermediates.

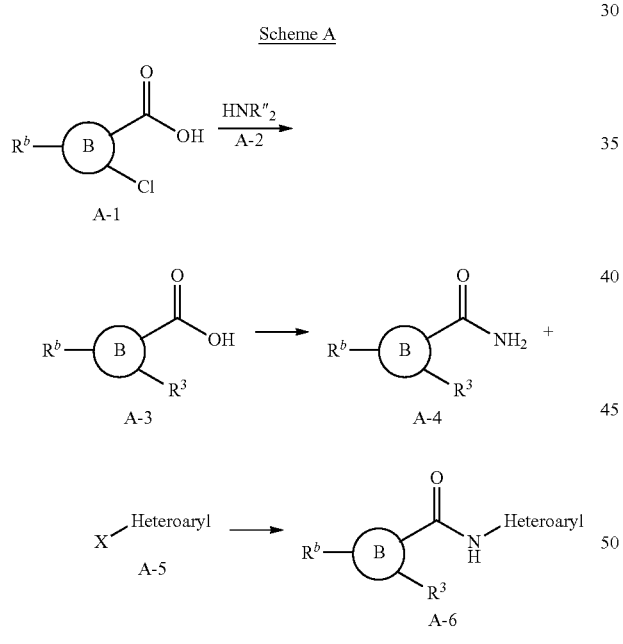

Scheme A $R^3$ is NR″$_2$; A is heteroaryl; X is halogen

The nucleophilic aromatic substitution may also occur in the presence of the carboxamide A-4, or alternative functional groups that can be converted to the carboxamide A-4 such as a halide, ester or cyano functional group, before being coupled to a heteroaryl halide A-5 to provide compounds of Formula A-6. Hydrolysis of ester B-1 to give the carboxylic acid A-3 allows direct amide coupling with an appropriately functionalized heteroarylamine B-2, by using amide coupling agents such as EDC or by forming the acid chloride from POCl$_3$, to afford compounds of Formula A-6.

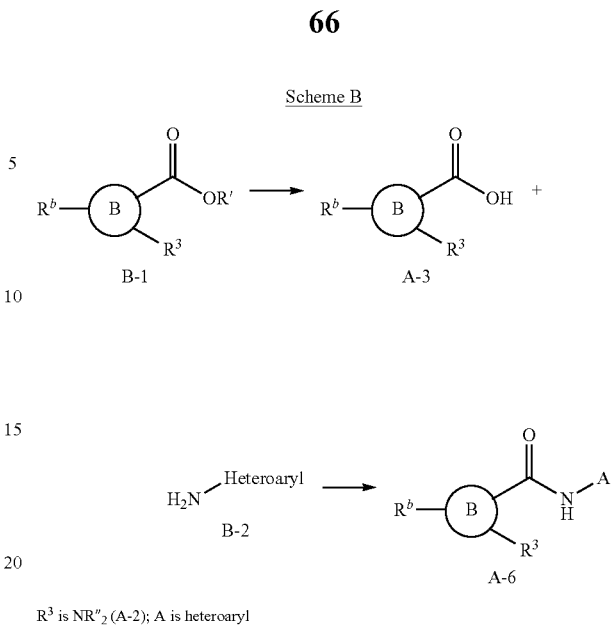

Scheme B $R^3$ is NR″$_2$ (A-2); A is heteroaryl

Those of skill in the art will appreciate that the amide coupling can occur first on an appropriately functionalized carboxylic acid (A-1) with a heteroaryl amine B-2, preferably using amide coupling agents such as EDC or by forming the acid chloride from POCl$_3$, or a C—N coupling between primary carboxamide C-2 and heteroaryl halide A-5 to afford intermediates of type C-1. Intermediates of type C-1 can undergo nucleophilic aromatic substitution reactions with secondary amines A-2 by displacing a heteroaryl chloride in the presence of a base, such as K$_2$CO$_3$ or DIPEA, or cross electrophile coupling reactions with alkyl halides to yield a compound of Formula A-6 as shown in Scheme C.

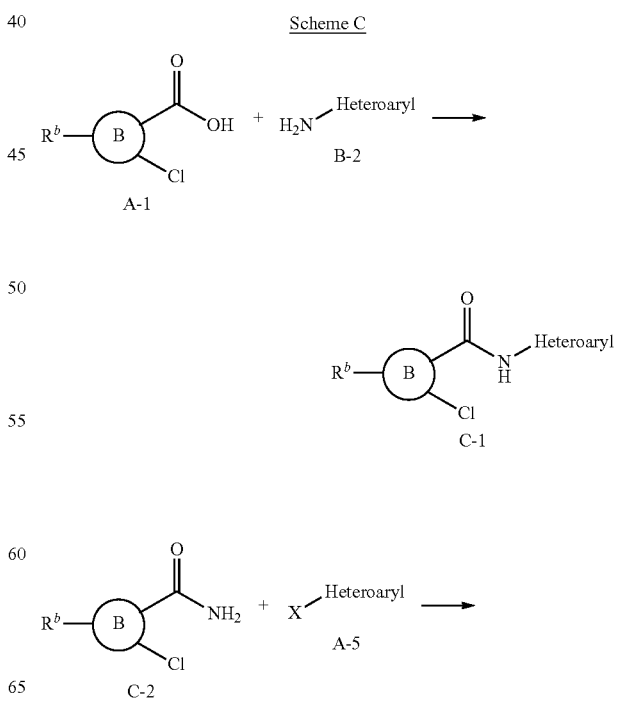

Scheme C

67

-continued

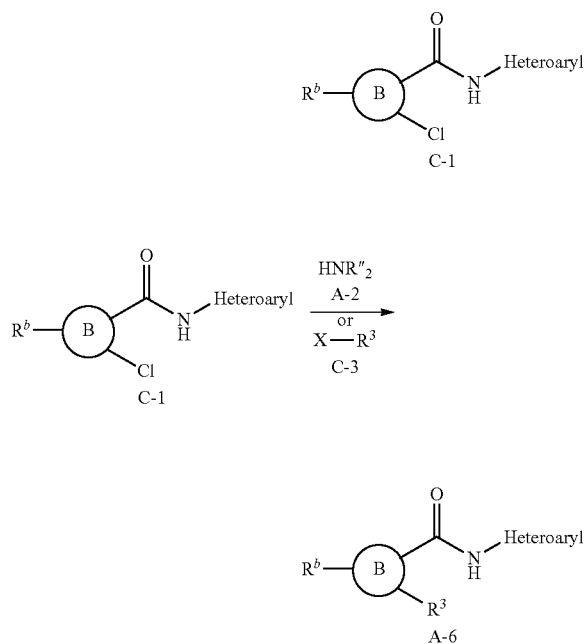

R³ is NR"₂, cycloalkyl or cycloheteroalkyl; X is halogen

The compound of Formula A-6 may also be prepared via reaction of heteroaryl chloride with an amine A-2, followed by halogenation of the adjacent position of the heteroaryl ring D-2. The heteroaryl halide D-2, such as a heteroaryl bromide, can be converted to a nitrile, which can be hydrolyzed to give a primary carboxamide A-4 and then coupled to a heteroaryl halide A-5 to afford compounds of Formula A-6. Alternatively, halide D-2 can be converted directly into amide A-6 via carbonylation in the presence of carbon monoxide and a catalyst, such as palladium. The resulting adduct may need to be deprotected using standard conditions to afford compounds of Formula A-6.

Scheme D

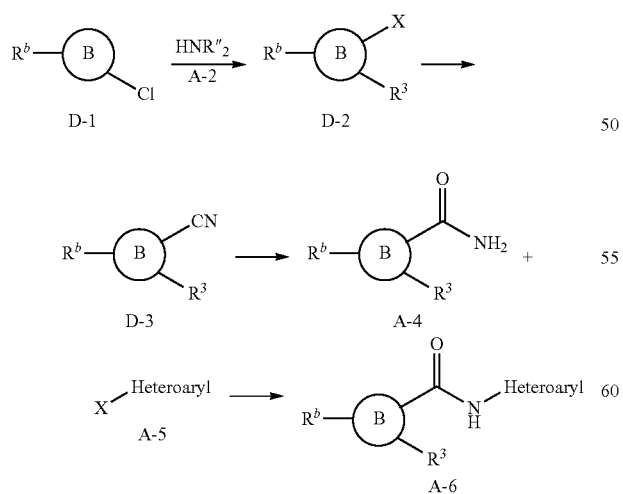

R³ is NR"₂; X is halogen

68

Intermediates

Intermediate 1

6-chloro-N,N-bis(2,4-dimethoxybenzyl)pyrazine-2-sulfonamide

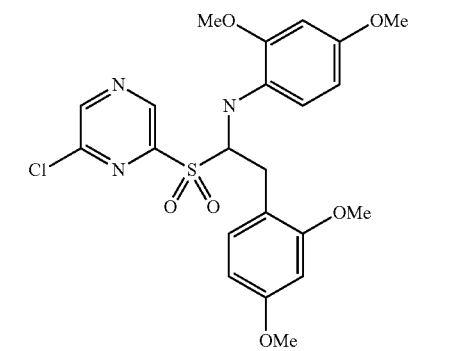 [SMILES: COc1ccc(CC(Nc2ccc(OC)cc2OC)S(=O)(=O)c2cncc(Cl)n2)c(OC)c1]

Step 1: 2-(benzylthio)-6-chloropyrazine To a solution of 2,6-dichloropyrazine (2.0 g, 13 mmol) in DMF (30 mL) was added K₂CO₃ (1.7 g, 12 mmol) and phenylmethanethiol (1.7 g, 13 mmol). The mixture was stirred at 30° C. for 13 hours, then diluted with water, extracted with EtOAc. The organic phase was separated, washed with brine, dried over Na₂SO₄, filtered and concentrated to give the title compound.

Step 2: 6-chloropyrazine-2-sulfonyl chloride A solution of 2-(benzylthio)-6-chloropyrazine (1 g crude) in CCl₄ (40 mL) and water (10 mL) was cooled 0° C., and then dichlorine (0.30 g, 4.2 mmol) was bubbled through the solution at 0° C. for 30 min. The resulting mixture was diluted with water and extracted with DCM. The organic phase was separated, washed with brine, dried over Na₂SO₄, filtered and concentrated to give the title compound.

Step 3: 6-chloro-N,N-bis(2,4-dimethoxybenzyl)pyrazine-2-sulfonamide To a solution of bis(2,4-dimethoxybenzyl)amine (0.45 g, 1.4 mmol) in DCM (8 mL) was added triethylamine (0.21 g, 2.1 mmol) and 6-chloropyrazine-2-sulfonyl chloride (0.30 g crude). The mixture was stirred at 29° C. for 1 hour, then concentrated and purified by silica gel chromatography (0-18% petroleum ether/EtOAc) to give the title compound.

Intermediate 2

5-bromo-N,N-bis(2,4-dimethoxybenzyl)pyridine-3-sulfonamide

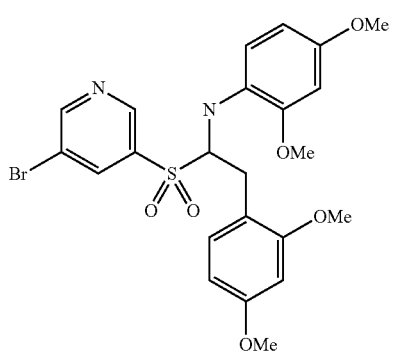 [SMILES: COc1ccc(CC(Nc2ccc(OC)cc2OC)S(=O)(=O)c2cncc(Br)c2)c(OC)c1]

A mixture of bis(2,4-dimethoxybenzyl)amine (0.99 g, 3.1 mmol) in DCM (3 mL) and Et₃N (0.65 mL, 4.7 mmol) was stirred at 25° C. for 5 min, then 5-bromopyridine-3-sulfonyl chloride (0.80 g, 3.1 mmol) was added. The mixture was stirred at 25° C. for 1 hour, then purified by silica gel chromatography (petroleum ether) to give the title compound.

Intermediate 3

3-bromo-5-(methylsulfonyl)pyridine

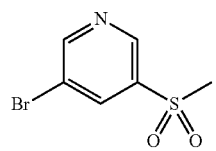

To a solution of 3-bromo-5-(methylthio)pyridine (0.20 g, 0.98 mmol) in DCM (5 mL) was added 3-chlorobenzoperoxoic acid (0.51 g, 2.9 mmol) slowly. The mixture was stirred at 21° C. for 13 hours, then diluted with DCM, and quenched with TN NaOH solution. The organic phase was separated, washed with brine, dried over Na₂SO₄, filtered and concentrated to give the title compound.

Intermediate 4

4-bromo-N,N-bis(2,4-dimethoxybenzyl)pyridine-2-sulfonamide

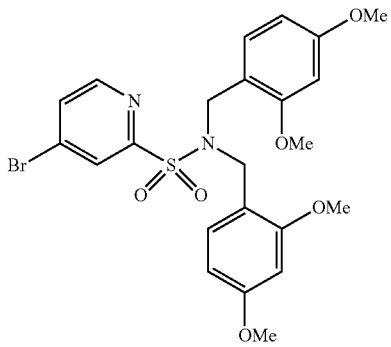 [SMILES: COc1ccc(CN(Cc2ccc(OC)cc2OC)S(=O)(=O)c2cc(Br)ccn2)c(OC)c1]

Step 1: 2-(benzylthio)-4-bromopyridine To a mixture of sodium hydride (32 g, 0.8 mol) in tetrahydrofuran (1.4 L) was added dropwise phenylmethanethiol (99 g, 0.8 mol) with stirring at 0° C. The mixture was stirred at 0° C. for 2 h, then a solution of 4-bromo-2-fluoropyridine (140 g, 0.8 mol) in tetrahydrofuran (1.4 L) was added to the mixture dropwise with stirring at 0° C. The resulting mixture was stirred at room temperature for 2 h, then cooled to 10° C., and quenched by the addition of water and extracted with ethyl acetate. The combined organic layers were dried over anhydrous magnesium sulfate, filtered and concentrated under reduced pressure to give a residue that was purified by silica gel chromatography (10% ethyl acetate/petroleum ether) to give the title compound.

Step 2: 4-bromopyridine-2-sulfonyl chloride To a solution of 2-(benzylthio)-4-bromopyridine (200 g, 0.72 mol) in DCM (2.8 L), AcOH (0.4 L) and water (0.8 L) was added 1,3-dichloro-5,5-dimethylimidazolidine-2,4-dione (424 g, 2.2 mol) dropwise with stirring at 0° C. The mixture was stirred at room temperature for 16 hours. Then the mixture was quenched with water and extracted with DCM. The combined organic layers were washed with sodium bicarbonate, dried over anhydrous magnesium sulfate, filtered and concentrated under reduced pressure to give a residue that was slurried with 3 volumes of PE and filtered to give the title compound.

Step 3: 4-bromo-N,N-bis(2,4-dimethoxybenzyl)pyridine-2-sulfonamide To a solution of 4-bromo-pyridine-2-sulfonyl chloride (90 g, 0.35 mol) in DCM (1.8 L) was added DIPEA (0.18 L, 1.1 mol), followed by the portionwise addition of bis(2,4-dimethoxybenzyl)amine (56 g, 0.18 mol). The mixture was stirred at 20° C. for 1.5 h, then diluted with water and extracted with DCM. The organic layer was dried over Na₂SO₄, filtered and concentrated under reduced pressure to give a residue that was purified by silica gel chromatography (10% ethyl acetate/petroleum ether) to give the title compound.

Intermediate 5

4-amino-N,N-bis(2,4-dimethoxybenzyl)pyridine-2-sulfonamide

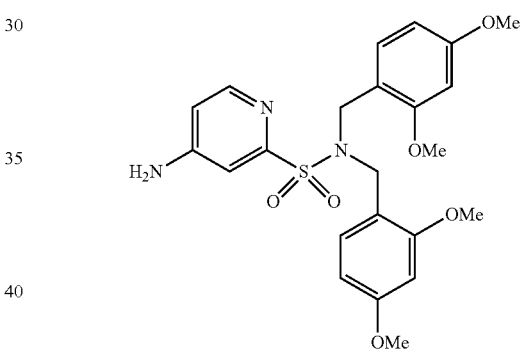

Step 1: 2-(benzylthio)-4-iodopyridine To a mixture of sodium hydride (54 g, 1.3 mol) in tetrahydrofuran (3.0 L) was added phenylmethanethiol (54 g, 1.3 mol) dropwise with stirring at 0° C. The mixture was stirred at 0° C. for 2 hours. To the mixture was added a solution of 2-fluoro-4-iodopyridine (300 g, 1.3 mol) in tetrahydrofuran (3.0 L) dropwise with stirring at 0° C. The resulting mixture was stirred at room temperature for 2 h, then cooled to 10° C., quenched by the addition of water and extracted with ethyl acetate. The combined organic layers were dried over anhydrous magnesium sulfate, filtered and concentrated under reduced pressure to give a residue that was purified by silica gel chromatography (10% ethyl acetate/petroleum ether) to give the title compound.

Step 2: 4-iodopyridine-2-sulfonyl chloride To a solution of a 2-(benzylthio)-4-iodopyridine (430 g, 1.3 mol) in DCM (6.0 L), AcOH (0.86 L) and water (1.7 L) was added 1,3-dichloro-5,5-dimethyl-imidazolidine-2,4-dione (780 g, 3.9 mol) dropwise with stirring at 0° C. The mixture was stirred at room temperature for 16 h, then quenched with water and extracted with DCM. The combined organic layers were washed with sodium bicarbonate, dried over anhydrous magnesium sulfate, filtered and concentrated under reduced pressure to give a residue that was was slurried with 3 volumes of PE and filtered to give the title compound.

Step 3: N, N-bis(2,4-dimethoxybenzyl)-4-iodopyridine-2-sulfonamide To a solution of 4-iodopyridine-2-sulfonyl chloride (250 g, 0.82 mol) in DCM (5.0 L) under an atmosphere of nitrogen was added DIPEA (0.43 L, 2.5 mol), then bis(2,4-dimethoxybenzyl)amine (130 g, 0.41 mol) portionwise. The mixture was stirred at 20° C. for 1.5 h, then diluted with water and extracted with DCM. The organic layer was dried over Na$_2$SO$_4$, filtered and concentrated under reduced pressure to give a residue that was purified by silica gel chromatography (10% ethyl acetate/petroleum ether) to give the title compound.

Step 4: 4-amino-N,N-bis(2,4dimethoxybenzyl)pyridine-2-sulfonamide To a solution of N,N-bis(2,4-dimethoxybenzyl)-4-iodopyridine-2-sulfonamide (70 g, 0.12 mol) in NMP (1.4 L) under an atmosphere of nitrogen was added ammonium acetate (92 g, 1.2 mol), copper(II) acetylacetonate (9.4 g, 0.036 mol), 2-acetylcyclohexanone (10 g, 0.072 mol) and Cs$_2$CO$_3$ (120 g, 0.36 mol) at room temperature. The mixture was stirred at 90° C. for 16 hours. Then the mixture was quenched with water and extracted with EtOAc. The combined organic layers were washed with brine, dried over anhydrous magnesium sulfate and concentrated under reduced pressure to give a residue that was slurried with 3 volumes of MTBE, then concentrated and recrystallized from acetonitrile to give the title compound.

Intermediate 6 tert-butyl tert-butyl((4-chloropyridin-2-yl)sulfonyl)carbamate

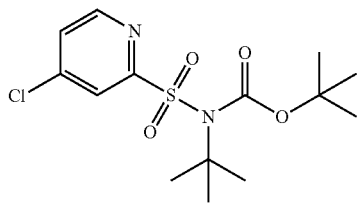 [SMILES: CC(C)(C)OC(=O)N(C(C)(C)C)S(=O)(=O)c1cc(Cl)ccn1]

Step 1: 2-(benzylthio)-4-chloropyridine To a mixture of 2-bromo-4-chloropyridine (10 g, 52 mmol) in dioxane (150 mL) was added XantPhos (4.5 g, 7.8 mmol), DIPEA (18 mL, 100 mmol), Pd$_2$(dba)$_3$ (2.4 g, 2.6 mmol) and phenylmethanethiol (6.1 mL, 52 mmol). The mixture was stirred at 100° C. for 13 h, then diluted in water and extracted with EtOAc. The combined organic layers were concentrated under reduced pressure to give a residue that was purified by silica gel chromatography (0-2% EtOAc/petroleum ether) to give the title compound.

Step 2: 4-chloropyridine-2-sulfonamide To a solution of 1,3-dichloro-5,5-dimethylimidazolidine-2,4-dione (22 g, 110 mmol) in acetonitrile (40 mL) at 0° C. was added acetic acid (4.0 mL) and water (3.2 mL). The mixture was stirred at 0° C. for 5 min, then 2-(benzylthio)-4-chloropyridine (10 g, 45 mmol) was added. The mixture was stirred at 0° C. for 0.5 h, then NH$_4$OH (56 g, 450 mmol) was added. The mixture was stirred at 0° C. for 0.5 h, then diluted in water and extracted with EtOAc. The organic layers were dried over Na$_2$SO$_4$, filtered and concentrated under pressure to give a residue that was purified by silica gel chromatography (50% EtOAc/petroleum ether) to give the title compound.

Step 3: tert-butyl tert-butyl((4-chloropyridin-2-yl)sulfonyl) carbamate To a mixture of 4-chloropyridine-2-sulfonamide (1.2 g, 6.2 mmol) in THF (40 mL) was added Boc$_2$O (3.2 mL, 14 mmol) and DMAP (0.76 g, 6.2 mmol) at 25° C. The mixture was stirred at 80° C. for 16 h. Then the mixture was concentrated under reduced pressure to give a residue that was purified by silica gel chromatography (20% EtOAc/petroleum ether) to give the title compound.

Intermediate 7 tert-butyl ((4-bromopyridin-2-yl)sulfonyl)(tert-butyl)carbamate

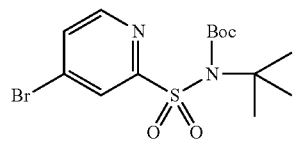 [SMILES: CC(C)(C)OC(=O)N(C(C)(C)C)S(=O)(=O)c1cc(Br)ccn1]

Step 1: 4-bromopyridine-2-sulfonamide To a solution of 4-bromopyridine-2-sulfonyl chloride (300 g, 1.3 mol) in acetonitrile (3.0 L) at 0° C. was added NH$_4$OH (1.5 kg, 13 mol) dropwise with stirring. The mixture was stirred at room temperature for 3 h, then quenched with water and extracted with EtOAc. The combined organic layers were washed with brine, dried over anhydrous magnesium sulfate, filtered and concentrated under reduced pressure to give a residue that was slurried with DCM to give the title compound.

Step 2: tert-butyl ((4-bromopyridin-2-yl)-sulfonyl)(tert-butyl)carbamate To a mixture of 4-bromopyridine-2-sulfonamide (50 g, 0.21 mol) in 2-methyltetrahydrofuran (1.0 L) at 25° C. was added Boc$_2$O (230 g, 1.1 mol) and DMAP (26 g, 0.21 mol). The mixture was stirred at 25° C. for 0.5 hour, then the mixture was stirred at 70° C. for 16 hours. The mixture was then cooled to 15° C., quenched with water and extracted with ethyl acetate. The combined organic layers were dried over anhydrous magnesium sulfate, filtered and concentrated under reduced pressure to give a residue that was purified by silica gel chromatography (1:30-1:24 ethyl acetate/petroleum ether), and then slurried with n-hexane to give the title compound.

Intermediate 8 tert-butyl ((4-aminopyridin-2-yl)sulfonyl)(tert-butyl)carbamate

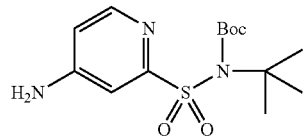 [SMILES: CC(C)(C)OC(=O)N(C(C)(C)C)S(=O)(=O)c1cc(N)ccn1]

Step 1: 4-iodopyridine-2-sulfonamide To a solution of 4-iodopyridine-2-sulfonyl chloride (550 g, 1.8 mol) in acetonitrile (11.0 L) at 0° C. was added NH4OH (2.1 kg, 18 mol) dropwise with stirring. The mixture was stirred at room temperature for 3 h, then quenched with water and extracted with EtOAc. The combined organic layers were washed with brine, dried over anhydrous magnesium sulfate, filtered and concentrated under reduced pressure to give a residue that was slurried with DCM to give the title compound.

Step 2: tert-butyl tert-butyl((4-iodopyridin-yl) sulfonyl)carbamate To a mixture of 4-iodopyridine-2-sulfonamide (125 g, 0.44 mol) in 2-methyltetrahydrofuran (2.5 L) at 25° C. was added Boc2O (480 g, 2.2 mol) and DMAP (11 g, 0.088 mol). The mixture was stirred at 25° C. for 0.5 hour, then the mixture was stirred at 70° C. for 16 hours. The mixture was then cooled to 15° C., quenched with water and extracted with ethyl acetate. The combined organic layers were dried over anhydrous magnesium sulfate, filtered and concentrated under reduced pressure to give a residue that was purified by silica gel chromatography (1:30-1:24 ethyl acetate/petroleum ether) to give the title compound.

Step 3: tert-butyl ((4-aminopyridin-2-yl)sulfonyl)(tert-butyl)carbamate To a solution of tert-butyl tert-butyl((4-iodopyridin-2-yl)sulfonyl)carbamate (50 g, 0.11 mol) in DMF (1.0 L) under an atmosphere of nitrogen was added NH4OH (64 g, 0.57 mol), copper(II) acetylacetonate (8.9 g, 0.033 mol), 2-acetylcyclohexanone (9.6 g, 0.066 mol) and Cs2CO3 (37 g, 0.11 mol) at room temperature. The mixture was stirred at 60° C. for 16 h, then quenched with water and extracted with EtOAc. The combined organic layers were washed with brine, dried over anhydrous magnesium sulfate and concentrated under reduced pressure to give a residue that was slurried with petroleum ether to give the title compound.

Intermediate 9

5,5-difluoroazepan-2-one

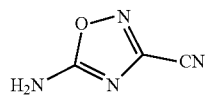

Step 1: tert-butyl (3-carbamoyl-1,2,4-oxadiazol-5-yl)carbamate Ammonia gas was bubbled through a solution of ethyl 5-((tert-butoxycarbonyl)amino)-1,2,4-oxadiazole-3-carboxylate (0.10 g, 0.39 mmol) in EtOH (3 mL) at 20° C. for 15 minutes. The mixture was stirred at 20° C. for 1 hour, then concentrated under reduced pressure to give the title compound.

Step 2: 5-amino-1,2,4-oxadiazole-3-carbonitrile To a solution of tert-butyl (3-carbamoyl-1,2,4-oxadiazol-5-yl)carbamate (20 mg, 0.088 mmol) in DCM (2 mL) at 20° C. was added phosphoryl trichloride (27 mg, 0.17 mmol) and a drop of DMF. The mixture was stirred at 40° C. for 1 h. Then the mixture was cooled to rt, diluted with water, treated with 2N NaOH to pH=8 and extracted with EtOAc. The combined organic layers were dried over Na2SO4, filtered and concentrated under reduced pressure to give the title compound.

Intermediate 10

(R and S)-4,4-difluoro-5-methylazepane hydrochloride

Step 1: 1-(tert-butyl) 4-ethyl 4-methyl-5-oxoazepane-1,4-dicarboxylate To a solution of 1-(tert-butyl) 4-ethyl 5-oxoazepane-1,4-dicarboxylate (1.0 g, 3.50 mmol) in DMF (12 mL) was added NaH (0.14 g, 3.5 mmol) at 0° C. over 1 min. After stirring for 1 h at 0° C., MeI (0.79 mL, 13 mmol) was added to the mixture at 0° C. The mixture was stirred at 20° C. for 2 h, then quenched with water and extracted with EtOAc. The combined organic layers were washed with brine, dried over anhydrous Na2SO4, filtered and concentrated under reduced pressure to give a residue that was purified by silica gel chromatography (04% ethyl acetate/petroleum ether) to give the title compound.

Step 2: tert-butyl 4-methyl-5-oxoazepane-1-carboxylate A mixture of KOH (4.2 mL, 8.3 mmol) and 1-(tert-butyl) 4-ethyl 4-methyl-5-oxoazepane-1,4-dicarboxylate (0.50 g, 1.7 mmol) in dioxane (5 mL) was stirred at 100° C. for 12 h. The mixture was quenched with water and extracted with EtOAc. The organic layer was separated, washed with brine, dried over anhydrous Na2SO4, filtered and concentrated under reduced pressure to give the title compound.

Step 3: tert-butyl 4,4-difluoro-5-methylazepane-1-carboxylate A mixture of tert-butyl 4-methyl-5-oxoazepane-1-carboxylate (0.37 g, 1.6 mmol) and BAST (0.90 mL, 4.9 mmol) in CHCl3 (5 mL) was degassed and backfilled with nitrogen three times. The mixture was heated to 55° C. for 12 h, then quenched with water and extracted with EtOAc. The organic layer was separated, washed with brine, concentrated and filtered under reduced pressure to give a residue that was purified by silica gel chromatography (0-4% petroleum ether/ethyl acetate) to give the title compound.

Step 4: (R and S)-4,4-difluoro-5-methylazepane hydrochloride A mixture of tert-butyl 4,4-difluoro-5-methylazepane-1-carboxylate (0.30 g, 1.2 mmol) in MeOH (2 mL) and HCl/dioxane (2 mL) was stirred at 20° C. for 12 h. Then the mixture was concentrated under reduced pressure to give the title compound.

Intermediate 11

4,4-Dichloro-3-methylpiperidine hydrochloride

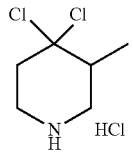

Step 1: Benzyl 4,4-dichloro-3-methylpiperidine-1-carboxylate Tungsten(VI) chloride (1.6 g, 4.1 mmol) was added to a solution of benzyl 3-methyl-4-oxopiperidine-1-carboxylate (0.34 g, 1.4 mmol) in DCM (16 mL). The mixture was heated at 40° C. for 10 minutes, then quenched with aqueous sodium hydrogen carbonate (saturated) and extracted with dichloromethane. The combined organic layers were dried over MgSO$_4$, filtered and concentrated under reduced pressure to give a residue that was purified by silica gel chromatography (0-100% EtOAc/hexanes) to give the title compound.

Step 2: 4,4-Dichloro-3-methylpiperidine hydrochloride A solution of benzyl 4,4-dichloro-3-methylpiperidine-1-carboxylate (0.39 g, 1.3 mmol) in EtOH was added to a suspension of Pd—C (0.14 g, 0.13 mmol) in nitrogen degassed EtOH (13 mL total). The mixture was evacuated and backfilled with hydrogen, and then stirred under a balloon of hydrogen for 1 hour. The reaction mixture was purged with nitrogen, and then filtered through a pad of Celite™. The filtrate was treated with 4M HCl (1.6 mL, 6.4 mmol) in dioxane, stirred for 10 minutes, and then concentrated under reduced pressure to give the title compound.

Intermediate 12

4,4-Dichloroazepane hydrochloride

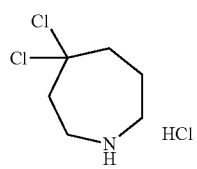

Step 1: Benzyl 4,4-dichloroazepane-1-carboxylate Tungsten(VI) chloride (1.2 g, 3.1 mmol) was added to a solution of benzyl 4-oxoazepane-1-carboxylate (0.26 g, 1.0 mmol) in DCM (10 mL). The mixture was heated at 40° C. for 10 minutes, then quenched with aqueous sodium hydrogen carbonate (saturated) and extracted with dichloromethane. The combined organic layers were dried over MgSO$_4$, filtered and concentrated under reduced pressure to give a residue that was purified by silica gel chromatography (0-100% EtOAc/hexanes) to give the title compound.

Step 2: 4,4-Dichloroazepane hydrochloride A solution of benzyl 4,4-dichloroazepane-1-carboxylate (0.12 g, 0.40 mmol) in EtOH was added to a suspension of Pd—C (43 mg, 0.040 mmol) in nitrogen degassed EtOH (4 mL total). The mixture was evacuated and backfilled with hydrogen, then stirred under a balloon of hydrogen for 1 hour. The mixture was purged with nitrogen, and then filtered through a pad of Celite™. The filtrate was treated with 4M HCl (0.50 mL, 2.0 mmol) in dioxane, stirred for 10 minutes, and then concentrated under reduced pressure to give the title compound.

Intermediate 13

(R)-2-(trifluoromethyl)-1,4-oxazepane hydrobromide

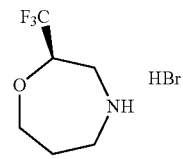 [SMILES: FC(F)(F)[C@H]1CNCCCO1 ; Br]

Step 1: (R)-3-((3,3,3-trifluoro-2-hydroxypropyl)amino)propan-1-ol (R)-2-(trifluoro-methyl)oxirane (3.7 g, 33 mmol) was added to a stirred solution of 3-amino-1-propanol (2.5 g, 33 mmol) in THF (33 mL) at 0° C. The mixture was stirred at 0° C. for 1 hour, then warmed to ambient temperature for 16 hours. Then the mixture was concentrated and azeotroped with THF to give the title compound.

Step 2: (R)—N-(3-hydroxypropyl)-4-methyl-N-(3,3,3-trifluoro-2-hydroxypropyl)benzenesulfonamide Tosyl-Cl (6.7 g, 35 mmol) was added to a solution of (R)-3-((3,3,3-trifluoro-2-hydroxypropyl)amino)propan-1-ol (6.0 g, 32 mmol) and TEA (8.9 mL, 64 mmol) in dichloromethane (80 mL) at 0° C. The mixture was stirred at 0° C. for 1 hour, then warmed to ambient temperature for 16 hours. The mixture was then diluted with EtOAc. The organic layer was separated, washed with brine, dried over MgSO$_4$, filtered and concentrated under reduced pressure to give a residue that was purified by silica gel chromatography (0-100% EtOAc/hexanes) to give the title compound.

Step 3: (R)-4-tosyl-2-(trifluoromethyl)-1,4-oxazepane To a stirred solution of (R)—N-(3-hydroxypropyl)-4-methyl-N-(3,3,3-trifluoro-2-hydroxypropyl)benzenesulfonamide (4.0 g, 12 mmol) in THF (120 mL) at 0° C. was added sodium hydride (1.2 g, 29 mmol). The mixture was stirred 5 minutes, then treated with 1-(p-toluenesulfonyl)imidazole (2.6 g, 12 mmol) at 0° C. The resulting mixture was warmed to ambient temperature for 16 hours, then quenched with water and extracted with EtOAc. The organic layer was separated, washed with brine, dried over MgSO$_4$, filtered and concentrated to give a residue that was purified by column chromatography (0-100% EtOAc/hexanes) to give the title compound.

Step 4: (R)-2-(trifluoromethyl)-1,4-oxazepane hydrobromide To a mixture of (R)-4-tosyl-2-(trifluoromethyl)-1,4-oxazepane (3.0 g, 9.3 mmol) and phenol (1.6 mL, 19 mmol) at room temperature was added HBr in AcOH (1.7 mL, 9.3 mmol). The mixture was heated to 80° C. for 6 hours. Then the mixture was cooled to ambient temperature, concentrated under reduced pressure and azeotroped with toluene. The resulting residue was triturated with Et$_2$O, collected by filtration, washed with Et$_2$O and dried under reduced pressure to give the title compound.

Intermediate 14

(2S,6R)-2-methyl-6-(trifluoromethyl)morpholine hydrochloride

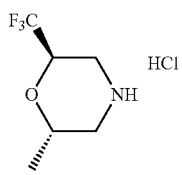

Step 1: (R)-3-(benzylamino)-1,1,1-trifluoropropan-2-ol To a solution of lithium trifluoromethanesulfonate (1.4 g, 9.2 mmol) in acetonitrile (23 mL) was added (R)-(+)-3,3,3-trifluoro-1,2-epoxypropane (5.5 g, 49 mmol) slowly at −10° C. After 5 minutes, benzylamine (5.1 mL, 47 mmol) was added slowly. The reaction mixture was stirred at ambient temperature for 18 hours. Then the mixture was concentrated under reduced pressure to give a residue that was purified by silica gel chromatography (0-100% EtOAc/hexanes) to give the title compound.

Step 2: N-benzyl-2-bromo-N—((R)-3,3,3-trifluoro-2-hydroxypropyl)propanamide To a solution of (R)-3-(benzylamino)-1,1,1-trifluoropropan-2-ol (3.0 g, 14 mmol) in DCM (55 mL) was added TEA (2.5 mL, 18 mmol), followed by 2-bromopropionyl chloride (1.5 mL, 15 mmol) at 0° C. The reaction mixture was stirred at 0° C. for 30 minutes, then warmed to ambient temperature for 4 hours. Then the mixture was concentrated under reduced pressure. The resulting residue was suspended in EtOAc, filtered through a pad of silica gel, washed with EtOAc, and concentrated under reduced pressure to give the title compound.

Step 3: (6R)-4-benzyl-2-methyl-6-(trifluoromethyl)morpholin-3-one To a stirred solution of N-benzyl-2-bromo-N—((R)-3,3,3-trifluoro-2-hydroxypropyl)propanamide (4.0 g, 11 mmol) in THF (45 mL) at 0° C. was added portionwise NaH (0.68 g, 17 mmol). The mixture was warmed to ambient temperature and stirred for 3 hours. Then the mixture was diluted with ½ saturated brine and extracted with DCM. The combined organic layers were filtered through a pad of Celite™, washing with dichloromethane, and concentrated to give a residue that was purified by silica gel chromatography (0-50% EtOAc/hexanes) to give the title compound.

Step 4: (2S,6R)-4-benzyl-2-methyl-6-(trifluoromethyl) morpholine To a solution of (6R)-4-benzyl-2-methyl-6-(trifluoromethyl)morpholin-3-one (3.0 g, 11 mmol) in THF (55 mL) at ambient temperature was added LAH (11 mL, 22 mmol) portionwise over 20 minutes. The reaction mixture was heated to reflux for 1 hour, then cooled to rt. The mixture was then diluted with ether, cooled to 0° C. and slowly treated with water (0.9 mL), followed by 15% aqueous sodium hydroxide (0.9 mL), and then water (2.7 mL). Then mixture was warmed to ambient temperature with stirring for 15 minutes, then treated with anhydrous magnesium sulfate and stirred for 1 hour. The resulting mixture was filtered to remove solids, and the filter cake was washed with Et₂O. The filtrate was concentrated under reduced pressure to give a residue that was purified by silica gel chromatography (0-100% EtOAc/hexanes) to give the title compound.

Step 5: (2S,6R)-2-methyl-6-(trifluoromethyl)morpholine hydrochloride To a stirred solution of (2S,6R)-4-benzyl-2-methyl-6-(trifluoromethyl)morpholine (0.30 g, 1.2 mmol) in DCE (1.2 mL) was added ACE-Cl (0.13 mL, 1.2 mmol). The mixture was heated to reflux for 16 hours, then cooled to rt and concentrated under reduced pressure to give a residue that was dissolved in MeOH (1.2 mL). The resulting mixture was heated to reflux for 4 hours. Then the mixture was cooled to ambient temperature and concentrated to give a residue that was triturated with Et₂O:hexanes (~1:3) to give a solid. The solid was filtered, collected and dried under reduced pressure to give the title compound.

Intermediate 15

(2R,6S and 2S,6R)-2-ethyl-6-(trifluoromethyl)morpholine hydrochloride

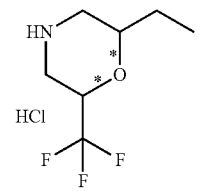

Step 1: N-benzyl-2-bromo-N-(3,3,3-trifluoro-2-hydroxypropyl)butanamide To a solution of 3-(benzylamino)-1,1,1-trifluoropropan-2-ol (1.2 g, 5.2 mmol) and TEA (2.2 mL, 16 mmol) in dichloromethane (25 mL) was added dropwise 2-bromobutanoyl chloride (1.0 g, 5.4 mmol) at 0° C. The mixture was stirred at 0° C. for 5 min then warmed to 15° C. for 1 hour. The mixture was concentrated under reduced pressure to give a residue that was purified by silica gel chromatography (18-25% ethyl acetate/petroleum ether) to give the title compound.

Step 2: 4-benzyl-2-ethyl-6-(trifluoromethyl)morpholin-3-one To a stirred suspension of NaH (0.17 g, 4.2 mmol) in THF (10 mL) at 0° C. was added a solution of N-benzyl-2-bromo-N-(3,3,3-trifluoro-2-hydroxypropyl)butanamide (1.4 g, 3.8 mmol) in THF (5 mL). The mixture was stirred at room temperature for 1 hour. The mixture was cooled to 0° C. and treated with MeOH (0.5 mL) until no more gas evolved. The mixture was concentrated under reduced pressure to a residue that was dissolved in water and extracted with EtOAc. The organic layers were washed with brine, dried over Na₂SO₄, filtered and concentrated under reduced pressure to give the title compound.

Step 3: (2R,6S and 2S,6R)-4-benzyl-2-ethyl-6-(trifluoromethyl)morpholine To a stirred solution of 4-benzyl-2-ethyl-6-(trifluoromethyl)morpholin-3-one (1.2 g) in THF (5 mL) at 0° C. was added dropwise BH₃.THF (21 mL, 21 mmol). The mixture was heated to 80° C. for 12 hours, then cooled to rt and quenched by the dropwise addition of MeOH (5 mL). The reaction mixture was concentrated under reduced pressure. The resulting residue was dissolved in MeOH (50 mL) and refluxed for 1 hour. Then the mixture was concentrated under reduced pressure to give a residue that was purified by silica gel chromatography to give the title compound.

Step 4: (2R,6S and 2S,6R)-2-ethyl-6-(trifluoromethyl) morpholine hydrochloride To a solution of (2R,6S and 2S,6R)-4-benzyl-2-ethyl-6-(trifluoromethyl)morpholine (0.40 g, 1.5 mmol) in THF (10 mL) under an atmosphere of nitrogen was added Pd/C (0.078 g, 0.073 mmol). The mixture was degassed and backfilled with hydrogen (three times). Then the mixture was stirred under hydrogen (50 psi) at 20° C. for 12 hours. The reaction mixture was filtered, and the filtrate was treated with HCl/EtOAc and concentrated under reduced pressure to give the title compound.

Intermediate 16

2,2-dimethyl-6-(trifluoromethyl)morpholine hydrochloride

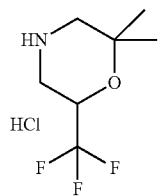

Step 1: 3-(benzyl(2-methylallyl)amino)-1,1,1-trifluoropropan-2-ol To a mixture of 3-(benzylamino)-1,1,1-trifluoropropan-2-ol (2.2 g, 10 mmol), K₂CO₃ (2.8 g, 20 mmol) in THF (20 mL) was added 3-bromo-2-methylprop-1-ene (1.8 g, 13 mmol) at 20° C. The mixture was stirred at 20° C. for 16 hours, then filtered. The filtrate was concentrated under reduced pressure to give a residue that was purified by silica gel chromatography (5% ethyl acetate/petroleum ether) to give the title compound.

Step 2: 4-benzyl-2,2-dimethyl-6-(trifluoromethyl)morpholine To a solution of Hg(OAc)₂ (0.50 g, 1.6 mmol) in THF (5 mL) and water (5 mL) was added 3-(benzyl(2-methylallyl)amino)-1,1,1-trifluoropropan-2-ol (0.42 g, 1.5 mmol). The mixture was stirred at 15° C. for 3 hours. Then the mixture was treated with NaOH (1.2 mL, 3.1 mmol, 2.5 M in water), followed by NaBH₄ (67 mg, 1.8 mmol). The reaction mixture was stirred at 15° C. for 16 h, then extracted with EtOAc. The combined organic layers were dried over Na₂SO₄, filtered and concentrated under reduced pressure to give a residue that was purified by silica gel chromatography (3% ethyl acetate/petroleum ether) to give the title compound.

Step 3: 2,2-dimethyl-6-(trifluoromethyl)morpholine hydrochloride To a solution of 4-benzyl-2,2-dimethyl-6-(trifluoromethyl)morpholine (0.25 g, 0.92 mmol) in THF (5 mL) under an atmosphere of nitrogen was added Pd/C (49 mg). The mixture was degassed and backfilled with hydrogen (three times). The reaction mixture was stirred under hydrogen (55 psi) at 15° C. for 12 hours, then filtered. The filtrate was treated with HCl/EtOAc (1 mL), and then concentrated under reduced pressure to give the title compound.

Intermediate 17

2-(azepan-1-yl)-5-(trifluoromethyl)nicotinic acid

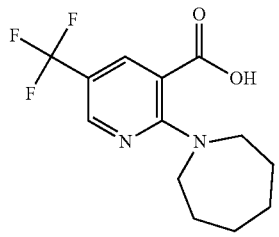 [SMILES: O=C(O)c1cc(C(F)(F)F)cnc1N1CCCCCC1]

To a mixture of 2-chloro-5-(trifluoromethyl)nicotinic acid (0.50 g, 2.2 mmol) in DMF (10 mL) was added K₂CO₃ (0.92 g, 6.6 mmol) and hexamethyleneimine (0.26 g, 2.7 mmol). The mixture was stirred at ambient temperature for 16 hours. Then the mixture was diluted with EtOAc, washed with 5% aqueous AcOH and brine, then dried over MgSO₄, filtered and concentrated to give the title compound.

Intermediate 18

2-(azepan-1-yl)-5-(trifluoromethyl)nicotinamide

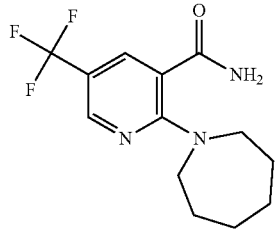 [SMILES: NC(=O)c1cc(C(F)(F)F)cnc1N1CCCCCC1]

To a solution of 2-(azepan-1-yl)-5-(trifluoromethyl)nicotinic acid (0.20 g, 0.69 mmol) in DMF (8 mL) was added triethylamine (0.19 mL, 1.4 mmol), HATU (0.32 g, 0.83 mmol) and ammonia hydrochloride (56 mg, 1.0 mmol). The mixture was stirred at 30° C. for 12 hours, then diluted with water and extracted with EtOAc. The combined organic layers were washed with brine, dried over Na₂SO₄, filtered and concentrated to give a residue that was purified by silica gel chromatography (50% petroleum ether/EtOAc) to give the title compound.

Intermediate 19

2-chloro-5-(trifluoromethyl)nicotinamide

A mixture of (COCl)₂ (0.093 mL, 1.1 mmol) and 2-chloro-5-(trifluoromethyl)nicotinic acid (200 mg, 0.89 mmol) in DCM (10 mL) was stirred at 0° C. for 2 h. Then the mixture was concentrated under reduced pressure, dissolved in THF (10 mL) and treated with NH₃·H₂O (5.0 mL, 36 mmol) at 20° C. for 2 h. The mixture was extracted with EtOAc and the combined organic layers were washed with water, brine, dried over Na₂SO₄, filtered and concentrated under reduced pressure to give the title compound.

Intermediate 20

2-(4,4-difluoropiperidin-1-yl)-5-(trifluoromethyl)nicotinamide

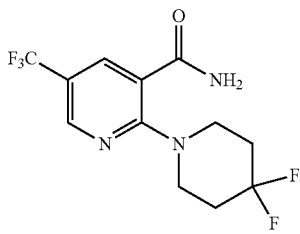 [SMILES: NC(=O)c1cc(C(F)(F)F)cnc1N1CCC(F)(F)CC1]

Step 1: 3-bromo-2-(4,4-difluoropiperidin-1-yl)-5-(trifluoromethyl)pyridine To a solution of 3-bromo-2-chloro-5-(trifluoromethyl)pyridine (48 g, 180 mmol) and 4,4-difluoropiperidine hydrochloride (36 g, 230 mmol) in NMP was added triethylamine (47 g, 460 mmol). The mixture was heated to 100° C. for 1 h, then cooled to rt and diluted in EtOAc. The organic layer was washed with water, citric acid, then brine, dried over Na₂SO₄, filtered and concentrated under reduced pressure to give the title compound.

Step 2: 2-(4,4-difluoropiperidin-1-yl)-5-(trifluoromethyl)nicotinonitrile To a solution of 3-bromo-2-(4,4-difluoropiperidin-1-yl)-5-(trifluoromethyl)pyridine (40 g, 120 mmol) in degassed DMA (400 mL) was added allylpalladium(II) chloride (1.3 g, 3.5 mmol), Xantphos (4.0 g, 7.0 mmol) and potassium ferrocyanide (20 g, 46 mmol). The mixture was heated to 100° C. for 16 hours, then filtered through diatomite with rinsed with EtOAc. The filtrate was washed with water, dried over Na₂SO₄ and concentrated to give a residue that was purified by silica gel chromatography (0-10% EtOAc/petroleum ether) to give the title compound.

Step 3: 2-(4,4-difluoropiperidin-1-yl)-5-(trifluoromethyl)nicotinamide To a solution of 2-(4,4-difluoropiperidin-1-yl)-5-(trifluoromethyl)nicotinonitrile (35 g, 120 mmol) in DCE under an atmosphere of nitrogen was added Cu(OTf)₂, followed by N,N-diethylhydroxylamine and trifluoromethanesulfonic acid. The mixture was heated to 50° C. for 2 h, then quenched into water and extracted with DCM. The organic layers were washed with citric acid then brine, dried over Na₂SO₄, filtered and concentrated to give a residue that was slurried in 1:1 Et₂O and petroleum ether and filtered to give the title compound.

Intermediate 21

2-chloro-N-(2-sulfamoylpyridin-4-yl)-5-(trifluoromethyl)nicotinamide

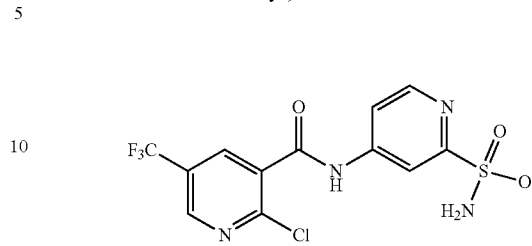

Step 1: tert-butyl tert-butyl((4-(2-chloro-5-(trifluoromethyl)nicotinamido)pyridin-2-yl)sulfonyl)carbamate To a solution of 2-chloro-5-(trifluoromethyl)pyridine-3-carboxylic acid (0.81 g, 3.6 mmol) and tert-butyl (4-aminopyridin-2-yl)sulfonyl(tert-butyl)carbamate (1.2 g, 3.6 mmol) in pyridine (18 mL) at 0° C. was added POCl₃ (0.37 mL, 3.9 mmol). The mixture was stirred at 0° C. for 1 hour, then quenched with brine (saturated), and extracted with ethyl acetate. The organic phase was dried over MgSO₄, filtered and concentrated under reduced pressure to give a residue that was purified on silica gel, eluting with a gradient of 0-100% EtOAc/hexanes over 15 column volumes, to give the title compound.

Step 2: 2-chloro-N-(2-sulfamoylpyridin-4-yl)-5-(trifluoromethyl)nicotinamide To a stirred solution of tert-butyl tert-butyl((4-(2-chloro-5-(trifluoromethyl)nicotinamido)pyridin-2-yl)sulfonyl)carbamate (1.7 g, 3.1 mmol) in DCM (25 mL) at 0° C. was added TFA (6.3 mL). The mixture was warmed to room temperature and stirred for 4 hours, then concentrated under reduced pressure. The resulting residue was dissolved in EtOAc. The organic phase was separated, washed with saturated aqueous NaHCO₃, dried over MgSO₄, filtered and concentrated under reduced pressure. The resulting residue was heated to 80° C. in EtOAc, then cooled to rt. The resulting solid filtered to give the title compound.

Intermediate 22

N-(2-(N,N-bis(2,4-dimethoxybenzyl)sulfamoyl)pyridin-4-yl)-2-chloro-5-(trifluoromethyl)nicotinamide

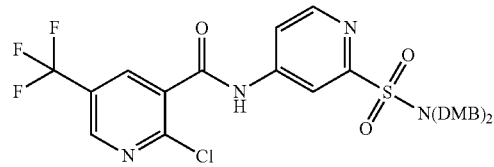

To a solution of 2-chloro-5-(trifluoromethyl)nicotinic acid (0.20 g, 0.89 mmol) and 4-amino-N,N-bis(2,4-dimethoxybenzyl)pyridine-2-sulfonamide (0.42 g, 0.89 mmol) in pyridine (1.0 mL) was added POCl₃ (0.083 mL, 0.89 mmol) at 0° C. The mixture was stirred at 0° C. for 10 minutes, then quenched with water and extracted with EtOAc. The combined organic layers were washed with brine, dried over Na₂SO₄, filtered and concentrated to give a residue that was purified by silica gel chromatography (25-30% ethyl acetate/petroleum ether) to give the title compound.

Intermediate 23

2-(4,4-Dichloropiperidin-1-yl)-5-(trifluoromethyl)nicotinic acid

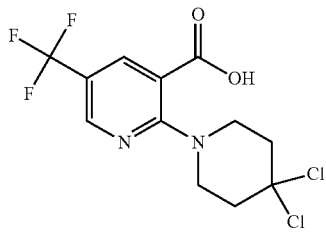 [SMILES: O=C(O)c1cc(C(F)(F)F)cnc1N1CCC(Cl)(Cl)CC1]

Step 1: Methyl 2-(4-oxopiperidin-1-yl)-5-(trifluoromethyl)nicotinate A mixture of methyl 2-chloro-5-(trifluoromethyl)nicotinate (0.27 g, 1.1 mmol), piperidin-4-one hydrochloride (0.15 g, 1.1 mmol) and DIPEA (0.59 mL, 3.4 mmol) in NMP (5.6 mL) was heated at 70° C. for 16 hours. Then the reaction mixture was quenched with aqueous potassium phosphate monobasic (saturated) and extracted with ethyl acetate. The combined organic layers were dried over MgSO$_4$, filtered and concentrated under reduced pressure to give a residue that was purified by silica gel chromatography (0-100% EtOAc/hexanes) to give the title compound.

Step 2: Methyl 2-(4,4-dichloropiperidin-1-yl)-5-(trifluoromethyl)nicotinate Tungsten(VI) chloride (1.2 g, 2.8 mmol) was added to a solution of methyl 2-(4-oxopiperidin-1-yl)-5-(trifluoromethyl)nicotinate (0.29 g, 0.95 mmol) in DCM (19 mL). The mixture was heated at 40° C. for 10 minutes, then diluted with DCM. The organic layer was separated, washed with saturated aqueous NaHCO$_3$ solution. dried over MgSO$_4$, filtered and concentrated under reduced pressure to give the title compound.

Step 3: 2-(4,4-Dichloropiperidin-1-yl)-5-(trifluoromethyl)nicotinic acid To a solution of methyl 2-(4,4-dichloropiperidin-1-yl)-5-(trifluoromethyl)nicotinate (0.28 g, 0.78 mmol) in MeOH (3.9 mL) was added 1M NaOH (1.6 mL, 1.6 mmol). The mixture was heated at 100° C. for 5 minutes under microwave irradiation. Then the mixture was quenched with hydrochloric acid (1M) and extracted with ethyl acetate. The organic layers were dried over MgSO$_4$, filtered and concentrated under reduced pressure to give the title compound.

Intermediate 24

2-chloro-6-methylnicotinamide

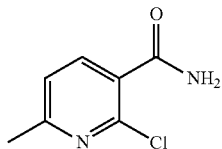

A mixture of (COCl)$_2$ (3.8 mL, 44 mmol) and 2-chloro-6-methylnicotinic acid (5.0 g, 29 mmol) in DCM (30 mL) was stirred at 20° C. for 2 hours. Then the mixture was concentrated under reduced pressure to give a residue that was treated with THF (30 mL) and NH$_3$·H$_2$O (30 mL) at 20° C. for 2 hours. The resulting mixture was filtered and the filtrate was concentrated under reduced pressure to give the title compound.

Intermediate 25

2-(4,4-difluoropiperidin-1-yl)-6-methylnicotinamide

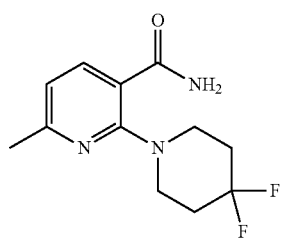 [SMILES: Cc1ccc(C(N)=O)c(N2CCC(F)(F)CC2)n1]

To a solution of 2-chloro-6-methylnicotinamide (3.0 g, crude) in NMP (50 mL) were added DIPEA (2.3 g, 18 mmol) and 4,4-difluoropiperidine hydrochloride (2.8 g, 18 mmol). The mixture was stirred at 160° C. for 3 hours, then diluted with water and extracted with EtOAc. The combined organic layers were washed with brine, dried over Na$_2$SO$_4$, filtered and concentrated under reduced pressure to a residue that was purified by silica gel chromatography (0-25% EtOAc/petroleum ether) to give the title compound.

Intermediate 26

N-(2-(N,N-bis(2,4-dimethoxybenzyl)sulfamoyl)pyridin-4-yl)-5-bromo-2-(4,4-difluoropiperidin-1-yl)-6-methylnicotinamide

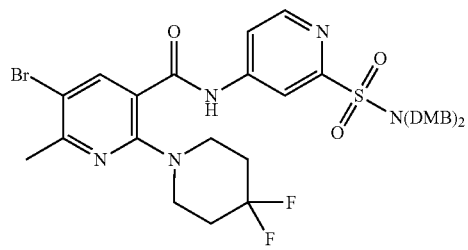

Step 1: 5-bromo-2-(4,4-difluoropiperidin-1-yl)-6-methylnicotinamide To a solution of 2-(4,4-difluoropiperidin-1-yl)-6-methylnicotinamide (1.3 g, 5.1 mmol) in DMF (20 mL) was added 1-bromopyrrolidine-2,5-dione (1.1 g, 6.1 mmol). The mixture was stirred at 11° C. for 2 hours, then diluted with water and extracted with EtOAc. The combined organic layers were dried over anhydrous Na$_2$SO$_4$, filtered and concentrated to give a residue which was purified by silica gel chromatography (0-22% EtOAc/petroleum ether) to give the title compound.

Step 2: N-(2-(N,N-bis(2,4-dimethoxybenzyl)sulfamoyl)pyridin-4-yl)-5-bromo-2-(4,4-difluoropiperidin-1-yl)-6-methylnicotinamide To a solution of 5-bromo-2-(4,4-difluoro-piperidin-1-yl)-6-methylnicotinamide (200 mg, 0.37 mmol) in 1,4-dioxane (4 mL) were added 4-bromo-N,N-bis (2,4-dimethoxybenzyl)pyridine-2-sulfonamide (150 mg, 0.45 mmol), Xantphos-Pd-G2 (33 mg, 0.037 mmol) and Cs$_2$CO$_3$ (365 mg, 1.1 mmol) under an inert atmosphere in a glove box. The mixture was stirred at 100° C. for 12 hours, then diluted with water and extracted with EtOAc. The combined organic layers were dried over anhydrous Na₂SO₄, filtered and concentrated to give a residue that was purified by silica gel chromatography (PE/EtOAc=3:1) to give the title compound.

Intermediate 27

6-chloro-2-(4,4-difluoropiperidin-1-yl)-4-methylnicotinamide

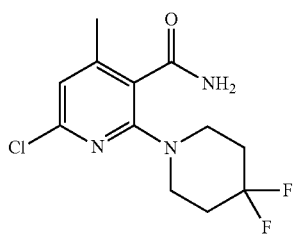 [SMILES: Cc1cc(Cl)nc(N2CCC(F)(F)CC2)c1C(N)=O]

Step 1: 6-chloro-2-(4,4-difluoropiperidin-1-yl)-4-methylnicotinonitrile To a mixture of 2,6-dichloro-4-methylnicotinonitrile (50 mg, 0.27 mmol) in DMF (1 mL) was added K₂CO₃ (0.11 g, 0.80 mmol) and 4,4-difluoropiperidine hydrochloride (46 mg, 0.29 mmol) under nitrogen. The mixture was stirred at 10° C. for 1 h, then at 90° C. for 16 h. Then the mixture was dissolved in water and extracted with EtOAc. The organic layer was separated, washed with brine, dried over anhydrous Na₂SO₄, filtered and concentrated under reduced pressure to give a residue that was purified by silica gel chromatography (PE/ethyl acetate=10/1) to give the title compound.

Step 2: 6-chloro-2-(4,4-difluoropiperidin-1-yl)-4-methylnicotinamide To a mixture of 6-chloro-2-(4,4-difluoropiperidin-1-yl)-4-methylnicotinonitrile (0.42 g, 1.6 mmol) in DMSO (4 mL) was added K₂CO₃ (0.65 g, 4.7 mmol) under nitrogen. The mixture was stirred at 0° C. for 1 h, then hydrogen peroxide (0.53 g, 7.8 mmol) was added. The mixture was stirred at 15° C. for 16 h, then dissolved in water and extracted with EtOAc. The organic layer was washed with brine, dried over anhydrous Na₂SO₄, filtered and concentrated under reduced pressure to give a residue that was purified by silica gel chromatography (0-30% ethyl acetate/petroleum ether gradient) to give the title compound.

Intermediate 28

2,6-dichloronicotinamide

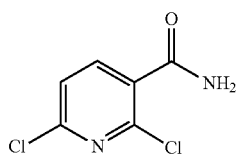 [SMILES: NC(=O)c1ccc(Cl)nc1Cl]

To a mixture of 2,6-dichloronicotinic acid (10 g, 52 mmol) and (COCl)₂ (6.8 mL, 78 mmol) in dichloromethane (20 mL) was added DMF (0.040 mL, 0.52 mmol). The mixture was stirred at 20° C. for 2 h, then concentrated under reduced pressure. The resulting residue was dissolved in THF (20 mL) and NH₃·H₂O (30 mL), and the mixture was stirred at 20° C. for 2 h. The mixture was filtered and the filtrate was concentrated under reduced pressure to give the title compound.

Intermediate 29

6-chloro-2-(4,4-difluoropiperidin-1-yl)nicotinamide

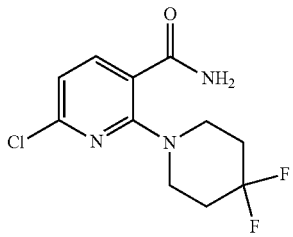 [SMILES: NC(=O)c1ccc(Cl)nc1N1CCC(F)(F)CC1]

A mixture of DIPEA (1.5 mL, 8.8 mmol), 4,4-difluoropiperidine hydrochloride (0.55 g, 3.5 mmol) and 2,6-dichloronicotinamide (0.56 g, 2.9 mmol) in NMP (10 mL) was stirred at 130° C. for 10 h. Then the mixture was quenched with water and extracted with EtOAc. The combined organic layers were washed with brine, dried over anhydrous Na₂SO₄, filtered and concentrated to give a residue that was purified by flash silica gel chromatography (0-26% ethyl acetate/PE) to give the title compound.

Intermediate 30

6-chloro-2-(4,4-difluoropiperidin-1-yl)-5-iodonicotinamide

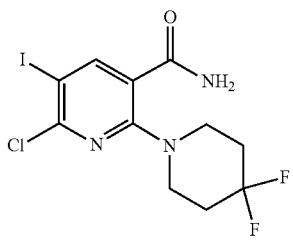 [SMILES: NC(=O)c1cc(I)c(Cl)nc1N1CCC(F)(F)CC1]

To a stirred solution of 6-chloro-2-(4,4-difluoropiperidin-1-yl)nicotinamide (0.30 g, 1.1 mmol) in acetonitrile (8.0 mL) was added NIS (0.73 g, 3.3 mmol) at 15° C. The mixture was stirred at 45° C. for 12 h. Then the mixture was diluted with EtOAc, washed with Na₂SO₃ aqueous solution, brine, dried over anhydrous sodium sulfate, filtered and concentrated under reduced pressure. The resulting residue was purified by silica gel chromatography (33% ethyl acetate/petroleum ether) to give the title compound.

Intermediate 31 methyl 6-chloro-2-(4,4-difluoroazepan-1-yl)nicotinate

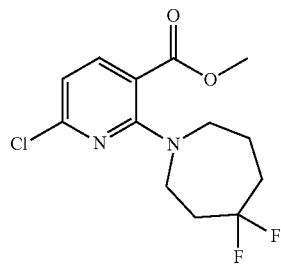 [SMILES: COC(=O)c1ccc(Cl)nc1N1CCCC(F)(F)CC1]

Step 1: methyl 2,6-dichloronicotinate To a solution of 2,6-dichloronicotinic acid (5.0 g, 26 mmol) in DCM (50 mL) and MeOH (50 mL) was added (diazomethyl)trimethyl silane (39 mL, 78 mmol). The mixture was stirred at 25° C. for 13 h, then diluted with water and extracted with DCM. The organic phase was washed with brine, dried over $Na_2SO_4$, filtered and concentrated to give a residue that was purified by silica gel chromatography (0-6% EtOAc/petroleum ether) to give the title compound.

Step 2: methyl 6-chloro-2-(4,4-difluoroazepan-1-yl)nicotinate To a solution of methyl 2,6-dichloronicotinate (1.8 g, 8.7 mmol) in THF (15 mL) and DMF (15 mL) was added N-ethyl-N-isopropylpropan-2-amine (2.3 g, 17 mmol) and 4,4-difluoroazepane hydrochloride (1.5 g, 8.7 mmol). The mixture was stirred at 70° C. for 11 h, then diluted with water and extracted with EtOAc. The combined organic layers were dried over anhydrous $Na_2SO_4$, filtered and concentrated to give a residue that was purified by silica gel chromatography (0-15% EtOAc/petroleum ether) to give the title compound.

Intermediate 32

5-chloro-6-cyclopropyl-2-(4,4-difluoroazepan-1-yl)nicotinamide

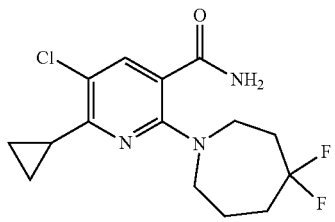 [SMILES: NC(=O)c1cc(Cl)c(C2CC2)nc1N1CCCC(F)(F)CC1]

Step 1: methyl 6-cyclopropyl-2-(4,4-difluoroazepan-1-yl)nicotinate A mixture of methyl 6-chloro-2-(4,4-difluoroazepan-1-yl)nicotinate (0.30 g, 0.98 mmol), Pd(dppf)Cl$_2$ (72 mg, 0.098 mmol), potassium cyclopropyltrifluoroborate (0.36 g, 2.5 mmol) and $K_2CO_3$ (0.41 g, 2.9 mmol) in dioxane (5 mL) and water (1 mL) was degassed and backfilled with nitrogen three times. The mixture was heated to 100° C. for 12 h. Then the mixture was cooled to room temperature, filtered and concentrated under reduced pressure to give a residue that was purified by silica gel chromatography (PE:EtOAc=5:1) to give the title compound.

Step 2: methyl 5-chloro-6-cyclopropyl-2-(4,4-difluoroazepan-1-yl)nicotinate To a solution of methyl 6-cyclopropyl-2-(4,4-difluoroazepan-1-yl)nicotinate (0.13 g, 0.42 mmol) in DMF (2.5 mL) was added NCS (0.11 g, 0.84 mmol). The mixture was stirred at 20° C. for 1 h, then heated to 30° C. for 12 h. The mixture was quenched with water and extracted with EtOAc. The combined organic layers were washed with brine, dried over anhydrous $Na_2SO_4$, filtered and concentrated under reduced pressure to give a residue that was purified by silica gel chromatography (ethyl acetate/PE=1/1, v/v) to give the title compound.

Step 3: 5-chloro-6-cyclopropyl-2-(4,4-difluoroazepan-1-yl)nicotinic acid A mixture of lithium hydroxide hydrate (79 mg, 1.9 mmol) and methyl 5-chloro-6-cyclopropyl-2-(4,4-difluoroazepan-1-yl)nicotinate (0.13 g, 0.38 mmol) in methanol (2.5 mL) and water (1 mL) was stirred at 50° C. for 12 h. The mixture was quenched with HCl (1M, 10 mL) and concentrated under reduced pressure to give the title compound.

Step 4: 5-chloro-6-cyclopropyl-2-(4,4-difluoroazepan-1-yl)nicotinamide To a solution of 5-chloro-6-cyclopropyl-2-(4,4-difluoroazepan-1-yl)nicotinic acid (0.11 g, 0.33 mmol) in DCM (5 mL) was added oxalyl dichloride (0.13 g, 1.0 mmol). The mixture was stirred at 30° C. for 1 h.

Then the mixture was concentrated under vacuum to give a residue that was dissolved in THF (2.0 mL) and treated with a solution of $NH_3 \cdot H_2O$ (0.5 mL) in THF (5.0 mL) at 30° C. The reaction mixture was stirred at 30° C. for 1 h, then washed with water and extracted with EtOAc. The combined organic layers were washed with brine, dried over $Na_2SO_4$, filtered and concentrated under reduced pressure to give a residue which was purified by silica gel chromatography (PE:EtOAc=2:1) to give the title compound.

Intermediate 33

2,5-dichloro-6-cyclobutyl-N-(2-sulfamoylpyridin-4-yl)nicotinamide

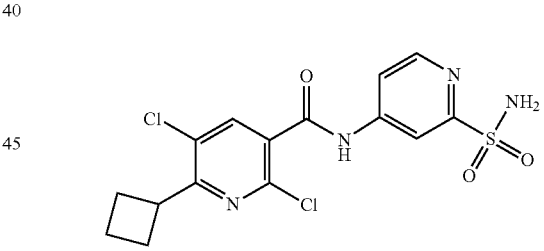

Step 1: methyl 2,5-dichloro-6-cyclobutylnicotinate To a mixture of sulfuric acid (0.78 mL, 15 mmol) and cyclobutanecarboxylic acid (2.8 mL, 29 mmol) in water (10 mL) was added methyl 2,5-dichloronicotinate (3.0 g, 15 mmol) followed by (nitrooxy)silver (0.74 g, 4.4 mmol). Then a solution of $(NH_4)_2S_2O_8$ (6.6 g, 29 mmol) in water (10 mL) was added. The reaction mixture was stirred at 20° C. for 13 h, then extracted with EtOAc, dried over $Na_2SO_4$, filtered and concentrated to give a residue that was purified by silica gel chromatography (petroleum ether:ethyl acetate=5:1) to give the title compound.

Step 2: 2,5-dichloro-6-cyclobutylnicotinic acid A mixture of methyl 2,5-dichloro-6-cyclobutylnicotinate (2.2 g, 8.5 mmol) and lithium hydroxide hydrate (1.4 g, 34 mmol) in MeOH (9 mL) and water (3 mL) was stirred at 20° C. for 3 h. Then the mixture was concentrated under reduced pressure. The resulting residue dissolved in water, acidified with TN HCl to pH ~3, and extracted with EtOAc. The organic layer was washed with brine, dried over anhydrous Na₂SO₄, filtered and concentrated to give the title compound.

Step 3: tert-butyl tert-butyl((4-(2,5-dichloro-6-cyclobutylnicotinamido)pyridin-2-yl)sulfonyl)-carbamate To a mixture of 2,5-dichloro-6-cyclobutylnicotinic acid (1.6 g crude) and tert-butyl ((4-aminopyridin-2-yl)sulfonyl)(tert-butyl)carbamate (2.1 g, 6.5 mmol) in pyridine (8 mL) at 0° C. was added dropwise POCl₃ (1.2 mL, 13 mmol). The mixture was stirred at 0° C. for 15 minutes, then quenched with water and extracted with EtOAc. The organic layer was washed with brine, dried over Na₂SO₄, filtered and concentrated under reduced pressure to give the title compound.

Step 4: 2,5-dichloro-6-cyclobutyl-N-(2-sulfamoylpyridin-4-yl)nicotinamide A mixture of tert-butyl tert-butyl((4-(2,5-dichloro-6-cyclobutylnicotinamido)pyridin-2-yl)sulfonyl)carbamate (2.5 g crude) and TFA (3 mL) in dichloromethane (9 mL) was stirred at 20° C. for 2 h. Then the mixture was concentrated under reduced pressure to give a residue that was purified by silica gel chromatography (petroleum ether:ethyl acetate=1:1) to give the title compound.

Intermediate 34

2-chloro-6-cyclobutyl-N-(2-sulfamoylpyridin-4-yl)nicotinamide

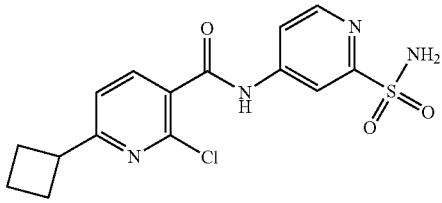 [SMILES: NS(=O)(=O)c1cc(NC(=O)c2ccc(C3CCC3)nc2Cl)ccn1]

Step 1: 2-chloro-6-cyclobutylnicotinonitrile To a solution of 2-chloronicotinonitrile (6.0 g, 43 mmol) and cyclobutanecarboxylic acid (8.7 g, 87 mmol) in water (20 mL) was added AgNO₃ (2.2 g, 13 mmol) and (NH₄)₂S₂O₈ (20 g, 87 mmol). The mixture was stirred at 20° C. for 60 minutes, then diluted with water and extracted with EtOAc. The organic layer was washed with brine, dried over anhydrous Na₂SO₄, filtered and concentrated to give a residue that was purified by silica gel chromatography (0-5% ethyl acetate/petroleum ether) to give the title compound.

Step 2: 2-chloro-6-cyclobutylnicotinamide To a mixture of 2-chloro-6-cyclobutylnicotinonitrile (0.60 g, 3.1 mmol) in DMSO (2 mL) was added K₂CO₃ (0.86 g, 6.2 mmol), followed by H₂O₂ (0.55 mL, 6.2 mmol). The mixture was stirred at 20° C. for 1 hour, then diluted with water and extracted with EtOAc. The organic phase was washed with brine, dried over anhydrous Na₂SO₄, filtered, and concentrated to give a residue that was purified by silica gel chromatography (petroleum ether/EtOAc=3:1) to give the title compound.

Step 3: N-(2-(N,N-bis(2,4-dimethoxybenzyl)sulfamoyl)pyridin-4-yl)-2-chloro-6-cyclobutylnicotinamide To a solution of 2-chloro-6-cyclobutylnicotinamide (0.40 g, 1.9 mmol) in dioxane (20 mL) was added Cs₂CO₃ (1.9 g, 5.7 mmol), 4-bromo-N,N-bis(2,4-dimethoxy-benzyl)pyridine-2-sulfonamide (1.1 g, 2.1 mmol) and XantPhos Pd G2 (0.17 g, 0.19 mmol). The mixture was degassed and backfilled with nitrogen three times, then stirred at 20° C. for 13 h. The mixture was then diluted with water and extracted with EtOAc. The organic layer was washed with brine, dried over anhydrous Na₂SO₄, filtered and concentrated to give a residue that was purified by silica gel chromatography (0-25% ethyl acetate/petroleum ether) to give the title compound.

Step 4: 2-chloro-6-cyclobutyl-N-(2-sulfamoylpyridin-4-yl)nicotinamide To a solution of N-(2-(N,N-bis(2,4-dimethoxybenzyl)sulfamoyl)pyridin-4-yl)-2-chloro-6-cyclobutylnicotinamide (0.67 g, 1.0 mmol) in dichloromethane (5 mL) was added TFA (5 mL). The mixture was stirred at 20° C. for 2 h. Then the mixture was concentrated under reduce pressure to give the title compound.

Intermediate 35 methyl 6-cyclobutyl-2-(4,4-difluoroazepan-1-yl)nicotinate

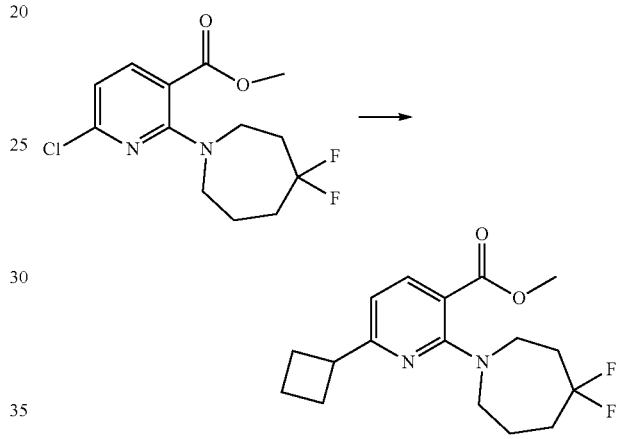

A mixture of nickel(II) iodide (61 mg, 0.20 mmol), pyridine-2,6-bis(carboximidamide) (32 mg, 0.20 mmol) and zinc (0.26 g, 3.9 mmol) were charged in a vial and the vial was evacuated and backfilled with nitrogen. DMA (4 mL) was added and the mixture was stirred for 5 minutes at 25° C. A solution of methyl 6-chloro-2-(4,4-difluoroazepan-1-yl)nicotinate (0.30 g, 0.98 mmol), bromocyclobutane (0.27 g, 2.0 mmol) and sodium iodide (0.30 g, 2.0 mmol) in DMA (4 mL) was added to the mixture. The mixture was heated to 100° C. for 13 h. Then the mixture was filtered and the filtrate was diluted with water and extracted with EtOAc. The combined organic layers were washed with brine, dried over anhydrous Na₂SO₄, filtered and concentrated under reduced pressure to give a residue that was purified by silica gel chromatography (PE:EtOAc=5:1) to give the title compound.

Intermediate 36 methyl 5-bromo-2-(4,4-difluoropiperidin-1-yl)-6-(trifluoromethyl)nicotinate

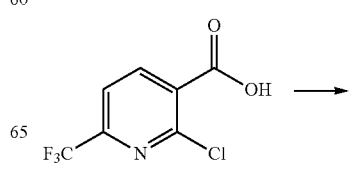

-continued

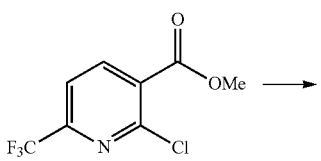

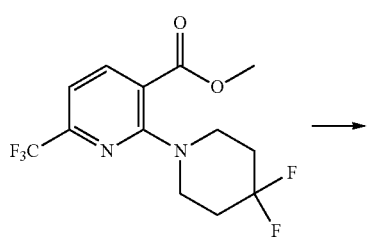

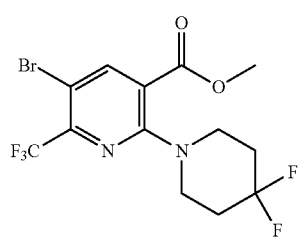

Step 1: methyl 2-chloro-6-(trifluoromethyl)nicotinate To a solution of 2-chloro-6-(trifluoromethyl)nicotinic acid (0.50 g, 2.2 mmol) in DCM (10 mL) and MeOH (1.1 mL) at 25° C. under an atmosphere of nitrogen was added dropwise (trimethylsilyl)diazomethane (1.8 mL, 3.6 mmol; 2 M in diethyether). The mixture was stirred at 25° C. for 1 h. Then the mixture was quenched with AcOH (76 µl, 1.3 mmol), and concentrated under reduced pressure. The resulting residue was dissolved in EtOAc. The organic layer was separated, washed with water, saturated NaHCO₃, dried over MgSO₄, filtered and concentrated to give a residue that was purified by silica gel chromatography (0-30% ethyl acetate:ethanol (3:1)/hexanes) to give the title compound.

Step 2: methyl 2-(4,4-difluoropiperidin-1-yl)-6-(trifluoromethyl)nicotinate To a solution of methyl 2-chloro-6-(trifluoromethyl)nicotinate (0.28 g, 1.2 mmol) in N-methyl-2-pyrrolidinone (12 mL) was added 4,4-difluoropiperidine (0.15 mL, 1.3 mmol) and K₂CO₃ (0.32 g, 2.3 mmol). The mixture was stirred at 60° C. for 4 h, then cooled to rt, diluted with water and extracted with EtOAc. The organic phase was washed with water, dried over MgSO₄, filtered and concentrated under reduced pressure to give a residue that was purified by silica gel chromatography (0-30% ethyl acetate:ethanol (3:1)/hexanes) to give the title compound.

Step 3: methyl 5-bromo-2-(4,4-difluoropiperidin-1-yl)-6-(trifluoromethyl)nicotinate To a solution of methyl 2-(4,4-difluoropiperidin-1-yl)-6-(trifluoromethyl)nicotinate (0.10 g, 0.31 mmol) in acetonitrile (1.5 mL) at 25° C. was added NBS (66 mg, 0.37 mmol). The mixture was stirred at 25° C. for 2 h, then quenched with water and extracted with EtOAc. The organic layer was separated, washed with saturated NaHCO₃, dried over MgSO₄, filtered and concentrated to give a residue that was purified by silica gel chromatography (0-20% ethyl acetate/hexanes) to give the title compound.

Intermediate 37

2-chloro-N-(2-sulfamoylpyridin-4-yl)-6-(trifluoromethyl)nicotinamide

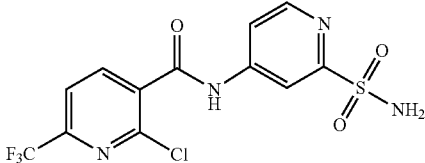 [SMILES: NS(=O)(=O)c1cc(NC(=O)c2ccc(C(F)(F)F)nc2Cl)ccn1]

Step 1: tert-butyl tert-butyl((4-(2-chloro-6-(trifluoromethyl)nicotinamido)pyridin-2-yl)sulfonyl)carbamate To a solution of 2-chloro-6-(trifluoromethyl)nicotinic acid (1.0 g, 4.4 mmol) and tert-butyl (4-aminopyridin-2-yl)sulfonyl (tert-butyl)carbamate (1.5 g, 4.4 mmol) in pyridine (10 mL) was added POCl₃ (1.2 mL, 13 mmol). The mixture was stirred at 0° C. 10 min, then quenched with water and extracted with EtOAc. The organic layer was separated, washed with saturated brine, dried over by Na₂SO₄, filtered and concentrated to give a residue that was purified by silica gel chromatography (0-30% petroleum ether/ethyl acetate) to give the title compound.

Step 2: 2-chloro-N-(2-sulfamoylpyridin-4-yl)-6-(trifluoromethyl)nicotinamide To a mixture of tert-butyl tert-butyl ((4-(2-chloro-6-(trifluoromethyl)nicotinamido)pyridin-2-yl) sulfonyl)-carbamate (1.0 g, 1.9 mmol) in dichloromethane (16 mL) was added TFA (8.0 mL, 104 mmol). The mixture was stirred at 20° C. for 1 h, then concentrated under reduced pressure to give the title compound.

Intermediate 38

1-(6-chloro-5-(trifluoromethyl)pyridin-2-yl)-4,4-difluoroazepane

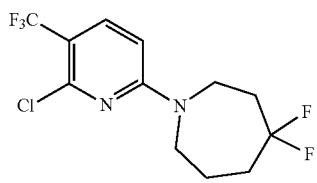 [SMILES: FC1(F)CCCN(c2ccc(C(F)(F)F)c(Cl)n2)CC1]

A mixture of 2,6-dichloro-3-(trifluoromethyl)pyridine (3.0 g, 14 mmol), DIPEA (7.3 mL, 42 mmol) and 4,4-difluoroazepane hydrochloride (2.9 g, 17 mmol) in DMF (10 mL) was stirred at 20° C. for 10 h. Then the mixture was diluted with water and extracted with EtOAc. The organic layer was washed with brine, dried over anhydrous Na₂SO₄, filtered and concentrated to give a residue that was purified by silica gel chromatography (0-25% ethyl acetate/PE) to give the title compound.

Intermediate 39 tert-butyl ((4-(5-bromo-2-(4,4-difluoropiperidin-1-yl)nicotinamido)pyridin-2-yl)sulfonyl) (tert-butyl) carbamate

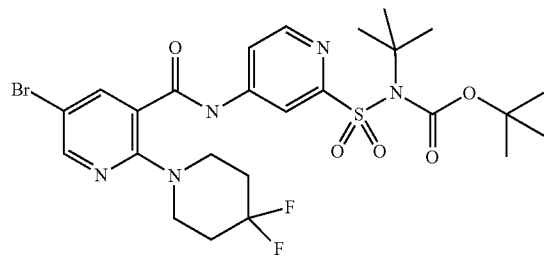

Step 1: 5-bromo-2-(4,4-difluoropiperidin-1-yl)pyridine-3-carboxylic acid To a mixture of 5-bromo-2-chloropyridine-3-carboxylic acid (8.0 g, 34 mmol) in NMP (80 mL) was added DIPEA (14 g, 0.11 mol) and 4,4-difluoropiperidine (4.5 g, 37 mmol) under nitrogen. The mixture was stirred at 120° C. for 16 hours, then cooled to 0° C., quenched with 6M HCl and extracted with EtOAc. The organic layer was separated, washed with brine and dried under reduced pressure to give a residue that was recrystallized from hexane to give the title compound.

Step 2: tert-butyl N-([4-[5-bromo-2-(4,4-difluoropiperidin-1-yl)pyridine-3-amido]pyridin-2-yl]sulfonyl)-N-tert-butylcarbamate To a solution of 5-bromo-2-(4,4-difluoropiperidin-1-yl)pyridine-3-carboxylic acid (9.0 g, 28 mmol) and tert-butyl (4-aminopyridin-2-yl)sulfonyl (tert-butyl)carbamate (9.2 g, 28 mmol) in pyridine (90 mL) was added POCl$_3$ (3.0 g, 20 mmol) at 0° C. The mixture was stirred at room temperature for 2 hours. Then the mixture was cooled to 0° C., quenched with water and extracted with EtOAc. The organic layer was separated, washed with saturated brine, and dried under reduced pressure to give a residue that was purified by silica gel chromatography (33% ethyl acetate/hexane) to give the title compound.

Intermediate 40

4,4-difluoroazepane hydrochloride

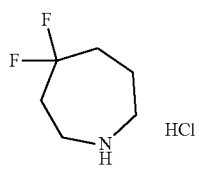

Step 1: tert-butyl 4,4-difluoroazepane-1-carboxylate To a solution of tert-butyl 4-oxoazepane-1-carboxylate (80 g, 0.38 mol) in DCM (0.56 L) at 0° C. was added dropwise a solution of diethylamino-sulfur trifluoride (240 g, 1.5 mol) in DCM (1.4 L). The mixture was stirred at 0° C. for 3.5 hours, then quenched into aqueous sodium hydrogen carbonate (saturated) and extracted with dichloromethane. The combined organic layers were dried over Na$_2$SO$_4$, filtered and concentrated under reduced pressure to give a residue that was purified by silica gel chromatography (6-50% EtOAc/hexanes) to give the title compound.

Step 2: 4,4-dichloroazepane hydrochloride A mixture of tert-butyl 4,4-difluoroazepane-1-carboxylate (105 g, 1.0 mol) and 4M HCl in dioxane (1.0 L, 4.0 mol) was stirred at room temperature for 1 hour. Then the mixture was concentrated under reduced pressure to give the title compound.

Intermediate 41

2,5-dichloro-4,6-dimethyl-N-(2-sulfamoylpyridin-4-yl)nicotinamide

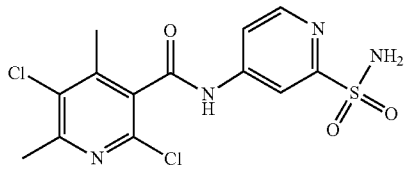 [SMILES: Cc1nc(Cl)c(C(=O)Nc2ccnc(S(N)(=O)=O)c2)c(C)c1Cl]

Step 1: 2,5-dichloro-4,6-dimethylnicotinamide To a mixture of 2,5-dichloro-4,6-dimethylnicotinonitrile (1.0 g, 5.0 mmol) and K$_2$CO$_3$ (1.4 g, 10 mmol) in DMSO (10 mL) was added H$_2$O$_2$ (0.87 mL, 10 mmol). The mixture was stirred at 20° C. for 2 h. Then the mixture was diluted with water and extracted with EtOAc. The combined organic layers were washed with brine, dried over anhydrous Na$_2$SO$_4$, filtered and concentrated to give a residue that was purified by silica gel chromatography (petroleum ether/ethyl acetate 1:2) to give the title compound.

Step 2: tert-butyl tert-butyl((4-(2,5-dichloro-4,6-dimethylnicotinamido)pyridin-2-yl)sulfonyl)carbamate To a solution of 2,5-dichloro-4,6-dimethylnicotinamide (1.0 g, 4.6 mmol) in 1,4-dioxane (15 mL) was added Cs$_2$CO$_3$ (3.0 g, 9.1 mmol), XantPhos-Pd-G2 (0.41 g, 0.46 mmol) and tert-butyl ((4-bromopyridin-2-yl)sulfonyl)(tert-butyl)carbamate (Intermediate 7, 2.0 g, 5.0 mmol). The reaction mixture was degassed and backfilled with nitrogen three times, then stirred at 100° C. for 13 h. The mixture was diluted with water, and extracted with EtOAc. The combined organic layers were washed with brine, dried over anhydrous Na$_2$SO$_4$, filtered and concentrated to give the title compound which was used in the next step without further purification.

Step 3: 2,5-dichloro-4,6-dimethyl-N-(2-sulfamoylpyridin-4-yl)nicotinamide A solution of tert-butyl tert-butyl((4-(2,5-dichloro-4,6-dimethylnicotinamido)pyridin-2-yl)sulfonyl)carbamate (1.9 g crude) in DCM (10 mL) and TFA (20 mL) was stirred at 20° C. for 2 h. The reaction mixture was concentrated under reduced pressure. The resulting residue was diluted with water and extracted with EtOAc. The combined organic layers were washed with brine, dried over anhydrous Na$_2$SO$_4$, filtered and concentrated under reduced pressure to give a residue that was purified by silica gel chromatography (petroleum ether/ethyl acetate 1:2) give the title compound.

EXAMPLES

Example 1

2-(4,4-difluoropiperidin-1-yl)-N-(6-sulfamoylpyrazin-2-yl)-5-(trifluoromethyl)nicotinamide

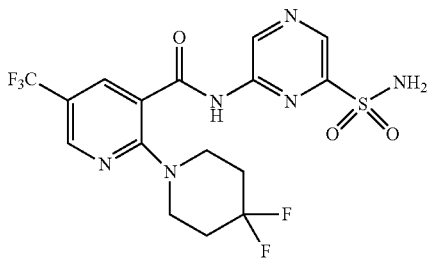 [SMILES: NS(=O)(=O)c1cncc(NC(=O)c2cc(C(F)(F)F)cnc2N2CCC(F)(F)CC2)n1]

Step 1: N-(6-(N,N-bis(2,4-dimethoxybenzyl)sulfamoyl)pyrazin-2-yl)-2-(4,4-difluoropiperidin-1-yl)-5-(trifluoromethyl)nicotinamide To a solution of 2-(4,4-difluoropiperidin-1-yl)-5-(trifluoromethyl)nicotinamide (Intermediate 20, 50 mg, 0.16 mmol) in 1,4-dioxane (1.5 mL) were added Cs$_2$CO$_3$ (110 mg, 0.32 mmol), 6-chloro-N,N-bis(2,4-dimethoxybenzyl)pyrazine-2-sulfonamide (120 mg, 0.243 mmol) and Brettphos-Pd-G3 (22 mg, 0.024 mmol). The mixture was stirred at 100° C. for 13 hours, then filtered, diluted with water and extracted with EtOAc. The combined organic layers were washed with brine, dried over Na$_2$SO$_4$, filtered and concentrated to give a residue which was purified by silica gel chromatography (PE/EtOAc=2:1) to give the title compound.

Step 2: 2-(4,4-difluoropiperidin-1-yl)-N-(6-sulfamoylpyrazin-2-yl)-5-(trifluoromethyl)-nicotinamide To a solution of N-(6-(N,N-bis(2,4-dimethoxybenzyl)sulfamoyl)pyrazin-2-yl)-2-(4,4-difluoropiperidin-1-yl)-5-(trifluoromethyl)nicotinamide (60 mg, 0.078 mmol) in DCM (3 mL) was added TFA (0.5 mL). The mixture was stirred at 28° C. for 2 hours. Then the mixture was concentrated under reduced pressure to give a residue that was purified by reverse phase chromatography (45-100% MeCN/water with 0.1% TFA, C18 column) to give the title compound. LRMS m/z (M+H): calculated 467.1, observed 466.9. $^1$H NMR δ (ppm) (400 MHz, CD$_3$OD): 9.71 (s, 1H), 8.90 (s, 1H), 8.59 (d, J=1.2 Hz, 1H), 8.18 (d, J=1.6 Hz, 1H), 3.67-3.70 (m, 4H), 2.04-2.13 (m, 4H).

Example 2

2-(4,4-difluoropiperidin-1-yl)-N-(4-hydroxypyrimidin-2-yl)-5-(trifluoromethyl)nicotinamide

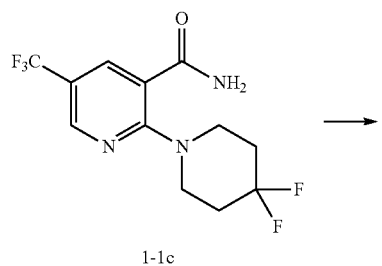

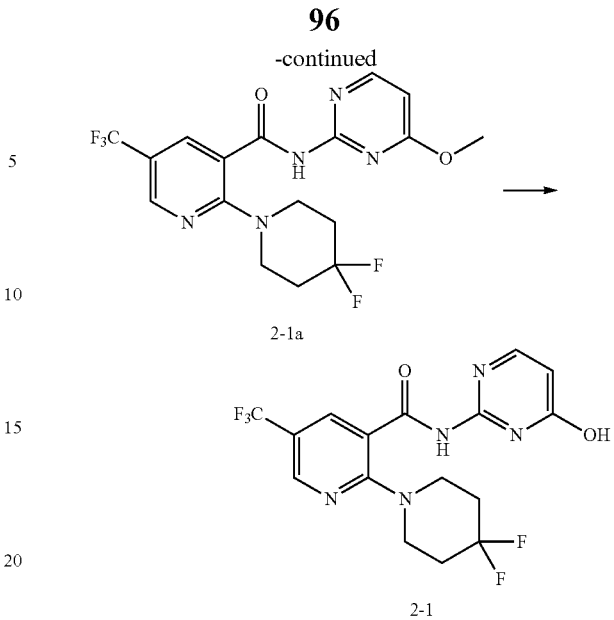

Step 1: 2-(4,4-difluoropiperidin-1-yl)-N-(4-methoxypyrimidin-2-yl)-5-(trifluoromethyl)-nicotinamide To a solution of 2-chloro-4-methoxypyrimidine (40 mg, 0.28 mmol) in dioxane (3 mL) were added Cs$_2$CO$_3$ (0.27 g, 0.83 mmol), 2-(4,4-difluoropiperidin-1-yl)-5-(trifluoromethyl)-nicotinamide (Intermediate 20, 94 mg, 0.30 mmol) and Brettphos Pd G3 (50 mg, 0.055 mmol). The mixture was stirred at 100° C. for 16 h under nitrogen. Then the mixture was purified by silica gel chromatography (petroleum ether:EtOAc=3:1) to give the title compound.

Step 2: 2-(4,4-difluoropiperidin-1-yl)-N-(4-hydroxypyrimidin-2-yl)-5-(trifluoromethyl)-nicotinamide To a solution of 2-(4,4-difluoropiperidin-1-yl)-N-(4-methoxypyrimidin-2-yl)-5-(trifluoromethyl)nicotinamide (60 mg, 0.14 mmol) in acetonitrile (1 mL) were added sodium iodide (86 mg, 0.57 mmol) and TMS-Cl (62 mg, 0.57 mmol) at 25° C. After 5 min, the mixture was heated at 50° C. for 3 hours. Then the mixture was purified by reverse phase chromatography to give the title compound. LRMS m/z (M+H): calculated 404.1, observed 404.2. $^1$H NMR δ (ppm) (400 MHz, CDCl$_3$): 8.71 (s, 1H), 8.45 (s, 1H), 7.75 (d, J=7.2 Hz, 1H), 6.31 (d, J=7.2 Hz, 1H), 3.52-3.60 (m, 4H), 2.15-2.29 (m, 4H).

Example 3

5-(2-(4,4-difluoropiperidin-1-yl)-5-(trifluoromethyl)nicotinamido)picolinic acid

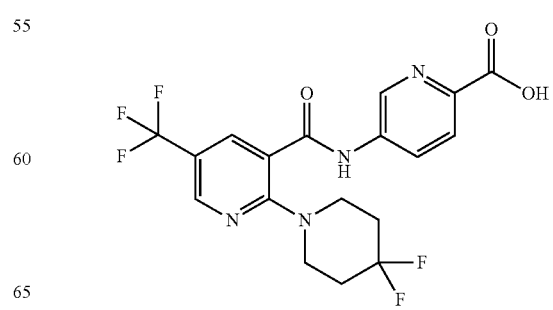

Brettphos Pd G3 (18 mg, 0.019 mmol) was added to a stirred mixture of 2-(4,4-difluoro-piperidin-1-yl)-5-(trifluoromethyl)nicotinamide (Intermediate 20, 40 mg, 0.13 mmol), Cs₂CO₃ (130 mg, 0.39 mmol), and methyl 5-bromopicolinate (33 mg, 0.15 mmol) in 1,4-dioxane (2 mL). The mixture was stirred at 100° C. for 18 h, then cooled to rt, treated with water and extracted with ethyl acetate. The combined organic layers were dried over Na₂SO₄, filtered and concentrated under reduced pressure to give a residue that was purified by reverse phase chromatography (40-100% AcCN/water with 0.1% TFA, C18 column) to give the title compound. LRMS m/z (M+H): calculated 431.1, observed 431.2. ¹H NMR δ (ppm) (400 MHz, CD₃OD): 9.10 (s, 1H), 8.56 (s, 1H), 8.49 (d, J=8.4 Hz, 1H), 8.28 (d, J=8.3 Hz, 1H), 8.13 (d, J=1.6 Hz, 1H), 3.59-3.84 (m, 4H), 1.84-2.23 (m, 4H).

Example 4

4-(2-(4,4-difluoropiperidin-1-yl)-5-(trifluoromethyl)nicotinamido)picolinic acid

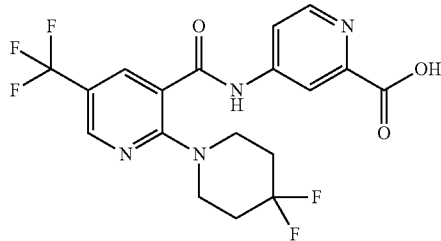 [SMILES: O=C(O)c1cc(NC(=O)c2cc(C(F)(F)F)cnc2N2CCC(F)(F)CC2)ccn1]

Brettphos Pd G3 (8.8 mg, 9.7 μmol) was added to a stirred mixture of 2-(4,4-difluoropiperidin-1-yl)-5-(trifluoromethyl)nicotinamide (Intermediate 20, 20 mg, 0.065 mmol), Cs₂CO₃ (63 mg, 0.19 mmol), and methyl 4-bromopicolinate (17 mg, 0.078 mmol) in 1,4-dioxane (2 mL). The mixture was stirred at 100° C. for 18 h, then cooled to rt, treated with water and extracted with ethyl acetate. The combined organic layers were dried over Na₂SO₄, filtered and concentrated to give a residue that was purified by reverse phase chromatography (40-100% AcCN/water with 0.1% TFA, C18 column) to give the title compound. LRMS m/z (M+H): calculated 431.1, observed 431.2. ¹H NMR δ (ppm) (400 MHz, CD₃OD): 8.64 (d, J=6.1 Hz, 1H), 8.60 (s, 2H), 8.31-8.37 (m, 1H), 8.18 (d, J=2.2 Hz, 1H), 3.63-3.75 (m, 4H), 1.96-2.15 (m, 4H).

Example 5

N-(6-cyanopyridin-3-yl)-2-(4,4-difluoropiperidin-1-yl)-5-(trifluoromethyl)nicotinamide

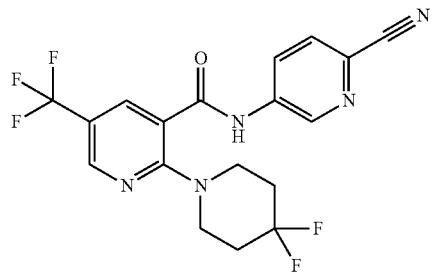 [SMILES: N#Cc1ccc(NC(=O)c2cc(C(F)(F)F)cnc2N2CCC(F)(F)CC2)cn1]

To a solution of 2-(4,4-difluoropiperidin-1-yl)-5-(trifluoromethyl)nicotinamide (Intermediate 20, 20 mg, 0.065 mmol) in 1,4-dioxane (2 mL) were added Cs₂CO₃ (63 mg, 0.19 mmol), 5-bromo-picolinonitrile (12 mg, 0.065 mmol) and Brettphos Pd G3 (8.8 mg, 9.7 μmol) with stirring at 25° C. The reaction mixture was stirred at 100° C. for 12 h, then cooled to rt, treated with water and extracted with ethyl acetate. The combined organic layers were dried over Na₂SO₄, filtered and concentrated to give a residue that was purified by reverse phase chromatography (AcCN/water with 0.1% TFA, C18 column) to give the title compound. LRMS m/z (M+H): calculated 412.1, observed 412.0. ¹H NMR δ (ppm) (400 MHz, CDCl₃): 10.23 (s, 1H), 8.80 (d, J=1.6 Hz, 1H), 8.69 (s, 1H), 8.63 (dd, J=8.8, 2.2 Hz, 1H), 8.49 (d, J=1.6 Hz, 1H), 7.82 (d, J=8.8 Hz, 1H), 6.30 (s, 2H), 3.51-3.67 (m, 4H), 2.09-2.28 (m, 4H).

Example 6

2-(azepan-1-yl)-N-(5-(methylsulfonyl)pyridin-3-yl)-5-(trifluoromethyl)nicotinamide

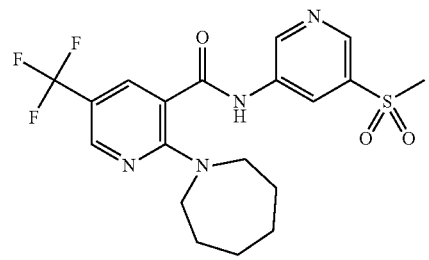 [SMILES: CS(=O)(=O)c1cncc(NC(=O)c2cc(C(F)(F)F)cnc2N2CCCCCC2)c1]

To a solution of 2-(azepan-1-yl)-5-(trifluoromethyl)nicotinamide (Intermediate 18, 30 mg, 0.10 mmol) in dioxane (1.5 mL) was added Cs₂CO₃ (68 mg, 0.21 mmol), 3-bromo-5-(methyl-sulfonyl)pyridine (25 mg) and Brettphos-Pd-G3 (9.5 mg, 10 μmol). The mixture was stirred at 100° C. for 13 hours. Then the mixture was filtered, diluted with DMF (3 mL), and purified by reverse phase chromatography (40-100% MeCN in water with 0.1% TFA, C18 column) to give the title compound. LRMS m/z (M+H): calculated 443.1, observed 443.0. ¹H NMR δ (ppm) (400 MHz, CD₃OD): 9.07 (d, J=2.4 Hz, 1H), 8.85 (d, J=2.0 Hz, 1H), 8.81 (t, J=2.0 Hz, 1H), 8.46 (d, J=1.2 Hz, 1H), 8.02 (d, J=2.4 Hz, 1H), 3.60-3.67 (m, 4H), 3.24 (s, 3H), 1.85 (br s, 4H), 1.55 (br s, 4H).

Example 7

2-(3-(hydroxymethyl)piperidin-1-yl)-N-(2-sulfamoylpyridin-4-yl)-5-(trifluoromethyl)nicotinamide

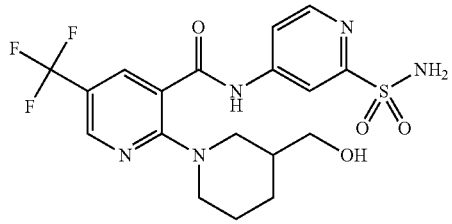 [SMILES: NS(=O)(=O)c1cc(NC(=O)c2cc(C(F)(F)F)cnc2N2CCCC(CO)C2)ccn1]

Step 1: 2-(3-(hydroxymethyl)piperidin-1-yl)-5-(trifluoromethyl)nicotinamide To a solution of 2-chloro-5-(trifluoromethyl)nicotinamide (Intermediate 19, 60 mg, 0.27 mmol) in DMA (1.0 mL) was added piperidin-3-ylmethanol (31 mg, 0.27 mmol) and DIPEA (0.14 mL, 0.80 mmol) dropwise with stirring at 25° C. The reaction mixture was stirred at 100° C. for 12 h, then treated with water and extracted with EtOAc. The combined organic layers were washed with brine, dried over $Na_2SO_4$, filtered and concentrated under reduced pressure to give a residue that was purified by silica gel chromatography (petroleum ether/ethyl acetate 1:2) to give the title compound.

Step 2: tert-butyl tert-butyl((4-(2-(3-(hydroxymethyl)piperidin-1-yl)-5-(trifluoromethyl)-nicotinamido)pyridin-2-yl)sulfonyl)carbamate To a solution of 2-(3-(hydroxymethyl)piperidin-1-yl)-5-(trifluoromethyl)nicotinamide (20 mg, 0.066 mmol) in 1,4-dioxane (1.0 mL) were added tert-butyl tert-butyl((4-chloropyridin-2-yl)sulfonyl)carbamate (23 mg, 0.066 mmol), cesium carbonate (21 mg, 0.066 mmol) and Brettphos Pd G3 (60 mg, 0.066 mmol) at 25° C. The reaction mixture was stirred at 100° C. for 12 h under a nitrogen atmosphere. The mixture was then treated with water and extracted with EtOAc. The combined organic layers were washed with brine, dried over $Na_2SO_4$, filtered and concentrated under reduced pressure to give the title compound.

Step 3: 2-(3-(hydroxymethyl)piperidin-1-yl)-N-(2-sulfamoylpyridin-4-yl)-5-(trifluoromethyl)-nicotinamide To a solution of tert-butyl tert-butyl((4-(2-(3-(hydroxymethyl)piperidin-1-yl)-5-(trifluoromethyl)nicotinamido)pyridin-2-yl)sulfonyl)carbamate (20 mg, 0.032 mmol) in DCM (2.0 mL) was added TFA (1.0 mL) dropwise with stirring at 25° C. The reaction mixture was stirred at 25° C. for 3 h. Then the mixture was concentrated under reduced pressure and purified by reversed phase chromatography (MeCN in water with 0.1% TFA, C18 column) to give the title compound. LRMS m/z (M+H): calculated 460.1; observed 460.2. $^1$H NMR δ (ppm) (400 MHz, $CDCl_3$): 10.77 (s, 1H), 8.56 (s, 1H), 8.54 (s, 1H), 8.40-8.44 (m, 1H), 8.02 (s, 1H), 7.98-7.99 (m, 1H), 5.10 (s, 2H), 3.63-3.66 (m, 2H), 3.56-3.57 (m, 2H), 2.91-2.98 (m, 2H), 1.84-1.88 (m, 2H), 1.15-1.21 (m, 2H), 0.76-0.77 (m, 1H).

Example 8

2-(azepan-1-yl)-N-(5-carbamoylpyridin-3-yl)-5-(trifluoromethyl)nicotinamide

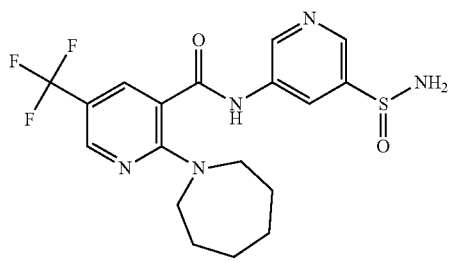 [SMILES: NS(=O)c1cncc(NC(=O)c2cc(C(F)(F)F)cnc2N2CCCCCC2)c1]

Step 1: 2-(azepan-1-yl)-N-(5-cyanopyridin-3-yl)-5-(trifluoromethyl)nicotinamide To a solution of 2-(azepan-1-yl)-5-(trifluoromethyl)nicotinamide (Intermediate 18, 45 mg, 0.16 mmol) in 1,4-dioxane (1.5 mL) were added $Cs_2CO_3$ (100 mg, 0.31 mmol), 5-bromonicotinonitrile (29 mg, 0.16 mmol) and Brettphos-Pd-G3 (14 mg, 0.016 mmol). The reaction was stirred at 100° C. for 13 hours, then diluted with water and extracted with EtOAc. The combined organic layers was washed with brine, dried over $Na_2SO_4$, filtered and concentrated to give a residue that was purified by silica gel chromatography (petroleum ether/EtOAc=3:1) to give the title compound.

Step 2: 2-(azepan-1-yl)-N-(5-carbamoylpyridin-3-yl)-5-(trifluoromethyl)nicotinamide To a solution of 2-(azepan-1-yl)-N-(5-cyanopyridin-3-yl)-5-(trifluoromethyl)nicotinamide (42 mg, 0.11 mmol) in DMSO (3.0 mL) was added $K_2CO_3$ (30 mg, 0.22 mmol). The mixture was stirred at 20° C. for 20 min, then warmed to 30° C. and hydrogen peroxide (1.0 mL, 0.11 mmol) was added dropwise. The mixture was stirred at 30° C. for 60 min. Then the mixture was filtered, treated with saturated $Na_2SO_3$ solution (1 mL), filtered, diluted with DMF (3 mL) and purified by reverse phase chromatography (30-100% MeCN in water with 0.1% TFA, C18 column) to give the title compound. LRMS m/z (M+H): calculated 408.2, observed 408.0. $^1$H NMR δ (ppm) (400 MHz, $CD_3OD$): 9.16 (d, J=2.4 Hz, 1H), 8.84 (d, J=2.0 Hz, 1H), 8.74 (d, J=2.0 Hz, 1H), 8.46 (d, J=1.6 Hz, 1H), 8.01 (d, J=1.6 Hz, 1H), 3.58-3.69 (m, 4H), 1.84 (br s, 4H), 1.54-1.56 (m, 4H).

Example 9

2-(4,4-difluoro-1-piperidyl)-6-methyl-N-(5-sulfamoyl-3-pyridyl)pyridine-3-carboxamide

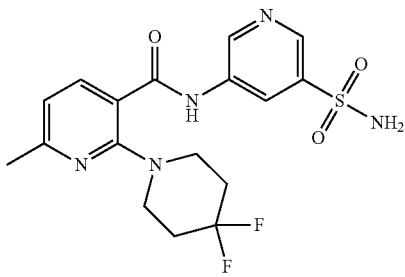 [SMILES: Cc1ccc(C(=O)Nc2cncc(S(N)(=O)=O)c2)c(N2CCC(F)(F)CC2)n1]

Step 1: N-(5-(N,N-bis(2,4-dimethoxybenzyl)sulfamoyl)pyridin-3-yl)-2-(4,4-difluoropiperidin-1-yl)-6-methylnicotinamide A mixture of $Cs_2CO_3$ (0.19 g, 0.59 mmol), Brettphos Pd G3 (18 mg, 0.020 mmol), 5-bromo-N,N-bis(2,4-dimethoxybenzyl)pyridine-3-sulfonamide (0.13 g, 0.24 mmol), 2-(4,4-difluoropiperidin-1-yl)-6-methylnicotinamide (Intermediate 25, 50 mg, 0.20 mmol) and dioxane (2 ml) at 20° C. was sparged with a stream of nitrogen for 2 min. The tube was sealed and heated to 100° C. for 10 h. Then the mixture was cooled to rt, quenched with water and extracted with EtOAc. The organic layer was washed with brine, dried over anhydrous $Na_2SO_4$, filtered and concentrated under reduced pressure to give a residue that was purified by silica gel chromatography (ethyl acetate/PE=1/1) to give the title compound.

Step 2: 2-(4,4-difluoropiperidin-1-yl)-6-methyl-N-(5-sulfamoylpyridin-3-yl)nicotinamide (9) To a solution of N-(5-(N,N-bis(2,4-dimethoxybenzyl)sulfamoyl)pyridin-3-yl)-2-(4,4-difluoro-piperidin-1-yl)-6-methylnicotinamide (50 mg, 0.070 mmol) in DCM (6 ml) was added TFA (0.027 ml, 0.35 mmol). The mixture was stirred at 20° C. for 2 h. Then the mixture was filtered and the filtrate was concentrated under reduced pressure to give a residue that was purified by reverse phase chromatography (30-100% MeCN in water with 0.1% TFA, C18 column) to give the title compound.

LRMS m/z (M+H): calculated 412.1, observed 412.1. ¹H NMR δ (ppm) (400 MHz, CD₃OD): 8.95 (br s, 1H), 8.82 (br d, J=10.96 Hz, 2H), 8.32 (d, J=2.63 Hz, 1H), 7.97 (d, J=2.63 Hz, 1H), 3.52 (br t, J=5.48 Hz, 4H), 1.98-2.11 (m, 4H).

with 0.1% TFA, C18 column) to give the title compound. LRMS m/z (M+H): calculated 446.1, observed 446.2. ¹H NMR δ (ppm) (400 MHz, CD₃OD): 8.76-8.95 (m, 3H), 6.90 (s, 1H), 3.44-3.62 (m, 4H), 2.33 (s, 3H), 1.72-2.06 (m, 4H).

TABLE 1

The compounds of Exmple 10 was prepared according to a synthetic procedure similar to the synthetic procedure for Example 9.

| Example | Compound | Name | Calc'd [M + H]⁺ | Observed [M + H]⁺ |
|---|---|---|---|---|
| 10 | 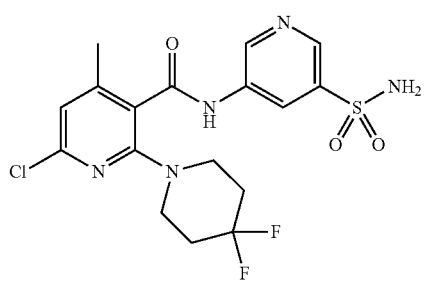 | 5-chloro-2-(4,4-difluoro-1-piperidyl)-N-(5-sulfamoyl-3-pyridyl)pyridine-3-carboxamide | 432.1 | 431.9 |

Example 11

6-chloro-2-(4,4-difluoropiperidin-1-yl)-4-methyl-N-(5-sulfamoylpyridin-3-yl)nicotinamide

Example 12

5,6-dicyclopropyl-2-(4,4-difluoropiperidin-1-yl)-N-(2-sulfamoylpyridin-4-yl)nicotinamide

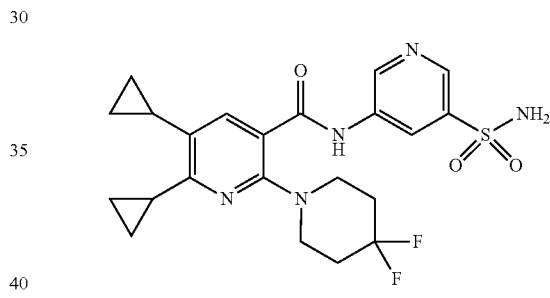

Step 1: N-(5-(N,N-bis(2,4-dimethoxybenzyl)sulfamoyl)pyridin-3-yl)-6-chloro-2-(4,4-difluoropiperidin-1-yl)-4-methylnicotinamide A mixture of tBu-Xphos Pd G3 (11 mg, 0.014 mmol), 6-chloro-2-(4,4-difluoropiperidin-1-yl)-4-methylnicotinamide (Intermediate 27, 40 mg, 0.14 mmol), sodium 2-methylpropan-2-olate (26 mg, 0.28 mmol), 5-bromo-N,N-bis(2,4-dimethoxybenzyl)pyridine-3-sulfonamide (0.11 g, 0.21 mmol), and THF (2.5 mL) at 20° C. was sparged with a stream of nitrogen for 1 min, then sealed and heated to 60° C. for 12 h. The mixture was quenched with water and extracted with EtOAc. The combined organic layers were washed with brine, dried over anhydrous Na₂SO₄, filtered and concentrated to give a residue that was purified by silica gel chromatography (petroleum ether: EtOAc=1:1) to give the title compound.

Step 2: 6-chloro-2-(4,4-difluoropiperidin-1-yl)-4-methyl-N-(5-sulfamoylpyridin-3-yl)-nicotinamide To a stirred solution of N-(5-(N,N-bis(2,4-dimethoxybenzyl)sulfamoyl)-pyridin-3-yl)-6-chloro-2-(4,4-difluoropiperidin-1-yl)-4-methylnicotinamide (50 mg, 0.067 mmol) in DCM (2 mL) was added TFA (1.0 mL, 13 mmol). The mixture was stirred at 20° C. for 1 h. Then the mixture was concentrated under reduced pressure to give a residue that was purified by reverse phase chromatography (35-100% MeCN in water Step 1: 5,6-dicyclopropyl-2-(4,4-difluoropiperidin-1-yl) nicotinamide To a stirred solution of 6-chloro-2-(4,4-difluoropiperidin-1-yl)-5-iodonicotinamide (Intermediate 30, 0.20 g, 0.50 mmol) in toluene (5.0 mL) and water (0.8 mL) was added potassium carbonate (0.21 g, 1.5 mmol), potassium cyclopropyltrifluoroborate (0.30 g, 2.0 mmol), Pd(PPh₃)₄ (80 mg, 0.069 mmol) at 15° C. under a nitrogen atmosphere. The mixture was stirred at 120° C. for 12 h, then cooled to room temperature and diluted with EtOAc. The organic layer was washed with brine, dried over anhydrous sodium sulfate, filtered and concentrated under reduced pressure to give a residue that was purified by silica gel chromatography (petroleum ether/EtOAc=1:1) to give the title compound.

Step 2: N-(2-(N,N-bis(2,4-dimethoxybenzyl)sulfamoyl)pyridin-4-yl)-5,6-dicyclopropyl-2-(4,4-difluoropiperidin-1-yl)nicotinamide A mixture of 5,6-dicyclopropyl-2-(4,4-difluoropiperidin-1-yl)nicotinamide (50 mg, 0.16 mmol), 4-bromo-N,N-bis(2,4-dimethoxybenzyl)pyridine-2-sulfonamide (125 mg, 0.23 mmol), sodium tert-butoxide (45 mg, 0.47 mmol), and tBuXphos-Pd-G3 (30 mg, 0.038 mmol) in THF (2 mL) was degassed and backfilled with nitrogen three times. The mixture was heated to 60° C. for 12 h, then diluted with EtOAc. The organic phase was dried over anhydrous sodium sulfate, filtered and concentrated under reduced pressure to give a residue that was purified by silica gel chromatography (petroleum ether/EtOAc=2:1) to give the title compound.

Step 3: 5,6-dicyclopropyl-2-(4,4-difluoropiperidin-1-yl)-N-(2-sulfamoylpyridin-4-yl)-nicotinamide A mixture of N-(2-(N,N-bis(2,4-dimethoxybenzyl)sulfamoyl)pyridin-4-yl)-5,6-dicyclopropyl-2-(4,4-difluoropiperidin-1-yl)nicotinamide (50 mg, 0.064 mmol) in CH$_2$Cl$_2$ (2 mL) and TFA (0.5 mL) was stirred at 20° C. for 4 h. Then the solvent was removed under reduced pressure to give a residue that was purified by silica gel chromatography (CH$_2$Cl$_2$/CH$_3$OH=20:1) to give the title compound. LRMS m/z (M+H): calculated 478.2, observed 478.1. $^1$H NMR δ (ppm) (400 MHz, CD$_3$OD): 8.56 (d, J=6.0 Hz, 1H), 8.43 (d, J=2.0 Hz, 1H), 7.84 (dd, J=5.6, 2.0 Hz, 1H), 7.65 (s, 1H), 3.34-3.39 (m, 4H), 2.51-2.70 (m, 1H), 1.96-2.10 (m, 5H), 0.99-1.13 (m, 6H), 0.59-0.69 (m, 2H).

Example 13

2-(4,4-difluoroazepan-1-yl)-N-(2-sulfamoylpyridin-4-yl)-5-(trifluoromethyl)nicotinamide

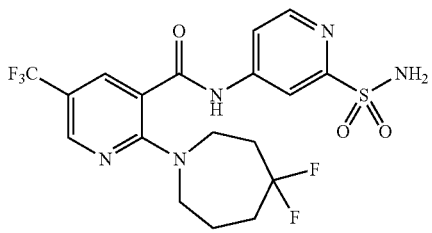 [SMILES: NS(=O)(=O)c1cc(NC(=O)c2cc(C(F)(F)F)cnc2N2CCCC(F)(F)CC2)ccn1]

Step 1: 2-(4,4-difluoroazepan-1-yl)-5-(trifluoromethyl)nicotinamide To a solution of 2-chloro-5-(trifluoromethyl)nicotinamide (Intermediate 19, 0.50 g, 2.2 mmol) in DMA (1 mL) was added 4,4-difluoroazepane hydrochloride (0.57 g, 3.3 mmol) and DIPEA (1.2 mL, 6.7 mmol) at 25° C. The mixture was stirred at 120° C. for 12 h, then diluted with EtOAc and washed with water. The organic layer was dried over anhydrous sodium sulfate, filtered and concentrated under reduced pressure to give a residue that was purified by silica gel chromatography (55% EtOAc/petroleum ether) to give the title compound.

Step 2: N-(2-(N,N-bis(2,4-dimethoxybenzyl)sulfamoyl)pyridin-4-yl)-2-(4,4-difluoroazepan-1-yl)-5-(trifluoromethyl)nicotinamide A mixture of tBuXphos Pd G3 (49 mg, 0.062 mmol), 2-(4,4-difluoroazepan-1-yl)-5-(trifluoromethyl)nicotinamide (200 mg, 0.62 mmol), sodium 2-methylpropan-2-olate (120 mg, 1.2 mmol), 4-bromo-N,N-bis(2,4-dimethoxybenzyl)pyridine-2-sulfonamide (400 mg, 0.74 mmol) and THF (2.5 mL) was sealed in a tube within a glove box under an inert atmosphere and heated to 60° C. for 12 h. Then the reaction mixture was quenched with water and extracted with EtOAc. The combined organic layers were washed with brine, dried over anhydrous Na$_2$SO$_4$, filtered and concentrated to give a residue that was purified by silica gel chromatography (petroleum ether in EtOAc) to give the title compound.

Step 3: 2-(4,4-difluoroazepan-1-yl)-N-(2-sulfamoylpyridin-4-yl)-5-(trifluoromethyl)nicotinamide To a mixture of N-(2-(N,N-bis(2,4-dimethoxybenzyl)sulfamoyl)pyridin-4-yl)-2-(4,4-difluoroazepan-1-yl)-5-(trifluoromethyl)nicotinamide (280 mg, 0.36 mmol) in DCM (2 mL) was added TFA (1.0 mL, 13 mmol) and stirred at 20° C. for 1 h. The mixture was then concentrated under reduced pressure to give a residue that was purified by reverse phase chromatography (33-100% MeCN in water with 0.1% TFA, C18 column) to give the title compound. LRMS m/z (M+H): calculated 480.1, observed 480.2. $^1$H NMR δ (ppm) (400 MHz, CD$_3$OD): 8.57 (d, J=5.6 Hz, 1H), 8.51 (s, 1H), 8.39 (d, J=1.6 Hz, 1H), 8.05 (d, J=1.6 Hz, 1H), 7.88 (dd, J=2.0, 5.2 Hz, 1H), 3.76-3.86 (m, 2H), 3.47 (s, 2H), 2.26-2.43 (m, 2H), 1.88-2.01 (m, 4H).

Example 14

5-cyclopropyl-2-(4,4-difluoropiperidin-1-yl)-6-methyl-N-(2-sulfamoylpyridin-4-yl)nicotinamide

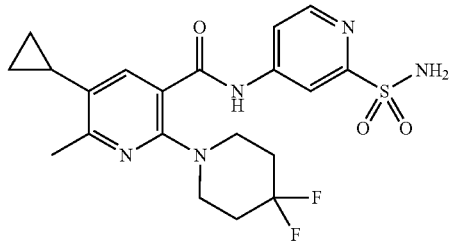 [SMILES: Cc1nc(N2CCC(F)(F)CC2)c(C(=O)Nc2ccnc(S(N)(=O)=O)c2)cc1C1CC1]

Step 1: N-(2-(N,N-bis(2,4-dimethoxybenzyl)sulfamoyl)pyridin-4-yl)-5-cyclopropyl-2-(4,4-difluoropiperidin-1-yl)-6-methylnicotinamide To a solution of N-(2-(N,N-bis(2,4-dimethoxybenzyl)sulfamoyl)pyridin-4-yl)-5-bromo-2-(4,4-difluoropiperidin-1-yl)-6-methylnicotinamide (Intermediate 26, 50 mg, 0.063 mmol) in toluene (2 mL) and water (0.4 mL) were added potassium cyclopropyltrifluoroborate (47 mg, 0.32 mmol), Pd(dppf)Cl$_2$ (9.2 mg, 0.013 mmol) and K$_2$CO$_3$ (18 mg, 0.13 mmol) and the mixture was degassed with nitrogen. The mixture was then stirred at 100° C. for 12 hours, diluted with water and extracted with EtOAc. The combined organic layers were dried over anhydrous Na$_2$SO$_4$, filtered and concentrated to give a residue that was purified by silica gel chromatography (petroleum ether/EtOAc=1:1) to give the title compound.

Step 2: 5-cyclopropyl-2-(4,4-difluoropiperidin-1-yl)-6-methyl-N-(2-sulfamoylpyridin-4-yl)nicotinamide To a solution of N-(2-(N,N-bis(2,4-dimethoxybenzyl)sulfamoyl)pyridin-4-yl)-5-cyclopropyl-2-(4,4-difluoropiperidin-1-yl)-6-methylnicotinamide (40 mg, 0.053 mmol) in DCM (2 mL) was added TFA (0.4 mL). The mixture was stirred at 11° C. for 2 hours. Then the mixture was filtered and purified by reverse phase chromatography (30-100% MeCN in water with 0.1% TFA, C18 column) to give the title compound. LRMS m/z (M+H): calculated 452.1, observed 452.1. $^1$H NMR δ (ppm) (400 MHz, CD$_3$OD): 8.59 (d, J=5.6 Hz, 1H), 8.42 (s, 1H), 7.85-7.87 (m, 1H), 7.76 (s, 1H), 3.46-3.48 (m, 4H), 2.66 (s, 3H), 2.04-2.13 (m, 4H), 1.88-1.96 (m, 1H), 1.01-1.04 (m, 2H), 0.68-0.71 (m, 2H).

Example 15

5-cyclobutyl-2-(4,4-difluoropiperidin-1-yl)-6-methyl-N-(2-sulfamoylpyridin-4-yl)nicotinamide

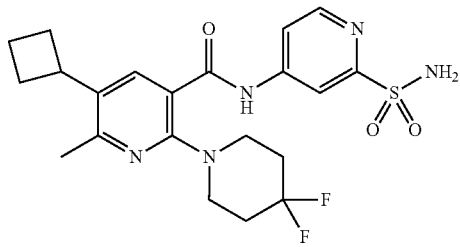 [SMILES: Cc1nc(N2CCC(F)(F)CC2)c(C(=O)Nc2ccnc(S(N)(=O)=O)c2)cc1C1CCC1]

Step 1: 5-bromo-2-(4,4-difluoropiperidin-1-yl)-6-methyl-N-(2-sulfamoylpyridin-4-yl)nicotinamide To a solution of N-(2-(N,N-bis(2,4-dimethoxybenzyl)sulfamoyl)pyridin-4-yl)-5-bromo-2-(4,4-difluoropiperidin-1-yl)-6-methylnicotinamide (Intermediate 26, 90 mg, 0.11 mmol) in DCM (3 mL) was added TFA (0.6 mL). The reaction mixture was stirred at 10° C. for 2 hours, then diluted with water and extracted with EtOAc. The combined organic layers were dried over anhydrous Na$_2$SO$_4$, filtered and concentrated to give a residue that was purified by silica gel chromatography (petroleum ether/EtOAc=1:1) to give the title compound.

Step 2: 5-cyclobutyl-2-(4,4-difluoropiperidin-1-yl)-6-methyl-N-(2-sulfamoylpyridin-4-yl)nicotinamide To a vial was added nickel(II) iodide (7.6 mg, 0.024 mmol), pyridine-2,6-bis(carboximidamide) (4.0 mg, 0.024 mmol) and zinc (32 mg, 0.49 mmol) and the vial was evacuated and backfilled with N$_2$. Then DMA (0.5 mL) was added and the mixture was stirred for 5 minutes at 12° C. A solution of 5-bromo-2-(4,4-difluoropiperidin-1-yl)-6-methyl-N-(2-sulfamoylpyridin-4-yl)nicotinamide (60 mg, 0.12 mmol), bromocyclobutane (33 mg, 0.24 mmol) and sodium iodide (37 mg, 0.24 mmol) in DMA (0.3 mL) was added to the vial. The mixture was stirred at 100° C. for 12 hours, then diluted with water and extracted with EtOAc. The combined organic layers were dried over anhydrous Na$_2$SO$_4$, filtered and concentrated to give a residue that was purified by reverse phase chromatography (30-100% MeCN in water with 0.1% TFA, C18 column) to give the title compound. LRMS m/z (M+H): calculated 466.2, observed 466.1. $^1$H NMR δ (ppm) (400 MHz, CD$_3$OD): 8.58 (d, J=4.8 Hz, 1H), 8.45 (d, J=2.0 Hz, 1H), 7.88 (d, J=6.4 Hz, 1H), 7.85-7.87 (m, 1H), 3.62-3.68 (m, 1H), 3.40-3.43 (m, 4H), 2.43 (s, 3H), 2.39-2.41 (m, 2H), 2.05-2.11 (m, 7H), 1.89-1.91 (m, 1H).

Example 16

5-(cyclopropylethynyl)-2-(4,4-difluoropiperidin-1-yl)-6-methyl-N-(2-sulfamoylpyridin-4-yl)nicotinamide

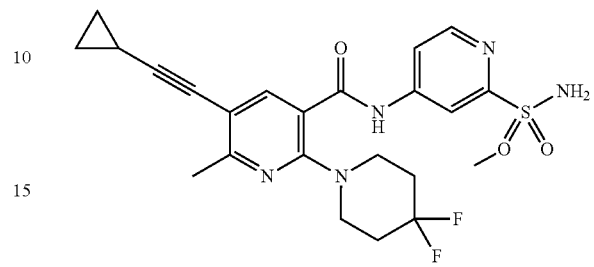

Step 1: N-(2-(N,N-bis(2,4-dimethoxybenzyl)sulfamoyl)pyridin-4-yl)-5-(cyclopropylethynyl)-2-(4,4-difluoropiperidin-1-yl)-6-methylnicotinamide A solution of N-(2-(N,N-bis(2,4-dimethoxy-benzyl)sulfamoyl)pyridin-4-yl)-5-bromo-2-(4,4-difluoropiperidin-1-yl)-6-methylnicotinamide (Intermediate 26, 80 mg, 0.10 mmol) in DMF (1 mL) under an atmosphere of nitrogen was added to a mixture of ethynylcyclopropane (6.7 mg, 0.10 mmol), copper(I) iodide (19 mg, 0.10 mmol), Pd(PPh$_3$)$_2$Cl$_2$ (7.1 mg, 10 μmol) and triethylamine (100 mg, 1.0 mmol). The mixture was heated to 100° C. for 13 hours, then diluted with water and extracted with EtOAc. The combined organic layers were dried over anhydrous Na$_2$SO$_4$, filtered and concentrated to give a residue that was purified by silica gel chromatography (petroleum ether/EtOAc=1:1) to give the title compound.

Step 2: 5-(cyclopropylethynyl)-2-(4,4-difluoropiperidin-1-yl)-6-methyl-N-(2-sulfamoylpyridin-4-yl)nicotinamide To a solution of N-(2-(N,N-bis(2,4-dimethoxybenzyl)sulfamoyl)pyridin-4-yl)-5-(cyclopropylethynyl)-2-(4,4-difluoropiperidin-1-yl)-6-methylnicotinamide (70 mg, 0.050 mmol) in DCM (2 mL) was added TFA (0.4 mL). The mixture was stirred at 18° C. for 2 hours. Then the mixture was filtered to give a residue that was purified by reverse phase chromatography (30-100% MeCN in water with 0.1% TFA, C18 column) to give the title compound. LRMS m/z (M+H): calculated 476.1, observed 476.0. $^1$H NMR δ (ppm) (400 MHz, CD$_3$OD): 8.57 (d, J=5.6 Hz, 1H), 8.42 (d, J=2.0 Hz, 1H), 7.84-7.86 (m, 1H), 7.80 (s, 1H), 3.49-3.52 (m, 4H), 2.53 (s, 3H), 1.97-2.06 (m, 4H), 1.51-1.53 (m, 1H), 0.90-0.92 (m, 2H), 0.74-0.77 (m, 2H).

Example 17

2-(4,4-difluoroazepan-1-yl)-6-methyl-N-(2-sulfamoylpyridin-4-yl)nicotinamide

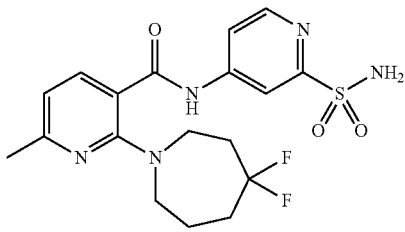 [SMILES: Cc1ccc(C(=O)Nc2ccnc(S(N)(=O)=O)c2)c(N2CCCC(F)(F)CC2)n1]

Step 1: 2-(4,4-difluoroazepan-1-yl)-6-methylnicotinamide To a stirred mixture of 2-chloro-6-methylnicotinamide (Intermediate 24, 0.50 g, 2.9 mmol) and 4,4-difluoroazepane hydrochloride (0.60 g, 3.5 mmol) was added DIPEA (1.5 mL, 8.8 mmol). The mixture was stirred at 160° C. for 3 h. Then the mixture was cooled to rt, diluted in water and extracted with ethyl acetate. The combined organic layers were washed with brine, dried over MgSO$_4$, filtered and concentrated under reduced pressure to give a residue, that was purified by flash silica gel chromatography (0-60% ethyl acetate/petroleum ether) to give the title compound.

Step 2: tert-butyl tert-butyl((4-(2-(4,4-difluoroazepan-1-yl)-6-methylnicotinamido)pyridin-2-yl)sulfonyl)carbamate A mixture of t-Bu Xphos-Pd-G3 (0.12 g, 0.15 mmol), sodium 2-methylpropan-2-olate (0.29 g, 3.0 mmol), 2-(4,4-difluoroazepan-1-yl)-6-methylnicotinamide (0.40 g, 1.5 mmol), tert-butyl (4-bromopyridin-2-yl)sulfonyl(tert-butyl)carbamate (0.62 g, 1.8 mmol) under an atmosphere of nitrogen was suspended in THF (15 mL). The mixture was stirred at 80° C. for 10 h, then cooled to rt, diluted with water and extracted with EtOAc. The combined organic layers were washed with brine, dried over MgSO$_4$, filtered and concentrated under reduced pressure to give a residue, that was purified by silica gel chromatography (petroleum ether: EtOAc=3:1) to give the title compound.

Step 3: 2-(4,4-difluoroazepan-1-yl)-6-methyl-N-(2-sulfamoylpyridin-4-yl)nicotinamide To a stirred mixture of tert-butyl tert-butyl((4-(2-(4,4-difluoroazepan-1-yl)-6-methylnicotinamido)-pyridin-2-yl)sulfonyl)carbamate (0.45, 0.77 mmol, 16-1b) in DCM (5 mL) was added TFA (2.5 mL, 32 mmol) dropwise at room temperature. The mixture was stirred at rt for 1 h. Then the mixture was concentrated under reduced pressure to give a residue, that was purified by reverse phase chromatography (18-100% MeCN in water with 0.1% TFA, C18 column) to give the title compound. LRMS m/z (M+H): calculated 426.1, observed 426.2. $^1$H NMR δ (ppm) (400 MHz, CD$_3$OD): 8.56 (d, J=6.4 Hz, 1H), 8.38 (s, 1H), 7.84-7.88 (m, 2H), 6.78 (d, J=8.0 Hz, 1H), 3.72-3.74 (m, 2H), 3.49-3.51 (m, 2H), 2.50 (s, 3H), 2.34-2.40 (m, 2H), 1.93-2.01 (m, 4H).

Example 18

6-(cyclopropylmethyl)-2-(4,4-difluoroazepan-1-yl)-N-(2-sulfamoylpyridin-4-yl)nicotinamide

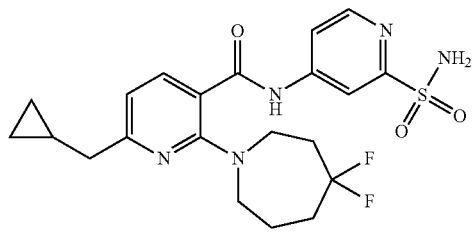 [SMILES: NS(=O)(=O)c1cc(NC(=O)c2ccc(CC3CC3)nc2N2CCCC(F)(F)CC2)ccn1]

Step 1: 6-chloro-2-(4,4-difluoroazepan-1-yl)nicotinamide To a solution of 2,6-dichloronicotinamide (Intermediate 28, 1.0 g, 5.2 mmol) in NMP (10 mL) were added 4,4-difluoroazepane hydrochloride (0.99 g, 5.8 mmol) and DIPEA (2.7 mL, 16 mmol). The mixture was stirred at 130° C. for 2 hours, then diluted with water and extracted with ethyl acetate. The combined organic layers were washed with brine, dried over anhydrous Na$_2$SO$_4$, filtered and concentrated to give a residue that was purified by silica gel chromatography (15% EtOAc) to give the title compound.

Step 2: 6-(cyclopropylmethyl)-2-(4,4-difluoroazepan-1-yl)nicotinamide To a solution of 6-chloro-2-(4,4-difluoroazepan-1-yl)nicotinamide (0.10 g, 0.34 mmol) in toluene (1.5 mL) was added Cs$_2$CO$_3$ (0.34 g, 1.0 mmol), potassium cyclopropylmethyltrifluoroborate (84 mg, 0.52 mmol) and DTBPF-Pd-G3 (61 mg, 0.069 mmol). The mixture was stirred at 100° C. for 10 hours under an atmosphere of nitrogen. Then the mixture was diluted with water and extracted with EtOAc. The combined organic layers were washed with brine, dried over Na$_2$SO$_4$, filtered and concentrated to give a residue that was purified by silica gel chromatography (petroleum ether/ethyl acetate=1/2) to give the title compound.

Step 3: N-(2-(N,N-bis(2,4-dimethoxybenzyl)sulfamoyl)pyridin-4-yl)-6-(cyclopropylmethyl)-2-(4,4-difluoroazepan-1-yl)nicotinamide To a solution of 6-(cyclopropylmethyl)-2-(4,4-difluoroazepan-1-yl)nicotinamide (15 mg, 0.048 mmol) in dioxane (1.5 mL) was added Cs$_2$CO$_3$ (47 mg, 0.14 mmol), 4-bromo-N,N-bis(2,4-dimethoxybenzyl)pyridine-2-sulfonamide (39 mg, 0.073 mmol) and Xantphos-Pd-G2 (4.3 mg, 4.8 μmol). The reaction mixture was degassed and backfilled with nitrogen three times. The mixture was stirred at 100° C. for 13 h, then diluted with water and extracted with EtOAc. The combined organic layers were washed with brine, dried over anhydrous Na$_2$SO$_4$, filtered and concentrated under reduced pressure to give the title compound.

Step 5: 6-(cyclopropylmethyl)-2-(4,4-difluoroazepan-1-yl)-N-(2-sulfamoylpyridin-4-yl)nicotinamide (18) A solution of N-(2-(N,N-bis(2,4-dimethoxybenzyl)sulfamoyl)pyridin-4-yl)-6-(cyclopropylmethyl)-2-(4,4-difluoroazepan-1-yl)nicotinamide (25 mg, crude) in dichloromethane (3 mL) and TFA (1 mL) was stirred at 20° C. for 2 h. Then the mixture was concentrated under reduced pressure and purified by reverse phase chromatography (39-100% MeCN in water with 0.1% 10 mM NH$_4$CO$_3$, C18 column) to give the title compound. LRMS m/z (M+H): calculated 466.2, observed 466.2. $^1$H NMR δ (ppm) (400 MHz, CD$_3$OD): 8.56 (d, J=5.6 Hz, 1H), 8.39 (d, J=2.0 Hz, 1H), 7.85-7.87 (m, 1H), 7.83 (d, J=8.0 Hz, 1H), 6.82 (d, J=8.0 Hz, 1H), 3.70-3.79 (m, 2H), 3.47 (t, J=6.0 Hz, 2H), 2.63 (d, J=7.2 Hz, 2H), 2.32-2.41 (m, 2H), 1.88-2.08 (m, 4H), 1.04-1.19 (m, 1H), 0.47-0.61 (m, 2H), 0.18-0.31 (m, 2H).

Example 19

2-(4,4-difluoroazepan-1-yl)-5,6-dimethyl-N-(2-sulfamoylpyridin-4-yl)nicotinamide

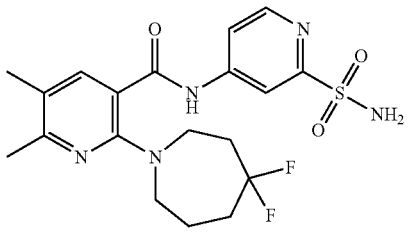 [SMILES: Cc1cc(C(=O)Nc2ccnc(S(N)(=O)=O)c2)c(N2CCCC(F)(F)CC2)nc1C]

Step 1: 2-chloro-5,6-dimethylnicotinoyl chloride 2-hydroxy-5,6-dimethylnicotinic acid (1.0 g, 6.0 mmol) was added to POCl$_3$ (5.0 mL, 54 mmol) slowly. The mixture was stirred for 30 min at 20° C., and stirred at 100° C. for 10 hours. Then the mixture was concentrated under reduced pressure to give the title compound.

Step 2: 2-chloro-5,6-dimethylnicotinamide To a solution of 2-chloro-5,6-dimethylnicotinoyl chloride (1.2 g, 5.9 mmol) in dichloromethane (5 mL) was added $NH_3 \cdot H_2O$ (5.0 mL, 36 mmol). The mixture was stirred at 20° C. for 1 h, then diluted with water and extracted with EtOAc. The combined organic layers were washed with brine, dried over $Na_2SO_4$, filtered and concentrated to give the title compound.

Step 3: 2-(4,4-difluoroazepan-1-yl)-5,6-dimethylnicotinamide To a solution of 2-chloro-5,6-dimethylnicotinamide (0.40 g, 2.2 mmol) in NMP (5 mL) were added 4,4-difluoroazepane hydrochloride (0.56 g, 3.2 mmol) and DIPEA (1.1 mL, 6.5 mmol). The mixture was stirred at 200° C. for 0.5 hours under microwave irradiation. Then the mixture was diluted with water and extracted with EtOAc. The combined organic layers were washed with brine, dried over anhydrous $Na_2SO_4$, filtered and concentrated to give a residue that was purified by silica gel chromatography (dichloromethane/MeOH=20/1) to give the title compound.

Step 4: N-(2-(N,N-bis(2,4-dimethoxybenzyl)sulfamoyl) pyridin-4-yl)-2-(4,4-difluoroazepan-1-yl)-5,6-dimethylnicotinamide To a solution of 2-(4,4-difluoroazepan-1-yl)-5,6-dimethylnicotinamide (0.26 g, 0.92 mmol) in dioxane (4 mL) were added $Cs_2CO_3$ (0.90 g, 2.7 mmol), XantPhos Pd G2 (82 mg, 0.092 mmol) and 4-bromo-N,N-bis(2,4-dimethoxybenzyl)-pyridine-2-sulfonamide (0.59 g, 1.1 mmol). The mixture was degassed and backfilled with nitrogen three times. Then the mixture was stirred at 100° C. for 13 h, and concentrated under reduced pressure to give the title compound.

Step 5: 2-(4,4-difluoroazepan-1-yl)-5,6-dimethyl-N-(2-sulfamoylpyridin-4-yl)nicotinamide To a solution of N-(2-(N,N-bis(2,4-dimethoxybenzyl)sulfamoyl)pyridin-4-yl)-2-(4,4-difluoroazepan-1-yl)-5,6-dimethylnicotinamide (0.65 g crude) in dichloromethane (3 mL) was added TFA (3 mL). The mixture was stirred at 20° C. for 2 h. The mixture was concentrated under reduced pressure and purified by reverse phase chromatography (23-100% MeCN in water with 0.1% TFA, C18 column) to give the title compound. LRMS m/z (M+H): calculated 440.2, observed 440.2. $^1$H NMR δ (ppm) (400 MHz, $CD_3OD$): 8.54 (d, J=5.6 Hz, 1H), 8.39 (d, J=2.0 Hz, 1H), 7.83-7.85 (m, 1H), 7.55 (s, 1H), 3.62-3.70 (m, 2H), 3.34-3.41 (m, 2H), 2.40 (s, 3H), 2.27-2.39 (m, 2H), 2.22 (s, 3H), 1.81-2.07 (m, 4H).

Example 20

5-cyclopropyl-2-(4,4-difluoropiperidin-1-yl)-N-(2-sulfamoylpyridin-4-yl)-6-(2,2,2-trifluoroethoxy) nicotinamide

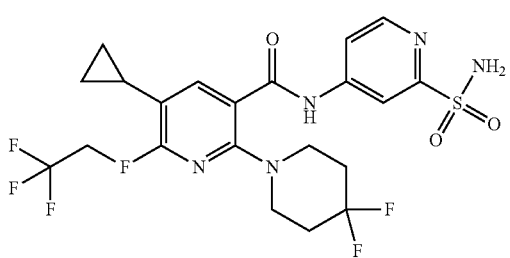

Step 1: 6-chloro-5-cyclopropyl-2-(4,4-difluoropiperidin-1-yl)nicotinamide To a stirred solution of 6-chloro-2-(4,4-difluoropiperidin-1-yl)-5-iodonicotinamide (Intermediate 30, 0.70 g, 1.7 mmol) in toluene (10 mL) and water (1.0 mL) were added potassium cyclopropyltrifluoroborate (0.52 g, 3.5 mmol), potassium carbonate (0.72 g, 5.2 mmol) and $Pd(PPh_3)_4$ (0.20 g, 0.17 mmol) under a nitrogen atmosphere. The mixture was stirred at 110° C. for 12 h, then cooled to room temperature and diluted with EtOAc. The organic layer was washed with brine, dried over anhydrous sodium sulfate, filtered and concentrated under reduced pressure to give a residue that was purified by silica gel chromatography (petroleum ether/ethyl acetate=1:1) to give the title compound.

Step 2: 5-cyclopropyl-2-(4,4-difluoropiperidin-1-yl)-6-(2,2,2-trifluoroethoxy)nicotinamide To a stirred solution of 2,2,2-trifluoroethanol (0.32 g, 3.2 mmol) in DMF (3 mL) was added $Cs_2CO_3$ (0.62 g, 1.9 mmol) at 0° C. The mixture was stirred at 0° C. for 10 min, then 6-chloro-5-cyclopropyl-2-(4,4-difluoropiperidin-1-yl)nicotinamide (0.20 g, 0.63 mmol) was added. The reaction was stirred at 100° C. for 12 h. Then the mixture was cooled to room temperature, filtered and the filtrate was purified by reverse phase chromatography (53-100% MeCN in water with 0.1% TFA, C18 column) to give the title compound.

Step 3: N-(2-(N,N-bis(2,4-dimethoxybenzyl)sulfamoyl) pyridin-4-yl)-5-cyclopropyl-2-(4,4-difluoropiperidin-1-yl)-6-(2,2,2-trifluoroethoxy)nicotinamide A mixture of 5-cyclopropyl-2-(4,4-difluoropiperidin-1-yl)-6-(2,2,2-trifluoroethoxy)nicotinamide (50 mg, 0.13 mmol), 4-bromo-N,N-bis(2,4-dimethoxybenzyl)pyridine-2-sulfonamide (78 mg, 0.14 mmol), $Cs_2CO_3$ (0.13 g, 0.39 mmol), and XantPhos Pd G2 (12 mg, 0.014 mmol) in dioxane (1.2 mL) was degassed and backfilled with nitrogen three times. The mixture was heated to 100° C. for 12 h, then cooled to room temperature and diluted with EtOAc. The organic layer was washed with brine, dried over anhydrous sodium sulfate, filtered and concentrated under reduced pressure to give the title compound.

Step 4: 5-cyclopropyl-2-(4,4-difluoropiperidin-1-yl)-N-(2-sulfamoylpyridin-4-yl)-6-(2,2,2-trifluoroethoxy)nicotinamide (20) To a stirred solution of N-(2-(N,N-bis(2,4-dimethoxy-benzyl)sulfamoyl)pyridin-4-yl)-5-cyclopropyl-2-(4,4-difluoropiperidin-1-yl)-6-(2,2,2-trifluoroethoxy) nicotinamide (110 mg crude) in dichloromethane (2 mL) was added TFA (0.5 mL). The mixture was stirred at 20° C. for 2 h. Then the mixture was concentrated under reduced pressure to give a residue that was purified by reverse phase chromatography (55-100% MeCN in water with 0.1% TFA, C18 column) to give the title compound. LRMS m/z (M+H): calculated 536.1, observed 536.2. $^1$H NMR δ (ppm) (400 MHz, $CD_3OD$): 8.56 (d, J=5.6 Hz, 1H), 8.42 (d, J=1.6 Hz, 1H), 7.84 (dd, J=5.6, 1.6 Hz, 1H), 7.60 (s, 1H), 4.95 (q, J=8.8 Hz, 2H), 3.44 (t, J=5.6 Hz, 4H), 1.86-2.20 (m, 5H), 0.89-0.97 (m, 2H), 0.64-0.73 (m, 2H).

Example 21

5-chloro-6-cyclopropyl-2-(4,4-difluoroazepan-1-yl)-N-(2-sulfamoylpyridin-4-yl)nicotinamide

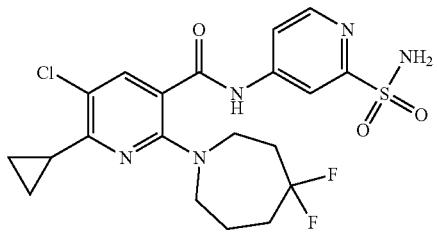 [SMILES: NS(=O)(=O)c1cc(NC(=O)c2cc(Cl)c(C3CC3)nc2N2CCCC(F)(F)CC2)ccn1]

Step 1: N-(2-(N,N-bis(2,4-dimethoxybenzyl)sulfamoyl)pyridin-4-yl)-5-chloro-6-cyclopropyl-2-(4,4-difluoroazepan-1-yl)nicotinamide A mixture of 5-chloro-6-cyclopropyl-2-(4,4-difluoroazepan-1-yl)nicotinamide (Intermediate 32, 12 mg, 0.036 mmol), 4-bromo-N,N-bis(2,4-dimethoxybenzyl)pyridine-2-sulfonamide (29 mg, 0.055 mmol), $Cs_2CO_3$ (36 mg, 0.11 mmol), Ruphos Pd G3 (6.1 mg, 7.3 μmol) and dioxane (1.5 mL) was degassed and backfilled with nitrogen three times. The mixture was stirred at 70° C. for 2.5 h, then diluted with water and extracted with EtOAc. The combined organic layers were washed with brine, dried over anhydrous $Na_2SO_4$, filtered and concentrated under reduced pressure to give a residue that was purified by silica gel chromatography (petroleum ether:EtOAc=2:1) to give the title compound.

Step 2: 5-chloro-6-cyclopropyl-2-(4,4-difluoroazepan-1-yl)-N-(2-sulfamoylpyridin-4-yl)nicotinamide (21) To a solution of N-(2-(N,N-bis(2,4-dimethoxybenzyl)sulfamoyl)pyridin-4-yl)-5-chloro-6-cyclopropyl-2-(4,4-difluoroazepan-1-yl)nicotinamide (15 mg, 0.019 mmol) in DCM (2 mL) was added TFA (0.4 mL). The mixture was stirred at 20° C. for 20 min. Then the mixture was concentrated under reduced pressure to give a residue that was purified by reverse phase chromatography (43-100% MeCN in water with 0.1% TFA, C18 column) to give the title compound. LRMS m/z (M+H): calculated 486.1, observed 486.0. $^1$H NMR δ (ppm) (400 MHz, $CD_3OD$): 8.55-8.58 (m, 1H), 8.39 (s, 1H), 7.86-7.87 (m, 1H), 7.76 (s, 1H), 3.65-3.67 (m, 2H), 3.38-3.41 (m, 2H), 2.31-2.52 (m, 1H), 2.28-2.32 (m, 2H), 1.91-1.97 (m, 4H), 1.06-1.10 (m, 4H).

Example 22

6-cyclopropyl-2-(4,4-difluoroazepan-1-yl)-N-(2-sulfamoylpyridin-4-yl)nicotinamide

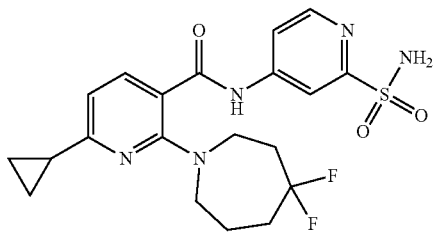 [SMILES: NS(=O)(=O)c1cc(NC(=O)c2ccc(C3CC3)nc2N2CCCC(F)(F)CC2)ccn1]

Step 1: N-(2-(N,N-bis(2,4-dimethoxybenzyl)sulfamoyl)pyridin-4-yl)-6-cyclopropyl-2-(4,4-difluoroazepan-1-yl)nicotinamide A mixture of 5-chloro-6-cyclopropyl-2-(4,4-difluoroazepan-1-yl)nicotinamide (Intermediate 32, 12 mg, 0.036 mmol), 4-bromo-N,N-bis(2,4-dimethoxy-benzyl)pyridine-2-sulfonamide (29 mg, 0.055 mmol), $Cs_2CO_3$ (36 mg, 0.119 mmol), Ruphos Pd G3 (6.1 mg, 7.3 μmol) and dioxane (1.5 mL) was degassed and backfilled with nitrogen three times. The mixture was stirred at 70° C. for 2.5 h, then diluted with water and extracted with EtOAc. The combined organic layers were washed with brine, dried over anhydrous $Na_2SO_4$, filtered and concentrated under reduced pressure to give a residue that was purified by silica gel chromatography (petroleum ether:EtOAc=2:1) to give the title compound.

Step 2: 6-cyclopropyl-2-(4,4-difluoroazepan-1-yl)-N-(2-sulfamoylpyridin-4-yl)nicotinamide To a solution of N-(2-(N,N-bis(2,4-dimethoxybenzyl)sulfamoyl)pyridin-4-yl)-6-cyclopropyl-2-(4,4-difluoroazepan-1-yl)nicotinamide (20 mg, 0.027 mmol) in dichloromethane (2 mL) was added TFA (0.4 mL). The mixture was stirred at 25° C. for 1 h. Then the mixture was concentrated under reduced pressure to give a residue that was purified by reverse phase chromatography (37-100% MeCN in water with 0.1% TFA, C18 column) to give the title compound. LRMS m/z (M+K): calculated 452.1, observed 452.2. $^1$H NMR δ (ppm) (400 MHz, $CD_3OD$): 8.53 (t, J=5.6 Hz, 1H), 8.36 (s, 1H), 7.83-7.85 (m, 1H), 7.66 (d, J=8.0 Hz, 1H), 6.72 (d, J=7.6 Hz, 1H), 3.63-3.66 (m, 2H), 3.36-3.39 (m, 2H), 2.23-2.33 (m, 2H), 1.90-2.03 (m, 5H), 0.93-1.02 (m, 4H).

Example 23

5-chloro-6-cyclobutyl-2-(4,4-difluoroazepan-1-yl)-N-(2-sulfamoylpyridin-4-yl)nicotinamide

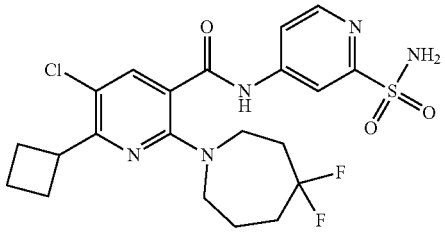 [SMILES: NS(=O)(=O)c1cc(NC(=O)c2cc(Cl)c(C3CCC3)nc2N2CCCC(F)(F)CC2)ccn1]

Step 1: methyl 5-chloro-6-cyclobutyl-2-(4,4-difluoroazepan-1-yl)nicotinate A mixture of NCS (0.11 g, 0.80 mmol) and methyl 6-cyclobutyl-2-(4,4-difluoroazepan-1-yl)nicotinate (Intermediate 35, 0.13 g, 0.40 mmol) in DMF (2.5 mL) was stirred at 20° C. for 1 h, then at 30° C. for 12 h. The mixture was then treated with water and extracted with EtOAc. The combined organic layers were washed with brine, dried over anhydrous $Na_2SO_4$, filtered and concentrated under reduced pressure to give a residue that was purified by silica gel chromatography (ethyl acetate/petroleum ether=5/1, v/v) to give the title compound.

Step 2: 5-chloro-6-cyclobutyl-2-(4,4-difluoroazepan-1-yl)nicotinic acid A mixture of lithium hydroxide hydrate (76 mg, 1.8 mmol) and methyl 5-chloro-6-cyclobutyl-2-(4,4-difluoroazepan-1-yl)nicotinate (130 mg, 0.36 mmol) in MeOH (2.5 mL) and water (1 mL) was stirred at 50° C. for 12 h. Then the reaction mixture was quenched with HCl (1M, 10 mL) and concentrated under reduced pressure to give the title compound.

Step 3: 5-chloro-6-cyclobutyl-2-(4,4-difluoroazepan-1-yl)nicotinamide To a solution of 5-chloro-6-cyclobutyl-2-(4,4-difluoroazepan-1-yl)nicotinic acid (0.11 g crude) in DCM (5 mL) was added oxalyl dichloride (0.12 g, 0.96 mmol). The mixture was stirred at 30° C. for 1 h. Then the mixture was concentrated at reduced pressure to give a residue that was treated with a solution of NH$_3$*H$_2$O (0.5 mL) in THF (5 mL). The reaction mixture was stirred at 30° C. for 1 h, then diluted with water and extracted with EtOAc. The combined organic layers were washed with brine, dried over Na$_2$SO$_4$, filtered and concentrated under reduced pressure to give a residue that was purified by silica gel chromatography (PE:EtOAc=1:1) to give the title compound.

Step 4: N-(2-(N,N-bis(2,4-dimethoxybenzyl)sulfamoyl)pyridin-4-yl)-5-chloro-6-cyclobutyl-2-(4,4-difluoroazepan-1-yl)nicotinamide A mixture of 5-chloro-6-cyclobutyl-2-(4,4-difluoroazepan-1-yl)nicotinamide (50 mg, 0.14 mmol), 4-bromo-N,N-bis(2,4-dimethoxy-benzyl)pyridine-2-sulfonamide (0.12 g, 0.22 mmol), Cs$_2$CO$_3$ (0.14 g, 0.44 mmol), Ruphos Pd G3 (24 mg, 0.029 mmol) and dioxane (3 mL) was degassed and backfilled with nitrogen three times. The mixture was stirred at 70° C. for 3 h, then diluted with water and extracted with EtOAc. The combined organic layers were washed with brine, dried over anhydrous Na$_2$SO$_4$, filtered and concentrated under reduced pressure to give a residue that was purified by silica gel chromatography (petroleum ether:EtOAc=2:1) to give the title compound.

Step 5: 5-chloro-6-cyclobutyl-2-(4,4-difluoroazepan-1-yl)-N-(2-sulfamoylpyridin-4-yl)nicotinamide (23) To a solution of N-(2-(N,N-bis(2,4-dimethoxybenzyl)sulfamoyl)pyridin-4-yl)-5-chloro-6-cyclobutyl-2-(4,4-difluoroazepan-1-yl)nicotinamide (0.13 g, 0.071 mmol) in DCM (2 mL) was added TFA (0.4 mL). The mixture was stirred at 20° C. for 1 h. The mixture was then concentrated under reduced pressure to give a residue that was purified by reverse phase chromatography (30-100% MeCN in water with 0.1% TFA, C18 column) to give the title compound. LRMS m/z (M+H): calculated 500.1, observed 500.0. $^1$H NMR δ (ppm) (400 MHz, CD$_3$OD): 8.53 (t, J=5.6 Hz, 1H), 8.38 (s, 1H), 7.84-7.86 (m, 1H), 7.72 (s, 1H), 3.91-3.99 (m, 1H), 3.75-3.78 (m, 2H), 3.40-3.43 (m, 2H), 2.29-2.43 (m, 6H), 1.87-2.13 (m, 6H).

Example 24

6-cyclobutyl-2-(4,4-difluoroazepan-1-yl)-N-(2-sulfamoylpyridin-4-yl)nicotinamide

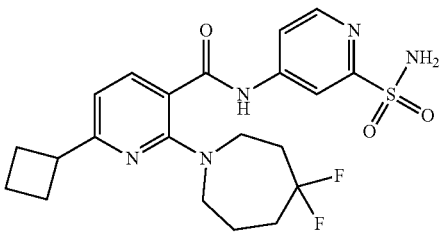 [SMILES: NS(=O)(=O)c1cc(NC(=O)c2ccc(C3CCC3)nc2N2CCCC(F)(F)CC2)ccn1]

Step 1: 6-cyclobutyl-2-(4,4-difluoroazepan-1-yl)nicotinic acid A mixture of lithium hydroxide hydrate (32 mg, 0.77 mmol) and methyl 6-cyclobutyl-2-(4,4-difluoroazepan-1-yl)nicotinate (Intermediate 35, 50 mg, 0.15 mmol) in methanol (2.5 mL) and water (1 mL) was stirred at 50° C. for 12 h. Then the mixture was quenched with HCl (1M, 10 mL) and concentrated under reduced pressure to give the title compound.

Step 2: 6-cyclobutyl-2-(4,4-difluoroazepan-1-yl)nicotinamide To a solution of 6-cyclobutyl-2-(4,4-difluoroazepan-1-yl)nicotinic acid (45 mg, crude) in DCM (5 mL) was added oxalyl dichloride (55 mg, 0.43 mmol). The mixture was stirred at 30° C. for 1 h. The mixture was concentrated under reduced pressure to give a residue that was dissolved in THF (2 mL) and treated with a solution of NH$_3$*H$_2$O (0.5 mL) in THF (3 mL). The mixture was stirred at 30° C. for 1 h. The mixture was diluted with water and extracted with EtOAc. The combined organic layers were washed with brine, dried over Na$_2$SO$_4$, filtered and concentrated under reduced pressure to give a residue that was purified by silica gel chromatography (PE:EtOAc=2:1) to give the title compound.

Step 3: N-(2-(N,N-bis(2,4-dimethoxybenzyl)sulfamoyl)pyridin-4-yl)-6-cyclobutyl-2-(4,4-difluoroazepan-1-yl)nicotinamide A mixture of 6-cyclobutyl-2-(4,4-difluoroazepan-1-yl)nicotinamide (30 mg, 0.097 mmol), Cs$_2$CO$_3$ (95 mg, 0.29 mmol), 4-bromo-N,N-bis(2,4-dimethoxybenzyl)pyridine-2-sulfonamide (78 mg, 0.14 mmol), Ruphos Pd G3 (16 mg, 0.019 mmol) and dioxane (3 mL) was degassed and backfilled with nitrogen three times. The mixture was stirred at 70° C. for 3 h, then diluted with water and extracted with EtOAc. The combined organic layers were washed with brine, dried over anhydrous Na$_2$SO$_4$, filtered and concentrated under reduced pressure to give a residue that was purified by silica gel chromatography (petroleum ether:EtOAc=2:1) to give the title compound.

Step 4: 6-cyclobutyl-2-(4,4-difluoroazepan-1-yl)-N-(2-sulfamoylpyridin-4-yl)nicotinamide (24) A mixture of N-(2-(N,N-bis(2,4-dimethoxybenzyl)sulfamoyl)pyridin-4-yl)-6-cyclobutyl-2-(4,4-difluoroazepan-1-yl)nicotinamide (60 mg, 0.078 mmol) in DCM (2 mL) and TFA (0.4 mL) was stirred at 25° C. for 1 h. Then the mixture was concentrated under reduced pressure to give a residue that was purified by reverse phase chromatography (23-100% MeCN in water with 0.1% TFA, C18 column) to give the title compound. LRMS m/z (M+H): calculated 466.2, observed 466.0. $^1$H NMR δ (ppm) (400 MHz, CD$_3$OD): 8.53 (t, J=5.6 Hz, 1H), 8.36 (s, 1H), 7.83-7.85 (m, 1H), 7.76 (d, J=7.6 Hz, 1H), 6.67 (d, J=7.6 Hz, 1H), 3.75-3.77 (m, 2H), 3.58-3.60 (m, 1H), 3.44-3.36 (m, 2H), 2.30-2.39 (m, 6H), 1.93-1.97 (m, 6H).

Example 25

2-(5,5-Difluoro-2-oxoazepan-1-yl)-N-(2-sulfamoylpyridin-4-yl)-5-(trifluoromethyl)nicotinamide

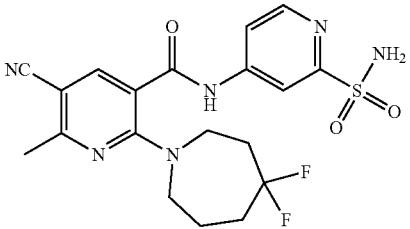 [SMILES: Cc1nc(N2CCCC(F)(F)CC2)c(C(=O)Nc2ccnc(S(N)(=O)=O)c2)cc1C#N]

Step 1: Ethyl 5-cyano-2-(4,4-difluoroazepan-1-yl)-6-methylnicotinate To a stirred solution of ethyl 2-chloro-5-cyano-6-methylnicotinate (0.50 g, 2.2 mmol), and 4,4-difluoroazepane (0.45 g, 3.3 mmol) in NMP (15 mL) was added N-ethyl-N-isopropylpropan-2-amine (0.86 g, 6.7 mmol). The mixture was stirred at 70° C. for 2 hours, then cooled to room temperature, treated with water and extracted with EtOAc. The combined organic layers were washed with brine, dried over MgSO$_4$, filtered and concentrated to give a residue that was purified by silica gel chromatography (EtOAc in hexane) to give the title compound.

Step 2: 5-cyano-2-(4,4-difluoroazepan-1-yl)-6-methylnicotinic acid To a stirred solution of ethyl 5-cyano-2-(4,4-difluoroazepan-1-yl)-6-methylnicotinate (0.70 g, 2.2 mmol) and ethanol (8.7 mL) was added 1N NaOH (2.2 mL, 2.2 mmol). The mixture was stirred at 55° C. for 4 hours. Then the mixture was acidified with 0.1 N HCl and extracted with EtOAc. The combined organic layers were washed with brine, dried over MgSO₄, filtered and concentrated to give the title compound.

Step 3: 5-cyano-2-(4,4-difluoroazepan-1-yl)-6-methylnicotinamide To a solution of oxalyl chloride (1.9 mL, 3.8 mmol) and 5-cyano-2-(4,4-difluoroazepan-1-yl)-6-methylnicotinic acid (0.75 g, 2.5 mmol) in DCM (6.4 mL) was added a drop of DMF. The mixture was heated at reflux for 1 hour. Then the mixture was concentrated under reduced pressure to give a residue that was dissolved in THF (6.4 mL) and treated with ammonium hydroxide (1.8 mL, 13 mmol) at 0° C. The reaction mixture was stirred at 0° C. for 1 hour, then diluted with water and extracted with ethyl acetate. The combined organic layers were dried over MgSO₄, filtered and concentrated under reduced pressure to give the title compound.

Step 4: 5-cyano-2-(4,4-difluoroazepan-1-yl)-N-(2-(N-(2,4-dimethoxybenzyl)-N-(2,5-dimethoxybenzyl)sulfamoyl) pyridin-4-yl)-6-methylnicotinamide A mixture of 5-cyano-2-(4,4-difluoroazepan-1-yl)-6-methylnicotinamide (0.60 g, 2.0 mmol), 4-bromo-N,N-bis(2,4-dimethoxybenzyl)pyridine-2-sulfonamide (1.3 g, 2.4 mmol), Xantphos Pd G3 (0.48 g, 0.51 mmol) and cesium carbonate (1.3 g, 4.1 mmol) in dioxane (2.0 mL) was sparged with nitrogen for 2 minutes. The mixture was heated at 100° C. in a sealed tube for 24 hours. Then the mixture was diluted with EtOAc, washed with water, brine, dried over MgSO₄ and concentrated under reduced pressure to give a residue that was purified by silica gel chromatography (EtOAc in hexane) to give the title compound.

Step 5: 5-cyano-2-(4,4-difluoroazepan-1-yl)-6-methyl-N-(2-sulfamoylpyridin-4-yl)nicotinamide To a stirred solution of N-(2-(N,N-bis(2,4-dimethoxybenzyl)sulfamoyl)pyridin-4-yl)-5-cyano-2-(4,4-difluoroazepan-1-yl)-6-methylnicotinamide (0.60 g, 0.80 mmol) in CH₂Cl₂ (4 mL) was added TFA (3.1 mL, 40 mmol). The mixture was stirred for 4 hours, and then quenched with MeOH. The resulting mixture was stirred for 5 minutes, then filtered to remove the solids. The filtrate was concentrated under reduced pressure and the resulting residue was dissolved in EtOAc. The organic layer was washed with saturated NaHCO₃, brine, dried over MgSO₄ and concentrated under reduced pressure to give a residue that was purified by silica gel chromatography (EtOAc in hexane) to give the title compound. LRMS m/z (M+H): calculated 451.1, observed 451.2. ¹H NMR δ (ppm) (500 MHz, DMSO-d₆): 11.11 (s, 1H), 8.60 (d, J=5.5 Hz, 1H), 8.27 (s, 1H), 8.20 (s, 1H), 7.82 (d, J=5.7 Hz, 1H), 7.45 (s, 2H), 3.70 (m, 2H), 3.42 (d, J=5.8 Hz, 2H), 3.32 (m, 2H), 2.55 (s, 3H), 2.32 (m, 2H), 2.08-1.80 (m, 2H).

Example 26

2-(4,4-difluoropiperidin-1-yl)-N-(2-sulfamoylpyridin-4-yl)nicotinamide

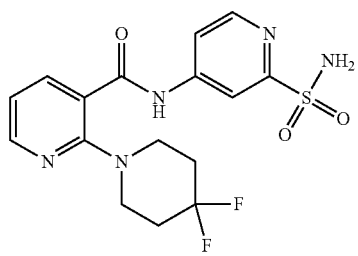 [SMILES: NS(=O)(=O)c1cc(NC(=O)c2cccnc2N2CCC(F)(F)CC2)ccn1]

Step 1: Methyl 2-(4,4-difluoropiperidin-1-yl)nicotinate A suspension of methyl 2-fluoro-nicotinate (0.12 g, 0.77 mmol) and potassium carbonate (0.13 g, 0.93 mmol) in N-methyl-2-pyrrolidinone (3.9 mL) was treated with 4,4-difluoropiperidine (0.096 mL, 0.85 mmol). The mixture was stirred at 60° C. for 18 h. Then the mixture was cooled to rt, diluted with water and extracted with EtOAc. The combined organic layers were dried over MgSO₄, filtered and concentrated under reduced pressure to give a residue that was purified by silica gel chromatography (0-30% ethyl acetate:ethanol (3:1)/hexanes) to give the title compound.

Step 2: 2-(4,4-difluoropiperidin-1-yl)nicotinic acid To a solution of methyl 2-(4,4-difluoropiperidin-1-yl)nicotinate (0.18 g, 0.71 mmol) in THF (2.8 mL) and MeOH (0.71 mL) was added aqueous LiOH (0.85 mL, 0.85 mmol, 1 M). The mixture was stirred at 50° C. for 3 h. Then the mixture was concentrated under reduced pressure to give a residue that was suspended in water, acidified with 1 N HCl and extracted with EtOAc. The combined organic layers were dried over MgSO₄, filtered and concentrated under reduced pressure to give the title compound.

Step 3: tert-butyl tert-butyl((4-(2-(4,4-difluoropiperidin-1-yl)nicotinamido)pyridin-2-yl)sulfonyl)carbamate To a solution of 2-(4,4-difluoropiperidin-1-yl)nicotinic acid (0.075 g, 0.31 mmol) and tert-butyl (4-aminopyridin-2-yl)sulfonyl(tert-butyl)carbamate (0.10 g, 0.31 mmol) in pyridine (1.5 mL) at 0° C. was added POCl₃ (32 µl, 0.34 mmol) dropwise via a syringe and the mixture stirred at 0° C. for 1 h. Then the reaction mixture was slowly quenched with brine and extracted with EtOAc. The combined organic layers were washed with water, brine, dried over MgSO₄, filtered and concentrated under reduced pressure to afford a residue that was purified by silica gel chromatography (0-30% ethyl acetate:ethanol (3:1)/hexanes) to give the title compound.

Step 4: 2-(4,4-difluoropiperidin-1-yl)-N-(2-sulfamoylpyridin-4-yl)nicotinamide (26) A solution of tert-butyl tert-butyl((4-(2-(4,4-difluoropiperidin-1-yl)nicotinamido) pyridin-2-yl)sulfonyl)-carbamate, (65 mg, 0.12 mmol) in DCM (1.2 mL) was treated with TFA (0.45 mL, 5.9 mmol) and the mixture was stirred at 25° C. for 3 h. Then the mixture was concentrated under reduced pressure. The resulting residue was suspended in saturated NaHCO₃ and extracted with EtOAc. The combined organic layers were dried over MgSO₄, filtered and concentrated under reduced pressure to give a residue that was purified by silica gel chromatography (0-25% ethyl acetate:ethanol (3:1)/hexanes) to give the title compound. LRMS m/z (M+H): calculated 398.1, observed 398.1. ¹H NMR δ (ppm) (500

MHz, CD₃OD): 8.59 (d, J=5.5 Hz, 1H), 8.42 (s, 1H), 8.35 (dd, J=4.9, 1.9 Hz, 1H), 7.98 (dd, J=7.5, 1.8 Hz, 1H), 7.86 (dd, J=5.5, 2.0 Hz, 1H), 7.06 (dd, J=7.5, 4.9 Hz, 1H), 3.52-3.46 (m, 4H), 2.05 (m, 4H).

Example 27

5-chloro-6-cyclopropyl-2-(4,4-difluoroazepan-1-yl)-N-(2-oxo-1,2-dihydropyridin-4-yl)nicotinamide

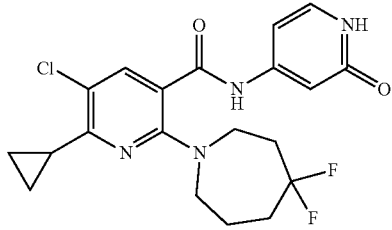

Step 1: methyl 6-cyclopropyl-2-(4,4-difluoroazepan-1-yl)nicotinate A mixture of methyl 6-chloro-2-(4,4-difluoroazepan-1-yl)nicotinate (Intermediate 31, 0.30 g, 0.98 mmol), Pd(dppf)Cl₂ (72 mg, 0.098 mmol), potassium cyclopropyltrifluoroborate (0.36 g, 2.5 mmol) and K₂CO₃ (0.41 g, 2.9 mmol) in dioxane (5 mL) and water (1 mL) was evacuated and backfilled with nitrogen three times. The mixture was heated to 100° C. for 12 h. Then the mixture was filtered and concentrated under reduced pressure to give a residue that was purified by silica gel chromatography (petroleum ether: EtOAc=5:1) to give the title compound.

Step 2: methyl 5-chloro-6-cyclopropyl-2-(4,4-difluoroazepan-1-yl)nicotinate A mixture of NCS (0.11 g, 0.84 mmol) and methyl 6-cyclopropyl-2-(4,4-difluoroazepan-1-yl)nicotinate (0.13 g, 0.42 mmol) in DMF (2.5 mL) was stirred at 20° C. for 1 h, then heated at 30° C. for 12 h. Then the mixture was diluted with water and extracted with EtOAc. The organic layer was washed with brine, dried over anhydrous Na₂SO₄, filtered and concentrated under reduced pressure to give a residue that was purified by silica gel chromatography (ethyl acetate/PE=1/1) to give the title compound.

Step 3: 5-chloro-6-cyclopropyl-2-(4,4-difluoroazepan-1-yl)nicotinic acid A mixture of methyl 5-chloro-6-cyclopropyl-2-(4,4-difluoroazepan-1-yl)nicotinate (0.20 g, 0.58 mmol) and LiOH H₂O (0.15 g, 3.5 mmol) in MeOH (6 mL) and water (0.2 mL) was stirred at 60° C. for 12 h. Then the mixture was treated with HCl/MeOH to pH ~6, and concentrated under reduced pressure to give the title compound.

Step 4: 5-chloro-6-cyclopropyl-2-(4,4-difluoroazepan-1-yl)nicotinamide To a solution of 5-chloro-6-cyclopropyl-2-(4,4-difluoroazepan-1-yl)nicotinic acid (0.14 g, 0.42 mmol) in dichloromethane (5 mL) was added oxalyl dichloride (0.11 mL, 1.3 mmol). The mixture was stirred at 30° C. for 1 h, and then concentrated under reduced pressure. The resulting residue was dissolved in THF (2 mL) and treated with a solution of NH₃·H₂O (0.5 mL) in THF (5.0 mL) at 30° C. The mixture was stirred at 30° C. for 1 h, then diluted with water and extracted with EtOAc. The organic layer was washed with brine, dried over Na₂SO₄, filtered and concentrated under reduced pressure to give a residue that was purified by reverse phase chromatography (42-100% MeCN in water with 0.1% TFA, C18 column) to give the title compound.

Step 5: 5-chloro-6-cyclopropyl-2-(4,4-difluoroazepan-1-yl)-N-(2-methoxypyridin-4-yl)nicotinamide A mixture of 5-chloro-6-cyclopropyl-2-(4,4-difluoroazepan-1-yl)nicotinamide (50 mg crude), t-BuONa (0.23 mL, 0.45 mmol), 4-chloro-2-methoxypyridine (35 mg, 0.24 mmol) and t-BuXPhos Pd G3 (10 mg, 0.015 mmol) in THF (10 mL) was degassed and backfilled with nitrogen three times. The mixture was heated to 60° C. for 12 h, then diluted with water and extracted with EtOAc. The combined organic layers were washed with brine, dried over anhydrous Na₂SO₄, filtered and concentrated to give a residue that was purified by silica gel chromatography (ethyl acetate/petroleum ether=1/5) to give the title compound.

Step 6: 5-chloro-6-cyclopropyl-2-(4,4-difluoroazepan-1-yl)-N-(2-oxo-1,2-dihydropyridin-4-yl)nicotinamide (27) A mixture of 5-chloro-6-cyclopropyl-2-(4,4-difluoroazepan-1-yl)-N-(2-methoxypyridin-4-yl)nicotinamide (60 mg, 0.14 mmol), KI (35 mg, 0.21 mmol), MeCN (1 mL) and TMSCl (0.053 mL, 0.41 mmol) was heated to 70° C. for 1 h. Then the mixture was concentrated under reduced pressure to give a residue that was purified by reverse phase chromatography (37-100% MeCN in water with 0.1% TFA, C18 column) to give the title compound. LRMS m/z (M+H): calculated 423.1, observed 422.9. ¹H NMR δ (ppm) (400 MHz, CD₃OD): 7.71 (s, 1H), 7.59 (d, J=7.2 Hz, 1H), 7.30 (d, J=1.6 Hz, 1H), 6.87-6.93 (m, 1H), 3.58-3.67 (m, 2H), 3.35 (t, J=6.0 Hz, 2H), 2.43-2.53 (m, 1H), 2.19-2.35 (m, 2H), 1.84-2.02 (m, 4H), 0.98-1.11 (m, 4H).

Example 28

2-(5,5-Difluoro-2-oxoazepan-1-yl)-N-(2-sulfamoylpyridin-4-yl)-5-(trifluoromethyl)nicotinamide

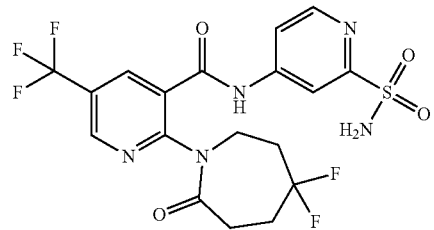 [SMILES: NS(=O)(=O)c1cc(NC(=O)c2cc(C(F)(F)F)cnc2N2CCC(F)(F)CCC2=O)ccn1]

Step 1: Methyl 2-(5,5-difluoro-2-oxoazepan-1-yl)-5-(trifluoromethyl)nicotinate To a suspension of 5,5-difluoro-2-azepanone (0.11 g, 0.71 mmol) in DMF (3.5 mL) was added NaH (43 mg, 1.1 mmol) at room temperature. The mixture was stirred for 10 min, then methyl 2-chloro-5-(trifluoromethyl)nicotinate (0.17 g, 0.71 mmol) was added. The mixture was stirred 16 h, then quenched with hydrochloric acid (1M) and extracted with ethyl acetate. The combined organic layers were dried over MgSO₄, filtered and concentrated under reduced pressure to give a residue that was purified by silica gel chromatography (0-100% EtOAc/hexanes) to give the title compound.

Step 2: 2-(5,5-Difluoro-2-oxoazepan-1-yl)-5-(trifluoromethyl)nicotinic acid To a solution of methyl 2-(5,5-difluoro-2-oxoazepan-1-yl)-5-(trifluoromethyl)nicotinate (49 mg, 0.14 mmol) in THF (350 μl) and water (350 μl) was added lithium hydroxide monohydrate (12 mg, 0.28 mmol). The mixture was stirred at rt for 1 hour, then quenched with hydrochloric acid (1M) and extracted with ethyl acetate. The combined organic layers were dried over MgSO₄, filtered and concentrated under reduced pressure to give the title compound.

Step 3: tert-Butyl tert-butyl((4-(2-(5,5-difluoro-2-oxoazepan-1-yl)-5-(trifluoromethyl)-nicotinamido)pyridin-2-yl) sulfonyl)carbamate To a solution of 2-(5,5-difluoro-2-oxoazepan-1-yl)-5-(trifluoromethyl)nicotinic acid (44 mg, 0.13 mmol) and tert-butyl (4-aminopyridin-2-yl)sulfonyl (tert-butyl)carbamate (43 mg, 0.13 mmol) in pyridine (650 µl) at 0° C. was added POCl₃ (13 µl, 0.14 mmol). The mixture was stirred 0° C. for 1 hour, then quenched with brine and extracted with ethyl acetate. The combined organic layers were dried over MgSO₄, filtered and concentrated under reduced pressure to give a residue that was purified by silica gel chromatography (0-100% EtOAc/hexanes) to give the title compound.

Step 4: 2-(5,5-Difluoro-2-oxoazepan-1-yl)-N-(2-sulfamoylpyridin-4-yl)-5-(trifluoromethyl)-nicotinamide To a solution of tert-butyl tert-butyl((4-(2-(5,5-difluoro-2-oxoazepan-1-yl)-5-(trifluoromethyl)nicotinamido)pyridin-2-yl)sulfonyl)carbamate (40 mg, 0.062 mmol) in DCM (0.3 mL) was added TFA (0.31 mL). The mixture was stirred at room temperature for 2 hours. Then the mixture was quenched with aqueous sodium hydrogen carbonate (saturated) and extracted with dichloromethane. The combined organic layers were dried over MgSO₄, filtered and concentrated under reduced pressure to give a residue that was purified by silica gel chromatography (0-100% EtOAc/hexanes) to give the title compound. LRMS m/z (M+H): calculated 494.1, observed 494.1. ¹H NMR δ (ppm) (600 MHz, DMSO-d₆): 11.30 (s, 1H), 9.02 (m, 1H), 8.57 (m, 1H), 8.44 (m, 1H), 8.19 (m, 1H), 7.78 (m, 1H), 7.43 (s, 2H), 4.19 (m, 2H), 2.65 (m, 2H), 2.34 (m, 2H), 2.16 (m, 2H).

TABLE 2

The compounds of Exmples 29-42 were prepared according to a synthetic procedure similar to the synthetic procedure for Example 28.

| Example | Compound | Name | Calc'd [M + H]⁺ | Observed [M + H]⁺ |
| --- | --- | --- | --- | --- |
| 29 | | 2-(4,4-Dichloropiperidin-1-yl)-N-(2-sulfamoylpyridin-4-yl)-5-(trifluoromethyl)-nicotinamide | 498.0 | 498.1 |
| 30 | | 2-(4,4-difluoroazepan-1-yl)-N-[1-(methylsulfonyl)-1H-pyrrolo[2,3-b]pyridin-3-yl]-5-(trifluoromethyl)pyridine-3-carboxamide | 518.1 | 518.3 |
| 31 | | 5-chloro-2-(4,4-difluoroazepan-1-yl)-6-methyl-N-[1-(methylsulfonyl)-1H-pyrazol-4-yl]pyridine-3-carboxamide | 448.1 | 448.3 |

TABLE 2-continued

The compounds of Exmples 29-42 were prepared according to a synthetic procedure similar to the synthetic procedure for Example 28.

| Example | Compound | Name | Calc'd [M + H]+ | Observed [M + H]+ |
|---|---|---|---|---|
| 32 | | 5-chloro-2-(4,4-difluoroazepan-1-yl)-4,6-dimethyl-N-[1-(methylsulfonyl)-pyrazol-4-yl]pyridine-3-carboxamide | 462.1 | 462.3 |
| 33 | | N-{1-[(2-aminoethyl)sulfonyl]-1H-pyrazol-4-yl}-5-chloro-2-(4,4-difluoroazepan-1-yl)-6-methylpyridine-3-carboxamide | 477.1 | 477.4 |
| 34 | | 2-(4,4-difluoroazepan-1-yl)-N-[1-(methylsulfonyl)-1H-indazol-3-yl]-5-(trifluoromethyl)pyridine-3-carboxamide | 518.1 | 518.3 |
| 35 | | 2-(4,4-difluoroazepan-1-yl)-N-[1-(methylsulfonyl)-1H-pyrrolo[3,2-c]pyridin-3-yl]-5-(trifluoromethyl)pyridine-3-carboxamide | 518.1 | 518.5 |
| 36 | | N-[1-(cyclopropylsulfonyl)-1H-pyrazol-4-yl]-2-(4,4-difluoroazepan-1-yl)-5-(trifluoromethyl)pyridine-3-carboxamide | 494.1 | 494.3 |

TABLE 2-continued

The compounds of Exmples 29-42 were prepared according to a synthetic procedure similar to the synthetic procedure for Example 28.

| Example | Compound | Name | Calc'd [M + H]+ | Observed [M + H]+ |
|---|---|---|---|---|
| 37 | | N-[5-cyclopropyl-1-(methylsulfonyl)-1H-pyrazol-4-yl]-2-(4,4-difluoroazepan-1-yl)-5-(trifluoromethyl)pyridine-3-carboxamide | 508.1 | 508.4 |
| 38 | | 2-cyclopropyl-4-(4,4-difluoroazepan-1-yl)-N-(2-sulfamoylpyridin-4-yl)pyrimidine-5-carboxamide | 453.1 | 453.4 |
| 39 | | 6-cyclopropyl-3-(4,4-difluoroazepan-1-yl)-N-(2-sulfamoylpyridin-4-yl)pyridazine-4-carboxamide | 453.1 | 453.4 |
| 40 | | 6-methyl-N-(2-sulfamoylpyridin-4-yl)-2-(3,4,4-trifluoroazepan-1-yl)nicotinamide | 444.1 | 444.4 |
| 41 | | 5-chloro-2-(4,4-difluoroazepan-1-yl)-6-methoxy-N-(2-sulfamoylpyridin-4-yl)pyridine-3-carboxamide | 476.1 | 476.3 |

TABLE 2-continued

The compounds of Exmples 29-42 were prepared according to a synthetic procedure similar to the synthetic procedure for Example 28.

| Example | Compound | Name | Calc'd [M + H]⁺ | Observed [M + H]⁺ |
|---|---|---|---|---|
| 42 | | N-[2-(tert-butylsulfamoyl)pyridin-4-yl]-5-chloro-2-(4,4-difluoroazepan-1-yl)-6-methoxypyridine-3-carboxamide | 532.1 | 532.4 |

Example 43

5-cyano-2-(4,4-difluoropiperidin-1-yl)-N-(2-sulfamoylpyridin-4-yl)-6-(trifluoromethyl)nicotinamide

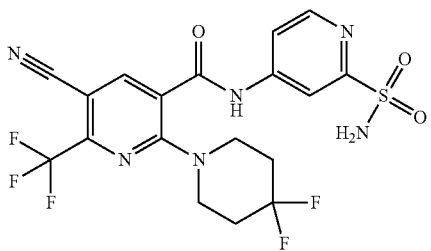 [SMILES: N#Cc1cc(C(=O)Nc2ccnc(S(N)(=O)=O)c2)c(N2CCC(F)(F)CC2)nc1C(F)(F)F]

Step 1: methyl 5-cyano-2-(4,4)-difluoropiperidin-1-yl)-6-(trifluoromethyl)nicotinate In a glove box, a solution of methyl 5-bromo-2-(4,4-difluoropiperidin-1-yl)-6-(trifluoromethyl)nicotinate (Intermediate 36, 96 mg, 0.24 mmol) in acetonitrile (1.6 mL) was treated with Xphos-Pd-G2 (19 mg, 0.024 mmol), dicyanozine (42 mg, 0.37 mmol) and potassium phosphate (30 µl, 0.36 mmol). The flask was sealed and the reaction mixture was stirred under nitrogen at 70° C. for 4 h. Then the mixture was cooled to rt, diluted with EtOAc and filtered through Celite™. The filtrate was concentrated under reduced pressure to give a residue that was purified by silica gel chromatography, (0-30% ethyl acetate:ethanol (3:1)/hexanes) to give the title compound.

Step 2: 5-cyano-2-(4,4-difluoropiperidin-1-yl)-6-(trifluoromethyl)nicotinic acid A solution of methyl 5-cyano-2-(4,4-difluoropiperidin-1-yl)-6-(trifluoromethyl)nicotinate (82 mg, 0.23 mmol) in THF (0.94 mL) and MeOH (0.24 mL) was treated with LiOH (0.24 mL, 0.24 mmol, 1.0 M in water). The mixture was stirred at 25° C. for 2 h. Then the mixture was concentrated and the resulting residue was dissolved in water, acidified with 1N HCl and extracted with EtOAc. The organic layer was dried over MgSO₄, filtered and concentrated to give the title compound.

Step 3: tert-butyl tert-butyl((4-(5-cyano-2-(4,4-difluoropiperidin-1-yl)-6-(trifluoromethyl)-nicotinamido)pyridin-2-yl)sulfonyl)carbamate A solution of 5-cyano-2-(4,4-difluoropiperidin-1-yl)-6-(trifluoromethyl)nicotinic acid (77 mg, 0.23 mmol) and tert-butyl (4-aminopyridin-2-yl)sulfonyl(tert-butyl)carbamate (76 mg, 0.23 mmol) in pyridine (1.1 mL) at 0° C. was treated with POCl₃ (0.024 mL, 0.25 mmol) dropwise via a syringe. The mixture was stirred at 0° C. for 1.5 h. Then the mixture was quenched with saturated aqueous NaCl and extracted with EtOAc. The organic layer was washed with brine, dried over MgSO₄, filtered and concentrated under reduced pressure to give a residue that was purified by silica gel chromatography (0-20% ethyl acetate/hexanes) to give the title compound.

Step 4: 5-cyano-2-(4,4-difluoropiperidin-1-yl)-N-(2-sulfamoylpyridin-4-yl)-6-(trifluoromethyl)-nicotinamide A solution of tert-butyl tert-butyl((4-(5-cyano-2-(4,4-difluoropiperidin-1-yl)-6-(trifluoromethyl)nicotinamido)pyridin-2-yl)sulfonyl)carbamate (50 mg, 0.077 mmol) in DCM (0.39 mL) was treated with TFA (0.30 mL, 3.9 mmol). The mixture was stirred at 25° C. for 5 h. Then the mixture was concentrated under reduced pressure and the resulting residue was suspended in NaHCO₃ and extracted with EtOAc. The organic layer was dried over MgSO₄, filtered and concentrated under reduced pressure to give a residue that was purified by silica gel chromatography (0-30% ethyl acetate:ethanol (3:1)/hexanes) to give the title compound. LRMS m/z (M+H): calculated 491.1, observed 491.2. ¹H NMR δ (ppm) (500 MHz, DMSO-$d_6$): 11.35 (s, 1H), 8.65 (d, J=5.4 Hz, 1H), 8.56 (s, 1H), 8.28 (d, J=1.5 Hz, 1H), 7.86-7.81 (m, 1H), 7.49 (s, 2H), 3.73-3.67 (m, 4H), 2.14-2.06 (m, 4H).

Example 44

5-(cyclopropylethynyl)-2-(4,4-difluoropiperidin-1-yl)-N-(2-sulfamoylpyridin-4-yl)-6-(trifluoromethyl)nicotinamide

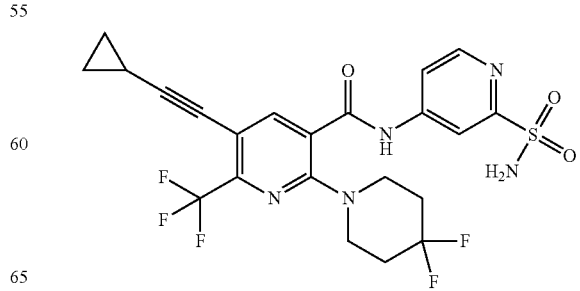

127

Step 1: methyl 5-(cyclopropylethynyl)-2-(4,4)-difluoropiperidin-1-yl)-6-(trifluoromethyl)-nicotinate In a glove box, to a vial containing methyl 5-bromo-2-(4,4-difluoropiperidin-1-yl)-6-(trifluoromethyl)nicotinate (Intermediate 36, 62 mg, 0.15 mmol) and cyclopropylacetylene (52 µl, 0.62 mmol) was added DMF (0.77 mL), followed by Pd(PPh$_3$)$_4$ (8.9 mg, 7.7 µmol), copper(I) iodide (1.5 mg, 7.7 µmol), and TEA (86 µl, 0.62 mmol). The vial was sealed and heated at 40° C. for 24 h. Then the mixture was diluted with EtOAc and washed with water, followed by brine. The organic layer was dried over MgSO$_4$, filtered and concentrated to give a residue that was purified by silica gel chromatography (0-10% ethyl acetate/hexanes) to give the title compound.

Step 2: 5-(cyclopropylethynyl)-2-(4,4-difluoropiperidin-1-yl)-6-(trifluoromethyl)nicotinic acid A solution of methyl 5-(cyclopropylethynyl)-2-(4,4-difluoropiperidin-1-yl)-6-(trifluoromethyl)-nicotinate (45 mg, 0.12 mmol) in THF (0.46 mL) and MeOH (0.12 mL) was treated with LiOH (0.12 mL, 0.12 mmol, 1.0 M in water). The mixture was stirred at 25° C. for 2 h, then concentrated under reduced pressure. The resulting residue was diluted with water, acidified with 1N HCl and extracted with EtOAc. The organic layer was dried over MgSO$_4$, filtered and concentrated to give the title compound.

Step 3: tert-butyl tert-butyl((4-(5-(cyclopropylethynyl)-2-(4,4-difluoropiperidin-1-yl)-6-(trifluoromethyl)nicotinamido)pyridin-2-yl)sulfonyl)carbamate A solution of 5-(cyclopropyl-ethynyl)-2-(4,4-difluoropiperidin-1-yl)-6-(trifluoromethyl)nicotinic acid (37 mg, 0.099 mmol) and tert-butyl (4-aminopyridin-2-yl)sulfonyl(tert-butyl)carbamate (33 mg, 0.099 mmol) in pyridine (0.49 mL) at 0° C. was treated with POCl$_3$ (10 µl, 0.11 mmol) dropwise via a syringe. The mixture was stirred at 0° C. for 1.5 h, then quenched with brine and extracted with EtOAc. The organic layer was washed with brine, dried over MgSO$_4$, filtered and concentrated under reduced pressure to give the title compound.

Step 4: 5-(cyclopropylethynyl)-2-(4,4-difluoropiperidin-1-yl)-N-(2-sulfamoylpyridin-4-yl)-6-(trifluoromethyl)nicotinamide A solution of tert-butyl tert-butyl((4-(5-(cyclopropylethynyl)-2-(4,4-difluoropiperidin-1-yl)-6-(trifluoromethyl)nicotinamido)pyridin-2-yl)sulfonyl) carbamate (67 mg, 0.098 mmol) in DCM (0.49 mL) was treated with TFA (0.38 mL, 4.9 mmol). The mixture was stirred at 25° C. for 5 h, then concentrated under reduced pressure. The resulting residue diluted in NaHCO$_3$ and extracted with EtOAc. The organic layer was dried over MgSO$_4$, filtered and concentrated under reduced pressure to give a residue that was purified by silica gel chromatography (0-30% ethyl acetate:ethanol (3:1)/hexanes) to give the title compound. LRMS m/z (M+H): calculated 430.1, observed 430.3. $^1$H NMR δ (ppm) (500 MHz, DMSO-d$_6$): 11.24 (s, 1H), 8.63 (d, J=5.4 Hz, 1H), 8.30 (d, J=1.7 Hz, 1H), 8.05 (s, 1H), 7.82 (d, J=3.6 Hz, 1H), 7.48 (s, 2H), 3.58-3.52 (m, 4H), 3.41-3.36 (m, 1H), 2.01 (d, J=18.2 Hz, 4H), 1.59 (td, J=8.1, 4.0 Hz, 1H), 0.97-0.89 (m, 2H), 0.76-0.69 (m, 2H).

128

Example 45

2-(azepan-1-yl)-N-(3-cyano-1,2,4-oxadiazol-5-yl)-5-(trifluoromethyl)pyridine-3-carboxamide

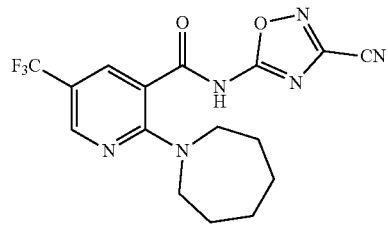 [SMILES: N#Cc1noc(NC(=O)c2cc(C(F)(F)F)cnc2N2CCCCCC2)n1]

To a solution of 2-(azepan-1-yl)-5-(trifluoromethyl)nicotinic acid (Intermediate 17, 20 mg, 0.069 mmol) in pyridine (1.0 mL) was added phosphoryl trichloride (11 mg, 0.069 mmol). The mixture was stirred at 20° C. for 5 min, then 5-amino-1,2,4-oxadiazole-3-carbonitrile (7.7 mg) was added and the resulting mixture was stirred at 50° C. for 2.5 h, then at 60° C. for 10 h. Then the mixture was cooled to rt, diluted with water and extracted with EtOAc. The organic layer was dried over Na$_2$SO$_4$, filtered and concentrated under reduced pressure to give a residue that was purified by reverse phase chromatography (MeCN in water with 0.1% TFA, C18 column) to give the title compound. LRMS m/z (M+H): calculated 381.1, observed 381.0. $^1$H NMR δ (ppm) (400 MHz, CD$_3$OD): 8.49 (s, 1H), 8.08 (s, 1H), 3.53-3.55 (m, 4H), 1.85-1.86 (m, 4H), 1.54-1.55 (m, 4H).

Example 46

5-(cyclopropylmethyl)-2-(4,4-difluoroazepan-1-yl)-N-(2-sulfamoylpyridin-4-yl)nicotinamide

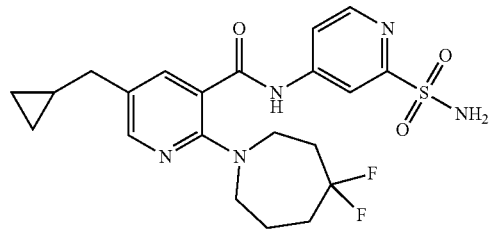 [SMILES: NS(=O)(=O)c1cc(NC(=O)c2cc(CC3CC3)cnc2N2CCCC(F)(F)CC2)ccn1]

Step 1: methyl 5-bromo-2-(4,4-difluoroazepan-1-yl)nicotinate To a solution of methyl 5-bromo-2-chloronicotinate (0.60 g, 2.4 mmol) in DMA (10 mL) was added 4,4-difluoroazepane (0.65 g, 4.8 mmol) and N-ethyl-N-isopropylpropan-2-amine (1.2 g, 9.6 mmol). The mixture was stirred at 100° C. for 2 h, then diluted with water and extracted with ethyl acetate. The organic layer was washed with brine, dried over anhydrous Na$_2$SO$_4$, filtered and concentrated under reduced pressure to give a residue that was purified by silica gel chromatography (30% EtOAc) to give the title compound.

Step 2: methyl 5-(cyclopropylmethyl)-2-(4,4-difluoroazepan-1-yl)nicotinate A mixture of methyl 5-bromo-2-(4,4-difluoroazepan-1-yl)nicotinate (0.50 g, 1.4 mmol), potassium (cyclopropyl-methyl)trifluoroborate (0.46 g, 2.9 mmol), P(tBu)$_3$-Pd-G2 (73 mg, 0.14 mmol) and Cs$_2$CO$_3$ (1.4 g, 4.3 mmol) in toluene (5 mL) was degassed and backfilled with nitrogen three times. The mixture was heated to 100° C. for 12 h. Then the mixture was cooled to rt, washed with water and extracted with EtOAc. The organic layer was washed with brine, dried over Na$_2$SO$_4$, filtered and concentrated under reduced pressure to give a residue that was purified by reverse phase chromatography (39-100% MeCN in water with 0.1% TFA, C18 column) to give the title compound.

Step 3: lithium 5-(cyclopropylmethyl)-2-(4,4-difluoroazepan-1-yl)nicotinate A mixture of methyl 5-(cyclopropylmethyl)-2-(4,4-difluoroazepan-1-yl)nicotinate (75 mg, 0.23 mmol) and LiOH H$_2$O (29 mg, 0.69 mmol) in MeOH (1.5 mL) and water (0.8 mL) was stirred at 45° C. for 13 h. Then the mixture was concentrated under reduced pressure to give the title compound.

Step 4: N-(2-(N,N-bis(2,4-dimethoxybenzyl)sulfamoyl) pyridin-4-yl)-5-(cyclopropylmethyl)-2-(4,4-difluoroazepan-1-yl)nicotinamide A mixture of 4-amino-N,N-bis(2,4-dimethoxy-benzyl)pyridine-2-sulfonamide (90 mg, 0.19 mmol), PyBOP (0.13 g, 0.25 mmol) and lithium 5-(cyclopropylmethyl)-2-(4,4-difluoroazepan-1-yl)nicotinate (40 mg crude) in DMF (4 mL) was stirred at 20° C. for 12 h. The reaction mixture was quenched with water and extracted with EtOAc. The organic layer was washed with brine, dried over Na$_2$SO$_4$, filtered and concentrated under reduced pressure to give a residue that was purified by silica gel chromatography (petroleum ether:EtOAc=1:1) to give the title compound.

Step 5: 5-(cyclopropylmethyl)-2-(4,4-difluoroazepan-1-yl)-N-(2-sulfamoylpyridin-4-yl)nicotinamide A mixture of N-(2-(N,N-bis(2,4-dimethoxybenzyl)sulfamoyl)pyridin-4-yl)-5-(cyclopropylmethyl)-2-(4,4-difluoroazepan-1-yl)nicotinamide (13 mg, 0.017 mmol) in dichloromethane (3 mL) and TFA (1 mL) was stirred at 20° C. for 0.5 h. Then the mixture was concentrated under reduced pressure to give a residue that was purified by reverse phase chromatography (34-100% MeCN in water with 0.1% 10 mM NH$_4$CO$_3$, C18 column) to give the title compound. LRMS m/z (M+H): calculated 466.2, observed 466.3. $^1$H NMR δ (ppm) (400 MHz, CD$_3$OD): 8.56 (d, J=5.2 Hz, 1H), 8.38 (s, 1H), 8.16 (d, J=2.0 Hz, 1H), 7.87 (d, J=5.6 Hz, 1H), 7.73 (d, J=1.6 Hz, 1H), 3.63-3.72 (m, 2H), 3.42 (t, J=6.0 Hz, 2H), 2.50 (d, J=7.2 Hz, 2H), 2.32 (d, J=10.0 Hz, 1H), 1.87-2.05 (m, 4H), 0.98 (br s, 1H), 0.49-0.57 (m, 2H), 0.23 (q, J=5.2 Hz, 2H).

Examples 47 and 48

(S)-2-(4,4-difluoro-3-methylpiperidin-1-yl)-N-(2-sulfamoylpyridin-4-yl)-5-(trifluoromethyl)nicotinamide (47) and (R)-2-(4,4-difluoro-3-methylpiperidin-1-yl)-N-(2-sulfamoylpyridin-4-yl)-5-(trifluoromethyl)nicotinamide (48)

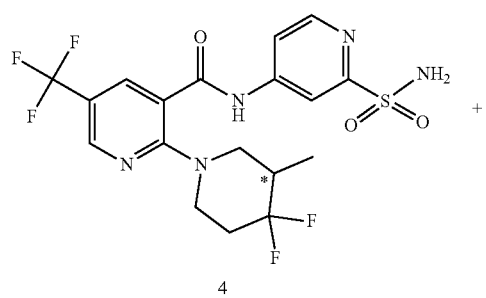

4

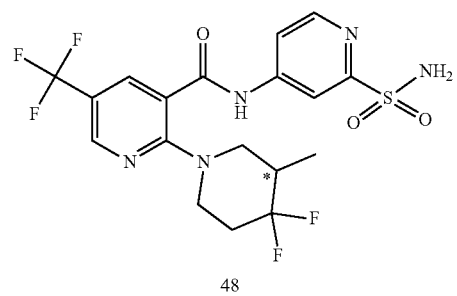

48

Step 1: (R and S)-2-(4,4-difluoro-3-methylpiperidin-1-yl)-N-(2-sulfamoylpyridin-4-yl)-5-(trifluoromethyl)nicotinamide To a solution of 2-chloro-N-(2-sulfamoylpyridin-4-yl)-5-(trifluoromethyl)nicotinamide (Intermediate 21, 75 mg, 0.20 mmol) in NMP (1 mL) were added 4,4-difluoro-3-methylpiperidine hydrochloride (34 mg, 0.2 mmol) and DIPEA (0.10 mL, 0.59 mmol). The mixture was heated at 70° C. for 4 hours, then quenched with aqueous potassium phosphate monobasic (saturated) and extracted with ethyl acetate. The combined organic layers were dried over MgSO$_4$, filtered and concentrated under reduced pressure to give a residue that was purified on silica gel (0-100% EtOAc/hexanes) to give the title compound.

Step 2: (R or S)-2-(4,4-difluoro-3-methylpiperidin-1-yl)-N-(2-sulfamoylpyridin-4-yl)-5-(trifluoromethyl)nicotinamide (47) and (S or R)-2-(4,4-difluoro-3-methylpiperidin-1-yl)-N-(2-sulfamoylpyridin-4-yl)-5-(trifluoromethyl) nicotinamide (48) (R and S)-2-(4,4-difluoro-3-methylpiperidin-1-yl)-N-(2-sulfamoylpyridin-4-yl)-5-(trifluoromethyl) nicotinamide (77 mg, 0.16 mmol) was purified by preparative SFC (AD-H, 25% EtOH/CO$_2$, 100 bar) to give the title compounds: enantiomer A (47) [(R or S)-2-(4,4-difluoro-3-methylpiperidin-1-yl)-N-(2-sulfamoylpyridin-4-yl)-5-(trifluoromethyl)nicotinamide; and enantiomer B (48) [(S or R)-2-(4,4-difluoro-3-methylpiperidin-1-yl)-N-(2-sulfamoylpyridin-4-yl)-5-(trifluoromethyl)-nicotinamide. Enantiomer A (47): LRMS m/z (M+H): calculated 480.1, observed 480.3, $^1$H NMR δ (ppm) (600 MHz, DMSO-d$_6$): 11.21 (s, 1H), 8.59 (d, J=4.9 Hz, 2H), 8.26 (s, 1H), 8.13 (d, J=2.0 Hz, 1H), 7.81 (d, J=3.7 Hz, 1H), 7.45 (s, 2H), 3.86 (t, J=13.7 Hz, 2H), 3.26-3.19 (m, 1H), 3.11-2.93 (m, 1H), 2.11 (m, 2H), 1.87 (m, 1H), 0.86 (d, J=6.8 Hz, 3H)]; Enantiomer B (48): LRMS m/z (M+H): calculated 480.1, observed 480.3, $^1$H NMR δ (ppm) (600 MHz, DMSO-d$_6$): 11.20 (s, 1H), 8.59 (d, J=5.1 Hz, 2H), 8.25 (s, 1H), 8.13 (d, J=2.2 Hz, 1H), 7.90-7.72 (m, 1H), 7.44 (s, 2H), 3.96-3.75 (m, 2H), 3.23 (t, J=10.9 Hz, 1H), 3.09-2.93 (m, 1H), 2.11 (s, 2H), 1.93 (s, 1H), 0.86 (d, J=6.8 Hz, 3H).

TABLE 3

The compounds of Examples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 49 | | (R or S)-2-(4,4-dichloro-3-methylpiperidin-1-yl)-N-(2-sulfamoylpyridin-4-yl)-5-(trifluoromethyl)nicotinamide | 512.1 | 512.1 | Chiral Method I, peak 1 |
| 50 | | (S or R)-2-(4,4-dichloro-3-methylpiperidin-1-yl)-N-(2-sulfamoylpyridin-4-yl)-5-(trifluoromethyl)nicotinamide | 512.1 | 512.1 | Chiral Method I, peak 2 |
| 51 | | 2-(4,4-Dichloroazepan-1-yl)-N-(2-sulfamoylpyridin-4-yl)-5-(trifluoromethyl)nicotinamide | 512.1 | 512.1 | 150° C. for 10 minutes in Step 3 |
| 52 | | 2-[(3S,5R)-4,4-difluoro-3,5-dimethyl-1-piperidyl]-N-(2-sulfamoyl-4-pyridyl)-5-(trifluoromethyl)pyridine-3-carboxamide | 494.1 | 494.1 | 150° C. for 10 minutes in Step 3 |
| 53 | | 5-chloro-2-[(3S,5R)-4,4-difluoro-3,5-dimethyl-1-piperidyl]-6-methyl-N-(2-sulfamoyl-4-pyridyl)pyridine-3-carboxamide | 474.1 | 474.1 | 200° C. for 10 minutes in Step 3 |

TABLE 3-continued

The compounds of Exmples 49-130 were prepared according to a synthetic procedure similar to the synthetic procedure for Examples 47 and 48.

| Example | Compound | Name | Calc'd [M + H]⁺ | Observed [M + H]⁺ | Conditions |
|---|---|---|---|---|---|
| 54 | | (S or R)-5-chloro-2-(4,4-difluoro-3-methylpiperidin-1-yl)-6-methyl-N-(2-sulfamoylpyridin-4-yl)nicotinamide | 460.1 | 460.1 | 200° C. for 90 minutes in Step 3, Chiral Method D, peak 2 |
| 55 | | (S or R)-5-chloro-2-(4,4-difluoro-3-methylpiperidin-1-yl)-6-methyl-N-(2-sulfamoylpyridin-4-yl)nicotinamide | 460.1 | 460.1 | 200° C. for 90 minutes in Step 3, Chiral Method D, peak 1 |
| 56 | | (S or R)-2-(3-methylpiperidin-1-yl)-N-(2-sulfamoylpyridin-4-yl)-5-(trifluoromethyl)nicotinamide | 444.1 | 444.1 | 100° C. for 10 minutes in Step 3; Chiral Method I, peak 2 |
| 57 | | (R or S)-2-(3-methylpiperidin-1-yl)-N-(2-sulfamoylpyridin-4-yl)-5-(trifluoromethyl)nicotinamide | 444.1 | 444.1 | 100° C. for 10 minutes in Step 3; Chiral Method I, peak 2 |
| 58 | | N-(2-sulfamoyl-4-pyridyl)-5-(trifluoromethyl)-2-[(1S,5S or 1R,5R)-1-(trifluoromethyl)-3-azabicyclo[3.2.0]heptan-3-yl]pyridine-3-carboxamide | 510.1 | 510.1 | Chiral Method D, peak 2 |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 59 | | N-(2-sulfamoyl-4-pyridyl)-5-(trifluoromethyl)-2-[(1R,5R or 1S,5S)-1-(trifluoromethyl)-3-azabicyclo[3.2.0]heptan-3-yl]pyridine-3-carboxamide | 510.1 | 510.1 | Chiral Method D, peak 1 |
| 60 | | N-(2-sulfamoylpyridin-4-yl)-2-((1R,5S)-6,6,7,7-tetrafluoro-3-azabicyclo[3.2.0]heptan-3-yl)-5-(trifluoromethyl)nicotinamide | 514.1 | 514.1 | 70° C. for 16 hours in Step 3 |
| 61 | | 2-[(1S,6S or 1R,6R)-7,7-difluoro-6-methyl-3-azabicyclo[4.1.0]heptan-3-yl]-N-(2-sulfamoyl-4-pyridyl)-5-(trifluoromethyl)pyridine-3-carboxamide | 492.1 | 492.1 | Chiral method A, peak 2 |
| 62 | | 2-[(1R,6R or 1S,6S)-7,7-difluoro-6-methyl-3-azabicyclo[4.1.0]heptan-3-yl]-N-(2-sulfamoyl-4-pyridyl)-5-(trifluoromethyl)pyridine-3-carboxamide | 492.1 | 492.1 | Chiral method A, peak 1 |
| 63 | | 2-((1R,5S)-8,8-difluoro-3-azabicyclo[3.2.1]octan-3-yl)-N-(2-sulfamoylpyridin-4-yl)-5-(trifluoromethyl)-nicotinamide | 492.1 | 492.1 | 150° C. for 10 minutes in Step 3 |

TABLE 3-continued

*The compounds of Exmples 49-130 were prepared according to a synthetic procedure similar to the synthetic procedure for Examples 47 and 48.*

| Example | Compound | Name | Calc'd [M + H]⁺ | Observed [M + H]⁺ | Conditions |
|---|---|---|---|---|---|
| 64 | | 2-((1R,5S or 1S,5R)-6,6-difluoro-3-azabicyclo-[3.2.0]heptan-3-yl)-N-(2-sulfamoylpyridin-4-yl)-5-(trifluoromethyl)-nicotinamide | 478.1 | 478.1 | Chiral Method D, peak 2 |
| 65 | | 2-((1S,5R or 1R,5S)-6,6-difluoro-3-azabicyclo-[3.2.0]heptan-3-yl)-N-(2-sulfamoylpyridin-4-yl)-5-(trifluoromethyl)-nicotinamide | 478.1 | 478.1 | Chiral Method D, peak 1 |
| 66 | | (R or S)-2-(1,1-difluoro-5-azaspiro[2.5]octan-5-yl)-N-(2-sulfamoyl-pyridin-4-yl)-5-(trifluoromethyl)nicotinamide | 492.1 | 492.1 | Chiral Method E, peak 1 |
| 67 | | (S or R)-2-(1,1-difluoro-5-azaspiro[2.5]octan-5-yl)-N-(2-sulfamoyl-pyridin-4-yl)-5-(trifluoromethyl)nicotinamide | 492.1 | 492.1 | Chiral Method E, peak 2 |
| 68 | | 2-((1R,5S)-3-azabicyclo[3.2.0]heptan-3-yl)-N-(2-sulfamoyl-pyridin-4-yl)-5-(trifluoromethyl)nicotinamide | 442.1 | 442.1 | 70° C. for 16 hours in Step 3 |

TABLE 3-continued

*The compounds of Exmples 49-130 were prepared according to a synthetic procedure similar to the synthetic procedure for Examples 47 and 48.*

| Example | Compound | Name | Calc'd [M + H]⁺ | Observed [M + H]⁺ | Conditions |
|---|---|---|---|---|---|
| 69 | | 2-((1S,6S or 1R,6R)-7,7-difluoro-3-azabicyclo[4.1.0]heptan-3-yl)-N-(2-sulfamoyl-pyridin-4-yl)-5-(trifluoro-methyl)nicotinamide | 478.1 | 478.1 | Chiral Method B, peak 1 |
| 70 | | 2-((1R,6R or 1S,6S)-7,7-difluoro-3-azabicyclo[4.1.0]heptan-3-yl)-N-(2-sulfamoyl-pyridin-4-yl)-5-(trifluoro-methyl)-nicotinamide | 478.1 | 478.1 | Chiral Method B, peak 2 |
| 71 | | 2-[(1R,4R or 1S,4S)-5,5-difluoro-2-azabicyclo[2.2.1]heptan-2-yl]-N-(2-sulfamoyl-4-pyridyl)-5-(trifluoromethyl)pyridine-3-carboxamide | 478.1 | 478.1 | Chiral Method C, peak 1 |
| 72 | | 2-[(1S,4S or 1R,4R)-5,5-difluoro-2-azabicyclo[2.2.1]heptan-2-yl]-N-(2-sulfamoyl-4-pyridyl)-5-(trifluoromethyl)pyridine-3-carboxamide | 478.1 | 478.1 | Chiral Method C, peak 2 |
| 73 | | (R or S)-2-(4,4-difluoro-2-methylpiperidin-1-yl)-N-(2-sulfamoylpyridin-4-yl)-5-(trifluoro-methyl)nicotinamide | 480.1 | 480.1 | 200° C. for 0.5 hour in Step 3; Chiral Method F peak 1 |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 74 | | (S or R)-2-(4,4-difluoro-2-methylpiperidin-1-yl)-N-(2-sulfamoylpyridin-4-yl)-5-(trifluoromethyl)nicotinamide | 480.1 | 480.1 | 200° C. for 0.5 hour in Step 3; Chiral Method F peak 2 |
| 75 | | 2-((3R,4s,5S)-4-hydroxy-3,4,5-trimeperthylpiridin-1-yl)-N-(2-sulfamoylpyridin-4-yl)-5-(trifluoromethyl)nicotinamide | 488.2 | 488.2 | 70° C. for 16 hours in Step 3 |
| 76 | | 2-((1R,5S)-6,6-difluoro-3-azabicyclo-[3.1.1]heptan-3-yl)-N-(2-sulfamoylpyridin-4-yl)-5-(trifluoromethyl)nicotinamide | 478.1 | 478.1 | 70° C. for 16 hours in Step 3 |
| 77 | | 2-[(3S,4S)-4-hydroxy-3-methyl-1-piperidyl]-N-(2-sulfamoyl-4-pyridyl)-5-(trifluoromethyl)-pyridine-3-carboxamide | 460.1 | 460.1 | 70° C. for 16 hours in Step 3 |
| 78 | | 2-[(3S,4r,5R)-4-hydroxy-3,5-dimethyl-1-piperidyl]-N-(2-sulfamoyl-4-pyridyl)-5-(trifluoromethyl)pyridine-3-carboxamide | 474.1 | 474.2 | 70° C. for 16 hours in Step 3 |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 79 | | 2-(6,7-dihydro-4H-thieno[3,2-c]pyridin-5-yl)-N-(2-sulfamoyl-4-pyridyl)-5-(trifluoromethyl)pyridine-3-carboxamide | 484.1 | 484.2 | |
| 80 | | N-(2-sulfamoyl-4-pyridyl)-5-(trifluoromethyl)-2-[3-(trifluoromethyl)-1-piperidyl]pyridine-3-carboxamide | 498.1 | 498.2 | |
| 81 | | 2-[3-(3,5-difluorophenyl)-1-piperidyl]-N-(2-sulfamoyl-4-pyridyl)-5-(trifluoromethyl)pyridine-3-carboxamide | 542.1 | 542.3 | |
| 82 | | N-(2-sulfamoyl-4-pyridyl)-5-(trifluoromethyl)-2-[4-(trifluoromethyl)-1-piperidyl]pyridine-3-carboxamide | 498.1 | 498.2 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 83 | | N-(2-sulfamoyl-4-pyridyl)-5-(trifluoromethyl)-2-[3-[[4-(trifluoromethyl)phenyl]methyl]-1-piperidyl]pyridine-3-carboxamide | 588.1 | 588.3 | |
| 84 | | N-(2-sulfamoyl-4-pyridyl)-2-thiomorpholino-5-(trifluoromethyl)pyridine-3-carboxamide | 448.1 | 448.2 | |
| 85 | | N-(2-sulfamoyl-4-pyridyl)-5-(trifluoromethyl)-2-[3-[4-(trifluoromethyl)phenyl]pyrrolidin-1-yl]pyridine-3-carboxamide | 560.1 | 560.2 | |
| 86 | | 2-(3-benzyl-6,8-dihydro-5H-imidazo[1,2-a]pyrazin-7-yl)-N-(2-sulfamoyl-4-pyridyl)-5-(trifluoromethyl)pyridine-3-carboxamide | 558.2 | 558.3 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 87 | | 2-[3,3-dimethyl-4-(2,2,2-trifluoroethyl)piperazin-1-yl]-N-(2-sulfamoyl-4-pyridyl)-5-(trifluoromethyl)pyridine-3-carboxamide | 541.1 | 541.3 | |
| 88 | | 2-(2,2-dimethyl-morpholin-4-yl)-N-(2-sulfamoyl-4-pyridyl)-5-(trifluoromethyl)pyridine-3-carboxamide | 460.1 | 460.2 | |
| 89 | | N-(2-sulfamoyl-4-pyridyl)-5-(trifluoromethyl)-2-[8-(trifluoromethyl)-3,4-dihydro-1H-isoquinolin-2-yl]pyridine-3-carboxamide | 546.1 | 546.2 | |
| 90 | | N-(2-sulfamoyl-4-pyridyl)-2-[4-(trifluoromethoxy)isoindolin-2-yl]-5-(trifluoro-methyl)pyridine-3-carboxamide | 548.1 | 548.2 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 91 | | N-(2-sulfamoyl-4-pyridyl)-5-(trifluoromethyl)-2-[2-[4-(trifluoromethyl)-phenyl]morpholin-4-yl]pyridine-3-carboxamide | 576.1 | 576.2 | |
| 92 | | N-(2-sulfamoyl-4-pyridyl)-2-(3,3,4,4-tetrafluoropyrrolidin-1-yl)-5-(trifluoromethyl)pyridine-3-carboxamide | 488.1 | 488.1 | |
| 93 | | N-(2-sulfamoyl-4-pyridyl)-5-(trifluoromethyl)-2-[3-(trifluoromethyl)azetidin-1-yl]pyridine-3-carboxamide | 470.1 | 470.2 | |
| 94 | | 2-(3-pyrazol-1-ylpyrrolidin-1-yl)-N-(2-sulfamoyl-4-pyridyl)-5-(trifluoromethyl)pyridine-3-carboxamide | 482.1 | 482.2 | |
| 95 | | 2-[2-(4-fluorophenyl)-1-piperidyl]-N-(2-sulfamoyl-4-pyridyl)-5-(trifluoromethyl)pyridine-3-carboxamide | 524.1 | 524.2 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 96 | | 2-(2,3,3a,5,6,6a-hexahydrofuro[3,2-b]pyrrol-4-yl)-N-(2-sulfamoyl-4-pyridyl)-5-(trifluoromethyl)pyridine-3-carboxamide | 458.1 | 458.2 | |
| 97 | | N-(2-sulfamoyl-4-pyridyl)-5-(trifluoromethyl)-2-[3-[4-(trifluoromethyl)phenoxy]azetidin-1-yl]pyridine-3-carboxamide | 562.1 | 562.2 | |
| 98 | | N-(2-sulfamoyl-4-pyridyl)-5-(trifluoromethyl)-2-[4-[3-(trifluoromethyl)phenoxy]-1-piperidyl]pyridine-3-carboxamide | 590.1 | 590.3 | |
| 99 | | 2-[4-(cyclopropylmethyl)-3-oxo-piperazin-1-yl]-N-(2-sulfamoyl-4-pyridyl)-5-(trifluoromethyl)-pyridine-3-carboxamide | 499.1 | 499.2 | |
| 100 | | N-(2-sulfamoyl-4-pyridyl)-2-[4-(2,2,2-trifluoroethyl)piperazin-1-yl]-5-(trifluoromethyl)-pyridine-3-carboxamide | 513.1 | 513.2 | |

TABLE 3-continued

The compounds of Exmples 49-130 were prepared according to a synthetic procedure similar to the synthetic procedure for Examples 47 and 48.

| Example | Compound | Name | Calc'd [M + H]⁺ | Observed [M + H]⁺ | Conditions |
|---|---|---|---|---|---|
| 101 | | 5-chloro-2-(4,4-difluoroazepan-1-yl)-N-(2-sulfamoyl-4-pyridyl)pyridine-3-carboxamide | 446.9 | 447.2 | 120° C. in Step 3 |
| 102 | | 2-((2R,6S)-2-methyl-6-(trifluoromethyl)morpholino)-N-(2-sulfamoyl-pyridin-4-yl)-5-(trifluoromethyl)nicotinamide | 514.1 | 514.1 | |
| 103 | | 2-((2S,6R)-2-methyl-6-(trifluoromethyl)morpholino)-N-(2-sulfamoyl-pyridin-4-yl)-5-(trifluoromethyl)nicotinamide | 514.4 | 514.1 | |
| 104 | | (S)-N-(2-sulfamoylpyridin-4-yl)-5-(trifluoromethyl)-2-(2-(trifluoromethyl)-1,4-oxazepan-4-yl)nicotinamide | 514.1 | 514.1 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 105 | | (R)-N-(2-sulfamoylpyridin-4-yl)-5-(trifluoromethyl)-2-(2-(trifluoromethyl)-1,4-oxazepan-4-yl)nicotinamide | 514.4 | 514.1 | |
| 106 | | 2-[(2R)-6,6-dimethyl-2-(trifluoromethyl)-1,4-oxazepan-4-yl]-N-(2-sulfamoyl-4-pyridyl)-5-(trifluoromethyl)pyridine-3-carboxamide | 542.1 | 542.2 | |
| 107 | | 2-(2,2-dimethyl-1,4-oxazepan-4-yl)-N-(2-sulfamoyl-4-pyridyl)-5-(trifluoromethyl)pyridine-3-carboxamide | 474.1 | 474.2 | |
| 108 | | 2-[(7S)-7-methyl-1,4-oxazepan-4-yl]-N-(2-sulfamoyl-4-pyridyl)-5-(trifluoromethyl)pyridine-3-carboxamide | 460.1 | 460.2 | |
| 109 | | N-[2-(tert-butylsulfamoyl)-4-pyridyl]-5-chloro-2-(4,4-difluoroazepan-1-yl)pyridine-3-carboxamide | 503.0 | 503.1 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 110 | | 2-[(2S)-2-methylmorpholin-4-yl]-N-(2-sulfamoyl-4-pyridyl)-5-(trifluoromethyl)pyridine-3-carboxamide | 446.1 | 446.1 | |
| 111 | | 2-[(2R)-2-methyl-1,4-oxazepan-4-yl]-N-(2-sulfamoyl-4-pyridyl)-5-(trifluoromethyl)pyridine-3-carboxamide | 460.1 | 460.1 | |
| 112 | | 2-(3-hydroxy-3-methyl-1-piperidyl)-N-(2-sulfamoyl-4-pyridyl)-5-(trifluoromethyl)pyridine-3-carboxamide | 460.1 | 460.2 | |
| 113 | | 2-(6-fluoro-1,1-dimethyl-isoindolin-2-yl)-N-(2-sulfamoyl-4-pyridyl)-5-(trifluoromethyl)pyridine-3-carboxamide | 510.1 | 510.2 | |
| 114 | | 2-(azepan-1-yl)-N-(2-methyl-5-sulfamoyl-thiophen-3-yl)-5-(trifluoromethyl)-pyridine-3-carboxamide | 463.1 | 463.2 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 115 | | 2-(4,4-difluoro-5-methylazepan-1-yl)-N-(2-sulfamoylpyridin-4-yl)-5-(trifluoromethyl)pyridine-3-carboxamide | 494.1 | 494.3 | |
| 116 | | 5-chloro-2-[(7R or 7S)-7-(difluoromethyl)-1,4-oxazepan-4-yl]-6-methyl-N-(2-sulfamoylpyridin-4-yl)pyridine-3-carboxamide | 476.9 | 477.0 | |
| 117 | | 5-chloro-2-[(7S or 7R)-7-(difluoromethyl)-1,4-oxazepan-4-yl]-6-methyl-N-(2-sulfamoylpyridin-4-yl)pyridine-3-carboxamide | 476.9 | 477.0 | |
| 118 | | (R or S)-N-(2-sulfamoylpyridin-4-yl)-5-(trifluoromethyl)-2-(7-(trifluoromethyl)-1,4-oxazepan-4-yl)nicotinamide | 514.1 | 514.2 | |
| 119 | | (S or R)-N-(2-sulfamoylpyridin-4-yl)-5-(trifluoromethyl)-2-(7-(trifluoromethyl)-1,4-oxazepan-4-yl)nicotinamide | 514.1 | 514.2 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 120 | | 2-[(2S,7R or 2R,7S)-2-methyl-7-(trifluoromethyl)-1,4-oxazepan-4-yl]-N-(2-sulfamoylpyridin-4-yl)-5-(trifluoromethyl)-pyridine-3-carboxamide | 528.1 | 528.2 | |
| 121 | | 2-((2R,7S or 2S,7R)-2-methyl-7-(trifluoromethyl)-1,4-oxazepan-4-yl)-N-(2-sulfamoylpyridin-4-yl)-5-(trifluoromethyl)-nicotinamide | 528.1 | 528.2 | |
| 122 | | 2-((2R,7R or 2S,7S)-2-methyl-7-(trifluoromethyl)-1,4-oxazepan-4-yl)-N-(2-sulfamoylpyridin-4-yl)-5-(trifluoromethyl)-nicotinamide | 528.1 | 528.2 | |
| 123 | | 2-((2S,7S or 2R,7R)-2-methyl-7-(trifluoromethyl)-1,4-oxazepan-4-yl)-N-(2-sulfamoyl-pyridin-4-yl)-5-(trifluoromethyl)-nicotinamide | 528.1 | 528.2 | |
| 124 | | (S or R)-5-chloro-2-(2-(difluoromethyl)morpholino)-6-methyl-N-(2-sulfamoylpyridin-4-yl)nicotinamide | 462.9 | 463.2 | |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 125 | | (R or S)-5-chloro-2-(2-(difluoromethyl)morpholino)-6-methyl-N-(2-sulfamoylpyridin-4-yl)nicotinamide | 462.9 | 463.2 | |
| 126 | | N-(2-sulfamoylpyridin-4-yl)-5-(trifluoromethyl)-2-[(2S)-2-(trifluoromethyl)pyrrolidin-1-yl]pyridine-3-carboxamide | 484.1 | 484.2 | 150° C. for 10 minutes in Step 3 |
| 127 | | (R)-N-(2-sulfamoylpyridin-4-yl)-5-(trifluoromethyl)-2-(2-(trifluoromethyl)pyrrolidin-1-yl)nicotinamide | 484.1 | 484.2 | 150° C. for 10 minutes in Step 3 |
| 128 | | N-(2-sulfamoylpyridin-4-yl)-5-(trifluoromethyl)-2-[3-(trifluoromethyl)pyrrolidin-1-yl]pyridine-3-carboxamide | 484.1 | 484.2 | 150° C. for 10 minutes in Step 3 |

TABLE 3-continued

The compounds of Exmples 49-130 were prepared according to a synthetic procedure similar to the synthetic procedure for Examples 47 and 48.

| Example | Compound | Name | Calc'd [M + H]+ | Observed [M + H]+ | Conditions |
|---|---|---|---|---|---|
| 129 | | (S or R)-2-(3-cyanopyrrolidin-1-yl)-N-(2-sulfamoylpyridin-4-yl)-5-(trifluoromethyl)-nicotinamide | 441.1 | 441.2 | 150° C. for 10 minutes in Step 3, Chiral Method K, peak 2 |
| 130 | | (R or S)-2-(3-cyanopyrrolidin-1-yl)-N-(2-sulfamoylpyridin-4-yl)-5-(trifluoromethyl)-nicotinamide | 441.1 | 441.2 | 150° C. for 10 minutes in Step 3, Chiral Method K, peak 1 |

Example 131

2-(4,4-difluoro-3-methylazepan-1-yl)-N-(2-sulfamoylpyridin-4-yl)-5-(trifluoromethyl)nicotinamide

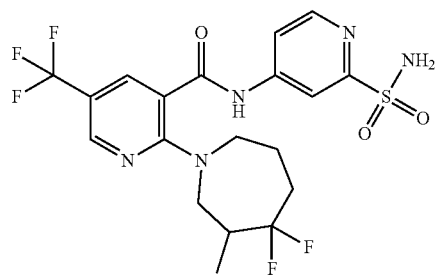 [SMILES: CC1CN(c2ncc(C(F)(F)F)cc2C(=O)Nc2ccnc(S(N)(=O)=O)c2)CCCC1(F)F]

A tube was charged with 2-chloro-N-(2-sulfamoylpyridin-4-yl)-5-(trifluoromethyl)nicotinamide (Intermediate 21, 0.10 g, 0.26 mmol), 4,4-difluoro-5-methylazepane hydrochloride (Intermediate 10, 80 mg crude), DIPEA (0.046 mL, 0.26 mmol) and NMP (1 mL). The mixture was heated to 150° C. for 10 min under microwave irradiation. Then the mixture was filtered and the filtrate was purified by reverse phase chromatography (37-100% MeCN in water with 0.1% 10 mM $NH_4CO_3$, C18 column) to give the title compound. LRMS m/z (M+H): calculated 494.1, observed 493.9. $^1$H NMR δ (ppm) (400 MHz, $CD_3OD$): 8.57 (d, J=5.6 Hz, 1H), 8.51 (d, J=1.2 Hz, 1H), 8.38 (d, J=1.6 Hz, 1H), 8.05 (d, J=1.6 Hz, 1H), 7.84-7.91 (m, 1H), 3.79-3.86 (m, 1H), 3.68-3.76 (m, 1H), 3.53-3.60 (m, 1H), 3.37-3.45 (m, 1H), 2.22-2.47 (m, 2H), 2.05-2.11 (m, 1H), 1.88-1.95 (m, 2H), 0.94 (d, J=7.2 Hz, 3H).

Example 132

2-(4,4-difluoroazepan-1-yl)-N-(2-sulfamoylpyridin-4-yl)-6-(trifluoromethyl)nicotinamide

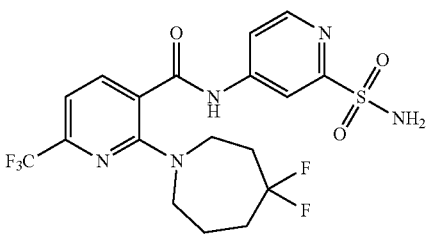 [SMILES: NS(=O)(=O)c1cc(NC(=O)c2ccc(C(F)(F)F)nc2N2CCCC(F)(F)CC2)ccn1]

A tube was charged with 2-chloro-N-(2-sulfamoylpyridin-4-yl)-6-(trifluoromethyl)nicotinamide (Intermediate 37, 21 mg, 0.16 mmol), DIPEA (0.023 mL, 0.13 mmol) and NMP (2 mL). The mixture was heated to 150° C. for 10 min under microwave irradiation. Then the mixture was purified by reverse phase chromatography (42-100% MeCN in water with 0.1% TFA, C18 column) to give the title compound. LRMS m/z (M+H): calculated 480.1, observed 479.9. $^1$H NMR δ (ppm) (400 MHz, $CD_3OD$): 8.57 (d, J=5.6 Hz, 1H), 8.36 (d, J=1.6 Hz, 1H), 7.96 (d, J=7.2 Hz, 1H), 7.86 (dd, J=1.6, 5.6 Hz, 1H), 7.12 (d, J=7.6 Hz, 1H), 3.74 (td, J=2.4, 5.6 Hz, 2H), 3.46 (t, J=5.6 Hz, 2H), 2.25-2.46 (m, 2H), 1.84-2.06 (m, 4H).

Examples 133 and 134

2-((2R,6S or 2S,6R)-2-ethyl-6-(trifluoromethyl)morpholino)-N-(2-sulfamoylpyridin-4-yl)-5-(trifluoromethyl)nicotinamide (133) and 2-((2S,6R or 2R,6S)-2-ethyl-6-(trifluoromethyl)-morpholino)-N-(2-sulfamoylpyridin-4-yl)-5-(trifluoromethyl)nicotinamide (134)

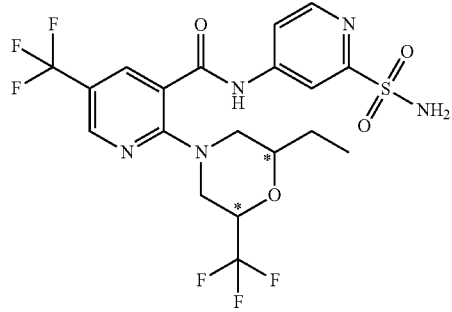

133

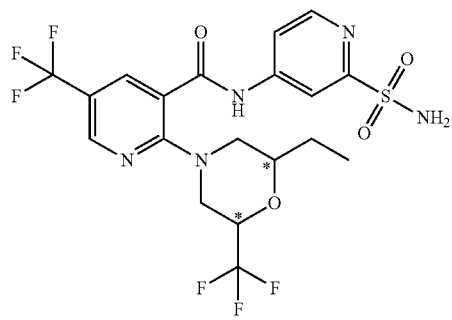

134

Step 1: N-(2-(N,N-bis(3,4-dimethylbenzyl)sulfamoyl)pyridin-4-yl)-2-((2R,6S and 2S,6R)-2-ethyl-6-(trifluoromethyl)morpholino)-5-(trifluoromethyl)nicotinamide A tube charged with (2R,6S and 2S,6R)-2-ethyl-6-(trifluoromethyl)morpholine hydrochloride (Intermediate 15, 0.17 g crude), N-(2-(N,N-bis(3,4-dimethylbenzyl)sulfamoyl)pyridin-4-yl)-2-chloro-5-(trifluoro-methyl)nicotinamide (Intermediate 22, 0.11 g, 0.51 mmol), K$_2$CO$_3$ (0.16 g, 1.1 mmol) and DMSO (1.5 mL) at 20° C. was sparged with nitrogen for 1 min, then sealed and heated at 80° C. for 12 h. Then the mixture was cooled to room temperature, diluted in water and extracted with EtOAc. The organic layer was washed with brine, dried over by Na$_2$SO$_4$, filtered and concentrated to give the title compound.

Step 2: 2-((2R,6S or 2S,6R)-2-ethyl-6-(trifluoromethyl)morpholino)-N-(2-sulfamoylpyridin-4-yl)-5-(trifluoromethyl)nicotinamide (133) and 2-((2S,6R or 2R,6S)-2-ethyl-6-(trifluoromethyl)morpholino)-N-(2-sulfamoylpyridin-4-yl)-5-(trifluoromethyl)nicotinamide (134) To a solution of N-(2-(N,N-bis(3,4-dimethylbenzyl)sulfamoyl)pyridin-4-yl)-2-((2R,6S and 2S,6R)-2-ethyl-6-(trifluoromethyl)morpholino)-5-(trifluoromethyl)nicotinamide (0.22 g crude) in dichloromethane (3 mL) was added TFA (1 mL). The mixture was stirred at 15° C. for 3 h, then concentrated under reduced pressure to give a residue that was purified by silica gel chromatography (ethyl acetate/petroleum ether=1/1) to give the title compound as a racemic mixture: 2-((2R,6S and 2S,6R)-2-ethyl-6-(trifluoromethyl)morpholino)-N-(2-sulfamoylpyridin-4-yl)-5-(trifluoromethyl)nicotinamide. The racemic mixture was separated by Chiral-SFC (Phenomenex-Amylose-1, 20% EtOH/CO$_2$) to give two enantiomers: enantiomer A (compound 133); and enantiomer B (compound 134). Enantiomer A: [LRMS m/z (M+H): calculated 528.1, observed 528.1; $^1$H NMR δ (ppm) (500 MHz, CD$_3$OD): 8.45-8.52 (m, 2H), 8.26-8.29 (m, 1H), 8.01 (d, J=2.5 Hz, 1H), 7.77-7.81 (m, 1H), 4.21-4.31 (m, 1H), 3.78-3.90 (m, 2H), 3.54-3.65 (m, 2H), 3.23-3.26 (m, 1H), 1.47-1.57 (m, 1H), 1.26-1.36 (m, 1H), 0.74-0.80 (m, 3H)]. Enantiomer B: [LRMS m/z (M+H): calculated 528.1, observed 528.2; $^1$H NMR δ (ppm) (500 MHz, CD$_3$OD): 8.44-8.54 (m, 2H), 8.26-8.29 (m, 1H), 8.01 (d, J=2.5 Hz, 1H), 7.77-7.81 (m, 1H), 4.21-4.31 (m, 1H), 3.78-3.90 (m, 2H), 3.54-3.65 (m, 2H), 3.22-3.27 (m, 1H), 1.47-1.57 (m, 1H), 1.26-1.36 (m, 1H), 0.74-0.80 (m, 3H)].

Examples 135 and 136

(R or S)-2-(2,2-dimethyl-6-(trifluoromethyl)morpholino)-N-(2-sulfamoylpyridin-4-yl)-5-(trifluoromethyl)nicotinamide (135) and (S or R)-2-(2,2-dimethyl-6-(trifluoromethyl)-morpholino)-N-(2-sulfamoylpyridin-4-yl)-5-(trifluoromethyl)nicotinamide (136)

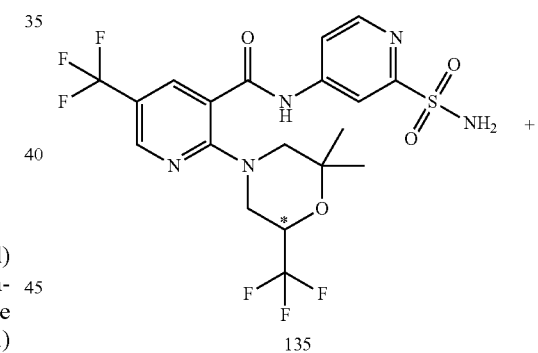

135

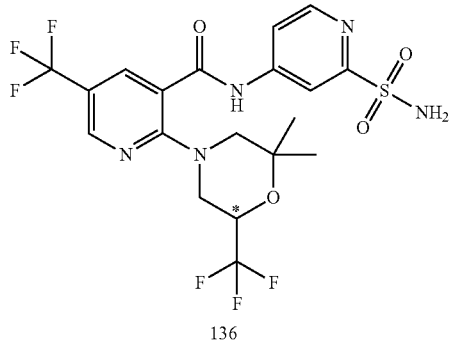

136

Step 1: (R and S)—N-(2-(N,N-bis(2,4-dimethoxybenzyl)sulfamoyl)pyridin-4-yl)-2-(2,2-dimethyl-6-(trifluoromethyl)morpholino)-5-(trifluoromethyl)nicotinamide A tube charged with N-(2-(N,N-bis(2,4-dimethoxybenzyl)sulfamoyl)pyridin-4-yl)-2-chloro-5-(trifluoromethyl)-nicotinamide (Intermediate 22, 0.16 g, 0.24 mmol), 2,2-dimethyl-6-(trifluoromethyl)morpholine hydrochloride (Intermediate 16, 0.10 g, 0.46 mmol), $K_2CO_3$ (0.16 g, 1.1 mmol) and DMSO (1.5 mL) was sparged with nitrogen for 1 min, then sealed and heated to 80° C. for 12 h. Then the mixture was cooled to rt, diluted in water and extracted with EtOAc. The organic layer was washed with brine, dried over by $Na_2SO_4$, filtered and concentrated to give the title compound.

Step 2: (R or S)-2-(2,2-dimethyl-6-(trifluoromethyl)morpholino)-N-(2-sulfamoylpyridin-4-yl)-5-(trifluoromethyl)nicotinamide (135) and (S or R)-2-(2,2-dimethyl-6-(trifluoromethyl)-morpholino)-N-(2-sulfamoylpyridin-4-yl)-5-(trifluoromethyl)nicotinamide (136) To a solution of (R and S)—N-(2-(N,N-bis(2,4-dimethoxybenzyl)sulfamoyl)pyridin-4-yl)-2-(2,2-dimethyl-6-(trifluoromethyl)morpholino)-5-(trifluoromethyl)nicotinamide (0.20 g crude) in dichloromethane (3 mL) was added TFA (1 mL). The mixture was stirred at 15° C. for 3 h. Then the mixture was concentrated under reduced pressure and purified by silica gel chromatography (ethyl acetate/petroleum ether=1/1) to give a racemic mixture of (R and S)-2-(2,2-dimethyl-6-(trifluoromethyl)-morpholino)-N-(2-sulfamoylpyridin-4-yl)-5-(trifluoromethyl)nicotinamide. The racemic material was separated by Chiral-SFC (ChiralPak IC, 15% MeOH/0.1% $NH_3·H_2O$) to give 2 enantiomers: enantiomer A (compound 135), and enantiomer B (compound 136). Enantiomer A (compound 135): [LRMS m/z (M+H): calculated 528.1, observed 528.1; $^1H$ NMR δ (ppm) (500 MHz, $CD_3OD$): 8.63 (d, J=5.5 Hz, 2H), 8.39 (s, 1H), 8.15 (d, J=2.0 Hz, 1H), 7.91-7.97 (m, 1H), 4.39-4.47 (m, 1H), 4.14-4.23 (m, 1H), 3.81-3.89 (m, 1H), 3.07-3.15 (m, 1H), 3.03 (d, J=13.5 Hz, 1H), 1.24 (d, J=10.0 Hz, 6H)]. Enantiomer B (compound 136): [LRMS m/z (M+H): calculated 528.1, observed 528.1; $^1H$ NMR δ (ppm) (500 MHz, $CD_3OD$): 8.48-8.52 (m, 2H), 8.27 (br s, 1H), 8.02 (d, J=2.0 Hz, 1H), 7.78-7.84 (m, 1H), 4.27-4.34 (m, 1H), 4.03-4.09 (m, 1H), 3.70-3.76 (m, 1H), 2.95-3.02 (m, 1H), 2.90 (d, J=13.5 Hz, 1H), 1.11 (d, J=10.0 Hz, 6H)].

Example 137

4-(2-(4,4-difluoroazepan-1-yl)-5-(trifluoromethyl)nicotinamido)picolinamide

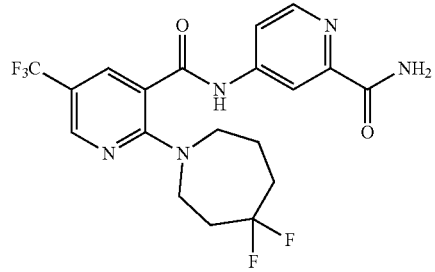 [SMILES: NC(=O)c1cc(NC(=O)c2cc(C(F)(F)F)cnc2N2CCCC(F)(F)CC2)ccn1]

Step 1: 4-(2-chloro-5-(trifluoromethyl)nicotinamido)picolinamide To a mixture of 2-chloro-5-(trifluoromethyl)nicotinic acid (0.20 g, 0.89 mmol) in pyridine (1 mL) was added 4-amino-pyridine-2-carboxamide (0.12 g, 0.89 mmol) and EDC (0.17 g, 0.89 mmol). The mixture was sonicated and heated at 50° C. for 6 hours, then stirred at ambient temperature for 2.5 days in a sealed vial. Then the mixture was concentrated under a stream of nitrogen with heating to 60° C. to give the title compound.

Step 2: 4-(2-(4,4-difluoroazepan-1-yl)-5-(trifluoromethyl)nicotinamido)picolinamide To a mixture of 4-(2-chloro-5-(trifluoromethyl)nicotinamido)picolinamide (0.31 g, 0.89 mmol) in DMSO (10 mL) was added $K_2CO_3$ (0.37 g, 2.7 mmol), 4,4-difluoroazepane hydrochloride (0.15 g, 0.89 mmol) and DIPEA (0.12 g, 0.89 mmol). The mixture was sonicated and stirred at 85° C. for 6 hours. Then the mixture was cooled to rt and diluted with EtOAc. The organic layer was washed with saturated aqueous $NaHCO_3$, water, brine, dried over $MgSO_4$ and concentrated to give a residue that was purified by silica gel chromatography (EtOAc/hexanes) to give the title compound. LRMS m/z (M+H): calculated 444.1, observed 444.1. $^1H$ NMR δ (ppm) (500 MHz, $CDCl_3$): 10.03 (s, 1H), 8.53 (m, 3H), 8.36 (s, 1H), 8.07 (d, 1H), 7.93 (m, 1H), 5.42 (d, 1H), 3.80 (m, 2H), 3.50 (m, 2H), 2.36 (m, 2H), 1.98 (m, 4H) ppm.

TABLE 4

The compounds of Exmples 138-142 were prepared according to a synthetic procedure similar to the synthetic procedure for Example 137.

| Example | Compound | Name | Calc'd [M + H]⁺ | Observed [M + H]⁺ |
|---|---|---|---|---|
| 138 | (structure) | 6-chloro-2-(4,4-difluoroazepan-1-yl)-N-(2-sulfamoyl-4-pyridyl)pyridine-3-carboxamide | 446.1 | 446.2 |

TABLE 4-continued

The compounds of Exmples 138-142 were prepared according to a synthetic procedure similar to the synthetic procedure for Example 137.

| Example | Compound | Name | Calc'd [M + H]+ | Observed [M + H]+ |
|---|---|---|---|---|
| 139 | | 2-(azepan-1-yl)-N-(2-sulfamoyl-4-pyridyl)-5-(trifluoromethyl)pyridine-3-carboxamide | 444.1 | 444.3 |
| 140 | | 2-(azepan-1-yl)-N-(2-methylsulfonyl-4-pyridyl)-5-(trifluoromethyl)-pyridine-3-carboxamide | 443.2 | 443.5 |
| 141 | | 2-(azepan-1-yl)-N-(6-sulfamoyl-2-pyridyl)-5-(trifluoromethyl)pyridine-3-carboxamide | 444.1 | 444.3 |
| 142 | | 2-(4,4-difluoroazepan-1-yl)-6-methoxy-N-(2-sulfamoylpyridin-4-yl)nicotinamide | 442.1 | 442.1 |

Example 143

N-(2-methoxypyridin-4-yl)-2-(6-azaspiro[2.5]octan-6-yl)-5-(trifluoromethyl)nicotinamide

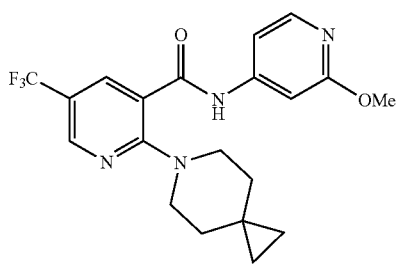 [SMILES: COc1cc(NC(=O)c2cc(C(F)(F)F)cnc2N2CCC3(CC2)CC3)ccn1]

Step 1: 2-chloro-N-(2-methoxypyridin-4-yl)-5-(trifluoromethyl)nicotinamide To a mixture of 2-chloro-5-(trifluoromethyl)nicotinic acid (0.10 g, 0.44 mmol) in pyridine (1 mL) was added 4-amino-2-methoxypyridine (0.066 g, 0.53 mmol) and EDC (0.13 g, 0.66 mmol). The mixture was sonicated and stirred at ambient temperature for 17 hours in a sealed vial. Then the mixture was concentrated under reduced pressure to give a residue that was purified by silica gel chromatography (EtOAc/hexanes) to give the title compound.

Step 2: N-(2-methoxypyridin-4-yl)-2-(6-azaspiro[2.5]octan-6-yl)-5-trifluoromethyl)nicotinamide To a mixture of 2-chloro-N-(2-methoxypyridin-4-yl)-5-(trifluoromethyl) nicotinamide (0.12 g, 0.89 mmol) in DMF (0.5 mL) was added 6-azaspiro[2.5]octane (84 mg, 0.75 mmol), and DIPEA (0.20 g, 1.5 mmol). The mixture was heated at 50° C. for 2 days. Then the mixture was diluted with EtOAc, washed with saturated aqueous NaHCO$_3$, water, brine, dried over MgSO$_4$, filtered and concentrated to give a residue that was purified by silica gel chromatography (EtOAc/hexanes) to give the title compound. LRMS m/z (M+H): calculated 407.2, observed 407.2 found; $^1$H NMR δ (ppm) (500 MHz, CDCl$_3$) □□ 10.67 (s, 1H), 8.66 (s, 3H), 8.56 (s, 1H), 8.15 (d, 1H), 7.18 (m, 2H), 3.97 (s, 3H), 3.36 (m, 4H), 1.59 (m, 4H), 0.42 (s, 4H) ppm.

TABLE 5

The compounds of Examples 144-146 were prepared according to a synthetic procedure similar to the synthetic procedure for Example 143.

| Example | Compound | Name | Calc'd [M + H]⁺ | Observed [M + H]⁺ |
|---|---|---|---|---|
| 144 | | 2-(4,4-difluoroazepan-1-yl)-N-(5-sulfamoyl-3-pyridyl)-5-(trifluoromethyl)pyridine-3-carboxamide | 480.1 | 480.2 |
| 145 | | 2-(azepan-1-yl)-N-(5-sulfamoyl-3-pyridyl)-5-(trifluoromethyl)pyridine-3-carboxamide | 444.1 | 444.2 |
| 146 | | 2-(4,4-difluoroazepan-1-yl)-N-(2-methoxy-4-pyridyl)-5-(trifluoromethyl)pyridine-3-carboxamide | 431.2 | 431.1 |

Example 147

2-((3S,5R)-4,4-difluoro-3,5-dimethylpiperidin-1l-yl)-N-(2-(methylsulfonyl)pyridin-4-yl)-5-(trifluoromethyl)nicotinamide

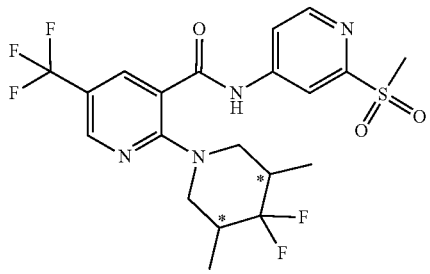 [SMILES: CC1CN(c2ncc(C(F)(F)F)cc2C(=O)Nc2ccnc(S(C)(=O)=O)c2)CC(C)C1(F)F]

Step 1: 2-chloro-N-(2-(methylsulfonyl)pyridin-4-yl)-5-(trifluoromethyl)nicotinamide To a solution 1: 2-chloro-5-(trifluoromethyl)pyridin-3-carboxylic acid (1.0 g, 4.4 mmol) and 2-(methylsulfonyl)pyridin-4-amine (0.76 g, 4.4 mmol) in pyridine (22 mL) at 0° C. was added POCl₃ (0.45 mL, 4.9 mmol). The mixture was stirred at 0° C. for 1 hour, then quenched with brine and extracted with ethyl acetate. The organic layer was dried over MgSO₄, filtered and concentrated under reduced pressure to give a residue that was triturated with Et₂O. The resulting solid was collected and dried under reduced pressure to give the title compound.

Step 2: 2-((3S,5R)-4,4-difluoro-3,5-dimethylpiperidin-1-yl)-N-(2-(methylsulfonyl)pyridin-4-5-(trifluoromethyl) nicotinamide To a solution of 2-chloro-N-(2-(methylsulfonyl)pyridin-4-yl)-5-(trifluoromethyl)nicotinamide (50 mg, 0.13 mmol) in NMP (0.66 mL) was added 4,4-difluoro-3,5-dimethylpiperidine hydrochloride (24 mg, 0.13 mmol) and DIPEA (69 µl, 0.40 mmol). The mixture was heated at 70° C. for 4 hours. Then the reaction was quenched with aqueous potassium phosphate monobasic (saturated) and extracted with ethyl acetate. The organic layer was dried over MgSO₄, filtered, and concentrated under reduced pressure to give a residue that was purified by silica gel chromatography (0-100% EtOAc/hexanes) to give the title compound. LRMS m/z (M+H): calculated 493.1, observed 493.2. ¹H NMR δ (ppm) (600 MHz, DMSO-d₆): 11.30 (s, 1H), 8.67 (d, J=5.4 Hz, 1H), 8.63-8.55 (m, 1H), 8.35 (d, J=1.5 Hz, 1H), 8.14 (d, J=2.0 Hz, 1H), 7.90 (dd, J=5.5, 1.9 Hz, 1H), 4.00-3.89 (m, 2H), 3.25 (s, 3H), 2.83 (t, J=12.8 Hz, 2H), 2.16-2.00 (m, 2H), 0.86 (d, J=6.8 Hz, 6H).

TABLE 6

The compounds of Exmples 148-155 were prepared according to a synthetic procedure similar to the synthetic procedure for Example 147.

| Example | Compound | Name | Calc'd [M + H]+ | Observed [M + H]+ | Conditions |
|---|---|---|---|---|---|
| 148 | | 2-[(3R or 3S)-4,4-difluoro-3-methyl-1-piperidyl]-N-(2-methylsulfonyl-4-pyridyl)-5-(trifluoromethyl)pyridine-3-carboxamide | 479.1 | 479.2 | Chiral Method G, peak 1 |
| 149 | | 2-[(3S or 3R)-4,4-difluoro-3-methyl-1-piperidyl]-N-(2-methylsulfonyl-4-pyridyl)-5-(trifluoromethyl)pyridine-3-carboxamide | 479.1 | 479.2 | Chiral Method G, peak 2 |
| 150 | | N-(2-cyano-4-pyridyl)-2-[(3S,5R)-4,4-difluoro-3,5-dimethyl-1-piperidyl]-5-(trifluoromethyl)pyridine-3-carboxamide | 440.1 | 440.1 | |
| 151 | | N-(2-methylsulfonyl-4-pyridyl)-2-[(1R,5S)-6,6,7,7-tetrafluoro-3-azabicyclo[3.2.0]heptan-3-yl]-5-(trifluoromethyl)pyridine-3-carboxamide | 513.1 | 513.1 | |
| 152 | | 2-[(1R,5S)-3-azabicyclo[3.2.0]heptan-3-yl]-N-(2-methylsulfonyl-4-pyridyl)-5-(trifluoromethyl)pyridine-3-carboxamide | 441.1 | 441.1 | |

TABLE 6-continued

The compounds of Exmples 148-155 were prepared according to a synthetic procedure similar to the synthetic procedure for Example 147.

| Example | Compound | Name | Calc'd [M + H]⁺ | Observed [M + H]⁺ | Conditions |
|---|---|---|---|---|---|
| 153 | | 2-[(1R,5S)-3-azabicyclo[3.2.0]heptan-3-yl]-N-(2-cyano-4-pyridyl)-5-(trifluoromethyl)pyridine-3-carboxamide | 388.1 | 388.1 | |
| 154 | | (S or R)-N-(2-cyanopyridin-4-yl)-2-(4,4-difluoro-3-methylpiperidin-1-yl)-5-(trifluoromethyl)nicotinamide | 426.1 | 426.2 | Chiral Method H, peak 2 |
| 155 | | (R or S)-N-(2-cyanopyridin-4-yl)-2-(4,4-difluoro-3-methylpiperidin-1-yl)-5-(trifluoromethyl)nicotinamide | 426.4 | 426.2 | Chiral Method H, peak 1 |

Example 156

4-(2-((3S,5R)-4,4-difluoro-3,5-dimethylpiperidin-1-yl)-5 (trifluoromethyl)nicotinamido)picolinamide

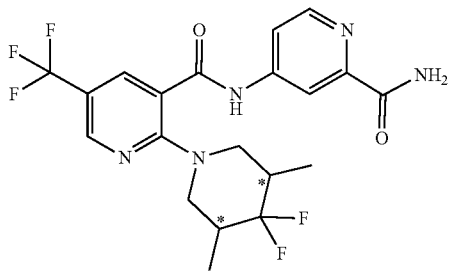 [SMILES: CC1CN(c2ncc(C(F)(F)F)cc2C(=O)Nc2ccnc(C(N)=O)c2)CC(C)C1(F)F]

Step 1: 2-chloro-N-(2-cyanopyridin-4-yl)-5-(trifluoromethyl)nicotinamide To a solution of 2-chloro-5-(trifluoromethyl)pyridine-3-carboxylic acid (1.0 g, 4.4 mmol) and 4-amino-picolinonitrile (0.53 g, 4.4 mmol) in pyridine (22 mL) at 0° C. was added POCl₃ (0.45 mL, 4.9 mmol). The mixture was stirred at 0° C. for 1 hour, then quenched with brine (saturated) and extracted with ethyl acetate. The organic layer was dried over MgSO₄, filtered and concentrated under reduced pressure to give a residue that was triturated with Et₂O. The resulting solid was collected, washed with Et₂O and dried under reduced pressure to give the title compound.

Step 2: N-(2-cyanopyridin-4-yl)-2-((3S,5R)-4,4-difluoro-3,5-dimethylpiperidin-1-yl)-5-(trifluoromethyl)nicotinamide To a solution of 2-chloro-N-(2-cyanopyridin-4-yl)-5-(trifluoromethyl)nicotinamide (90 mg, 0.28 mmol) in NMP (1.4 mL) was added 4,4-difluoro-3,5-dimethylpiperidine hydrochloride (51 mg, 0.28 mmol) and DIPEA (0.14 mL, 0.83 mmol). The mixture was heated at 70° C. for 16 h, then quenched with aqueous potassium phosphate monobasic (saturated) and extracted with ethyl acetate. The organic layer was dried over MgSO₄, filtered and concentrated under reduced pressure to give a residue that was purified by silica gel chromatography (0-100% EtOAc/hexanes) to give the title compound.

Step 3: 4-(2-((3S,5R)-4,4-difluoro-3,5-dimethylpiperidin-1-yl)-5-(trifluoromethyl)nicotinamido)-picolinamide N-(2-cyanopyridin-4-yl)-2-((3R,5S)-4,4-difluoro-3,5-dimethylpiperidin-1-yl)-5-(trifluoromethyl)nicotinamide (120 mg, 0.27 mmol) and 1 N NaOH (0.82 mL, 0.82 mmol) were combined in MeOH (1.4 mL). The mixture was heated at 70° C. for 4 hours, then quenched with water and extracted with DCM. The organic layer was dried over MgSO$_4$, filtered and concentrated under reduced pressure to give a residue that was purified by silica gel chromatography (0-100% EtOAc/hexanes) to give the title compound. LRMS m/z (M+H): calculated 458.1, observed 458.2. $^1$H NMR δ (ppm) (600 MHz, DMSO-d$_6$): 11.08 (s, 1H), 8.58 (s, 1H), 8.52 (d, J=5.4 Hz, 1H), 8.31 (s, 1H), 8.11 (d, J=2.1 Hz, 1H), 8.08 (s, 1H), 7.83 (d, J=3.7 Hz, 1H), 7.63 (s, 1H), 3.97 (d, J=13.6 Hz, 2H), 2.82 (t, J=12.5 Hz, 2H), 2.10 (s, 2H), 0.84 (d, J=6.8 Hz, 6H).

layer was washed with brine, dried over MgSO$_4$, filtered and concentrated under reduced pressure to give a residue that was purified by silica gel chromatography (0-30% ethyl acetate/hexanes) to give the title compound.

Step 2: tert-butyl ((4-(2-(4,4-difluoropiperidin-1-yl)-4-methoxynicotinamido)pyridin-2-yl)sulfonyl)carbamate To a solution of tert-butyl tert-butyl((4-(2-fluoro-4-methoxynicotinamido)pyridin-2-yl)sulfonyl)carbamate (57 mg, 0.12 mmol) in NMP (0.6 mL) was added 4,4-difluoropiperidine (15 µl, 0.13 mmol), followed by K$_2$CO$_3$ (33 mg, 0.24 mmol). The mixture was stirred at 110° C. for 4 h, then cooled to rt,

TABLE 7

The compounds of Exmples 157-158 were prepared according to a synthetic procedure similar to the synthetic procedure for Example 156.

| Example | Compound | Name | Calc'd [M + H]$^+$ | Observed [M + H]$^+$ | Conditions |
|---|---|---|---|---|---|
| 157 | | N-(2-carbamoyl-4-pyridyl)-2-[(3R or 3S)-4,4-difluoro-3-methyl-1-piperidyl]-5-(trifluoromethyl)-pyridine-3-carboxamide | 444.4 | 444.2 | Chiral Method J, peak 2 |
| 158 | | N-(2-carbamoyl-4-pyridyl)-2-[(3S or 3R)-4,4-difluoro-3-methyl-1-piperidyl]-5-(trifluoromethyl)-pyridine-3-carboxamide | 444.1 | 444.2 | Chiral Method J, peak 1 |

Example 159

2-(4,4-difluoropiperidin-1-yl)-4-methoxy-N-(2-sulfamoylpyridin-4-yl)nicotinamide

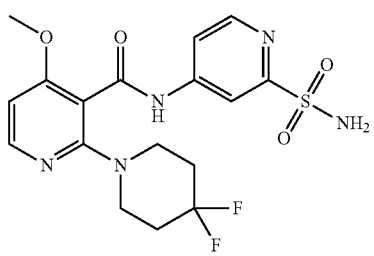 [SMILES: COc1ccnc(N2CCC(F)(F)CC2)c1C(=O)Nc1ccnc(S(N)(=O)=O)c1]

Step 1: tert-butyl tert-butyl((4-(2-fluoro-4-methoxynicotinamido)pyridin-2-yl)sulfonyl)carbamate A solution of 2-fluoro-4-methoxynicotinic acid (0.10 g, 0.58 mmol) and tert-butyl (4-aminopyridin-2-yl)sulfonyl(tert-butyl)carbamate (0.19 g, 0.58 mmol) in pyridine (2.9 mL) at 0° C. was treated with POCl$_3$ (0.060 mL, 0.64 mmol) dropwise via a syringe. The mixture was stirred at 0° C. for 1 h, then quenched with brine and diluted with EtOAc. The organic layer was acidified with 1 N HCl and extracted with EtOAc. The organic layer was dried over MgSO$_4$, filtered and concentrated under reduced pressure to give the title compound.

Step 3: 2-(4,4-difluoropiperidin-1-yl)-4-methoxy-N-(2-sulfamoylpyridin-4-yl)nicotinamide To a solution tert-butyl ((4-(2-(4,4-difluoropiperidin-1-yl)-4-methoxynicotinamido)pyridin-2-yl)sulfonyl)carbamate (0.12 g, 0.12 mmol) in DCM (0.6 mL) was added TFA (0.19 mL, 2.5 mmol). The mixture was stirred at 25° C. for 1 h, then concentrated under reduced pressure. The resulting residue was suspended in NaHCO$_3$ and extracted with EtOAc. The organic layer was dried over MgSO$_4$, filtered and concentrated under reduced pressure to give a residue that was purified by silica gel chromatography (0-50% ethyl acetate:ethanol (3:1)/hexanes) to give the title compound. LRMS m/z (M+H): calculated 428.1, observed 428.2. $^1$H NMR δ (ppm) (500 MHz, DMSO-d$_6$): 11.09 (s, 1H), 8.59 (d, J=5.5 Hz, 1H), 8.32 (s, 1H), 8.22 (d, J=5.8 Hz, 1H), 7.77 (d, J=3.5 Hz, 1H), 7.45 (s, 2H), 6.81 (d, J=5.9 Hz, 1H), 3.83 (s, 3H), 3.45-3.39 (m, 4H), 2.01-1.92 (m, 4H).

Examples 160 and 161

5-chloro-6-cyclobutyl-2-((2R,6S or 2S,6R)-2-methyl-6-(trifluoromethyl)morpholino)-N-(2-sulfamoylpyridin-4-yl)nicotinamide (160) and 5-chloro-6-cyclobutyl-2-((2S,6R or 2R,6S)-2-methyl-6-(trifluoromethyl)morpholino)-N-(2-sulfamoylpyridin-4-yl)nicotinamide (161)

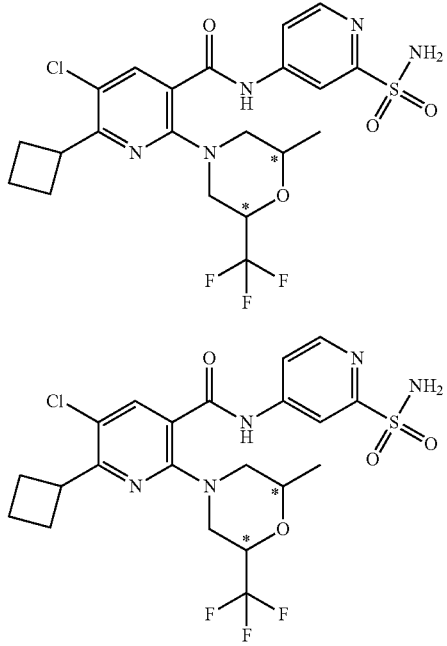

To a solution of racemic-(2R,6S and 2S,6R)-2-methyl-6-(trifluoromethyl)morpholine ((prepared similar to Intermediate 14, 0.26 mg, 1.6 mmol) in NMP (1 mL) were added 2,5-dichloro-6-cyclobutyl-N-(2-sulfamoylpyridin-4-yl)nicotinamide (Intermediate 33, 0.25 g, 0.62 mmol) and $K_2CO_3$ (0.43 g, 3.1 mmol). The mixture was stirred at 200° C. for 0.5 hour under microwave irradiation. Then the mixture was washed with water and extracted with EtOAc. The organic layer was washed with brine, dried over $Na_2SO_4$, filtered and concentrated under reduced pressure to give a residue that was purified by reverse phase chromatography (40-100% MeCN in water with 0.1% TFA, C18 column) to give a racemic mixture of 5-chloro-6-cyclobutyl-2-((2R,6S and 2S,6R)-2-methyl-6-(trifluoromethyl)morpholino)-N-(2-sulfamoylpyridin-4-yl)nicotinamide. The racemic mixture was separated by Chiral-SFC (Phenomenex-Amylose-1, 30% EtOH/$CO_2$) to give two enantiomers: enantiomer A (compound 160), and enantiomer B (compound 161). Enantiomer A (compound 160): [LRMS m/z (M+H): calculated 534.1, observed 534.3, $^1$H NMR δ (ppm) (400 MHz, $CD_3OD$): 8.57 (d, J=5.6 Hz, 1H), 8.38 (d, J=1.2 Hz, 1H), 7.82-7.87 (m, 2H), 4.40 (dd, J=7.2, 11.2 Hz, 1H), 4.18 (d, J=3.2 Hz, 1H), 4.00 (quin, J=8.4 Hz, 1H), 3.84 (dd, J=3.6, 13.2 Hz, 1H), 3.62 (dd, J=6.8, 13.2 Hz, 1H), 3.51 (dd, J=3.2, 12.8 Hz, 1H), 3.14 (dd, J=6.4, 12.8 Hz, 1H), 2.31-2.47 (m, 4H), 2.03-2.17 (m, 1H), 1.86-1.99 (m, 1H), 1.15 (d, J=6.0 Hz, 3H)]. Enantiomer B (compound 161): [LRMS m/z (M+H): calculated 534.1, observed 534.3, $^1$H NMR δ (ppm) (400 MHz, $CD_3OD$): 8.57 (d, J=5.6 Hz, 1H), 8.38 (d, J=1.6 Hz, 1H), 7.81-7.88 (m, 2H), 4.34-4.45 (m, 1H), 4.18 (d, J=3.2 Hz, 1H), 4.00 (quin, J=8.4 Hz, 1H), 3.84 (dd, J=3.6, 13.2 Hz, 1H), 3.62 (dd, J=6.4, 13.6 Hz, 1H), 3.51 (dd, J=3.2, 13.2 Hz, 1H), 3.14 (dd, J=6.4, 12.8 Hz, 1H), 2.30-2.47 (m, 4H), 2.05-2.16 (m, 1H), 1.88-1.99 (m, 1H), 1.11-1.19 (m, 1H), 1.15 (d, J=6.8 Hz, 2H)].

Examples 162 and 163

(R or S)-2-(4,4-difluoro-3-methylpiperidin-1-yl)-N-(2-sulfamoylpyridin-4-yl)-6-(trifluoromethyl)nicotinamide (162) and (S or R)-2-(4,4-difluoro-3-methylpiperidin-1-yl)-N-(2-sulfamoylpyridin-4-yl)-6-(trifluoromethyl)nicotinamide (163)

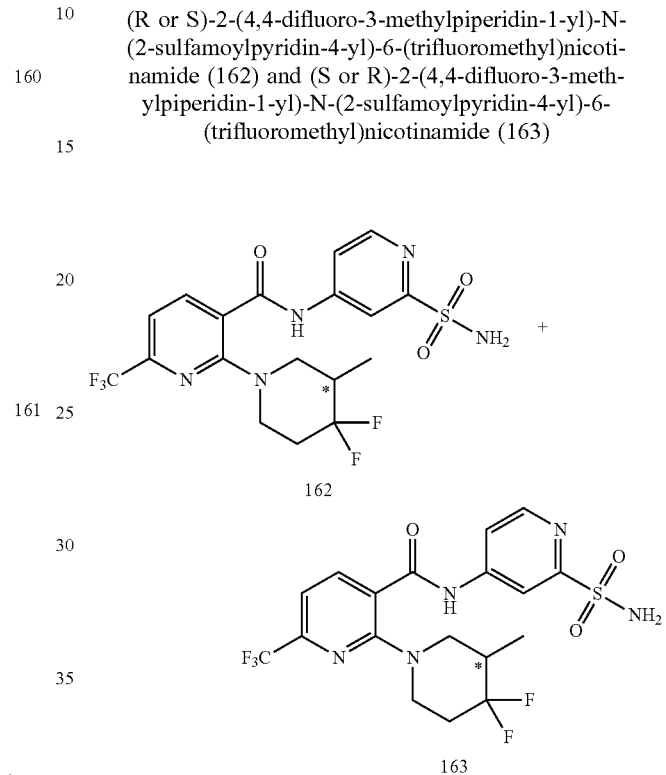

A tube was charged with 2-chloro-N-(2-sulfamoylpyridin-4-yl)-6-(trifluoromethyl)nicotinamide (Intermediate 37, 150 mg crude), racemic-4,4-difluoro-3-methylpiperidine (64 mg, 0.47 mmol), DIPEA (0.069 mL, 0.39 mmol) and NMP (2 mL). The mixture was heated to 150° C. for 10 min under microwave irradiation. Then the mixture was purified by reverse phase chromatography (43-100% MeCN in water with 0.1% TFA, C18 column) to give a racemic mixture: (R and S)-2-(4,4-difluoro-3-methylpiperidin-1-yl)-N-(2-sulfamoylpyridin-4-yl)-6-(trifluoromethyl)-nicotinamide. The racemic mixture was separated by Chiral-SFC (Phenomenex-Cellulose-2, 30% EtOH) to give two enantiomers: enantiomer A (compound 162), and enantiomer B (compound 163). Enantiomer A (compound 162): [LRMS m/z (M+H): calculated 480.1, observed 480.1, $^1$H NMR δ (ppm) (500 MHz, $CD_3OD$): 8.63 (d, J=5.5 Hz, 1H), 8.42 (d, J=1.5 Hz, 1H), 8.07 (d, J=7.5 Hz, 1H), 7.90 (dd, J=2.0, 5.5 Hz, 1H), 7.34 (d, J=7.5 Hz, 1H), 3.90-4.02 (m, 1H), 3.76-3.86 (m, 1H), 3.28-3.33 (m, 1H), 3.05 (dd, J=11.0, 13.0 Hz, 1H), 2.08-2.24 (m, 2H), 1.91-2.06 (m, 1H), 0.99 (d, J=7.0 Hz, 3H)]. Enantiomer B (compound 163): [LRMS m/z (M+H): calculated 480.1, observed 480.1, $^1$H NMR δ (ppm) (500 MHz, $CD_3OD$): 8.63 (d, J=5.5 Hz, 1H), 8.43 (d, J=1.5 Hz, 1H), 8.01-8.16 (m, 1H), 7.91 (dd, J=2.0, 5.5 Hz, 1H), 7.34 (d, J=7.5 Hz, 1H), 3.90-4.01 (m, 1H), 3.76-3.86 (m, 1H), 3.24-3.32 (m, 1H), 3.00-3.12 (m, 1H), 2.11-2.22 (m, 2H), 2.04-1.91 (m, 1H), 1.00 (d, J=7.0 Hz, 3H)].

Examples 164 and 165

(S or R)-5-chloro-2-(4,4-difluoro-3-methylpiperidin-1-yl)-N-(2-sulfamoylpyridin-4-yl)-6-(trifluoromethyl)nicotinamide (164) and (R or S)-5-chloro-2-(4,4-difluoro-3-methylpiperidin-1-yl)-N-(2-sulfamoylpyridin-4-yl)-6-(trifluoromethyl)nicotinamide (165)

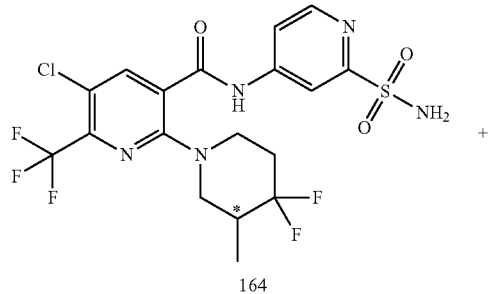

164

+

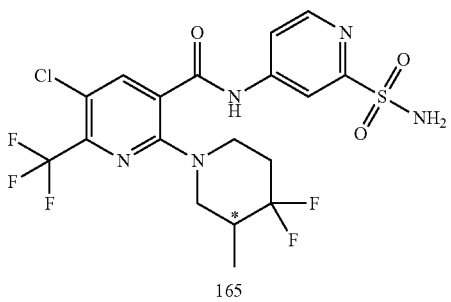

165

To a solution of 2-(4,4-difluoro-3-methylpiperidin-1-yl)-N-(2-sulfamoylpyridin-4-yl)-6-(trifluoromethyl)nicotinamide (racemic mixture of Examples 162 and 163, 0.21 g, 0.43 mmol) in acetonitrile (2.2 mL) at 25° C. was added NCS (70 mg, 0.52 mmol). The mixture was stirred at 80° C. for 2 h, then quenched with water and concentrated under reduced pressure. The resulting residue was extracted with EtOAc. The organic layer was washed with NaHCO$_3$, dried over MgSO$_4$, filtered and concentrated to give a residue that was purified by silica gel chromatography (0-60% ethyl acetate/hexanes) to give racemic mixture of (S and R)-5-chloro-2-(4,4-difluoro-3-methylpiperidin-1-yl)-N-(2-sulfamoylpyridin-4-yl)-6-(trifluoromethyl)-nicotinamide. The racemic mixture was separated by SFC (Lux-4, 15% EtOH/CO$_2$ (100 bar)) to give two enantiomers: enantiomer A (compound 164), and enantiomer B (compound 165). Enantiomer A (compound 164): [LRMS m/z (M, M+2): calculated 514.1, observed=514.2, 516.2. $^1$H NMR δ (ppm) (500 MHz, DMSO-d$_6$): 11.31 (s, 1H), 8.65 (d, J=5.4 Hz, 1H), 8.29 (s, 1H), 8.25 (s, 1H), 7.83 (d, J=5.4 Hz, 1H), 7.49 (s, 2H), 3.85-3.72 (m, 2H), 3.25-3.21 (m, 1H), 3.12-2.92 (m, 1H), 2.14 (m, 2H), 1.99 (m, 1H), 0.89 (d, J=6.8 Hz, 3H)]. Enantiomer B (compound 165): [LRMS m/z (M, M+2): calculated 514.1, observed=514.2, 516.2. $^1$H NMR δ (ppm) (500 MHz, DMSO-d$_6$): 11.31 (s, 1H), 8.65 (d, J=5.4 Hz, 1H), 8.29 (s, 1H), 8.25 (s, 1H), 7.83 (d, J=5.4 Hz, 1H), 7.49 (s, 2H), 3.85-3.72 (m, 2H), 3.25-3.21 (m, 1H), 3.12-2.92 (m, 1H), 2.14 (m, 2H), 1.99 (m, 1H), 0.89 (d, J=6.8 Hz, 3H)].

Example 166

6-cyclobutyl-2-((3S,5R)-4,4-difluoro-3,5-dimethylpiperidin-1-yl)-N-(2-sulfamoylpyridin-4-yl)nicotinamide

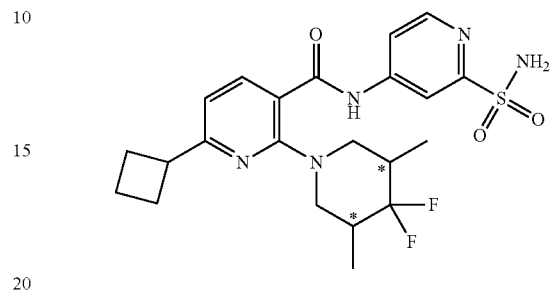

To a solution of 2-chloro-6-cyclobutyl-N-(2-sulfamoylpyridin-4-yl)nicotinamide (Intermediate 34, 50 mg crude) in NMP (2 mL) was added (3S,5R)-4,4-difluoro-3,5-dimethylpiperidine hydrochloride (38 mg, 0.20 mmol) and DIPEA (0.071 mL, 0.41 mmol). The mixture was stirred at 200° C. for 0.5 hour under microwave irradiation. Then the mixture was purified by reverse phase chromatography (Phenomenex-Amylose-1, 35% EtOH/0.1% NH$_3$H$_2$O) to give the title compound. LRMS m/z (M+H): calculated 480.2, observed 480.2. $^1$H NMR δ (ppm) (400 MHz, CD$_3$OD): 8.57 (d, J=5.6 Hz, 1H), 8.41 (d, J=1.2 Hz, 1H), 7.81-7.90 (m, 2H), 6.86 (d, J=8.0 Hz, 1H), 3.75 (d, J=12.4 Hz, 2H), 3.58-3.67 (m, 1H), 2.90 (t, J=12.4 Hz, 2H), 2.26-2.41 (m, 4H), 2.01-2.24 (m, 3H), 1.85-1.99 (m, 1H), 0.98 (d, J=6.6 Hz, 6H).

Examples 167 and 168

6-cyclobutyl-2-((2R,6S or 2S,6R)-2-methyl-6-(trifluoromethyl)morpholino)-N-(2-sulfamoylpyridin-4-yl)nicotinamide (167) and 6-cyclobutyl-2-((2S,6R or 2R,6S)-2-methyl-6-(trifluoromethyl)morpholino)-N-(2-sulfamoylpyridin-4-yl)nicotinamide (168)

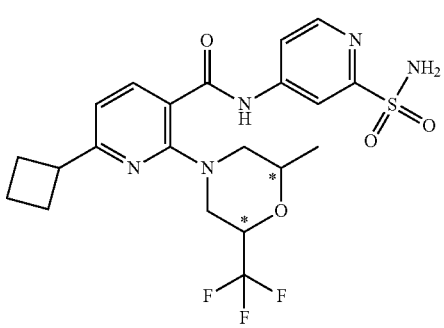

167

185

-continued

168

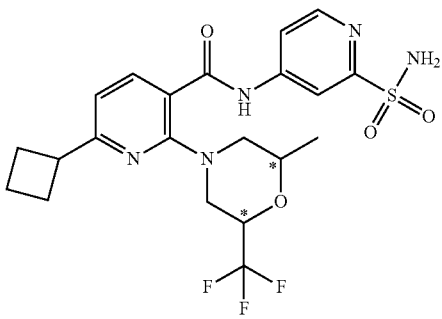

To a solution of 2-chloro-6-cyclobutyl-N-(2-sulfamoylpyridin-4-yl)nicotinamide (Intermediate 34, 90 mg, 0.24 mmol) in NMP (1.5 mL) was added DIPEA (95 mg, 0.74 mmol) and racemic-(2R,6S and 2S,6R)-2-methyl-6-(trifluoromethyl)morpholine hydrochloride (prepared similar to Intermediate 14, 0.10 g, 0.49 mmol). The mixture was stirred at 200° C. for 0.5 hour under microwave irradiation. Then the mixture was diluted with DMF and purified by reverse phase chromatography (50-100% MeCN in water with 0.1% TFA, C18 column) to give a racemic mixture of 6-cyclobutyl-2-((2R,6S and 2S,6R)-2-methyl-6-(trifluoromethyl)morpholino)-N-(2-sulfamoylpyridin-4-yl)nicotinamide. The racemic mixture was separated by SFC (Phenomenex-Amylose-1, 30% EtOH/0.1% NH$_3$*H$_2$O to give two enantiomers: enantiomer A (compound 167), and enantiomer B (compound 168). Enantiomer A (compound 167): [LRMS m/z (M+H): calculated 500.1, observed 500.2, $^1$H NMR δ (ppm) (400 MHz, CD$_3$OD): 8.56 (d, J=5.6 Hz, 1H), 8.39 (d, J=1.6 Hz, 1H), 7.84-7.86 (m, 1H), 7.81 (d, J=7.6 Hz, 1H), 6.86 (d, J=8.0 Hz, 1H), 4.31-4.47 (m, 1H), 4.14-4.20 (m, 1H), 3.82-3.86 (m, 1H), 3.60-3.68 (m, 1H), 3.54-3.59 (m, 1H), 3.45-3.49 (m, 1H), 3.08-3.14 (m, 1H), 2.32-2.37 (m, 4H), 2.00-2.18 (m, 1H), 1.84-1.98 (m, 1H), 1.14 (d, J=6.4 Hz, 3H)] and enantiomer B [LRMS m/z (M+H): calculated 500.1, observed 500.1, $^1$H NMR δ (ppm) (400 MHz, CD$_3$OD): 8.56 (d, J=5.6 Hz, 1H), 8.39 (d, J=1.6 Hz, 1H), 7.84-7.86 (m, 1H), 7.81 (d, J=8.0 Hz, 1H), 6.86 (d, J=7.6 Hz, 1H), 4.35-4.47 (m, 1H), 4.13-4.25 (m, 1H), 3.81-3.86 (m, 1H), 3.61-3.69 (m, 1H), 3.54-3.59 (m, 1H), 3.45-3.49 (m, 1H), 3.08-3.14 (m, 1H), 2.27-2.42 (m, 4H), 2.01-2.18 (m, 1H), 1.84-1.99 (m, 1H), 1.14 (d, J=6.0 Hz, 3H)].

Example 169

5-chloro-6-cyclobutyl-2-((3S,5R)-4,4-difluoro-3,5-dimethylpiperidin-1-yl)-N-(2-sulfamoylpyridin-4-yl)nicotinamide

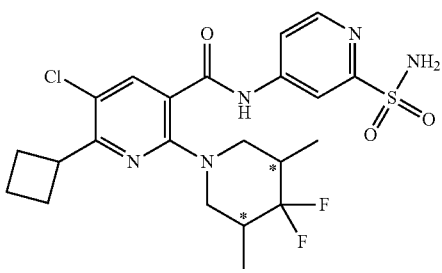 [SMILES: CC1CN(c2nc(C3CCC3)c(Cl)cc2C(=O)Nc2ccnc(S(N)(=O)=O)c2)CC(C)C1(F)F]

186

To a solution of 2,5-dichloro-6-cyclobutyl-N-(2-sulfamoylpyridin-4-yl)nicotinamide (Intermediate 33, 80 mg, 0.20 mmol) in NMP (1 mL) was added (3S,5R)-4,4-difluoro-3,5-dimethylpiperidine hydrochloride (74 mg, 0.50 mmol) and K$_2$CO$_3$ (0.14 g, 1.0 mmol). The mixture was stirred at 200° C. for 0.5 h under microwave irradiation. Then the mixture was washed with water and extracted with EtOAc. The combined organic layers were washed with brine, dried over Na$_2$SO$_4$, filtered and concentrated under reduced pressure to give a residue that was purified by reverse phase chromatography (55-100% MeCN in water with 0.1% TFA, C18 column), followed by SFC (Phenomenex-Amylose-1, 30% EtOH, 0.1% NH$_3$H$_2$O) to give the title compound. LRMS m/z (M+H): calculated 514.1, observed 514.3. $^1$H NMR δ (ppm) (400 MHz, CD$_3$OD): 8.58 (d, J=5.2 Hz, 1H), 8.39 (d, J=1.6 Hz, 1H), 7.82-7.88 (m, 2H), 3.95-4.03 (m, 1H), 3.78 (d, J=12.4 Hz, 2H), 2.92 (t, J=12.8 Hz, 2H), 2.32-2.44 (m, 4H), 2.06-2.21 (m, 3H), 1.94 (br s, 1H), 0.98 (d, J=7.2 Hz, 6H).

Example 170

6-chloro-2-(4,4-difluoropiperidin-1-yl)-4-methyl-N-(2-sulfamoylpyridin-4-yl)nicotinamide

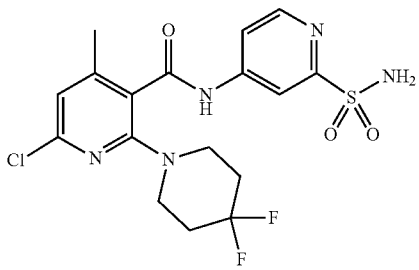 [SMILES: Cc1cc(Cl)nc(N2CCC(F)(F)CC2)c1C(=O)Nc1ccnc(S(N)(=O)=O)c1]

Step 1: N-(2-(N,N-bis(2,4-dimethoxybenzyl)sulfamoyl)pyridin-4-yl)-6-chloro-2-(4,4-difluoropiperidin-1-yl)-4-methylnicotinamide A mixture of tBu Xphos Pd G3 (0.12 g, 0.14 mmol), 6-chloro-2-(4,4-difluoropiperidin-1-yl)-4-methylnicotinamide (Intermediate 27, 0.42 g, 1.5 mmol), sodium 2-methylpropan-2-olate (0.28 g, 2.9 mmol), 4-bromo-N,N-bis(2,4-dimethoxybenzyl)pyridine-2-sulfonamide (1.0 g, 1.9 mmol) and THF (6 mL) at 20° C. was sparged with a stream of nitrogen for 1 min. The tube was sealed and heated to 70° C. for 10 h. Then the mixture was cooled to rt, quenched with water and extracted with EtOAc. The combined organic layers were washed with brine, dried over anhydrous Na$_2$SO$_4$, filtered and concentrated under reduced pressure to give a residue that was purified by silica gel chromatography (0-30% ethyl acetate/petroleum ether) to give the title compound.

Step 2: 6-chloro-2-(4,4-difluoropiperidin-1-yl)-4-methyl-N-(2-sulfamoylpyridin-4-yl)-nicotinamide To a mixture of N-(2-(N,N-bis(2,4-dimethoxybenzyl)sulfamoyl)pyridin-4-yl)-6-chloro-2-(4,4-difluoropiperidin-1-yl)-4-methylnicotinamide (0.45 g, 0.60 mmol) in DCM (4 mL) was added TFA (2 mL). The mixture was stirred at 15° C. for 16 h. Then the mixture was purified by reverse phase chromatography (20-50% MeCN in 0.05% NH$_4$OH, C18 column) to give the title compound. LRMS m/z (M+H): calculated 446.1, observed 446.2. $^1$H NMR δ (ppm) (500 MHz, CD$_3$OD): 8.59 (d, J=5.5 Hz, 1H), 8.39 (d, J=2.0 Hz, 1H), 7.84 (dd, J=2.0, 5.5 Hz, 1H), 6.92 (s, 1H), 3.44-3.54 (m, 4H), 2.33 (s, 3H), 1.86-2.01 (m, 4H).

Example 171

2-(4,4-difluoroazepan-1-yl)-5-(difluoromethoxy)-N-(2-sulfamoylpyridin-4-yl)nicotinamide

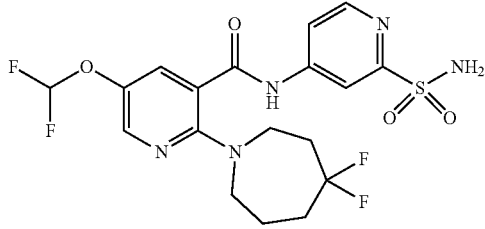 [SMILES: NS(=O)(=O)c1cc(NC(=O)c2cc(OC(F)F)cnc2N2CCCC(F)(F)CC2)ccn1]

Step 1: 5-bromo-2-(4,4-difluoroazepan-1-yl)nicotinonitrile To a solution of 5-bromo-2-chloronicotinonitrile (3.0 g, 14 mmol) in NMP (20 mL) were added 4,4-difluoroazepane (2.8 g, 21 mmol) and DIPEA (5.5 mL, 41 mmol). The mixture was stirred at 50° C. for 10 hours. Then the mixture was diluted in water and extracted with ethyl acetate. The combined organic layers were washed with brine, dried over anhydrous $Na_2SO_4$, filtered and concentrated to give a residue that was purified by silica gel chromatography (15% EtOAc) to give the title compound.

Step 2: (5-cyano-6-(4,4-difluoroazepan-1-yl)pyridin-3-yl)boronic acid A mixture of 5-bromo-2-(4,4-difluoroazepan-1-yl)nicotinonitrile (1.5 g, 4.7 mmol), $PdCl_2$(dppf) (0.35 g, 0.47 mmol)), bis(pinacolato)-diboron (2.4 g, 9.5 mmol) and potassium acetate (0.93 g, 9.5 mmol) in dioxane (20 mL) was degassed and backfilled with nitrogen three times. The mixture was heated to 80° C. for 2 h. Then the mixture was cooled to rt, filtered and concentrated to give the title compound.

Step 3: 2-(4,4-difluoroazepan-1-yl)-5-hydroxynicotinonitrile To a mixture of (5-cyano-6-(4,4-difluoroazepan-1-yl)pyridin-3-yl)boronic acid (1.7 g, 4.6 mmol) in THF (10 mL) and water (10 mL) was added aqueous KOH (0.26 g, 4.6 mmol) at 0° C., followed by $H_2O_2$ (0.40 mL, 4.6 mmol). The mixture was stirred at 20° C. for 2 hours. Then the mixture was quenched with aqueous sodium thiosulfate solution, acidified to pH=6 with aqueous hydrochloric acid (1.2 N), diluted with water and extracted with EtOAc. The combined organic layers were washed with brine, dried over anhydrous $Na_2SO_4$, filtered and concentrated to give a residue that was purified by silica gel chromatography (0-26% ethyl acetate/PE gradient) to give the title compound.

Step 4: 2-(4,4-difluoroazepan-1-yl)-5-(difluoromethoxy) nicotinonitrile 2-(4,4-difluoroazepan-1-yl)-5-hydroxynicotinonitrile (1.0 g, 4.0 mmol), $K_2CO_3$ (1.1 g, 7.9 mmol) and sodium chloro-difluoroacetate (1.2 g, 7.9 mmol) in DMF (10 mL) and water (2 mL) was stirred at 110° C. for 10 h. The mixture was diluted with water and extracted with EtOAc. The organic layers were washed with brine, dried over anhydrous $Na_2SO_4$, filtered and concentrated to give a residue that was purified by silica gel chromatography (0-25% ethyl acetate/PE) to give the title compound.

Step 5: 2-(4,4-difluoroazepan-1-yl)-5-(difluoromethoxyl) nicotinamide To a mixture of 2-(4,4-difluoroazepan-1-yl)-5-(difluoromethoxy)nicotinonitrile (0.25 g, 0.82 mmol) in DMSO (5 mL) was added $K_2CO_3$ (0.23 g, 1.6 mmol), followed by $H_2O_2$ (3.0 mL, 34 mmol). The mixture was stirred at 35° C. for 1 hour, then diluted with water and extracted with EtOAc. The combined organic layers were washed with brine, dried over anhydrous $Na_2SO_4$, filtered and concentrated to give a residue that was purified by silica gel chromatography (PE/EtOAc=1:1) to give the title compound.

Step 6: N-(2-(N,N-bis(2,4-dimethoxybenzyl)sulfamoyl) pyridin-4-yl)-2-(4,4-difluoroazepan-1-yl)-5-(difluoromethoxy)nicotinamide A mixture of 2-(4,4-difluoroazepan-1-yl)-5-(difluoro-methoxy)nicotinamide (0.10 g, 0.31 mmol), 5-bromo-N,N-bis(2,4-dimethoxybenzyl)pyridine-3-sulfonamide (0.25 g, 0.47 mmol), sodium 2-methylpropan-2-olate (90 mg, 0.93 mmol) and tBuXphos (21 mg, 0.031 mmol) in THF (4 mL) was degassed and backfilled with nitrogen three times. The mixture was heated to 70° C. for 10 hour. Then the mixture was cooled to rt, filtered and concentrated under reduced pressure. The resulting residue was purified by silica gel chromatography (petroleum ether/ethyl acetate=1/1) to give the title compound.

Step 7: 2-(4,4-difluoroazepan-1-yl)-5-(difluoromethoxy)-N-(2-sulfamoylpyridin-4-yl)nicotinamide A solution of N-(2-(N,N-bis(2,4-dimethoxybenzyl)sulfamoyl)pyridin-4-yl)-2-(4,4-difluoroazepan-1-yl)-5-(difluoromethoxy)nicotinamide (0.21 g, 0.24 mmol) in TFA (2 mL) and DCM (2 mL) was stirred at 20° C. for 1 hour. The mixture was concentrated under reduced pressure and purified by reverse phase chromatography (35-100% MeCN in water with 0.1% TFA, C18 column) to give the title compound. LRMS m/z (M+H): calculated 478.1, observed 478.2. $^1$H NMR δ (ppm) (400 MHz, $CD_3OD$): 8.56 (d, J=5.2 Hz, 1H), 8.38 (d, J=2.0 Hz, 1H), 8.16 (d, J=2.8 Hz, 1H), 7.86-7.88 (m, 1H), 7.69 (d, J=2.8 Hz, 1H), 6.50-6.97 (m, 1H), 3.66-3.74 (m, 2H), 3.42 (t, J=5.6 Hz, 2H), 2.24-2.39 (m, 2H), 1.85-2.02 (m, 4H).

Example 172

5-chloro-2-(4,4-difluoroazepan-1-yl)-6-methyl-N-(2-sulfamoylpyridin-4-yl)nicotinamide

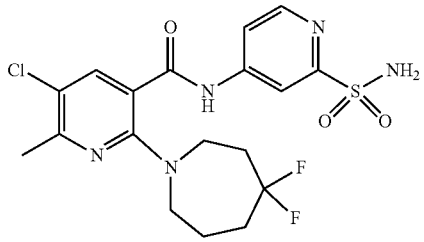 [SMILES: Cc1nc(N2CCCC(F)(F)CC2)c(C(=O)Nc2ccnc(S(N)(=O)=O)c2)cc1Cl]

Step 1: 2-(4,4-difluoroazepan-1-yl)-6-methylnicotinonitrile To a solution of 2-chloro-6-methylnicotinonitrile (1.0 g, 6.5 mmol) and 4,4-difluoroazepane (1.2 g, 8.5 mmol) in NMP (10 mL) was added triethylamine (2.0 g, 20 mmol). The mixture was stirred at 130° C. for 2 hours, then diluted in water and extracted with EtOAc. The combined organic layers were washed with brine, dried over $Na_2SO_4$, filtered and concentrated under reduced pressure to give a residue that was purified by silica gel chromatography (petroleum ether:ethyl acetate=5:1) to give the title compound.

Step 2: 5-chloro-2-(4,4-difluoroazepan-1-yl)-6-methylnicotinonitrile To a mixture of NCS (0.40 g, 3.0 mmol) and 2-(4,4-difluoroazepan-1-yl)-6-methylnicotinonitrile (0.50 g, 2.0 mmol) was added a drop of acetic acid in DMF (5 mL). The mixture was stirred at 20° C. for 12 hours. Then the mixture was washed with water and extracted with EtOAc. The combined organic layers were washed with brine, dried over $Na_2SO_4$, filtered and concentrated under reduced pressure to give a residue that was purified by silica gel chromatography (petroleum ether:ethyl acetate=5:1) to give the title compound.

Step 3: 5-chloro-2-(4,4-difluoroazepan-1-yl)-6-methylnicotinamide To a solution of 5-chloro-2-(4,4-difluoroazepan-1-yl)-6-methylnicotinonitrile (0.32 g, 1.1 mmol) in DMSO (8 mL) was added potassium hydroxide (0.25 g, 4.5 mmol) and hydrogen peroxide (0.38 g, 11 mmol). The mixture was stirred at 15° C. for 2 hours. Then the mixture was diluted with water and extracted with EtOAc. The combined organic layers were dried over anhydrous Na$_2$SO$_4$, filtered and concentrated to give a residue that was purified by silica gel chromatography (0-20% EtOAc/petroleum ether) to give the title compound.

Step 4: N-(2-(N,N-bis(2,4-dimethoxybenzyl)sulfamoyl)pyridin-4-yl)-5-chloro-2-(4,4-difluoroazepan-1-yl)-6-methylnicotinamide To a solution of 5-chloro-2-(4,4-difluoroazepan-1-yl)-6-methylnicotinamide (0.45 g, 1.5 mmol) in dioxane (1.5 mL) was added Cs$_2$CO$_3$ (1.4 g, 4.4 mmol), 5-bromo-N,N-bis(2,4-dimethoxybenzyl)pyridine-3-sulfonamide (1.2 g, 2.2 mmol) and XantPhos-Pd-G2 (0.13 g, 0.15 mmol). The reaction mixture was degassed and backfilled with nitrogen three times then stirred at 100° C. for 13 hours. Then the mixture was diluted with water and extracted with EtOAc. The organic layers were washed with brine, dried over anhydrous Na$_2$SO$_4$, filtered and concentrated under reduced pressure to give a residue that was purified by silica gel chromatography (petroleum ether:ethyl acetate=1:1) to give the title compound.

Step 5: 5-chloro-2-(4,4-difluoroazepan-1-yl)-6-methyl-N-(2-sulfamoylpyridin-4-yl)nicotinamide To a solution of N-(2-(N,N-bis(2,4-dimethoxybenzyl)sulfamoyl)pyridin-4-yl)-5-chloro-2-(4,4-difluoroazepan-1-yl)-6-methylnicotinamide (0.45 g, 0.59 mmol) in DCM (10 mL) was added TFA (3 mL). The mixture was stirred at 12° C. for 12 hours. Then the mixture was filtered and purified by reverse phase chromatography (30-100% MeCN in water with 0.1% TFA, C18 column) to give the title compound. LRMS m/z (M+H): calculated 460.1, observed 460.0. $^1$H NMR δ (ppm) (400 MHz, CD$_3$OD): 8.56 (d, J=5.4 Hz, 1H), 8.38 (d, J=1.6 Hz, 1H), 7.85 (dd, J=2.0, 5.4 Hz, 1H), 7.76 (s, 1H), 3.68-3.73 (m, 2H), 3.40 (t, J=5.6 Hz, 2H), 2.50 (s, 3H), 2.27-2.40 (m, 2H), 1.88-2.04 (m, 4H).

Example 173

4-(4,4-difluoroazepan-1-yl)-2-methyl-N-(2-sulfamoylpyridin-4-yl)pyrimidine-5-carboxamide

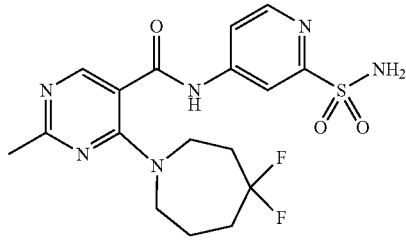 [SMILES: Cc1ncc(C(=O)Nc2ccnc(S(N)(=O)=O)c2)c(N2CCCC(F)(F)CC2)n1]

Step 1: 4-(4,4-difluoroazepan-1-yl)-2-methylpyrimidine-5-carbonitrile To a stirred solution of 4-chloro-2-methylpyrimidine-5-carbonitrile (0.24 g, 1.6 mmol) and 4,4-difluoroazepane hydrochloride (0.32 g, 1.9 mmol) in DMF (4 mL) was added DIPEA (0.9 mL, 5.2 mmol) at 20° C. The mixture was stirred at 80° C. for 12 h, then diluted with EtOAc. The organic layer was washed with water, brine, dried over anhydrous sodium sulfate, filtered and concentrated under reduced pressure to give the title compound.

Step 2: 4-(4,4-difluoroazepan-1-yl)-2-methylpyrimidine-5-carboxamide To a stirred solution of 4-(4,4-difluoroazepan-1-yl)-2-methylpyrimidine-5-carbonitrile (0.10 g, 0.40 mmol) and potassium carbonate (0.16 g, 1.2 mmol) in DMSO (4 mL) was added hydrogen peroxide (0.45 g, 4.0 mmol). The mixture was stirred at 20° C. for 2 h, then diluted with EtOAc. The organic layer was washed with water, saturated Na$_2$SO$_3$ aqueous solution, brine, dried over anhydrous sodium sulfate, filtered and concentrated under reduced pressure to give the title compound.

Step 3: N-(2-(N,N-bis(2,4-dimethoxybenzyl)sulfamoyl)pyridin-4-yl)-4-(4,4-difluoroazepan-1-yl)-2-methylpyrimidine-5-carboxamide A mixture of 4-(4,4-difluoroazepan-1-yl)-2-methylpyrimidine-5-carboxamide (30 mg, crude), 4-bromo-N,N-bis(2,4-dimethoxybenzyl)-pyridine-2-sulfonamide (66 mg, 0.12 mmol), Cs$_2$CO$_3$ (0.11 g, 0.33 mmol), and XantPhos-Pd-G2 (10 mg, 0.011 mmol) in dioxane (2.0 mL) was degassed and backfilled with nitrogen three times. The mixture was heated to 100° C. for 12 h, then cooled to 20° C. and diluted with EtOAc. The organic layer was washed with brine, dried over anhydrous sodium sulfate, filtered and concentrated under reduced pressure to give the title compound.

Step 4: 4-(4,4-difluoroazepan-1-yl)-2-methyl-N-(2-sulfamoylpyridin-4-yl)pyrimidine-5-carboxamide To a stirred solution of N-(2-(N,N-bis(2,4-dimethoxybenzyl)sulfamoyl)pyridin-4-yl)-4-(4,4-difluoroazepan-1-yl)-2-methylpyrimidine-5-carboxamide (60 mg crude) in DCM (4 mL) was added TFA (1 mL). The mixture was stirred at 20° C. for 2 h, then the solvent was removed under reduced pressure to give a residue that was purified by reverse phase chromatography (63-100% MeCN in water with 0.1% TFA, C18 column) to give the title compound. LRMS m/z (M+H): calculated 427.1, observed 427.1. $^1$H NMR δ (ppm) (400 MHz, CD$_3$OD): 8.61 (s, 2H), 8.35 (d, J=2.0 Hz, 1H), 7.85 (dd, J=5.6, 2.0 Hz, 1H), 3.98 (br s, 2H), 3.67 (br s, 2H), 2.64 (s, 3H), 2.37 (br s, 2H), 1.97-2.10 (m, 4H).

Example 174

2-(4,4-difluoroazepan-1-yl)-6-(difluoromethyl)-N-(2-sulfamoylpyridin-4-yl)nicotinamide

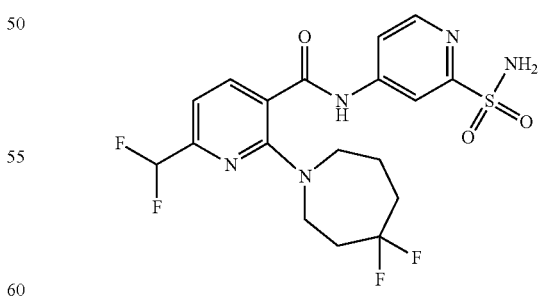

Step 1: (Z)-4-ethoxy-1,1-difluorobut-3-en-2-one A mixture of ethoxyethene (2.0 g, 28 mmol), N,N-dimethylpyridin-4-amine (0.20 g, 1.7 mmol) and 2,2-difluoroacetic anhydride (4.8 g, 28 mmol) in dichloromethane (50 mL) was stirred at 20° C. for 16 h. Then the mixture was dissolved in water and extracted with dichloromethane. The combined organic layers were washed with brine, dried over anhydrous Na$_2$SO$_4$, filtered and concentrated under reduced pressure to give a residue that was purified by silica gel chromatography (0-30% ethyl acetate/petroleum ether) to give the title compound.

Step 2: 6-(difluoromethyl)-2-hydroxynicotinonitrile (Z)-4-ethoxy-1,1-difluorobut-3-en-2-one (2.5 g, 17 mmol), 2-cyanoacetamide (2.1 g, 25 mmol) and sodium ethanolate (1.2 g, 18 mmol) were added to EtOH (20 mL). The mixture was heated to 90° C. for 12 h. Then the mixture was concentrated to give the title compound.

Step 3: 2-(4,4-difluoroazepan-1-yl)-6-(difluoromethyl) nicotinonitrile A mixture of 1,8-diazabicyclo[5.4.0]undec-7-ene (1.8 g, 12 mmol), 6-(difluoromethyl)-2-hydroxynicotinonitrile (1 g crude), 6-(difluoromethyl)-2-hydroxynicotinonitrile (1 g crude), benzotriazol-1-yloxytris-(dimethylamino)phosphonium hexafluorophosphate (0.52 g, 1.2 mmol) and 4,4-difluoroazepane hydrochloride (0.30 g, 1.8 mmol) in acetonitrile (2 mL) was stirred at 20° C. for 16 h. Then the mixture was purified by silica gel chromatography (petroleum ether/ethyl acetate=10/1) to give the title compound.

Step 4: 2-(4,4-difluoroazepan-1-yl)-6-(difluoromethyl) nicotinamide A mixture of K$_2$CO$_3$ (87 mg, 0.63 mmol), 2-(4,4-difluoroazepan-1-yl)-6-(difluoromethyl)nicotinonitrile (60 mg, 0.21 mmol) and hydrogen peroxide (120 mg, 1.0 mmol) in DMSO (1 mL) was stirred at 20° C. for 2 h. Then the mixture was diluted in water and saturated Na$_2$SO$_3$ and extracted with EtOAc. The combined organic layers were washed with brine, dried over anhydrous Na$_2$SO$_4$, filtered and concentrated under reduced pressure to give the title compound.

Step 5: N-(2-(N,N-bis(2,4-dimethoxybenzyl)sulfamoyl) pyridin-4-yl)-2-(4,4-difluoroazepan-1-yl)-6-(difluoromethyl)nicotinamide A mixture of 4-bromo-N,N-bis (2,4-dimethoxybenzyl)-pyridine-2-sulfonamide (92 mg, 0.17 mmol), XantPhos Pd G2 (10 mg, 0.011 mmol), Cs$_2$CO$_3$ (110 mg, 0.34 mmol) and 2-(4,4-difluoroazepan-1-yl)-6-(difluoromethyl)nicotinamide (35 mg, 0.12 mmol) in dioxane (2 mL) was degassed and backfilled with nitrogen three times. The mixture was heated to 100° C. for 6 h. Then the mixture was purified by silica gel chromatography (petroleum ether/ethyl acetate=2/1) to give the title compound.

Step 6: 2-(4,4-difluoroazepan-1-yl)-6-(difluoromethyl)-N-(2-sulfamoylpyridin-4-yl)nicotinamide A mixture of N-(2-(N,N-bis(2,4-dimethoxybenzyl)sulfamoyl)pyridin-4-yl)-2-(4,4-difluoro-azepan-1-yl)-6-(difluoromethyl)nicotinamide (22 mg, 0.029 mmol) in dichloromethane (1 mL) and TFA (1 mL) was stirred at 20° C. for 2 h. Then solvent was concentrated under reduced pressure to give a residue that was purified by reverse phase chromatography (20-50% MeCN in water with 0.05% NH$_4$OH, C18 column) to give the title compound. LRMS m/z (M+H): calculated 462.1, observed 462.2. $^1$H NMR δ (ppm) (500 MHz, CD$_3$OD): 8.52-8.62 (m, 1H), 8.39 (d, J=2.0 Hz, 1H), 7.94 (d, J=7.5 Hz, 1H), 7.88 (dd, J=2.0, 5.5 Hz, 1H), 7.04 (d, J=7.6 Hz, 1H), 6.40-6.71 (m, 1H), 3.75 (dd, J=2.5, 5.5 Hz, 2H), 3.46 (t, J=5.5 Hz, 2H), 2.24-2.41 (m, 2H), 1.87-2.03 (m, 4H).

Example 175

2-(4,4-difluoropiperidin-1-yl)-N-(2-sulfamoylpyridin-4-yl)-5-(trifluoromethyl) nicotinamide

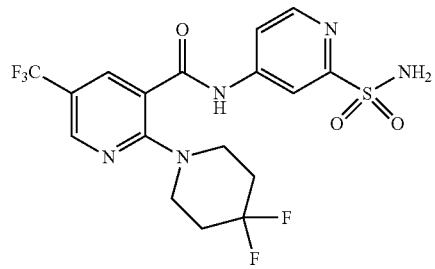 [SMILES: NS(=O)(=O)c1cc(NC(=O)c2cc(C(F)(F)F)cnc2N2CCC(F)(F)CC2)ccn1]

Step 1: tert-butyl tert-butyl((4-(2-(4,4-difluoropiperidin-1-yl)-5-(trifluoromethyl)nicotinamido) pyridin-2-yl)sulfonyl)carbamate A mixture of 2-(4,4-difluoropiperidin-1-yl)-5-(trifluoro-methyl)nicotinamide (Intermediate 20, 38 g, 123 mmol), tert-butyl (4-bromopyridin-2-yl)sulfonyl(tert-butyl) carbamate (51 g, 130 mmol), Brettphos-Pd-G3 (1.1 g, 1.2 mmol), cesium carbonate (60 g, 180 mmol) and dioxane was degassed with nitrogen sparge. The mixture was heated to 90° C. for 1 h. Then the mixture was cooled to rt, diluted in EtOAc and filtered. The organic layer was washed with citric acid, brine, dried over Na$_2$SO$_4$, filtered and concentrated to give the title compound.

Step 2: 2-(4,4-difluoropiperidin-1-yl)-N-(2-sulfamoylpyridin-4-yl)-5-(trifluoromethyl) nicotinamide To a solution of tert-butyl tert-butyl((4-(2-(4,4-difluoropiperidin-1-yl)-5-(trifluoromethyl) nicotinamido)pyridin-2-yl)sulfonyl)carbamate (80 g, 103 mmol) in DCM was added dropwise sulfuric acid (80 mL, 103 mmol). The mixture was stirred at rt for 1 h. Then the mixture was decanted into a solution of NH$_4$HCO$_3$, and filtered. The filtrate was extracted with DCM. The organic layer was evaporated and combined with filter cake. The resulting solid was dissolved in AcCN at 60° C., then water was added and the AcCN evaporated off, and the mixture was filtered to give the title compound. LRMS m/z (M+H): calculated 466.1, observed 466.0 (and 504 [M+K]). $^1$H NMR δ (ppm) (400 MHz, DMSO-d$_6$): 11.22 (1H, s), 8.64 (2H, d), 8.32 (1H, d), 8.18 (1H, d), 7.87 (1H, m), 7.47 (2H, s), 3.63 (4H, m), 2.12-1.98 (4H, m).

Example 176

4-(2-(4,4-difluoropiperidin-1-yl)-5-(trifluoromethyl) nicotinamido)pyridine-2-sulfonic acid

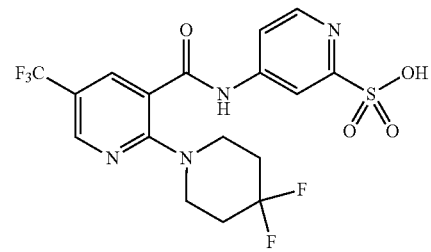 [SMILES: O=C(Nc1ccnc(S(=O)(=O)O)c1)c1cc(C(F)(F)F)cnc1N1CCC(F)(F)CC1]

To a vial of 2-(4,4-difluoropiperidin-1-yl)-N-(2-sulfamoylpyridin-4-yl)-5-(trifluoromethyl)-nicotinamide (Example 175, 80 mg, 0.17 mmol), potassium carbonate (47 mg, 0.34 mmol), 2-mesityl-2,5,6,7-tetrahydropyrrolo[2,1-c][1,2,4]triazol-4-ium chloride (2.3 mg, 8.6 µmol) and water (0.16 mL, 8.6 mmol) were added DMF (0.86 mL) and benzaldehyde (21 µl, 0.21 mmol). The vial was sealed and heated at 80° C. for 16 h. Then the mixture was concentrated under reduced pressure and purified by reverse phase chromatography (10%-100% MeCN in water with 0.1% TFA, C18 column) to give the title compound. LRMS m/z (M+H): calculated 466.4, observed 466.7. $^1$H NMR δ (ppm) (500 MHz, $CD_3OD$): 8.55 (s, 1H), 8.49 (s, 1H), 8.19 (s, 1H), 8.10 (s, 1H), 7.92 (s, 1H), 3.70-3.63 (m, 4H), 2.04 (tt, J=13.6, 5.6 Hz, 4H).

Example 177

2-(4,4-difluoroazepan-1-yl)-N-(2-sulfamoylpyridin-4-yl)-5-(trifluoromethoxy)nicotinamide

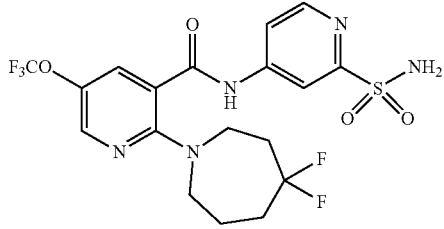 [SMILES: NS(=O)(=O)c1cc(NC(=O)c2cc(OC(F)(F)F)cnc2N2CCCC(F)(F)CC2)ccn1]

Step 1: 4,4-difluoro-1-(5-(trifluoromethoxy)pyridin-2-yl)azepane To a solution of 2-bromo-5-(trifluoromethoxy)pyridine (0.30 g, 1.2 mmol) in THF (3 mL) was added 4,4-difluoroazepane (0.25 g, 1.9 mmol), sodium 2-methylpropan-2-olate (0.36 g, 3.7 mmol) and Brettphos-Pd-G3 (0.17 g, 1.2 mmol) at 25° C. under a nitrogen atmosphere. The mixture was stirred at 60° C. for 12 h. Then the mixture was diluted with water and extracted with EtOAc. The combined organic layers were washed with brine, dried over $Na_2SO_4$, filtered and concentrated under reduced pressure to give a residue that was purified by silica gel column chromatography (5-20% petroleum ether/ethyl acetate) to give the title compound.

Step 2: 1-(3-bromo-5-(trifluoromethoxy)pyridin-2-yl)-4,4-difluoroazepane To a solution of 4,4-difluoro-1-(5-(trifluoromethoxy)pyridin-2-yl)azepane (0.20 g, 0.67 mmol) in DCM (3 mL) was added NBS (0.12 g, 0.67 mmol). The mixture was stirred at 20° C. for 10 h. Then the mixture was diluted with water and extracted with EtOAc. The combined organic layers were washed with brine, dried over $Na_2SO_4$, filtered and concentrated under reduced pressure to give a residue that was purified by silica gel column chromatography (5-20% petroleum ether/ethyl acetate) to give the title compound.

Step 3: 2-(4,4-difluoroazepan-1-yl)-5-(trifluoromethoxy)nicotinonitrile A solution of 1-(3-bromo-5-(trifluoromethoxy)pyridin-2-yl)-4,4-difluoroazepane (0.12 g, 0.32 mmol) in NMP (3 mL) was added $Zn(CN)_2$ (0.19 g, 1.6 mmol), $Pd(tBu_3P)_2$ (16 mg, 0.032 mmol) at 20° C. was degassed and backfilled with nitrogen three times, then the tube was sealed. The mixture was heated at 140° C. under microwave irradiation for 40 minutes. Then the mixture was dissolved in water and extracted with EtOAc. The combined organic layers were washed with brine, dried over anhydrous $Na_2SO_4$, filtered and concentrated to give a residue that was purified by silica gel chromatography (10% PE/ethyl acetate) to give the title compound.

Step 4: 2-(4,4-difluoroazepan-1-yl)-5-(trifluoromethoxy)nicotinamide To a solution of 2-(4,4-difluoroazepan-1-yl)-5-(trifluoromethoxy)nicotinonitrile (80 mg, 0.25 mmol) in DMSO (3 mL) was added $K_2CO_3$ (0.10 g, 0.75 mmol) and hydrogen peroxide (0.5 mL, 0.25 mmol). The mixture was stirred at 20° C. for 2 h. The mixture was quenched with aqueous $Na_2SO_3$, diluted with water and extracted with EtOAc. The organic layers were washed with brine, dried over $Na_2SO_4$, filtered and concentrated under reduced pressure to give a residue that was purified by silica gel chromatography (50% PE/ethyl acetate) to give the title compound.

Step 5: N-(2-(N,N-bis(2,4-dimethoxybenzyl)sulfamoyl)pyridin-4-yl)-2-(4,4-difluoroazepan-1-yl)-5-(trifluoromethoxy)nicotinamide To a solution of 2-(4,4-difluoroazepan-1-yl)-5-(trifluoromethoxy)nicotinamide (30 mg, 0.088 mmol) in dioxane (2 mL) was added 4-bromo-N,N-bis(2,4-dimethoxybenzyl)pyridine-2-sulfonamide (52 mg, 0.097 mmol), cesium carbonate (86 mg, 0.26 mmol) and Brettphos-Pd-G3 (80 mg, 0.088 mmol) at 20° C. under an atmosphere of nitrogen. The mixture was stirred at 100° C. for 12 h. Then the mixture was diluted in water and extracted with EtOAc. The organic layers were washed with brine, dried over $Na_2SO_4$, filtered and concentrated under reduced pressure to give a residue that was purified by silica gel chromatography (50% petroleum ether/ethyl acetate) to give the title compound.

Step 6: 2-(4,4-difluoroazepan-1-yl)-N-(2-sulfamoylpyridin-4-yl)-5-(trifluoromethoxy)-nicotinamide To a solution of N-(2-(N,N-bis(2,4-dimethoxybenzyl)sulfamoyl)pyridin-4-yl)-2-(4,4-difluoroazepan-1-yl)-5-(trifluoromethoxy)nicotinamide (30 mg, 0.038 mmol) in DCM (2 mL) was added TFA (1 mL). The mixture was stirred at 20° C. for 10 h then filtered and concentrated under reduced pressure to give a residue that was purified by reversed phase chromatography (MeCN in water with 0.1% TFA, C18 column) to give the title compound. LRMS m/z (M+H): calculated 496.1, observed 496.2. $^1$H NMR δ (ppm) (400 MHz, $CD_3OD$): 8.56 (d, J=5.6 Hz, 1H), 8.37 (d, J=1.6 Hz, 1H), 8.24 (d, J=2.0 Hz, 1H), 7.87 (dd, J=5.6, 2.0 Hz, 1H), 7.78 (d, J=2.0 Hz, 1H), 3.67-3.77 (m, 2H), 3.43 (t, J=5.6 Hz, 2H), 2.24-2.40 (m, 2H), 1.86-2.08 (m, 4H).

Example 178

2-(4,4-difluoropiperidin-1-yl)-5-fluoro-6-methyl-N-(2-sulfamoylpyridin-4-yl)nicotinamide

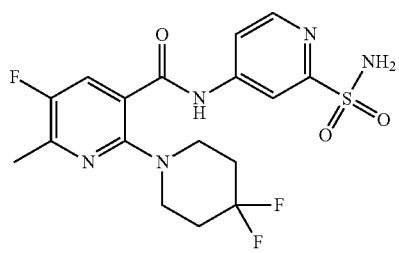 [SMILES: Cc1nc(N2CCC(F)(F)CC2)c(C(=O)Nc2ccnc(S(N)(=O)=O)c2)cc1F]

Step 1: 6-(4,4-difluoropiperidin-1-yl)-3-fluoro-2-methylpyridine To a stirred solution of 6-chloro-3-fluoro-2-methylpyridine (0.50 g, 3.4 mmol), and 4,4-difluoropiperidine hydrochloride (0.65 g, 4.1 mmol) in dioxane (10 mL) were added t-BuONa (0.99 g, 10 mmol) and Ruphos-Pd-G3 (0.29 g, 0.34 mmol) at 15° C. under a nitrogen atmosphere. The mixture was stirred at 110° C. for 12 h. Then the mixture was filtered through Celite™ and the filtrate was concentrated under reduced pressure. The resulting residue was purified by silica gel chromatography (EtOAc/hexane) to give the title compound.

Step 2: 3-bromo-2-(4,4-difluoropiperidin-1-yl)-5-fluoro-6-methylpyridine To a solution of 6-(4,4-difluoropiperidin-1-yl)-3-fluoro-2-methylpyridine (60 mg, 0.26 mmol) in acetonitrile (2 mL) was added NBS (56 mg, 0.31 mmol) at 0° C. The mixture was stirred at 0° C. for 2 h. Then the mixture was concentrated under reduced pressure, diluted with water and extracted with EtOAc. The combined organic layers were dried over anhydrous Na₂SO₄, filtered and concentrated to give a residue that was purified by silica gel chromatography (petroleum ether/ethyl acetate=10:1) to give the title compound.

Step 3: 2-(4,4-difluoropiperidin-1-yl)-5-fluoro-6-methylnicotinonitrile To a stirred solution of 3-bromo-2-(4,4-difluoropiperidin-1-yl)-5-fluoro-6-methylpyridine (20 mg, 0.065 mmol) in NMP (2 mL) was added dicyanozinc (38 mg, 0.32 mmol), and Pd(tBu₃P)₂ (6.6 mg, 0.013 mmol) at 15° C. under nitrogen. The mixture was stirred at 130° C. under microwave irradiation for 30 min. Then the mixture was cooled to room temperature and diluted with EtOAc. The organic layer was washed with water, brine, dried over anhydrous sodium sulfate, filtered and concentrated under reduced pressure to give a residue that was purified by silica gel chromatography (pet ether/EtOAc=10:1) to give the title compound.

Step 4: 2-(4,4-difluoropiperidin-1-yl)-5-fluoro-6-methylnicotinamide To a solution of 2-(4,4-difluoropiperidin-1-yl)-5-fluoro-6-methylnicotinonitrile (15 mg, 0.059 mmol) in DMSO (2 mL) was added KOH (16 mg, 0.29 mmol) and 30% H₂O₂ (0.060 mL, 0.59 mmol). The mixture was stirred at 15° C. for 1 h, then the mixture was quenched with saturated Na₂SO₃ and extracted with EtOAc. The combined organic layers were washed with brine, dried over Na₂SO₄, filtered and concentrated under reduced pressure to give a residue, which was purified by silica gel chromatography (petroleum ether/ethyl acetate=1:1) to give the title compound.

Step 5: N-(2-(N,N-bis(2,4-dimethoxybenzyl)sulfamoyl)pyridin-4-yl)-2-(4,4-difluoropiperidin-1-yl)-5-fluoro-6-methylnicotinamide A mixture of 4-bromo-N,N-bis(2,4-dimethoxybenzyl)-pyridine-2-sulfonamide (0.28 g, 0.53 mmol), 2-(4,4-difluoropiperidin-1-yl)-5-fluoro-6-methylnicotinamide (0.12 g, 0.44 mmol), Cs₂CO₃ (0.43 g, 1.3 mmol) and Xantphos Pd G2 (39 mg, 0.044 mmol) in dioxane (5 mL) was heated to 100° C. for 12 h under an atmosphere of nitrogen. Then the mixture was cooled to room temperature and diluted with EtOAc. The organic layer was washed with water, brine, dried over anhydrous sodium sulfate, filtered and concentrated under reduced pressure to give a residue that was purified by silica gel chromatography (pet ether/EtOAc=1:1) to give the title compound.

Step 6: 2-(4,4-difluoropiperidin-1-yl)-5-fluoro-6-methyl-N-(2-sulfamoylpyridin-4-yl)nicotinamide To a solution of N-(2-(N,N-bis(2,4-dimethoxybenzyl)sulfamoyl)pyridin-4-yl)-2-(4,4-difluoropiperidin-1-yl)-5-fluoro-6-methylnicotinamide (0.24 g, 0.33 mmol) in dichloromethane (5 mL) was added TFA (2 mL). The mixture was stirred at 20° C. for 1.5 h, then concentrated under reduced pressure to give a residue that was purified by reverse phase chromatography (35-100% MeCN in water with 0.1% TFA, C18 column) to give the title compound. LRMS m/z (M+H): calculated 430.1, observed 430.2. ¹H NMR δ (ppm) (400 MHz, CD₃OD): 8.59 (d, J=5.4 Hz, 1H), 8.45 (d, J=1.7 Hz, 1H), 7.86 (dd, J=5.5, 2.1 Hz, 1H), 7.80 (d, J=9.0 Hz, 1H), 3.43-3.37 (m, 4H), 2.47 (d, J=2.7 Hz, 3H), 2.18-1.95 (m, 4H).

Example 179

3-(4,4-difluoroazepan-1-yl)-N-(2-sulfamoylpyridin-4-yl)-6-(trifluoromethyl)pyridazine-4-carboxamide

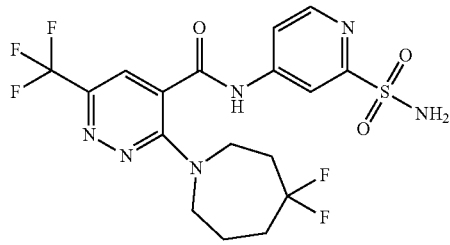 [SMILES: NS(=O)(=O)c1cc(NC(=O)c2cc(C(F)(F)F)nnc2N2CCCC(F)(F)CC2)ccn1]

Step 1: 4,4-difluoro-1-(6-(trifluoromethyl)pyridazin-3-yl)azepane A mixture of 4,4-difluoroazepane hydrochloride (0.34 g, 2.0 mmol), DIPEA (0.86 mL, 4.9 mmol), 3-chloro-6-(trifluoromethyl)pyridazine (0.30 g, 1.6 mmol) and NMP (5 mL) was sealed in a tube and heated to 150° C. for 10 minutes by microwave irradiation. Then the mixture was cooled to rt, diluted with water and extracted with ethyl acetate. The combined organic layers were dried (Na₂SO₄), filtered and concentrated under reduced pressure to give a residue that was purified by silica gel chromatography (0-30% petroleum ether/ethyl acetate) to give the title compound.

Step 2: 1-(4-bromo-6-(trifluoromethyl)pyridazin-3-yl)-4,4-difluoroazepane A mixture of 4,4-difluoro-1-(6-(trifluoromethyl)pyridazin-3-yl)azepane (0.30 g, 1.1 mmol) and 1,3-dibromo-5,5-dimethylimidazolidine-2,4-dione (0.91 g, 3.2 mmol) in acetic acid (5 mL) was stirred at 40° C. for 18 h. The mixture was cooled to rt, diluted in water and extracted with ethyl acetate. The combined organic fractions were dried over Na₂SO₄, filtered and concentrated under reduced pressure to give a residue that was purified by silica gel chromatography (0-10% petroleum ether/ethyl acetate) to give the title compound.

Step 3: 3-(4,4-difluoroazepan-1-yl)-6-(trifluoromethyl)pyridazine-4-carbonitrile To a solution of 1-(4-bromo-6-(trifluoromethyl)pyridazin-3-yl)-4,4-difluoroazepane (0.15 g, 0.42 mmol) in DMA (2 mL) was added dicyanozinc (0.25 g, 2.1 mmol), dppf (46 mg, 0.083 mmol) and Pd₂(dba)₃ (38 mg, 0.042 mmol) at 20° C. The mixture was degassed and backfilled with nitrogen three times, then stirred at 160° C. for 1 h. Then the mixture was diluted with water and extracted with EtOAc. The organic layer was washed with brine, dried over Na₂SO₄, filtered and concentrated under reduced pressure to give a residue that was purified by silica gel chromatography (PE/ethyl acetate=3/1) to give the title compound.

Step 4: 3-(4,4-difluoroazepan-1-yl)-6-(trifluoromethyl)pyridazine-4-carboxamide To a solution of 3-(4,4-difluoroazepan-1-yl)-6-(trifluoromethyl)pyridazine-4-carbonitrile (0.11 g, 0.36 mmol) in DMSO (2 mL) was added K₂CO₃ (0.25 g, 1.8 mmol), and hydrogen peroxide (0.12 g, 3.6 mmol). The mixture was stirred at 20° C. for 1 h, then diluted with water and extracted with EtOAc. The combined organic layer was washed with brine, dried over Na₂SO₄, filtered and concentrated under reduced pressure to give a residue that was purified by silica gel chromatography (petroleum ether/ethyl acetate=1/1) to give the title compound.

Step 5: N-(2-(N,N-bis(2,4-dimethoxybenzyl)sulfamoyl)pyridin-4-yl)-3-(4,4-difluoroazepan-1-6-(trifluoromethyl)pyridazine-4-carboxamide To a solution of 4-bromo-N,N-bis(2,4-dimethoxybenzyl)pyridine-2-sulfonamide (80 mg, 0.15 mmol) in dioxane (10 mL) was added 3-(4,4-difluoroazepan-1-yl)-6-(trifluoromethyl)pyridazine-4-carboxamide (40 mg, 0.12 mmol), Cs₂CO₃ (40 mg, 0.12 mmol) and Xantphos-Pd-G2 (11 mg, 0.012 mmol). The mixture was degassed with nitrogen and stirred at 100° C. for 12 h. Then the mixture was diluted with water and extracted with EtOAc. The combined organic layers were dried over anhydrous Na₂SO₄, filtered and concentrated under reduced pressure to give a residue that was purified by silica gel chromatography (50% EtOAc/petroleum ether) to give the title compound.

Step 6: 3-(4,4-difluoroazepan-1-yl)-N-(2-sulfamoylpyridin-4-yl)-6-(trifluoromethyl)pyridazine-4-carboxamide To a mixture of N-(2-(N,N-bis(2,4-dimethoxybenzyl)sulfamoyl)pyridin-4-yl)-3-(4,4-difluoroazepan-1-yl)-6-(trifluoromethyl)pyridazine-4-carboxamide (70 mg, 0.090 mmol) in dichloromethane (2 mL) was added TFA (1 mL, 13 mmol). The mixture was stirred at 20° C. for 2 h. Then the mixture was concentrated under reduced pressure to give a residue that was purified by reverse phase chromatography (25-100% MeCN in water with 0.1% TFA, C18 column) to give the title compound. LRMS m/z (M+H): calculated 481.1, observed 481.2. ¹H NMR δ (ppm) (500 MHz, CD₃OD): 8.63 (d, J=5.5 Hz, 1H), 8.40 (d, J=1.5 Hz, 1H), 7.98-8.11 (m, 1H), 7.90 (dd, J=1.5, 5.5 Hz, 1H), 3.98 (td, J=2.5, 5.5 Hz, 2H), 3.61 (t, J=5.5 Hz, 2H), 2.33-2.54 (m, 2H), 1.93-2.18 (m, 4H).

Example 180

5-(tert-butyl)-2-(4,4-difluoropiperidin-1-yl)-6-methyl-N-(2-sulfamoylpyridin-4-yl)nicotinamide

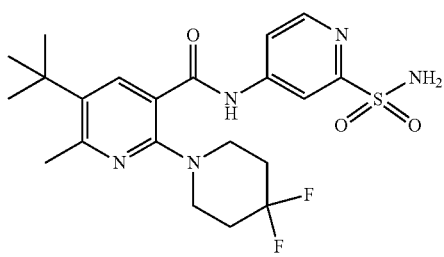 [SMILES: Cc1nc(N2CCC(F)(F)CC2)c(C(=O)Nc2ccnc(S(N)(=O)=O)c2)cc1C(C)(C)C]

Step 1: 3-(tert-butyl)-6-chloro-2-methylpyridine To a stirred solution of copper(I) bromide (2.9 g, 20 mmol) in THF (27 mL) at −78° C. was added tert-butylmagnesium chloride (25 mL, 42 mmol). The mixture was stirred at −78° C. for 30 minutes, then 3-bromo-6-chloro-2-methylpyridine (1.0 g, 5.0 mmol) in THF (3 mL) was dropwise added at −78° C. The mixture was stirred at −78° C. for 2 h, then stirred at 20° C. for 24 h. Then the reaction mixture was quenched with saturated NH₄Cl aqueous solution at 0° C. and extracted with EtOAc. The combined organic layers were dried over anhydrous sodium sulfate, filtered and concentrated under reduced pressure to give a residue that was purified by silica gel chromatography (petroleum ether/ethyl acetate=20:1) to give the title compound.

Step 2: 3-(tert-butyl)-6-(4,4-difluoropiperidin-1-yl)-2-methylpyridine To a stirred solution of 3-(tert-butyl)-6-chloro-2-methylpyridine (40 mg, 0.22 mmol) in dioxane (4 mL) under an atmosphere of nitrogen was added 4,4-difluoropiperidine hydrochloride (58 mg, 0.37 mmol), sodium tert-butoxide (95 mg, 0.99 mmol) and RuPhos-Pd-G3 (22 mg, 0.026 mmol). The mixture was stirred at 110° C. for 5 h, then cooled to room temperature and diluted with EtOAc. The organic layer was washed with brine, dried over anhydrous sodium sulfate, filtered and concentrated under reduced pressure to give the title compound.

Step 3: 3-bromo-5-(tert-butyl)-2-(4,4-difluoropiperidin-1-yl)-6-methylpyridine To a stirred solution of 3-(tert-butyl)-6-(4,4-difluoropiperidin-1-yl)-2-methylpyridine (35 mg crude) in dichloromethane (3 mL) was added NBS (28 mg, 0.16 mmol). The mixture was stirred at 20° C. for 30 minutes. Then the mixture was concentrated under reduced pressure to give a residue that was purified by silica gel chromatography (petroleum ether/ethyl acetate=10:1) to give the title compound.

Step 4: 5-(tert-butyl)-2-(4,4-difluoropiperidin-1-yl)-6-methylnicotinonitrile To a stirred solution of 3-bromo-5-(tert-butyl)-2-(4,4-difluoropiperidin-1-yl)-6-methylpyridine (40 mg, 0.12 mmol) in DMA (3 mL) were added dppf (25 mg, 0.045 mmol), dicyanozinc (45 mg, 0.38 mmol) and Pd₂(dba)₃ (21 mg, 0.023 mmol) under a nitrogen atmosphere. The mixture was stirred at 140° C. for 4 h, then cooled to room temperature and diluted with EtOAc. The organic layer was washed with water, brine, dried over anhydrous sodium sulfate, filtered and concentrated under reduced pressure to give a residue that was purified by silica gel chromatography (petroleum ether/ethyl acetate=20:1) to give the title compound.

Step 5: 5-(tert-butyl)-2-(4,4-difluoropiperidin-1-yl)-6-methylnicotinamide To a stirred solution of 5-(tert-butyl)-2-(4,4-difluoropiperidin-1-yl)-6-methylnicotinonitrile (40 mg) and potassium carbonate (60 mg, 0.43 mmol) in DMSO (2 mL) was added hydrogen peroxide (0.16 g, 1.4 mmol). The mixture was stirred at 20° C. for 3 h then diluted with EtOAc. The organic layer was washed with water, brine, dried over anhydrous sodium sulfate, filtered and concentrated under reduced pressure to give the title compound.

Step 6: N-(2-(N,N-bis(2,4-dimethoxybenzyl)sulfamoyl)pyridin-4-yl)-5-(tert-butyl)-2-(4,4-difluoropiperidin-1-yl)-6-methylnicotinamide A mixture of 5-(tert-butyl)-2-(4,4-difluoropiperidin-1-yl)-6-methylnicotinamide (26 mg, crude), 4-bromo-N,N-bis(2,4-dimethoxybenzyl)pyridine-2-sulfonamide (54 mg, 0.10 mmol), Cs₂CO₃ (82 mg, 0.25 mmol), and XantPhos-Pd-G2 (6.0 mg, 6.8 μmol) in dioxane (1.2 mL) was degassed and backfilled with nitrogen three times. The mixture was heated to 100° C. for 12 h, then cooled to rt and diluted with EtOAc. The organic layer was washed with brine, dried over anhydrous sodium sulfate, filtered and concentrated under reduced pressure to give the title compound.

Step 7: 5-(tert-butyl)-2-(4,4-difluoropiperidin-1-yl)-6-methyl-N-(2-sulfamoylpyridin-4-yl)nicotinamide To a stirred solution of N-(2-(N,N-bis(2,4-dimethoxybenzyl)sulfamoyl)pyridin-4-yl)-5-(tert-butyl)-2-(4,4-difluoropiperidin-1-yl)-6-methylnicotinamide (42 mg, crude) in DCM (3 mL) was added TFA (0.8 mL). The mixture was stirred at 20° C. for 2 h, then concentrated under reduced pressure to give a residue that was purified by reverse phase chromatography (50-100% MeCN in water with 0.1% TFA, C18 column) to give the title compound. LRMS m/z (M+H):

calculated 468.2, observed 468.2. ¹H NMR δ (ppm) (400 MHz, CD₃OD): 8.58 (d, J=5.2 Hz, 1H), 8.42 (d, J=1.6 Hz, 1H), 8.11 (br s, 1H), 7.86 (dd, J=5.2, 2.0 Hz, 1H), 3.47 (br s, 4H), 2.73 (s, 3H), 1.99-2.18 (m, 4H), 1.44 (s, 9H).

Example 181

5-cyclopropyl-2-(4,4-difluoropiperidin-1-yl)-N-(2-sulfamoylpyridin-4-yl)-6-(trifluoromethyl)nicotinamide

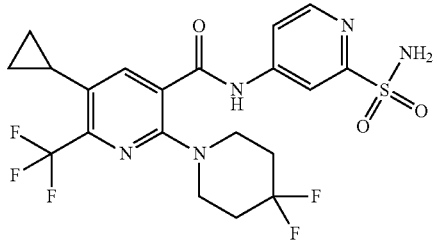 [SMILES: NS(=O)(=O)c1cc(NC(=O)c2cc(C3CC3)c(C(F)(F)F)nc2N2CCC(F)(F)CC2)ccn1]

Step 1: 2-(4,4-difluoropiperidin-1-yl)-6-(trifluoromethyl)pyridine To a solution of 2-chloro-6-(trifluoromethyl)pyridine (0.30 g, 1.7 mmol) in DMA (6 mL) was added 4,4-difluoropiperidine hydrochloride (0.31 g, 2.0 mmol) and DIPEA (0.87 mL, 5.0 mmol). The mixture was stirred at 120° C. for 12 h under nitrogen, then diluted with water and extracted with EtOAc. The combined organic layers were washed with brine, dried over anhydrous Na₂SO₄, filtered and concentrated to give a residue that was purified by silica gel chromatography (petroleum ether/ethyl acetate=10:1) to give the title compound.

Step 2: 3-bromo-6-(4,4-difluoropiperidin-1-yl)-2-(trifluoromethyl)pyridine To a solution of 2-(4,4-difluoropiperidin-1-yl)-6-(trifluoromethyl)pyridine (0.95 g, 3.6 mmol) in MeOH (20 mL) was added 1-bromopyrrolidine-2,5-dione (0.76 g, 4.3 mmol) at 0° C. The mixture was stirred at 15° C. for 2 h, then concentrated under reduced pressure, diluted with water and extracted with EtOAc. The combined organic layers were dried over anhydrous Na₂SO₄, filtered and concentrated to give a residue that was purified by silica gel chromatography (2% EtOAc) to give the title compound.

Step 3: 3-cyclopropyl-6-(4,4-difluoropiperidin-1-yl)-2-(trifluoromethyl)pyridine To a solution of 3-bromo-6-(4,4-difluoropiperidin-1-yl)-2-(trifluoromethyl)pyridine (0.25 mg, 0.72 mmol) in dioxane (3 mL) and water (3 mL) was added potassium cyclopropyltrifluoroborate (0.21 g, 1.4 mmol), Pd(dppf)Cl₂ (53 mg, 0.072 mmol) and K₂CO₃ (0.20 g, 1.4 mmol). The mixture was degassed with nitrogen and stirred at 100° C. for 12 h. The mixture was then filtered through Celite™ and the filtrate was concentrated. The resulting residue was diluted with water and extracted with EtOAc. The organic layer was separated, dried over anhydrous Na₂SO₄, filtered and concentrated to give a residue that was purified by silica gel chromatography (petroleum ether:EtOAc=10:1) to give the title compound.

Step 4: 3-bromo-5-cyclopropyl-2-(4,4-difluoropiperidin-1-yl)-6-(trifluoromethyl)pyridine To a solution of 3-cyclopropyl-6-(4,4-difluoropiperidin-1-yl)-2-(trifluoromethyl)pyridine (100 mg, 0.33 mmol) in DMF (2 mL) was added NBS (70 mg, 0.39 mmol). The mixture was stirred at rt for 2 h. The solution was diluted with water, and extracted with EtOAc. The organic layer was dried over anhydrous Na₂SO₄, filtered and concentrated to a residue that was purified by silica gel chromatography (petroleum ether/ethyl acetate=10:1) to give the title compound.

Step 5: 5-cyclopropyl-2-(4,4-difluoropiperidin-1-yl)-6-(trifluoromethyl)nicotinonitrile To a mixture of 3-bromo-5-cyclopropyl-2-(4,4-difluoropiperidin-1-yl)-6-(trifluoromethyl)pyridine (180 mg, 0.47 mmol), zinc (31 mg, 0.47 mmol), dicyanozinc (140 mg, 1.2 mmol) in DMF (5 mL) was added dppf (52 mg, 0.093 mmol) and Pd₂(dba)₃ (43 mg, 0.047 mmol) at 20° C. under nitrogen. The reaction mixture was heated to 160° C. for 2 h, then cooled to rt, quenched with H₂O and extracted with EtOAc. The organic layer was separated, washed with brine, dried over anhydrous Na₂SO₄, filtered and concentrated under reduced pressure to give a residue that was purified by silica gel chromatography (petroleum ether/ethyl acetate=10:1) to give the title compound.

Step 6: 5-cyclopropyl-2-(4,4-difluoropiperidin-1-yl)-6-(trifluoromethyl)nicotinamide To a solution of 5-cyclopropyl-2-(4,4-difluoropiperidin-1-yl)-6-(trifluoromethyl)nicotinitrile (0.13 g, 0.39 mmol) in DMSO (4 mL) was added KOH (0.11 g, 2.0 mmol) and H₂O₂ (0.40 mL, 3.9 mmol). The mixture was stirred at 15° C. for 1 h, then quenched with water and extracted with EtOAc. The organic layers was separated, washed with brine, dried over Na₂SO₄, filtered and concentrated under reduced pressure to a residue that was purified by silica gel chromatography (petroleum ether/ethyl acetate=1:1) to give the title compound.

Step 7: N-(2-(N,N-bis(2,4-dimethoxybenzyl)sulfamoyl)pyridin-4-yl)-5-cyclopropyl-2-(4,4-difluoropiperidin-1-yl)-6-(trifluoromethyl)nicotinamide In a glovebox, a mixture of 4-bromo-N,N-bis(2,4-dimethoxybenzyl)pyridine-2-sulfonamide (92 mg, 0.17 mmol), 5-cyclopropyl-2-(4,4-difluoropiperidin-1-yl)-6-(trifluoromethyl)nicotinamide (50 mg, 0.14 mmol), Cs₂CO₃ (0.14 g, 0.43 mmol) and Xantphos Pd G2 (13 mg, 0.014 mmol) in dioxane (3 mL) was heated to 100° C. for 12 h. Then the mixture was cooled to room temperature and diluted with EtOAc. The organic layer was washed with water, brine, dried over anhydrous sodium sulfate, filtered and concentrated under reduced pressure to give a residue that was purified by silica gel chromatography (petroleum ether:EtOAc=1:1) to give the title compound.

Step 8: 5-cyclopropyl-2-(4,4-difluoropiperidin-1-yl)-N-(2-sulfamoylpyridin-4-yl)-6-(trifluoromethyl)nicotinamide (181) To a solution of N-(2-(N,N-bis(2,4-dimethoxybenzyl)-sulfamoyl)pyridin-4-yl)-5-cyclopropyl-2-(4,4-difluoropiperidin-1-yl)-6-(trifluoromethyl)-nicotinamide (0.11 g, 0.14 mmol) in dichloromethane (3 mL) was added TFA (1 mL). The mixture was stirred at 20° C. for 1.5 h, then concentrated under reduced pressure to give a residue that was purified by reverse phase chromatography (42-100% MeCN in water with 0.1% TFA, C18 column) to give the title compound. LRMS m/z (M+H): calculated 506.1, observed 506.1. ¹H NMR δ (ppm) (400 MHz, CD₃OD): 8.60 (d, J=5.4 Hz, 1H), 8.40 (d, J=7.2 Hz, 1H), 7.88 (dd, J=5.4, 2.0 Hz, 1H), 7.68 (s, 1H), 3.57-3.46 (m, 4H), 2.22-2.09 (m, 1H), 2.08-1.92 (m, 4H), 1.12-0.98 (m, 2H), 0.84-0.73 (m, 2H).

Example 182

5-cyclopropyl-2-(4,4-difluoropiperidin-1-yl)-N-(2-sulfamoylpyridin-4-yl)-6-(trifluoromethoxy)nicotinamide

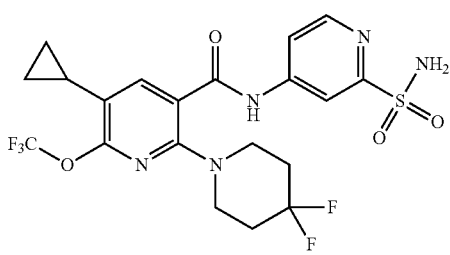 [SMILES: NS(=O)(=O)c1cc(NC(=O)c2cc(C3CC3)c(OC(F)(F)F)nc2N2CCC(F)(F)CC2)ccn1]

Step 1: 6-chloro-3-iodo-2-(trifluoromethoxy)pyridine To a stirred solution of 2-chloro-6-(trifluoromethoxy)pyridine (0.20 mg, 1.0 mmol) in THF (6 mL) was added lithium diisopropylamide (1.1 mL, 1.3 mmol) at −78° C. The mixture was stirred at −78° C. for 1 h, then a solution of diiodine (0.28 g, 1.1 mmol) in THF (1.0 mL) was added at −78° C. The mixture was warmed to 20° C. for 2 h, then diluted with EtOAc. The organic layer was washed with saturated $Na_2SO_3$ aqueous solution, brine, dried over anhydrous sodium sulfate, filtered and concentrated under reduced pressure to give a residue that was purified by silica gel chromatography (petroleum ether/ethyl acetate=20:1) to give the title compound.

Step 2: 6-chloro-3-cyclopropyl-2-(trifluoromethoxy)pyridine To a stirred solution of 6-chloro-3-iodo-2-(trifluoromethoxy)pyridine (0.20 g, 0.62 mmol) in toluene (5 mL) and water (0.6 mL) was added potassium carbonate (0.26 g, 1.9 mmol), potassium cyclopropyltrifluoroborate (0.16 g, 1.1 mmol) and $Pd(PPh_3)_4$ (75 mg, 0.065 mmol) at 20° C. under a nitrogen atmosphere. The mixture was stirred at 110° C. for 12 h, then cooled to room temperature and diluted with EtOAc. The organic layer was washed with brine, dried over anhydrous sodium sulfate, filtered and concentrated under reduced pressure to give a residue that was purified by silica gel chromatography (petroleum ether/ethyl acetate=20:1) to give the title compound.

Step 3: 3-cyclopropyl-6-(4,4-difluoropiperidin-1-yl)-2-(trifluoromethoxy)pyridine To a stirred solution of 6-chloro-3-cyclopropyl-2-(trifluoromethoxy)pyridine (0.10 g, 0.42 mmol) in dioxane (5 mL) was added 4,4-difluoropiperidine hydrochloride (0.11 g, 0.72 mmol), sodium 2-methylpropan-2-olate (0.12 g, 1.3 mmol) and RuPhos-Pd-G2 (50 mg, 0.060 mmol) under nitrogen atmosphere at 20° C. The mixture was stirred at 110° C. for 12 h, then cooled to room temperature and diluted with EtOAc. The organic layer was separated, washed with brine, dried over anhydrous sodium sulfate, filtered and concentrated under reduced pressure to give a residue that was purified by silica gel chromatography (petroleum ether/ethyl acetate=20:1) to give the title compound.

Step 4: 3-bromo-5-cyclopropyl-2-(4,4-difluoropiperidin-1-yl)-6-(trifluoromethoxy)pyridine To a stirred solution of 3-cyclopropyl-6-(4,4-difluoropiperidin-1-yl)-2-(trifluoromethoxy)pyridine (0.15 g, 0.46 mmol) in DCM (5 mL) was added NBS (91 mg, 0.51 mmol). The mixture was stirred at 20° C. for 30 min. Then the mixture solvent was removed under reduced pressure. The resulting residue was dissolved into EtOAc, and the EtOAc solution was washed with water, brine, dried over anhydrous sodium sulfate, filtered and concentrated under reduced pressure to give the title compound.

Step 5: 5-cyclopropyl-2-(4,4-difluoropiperidin-1-yl)-6-(trifluoromethoxy)nicotinonitrile To a stirred solution of 3-bromo-5-cyclopropyl-2-(4,4-difluoropiperidin-1-yl)-6-(trifluoromethoxy)-pyridine (150 mg, crude) in DMA (5 mL) was added dppf (42 mg, 0.076 mmol), dicyanozinc (0.13 g, 1.1 mmol), $Pd_2(dba)_3$ (35 mg, 0.038 mmol) under a nitrogen atmosphere at 20° C. The mixture was stirred at 140° C. for 4 h, then cooled to room temperature and diluted with EtOAc. The organic layer was washed with water, brine, dried over anhydrous sodium sulfate, filtered and concentrated under reduced pressure to give a residue that was purified by silica gel chromatography (petroleum ether/ethyl acetate=20:1) to give the title compound.

Step 6: 5-cyclopropyl-2-(4,4-difluoropiperidin-1-yl)-6-(trifluoromethoxy)nicotinamide To a stirred solution of 5-cyclopropyl-2-(4,4-difluoropiperidin-1-yl)-6-(trifluoromethoxy)-nicotinonitrile (50 mg, 0.14 mmol) in DMSO (1.5 mL) was added potassium carbonate (60 mg, 0.43 mmol) and hydrogen peroxide (0.16 g, 1.4 mmol). The mixture was stirred at 20° C. for 30 min, then diluted with EtOAc. The organic layer was separated, washed with water, brine, dried over anhydrous sodium sulfate, filtered and concentrated under reduced pressure to give the title compound.

Step 7: N-(2-(N,N-bis(2,4-dimethoxybenzyl)sulfamoyl)pyridin-4-yl)-5-cyclopropyl-2-(4,4-difluoropiperidin-1-yl)-6-(trifluoromethoxy)nicotinamide A mixture of 5-cyclopropyl-2-(4,4-difluoropiperidin-1-yl)-6-(trifluoromethoxy) nicotinamide (20 mg, crude), 4-bromo-N,N-bis(2,4-dimethoxybenzyl)pyridine-2-sulfonamide (36 mg, 0.067 mmol), $Cs_2CO_3$ (55 mg, 0.17 mmol), and XantPhos-Pd-G2 (6.0 mg, 6.7 μmol) in dioxane (1.2 mL) was degassed and backfilled with nitrogen three times. The mixture was heated to 100° C. for 12 h, then cooled to room temperature and diluted with EtOAc. The organic layer was washed with brine, dried over anhydrous sodium sulfate, filtered and concentrated under reduced pressure to give the title compound.

Step 8: 5-cyclopropyl-2-(4,4-difluoropiperidin-1-yl)-N-(2-sulfamoylpyridin-4-yl)-6-(trifluoromethoxy)nicotinamide To a stirred solution of N-(2-(N,N-bis(2,4-dimethoxybenzyl)sulfamoyl)pyridin-4-yl)-5-cyclopropyl-2-(4,4-difluoropiperidin-1-yl)-6-(trifluoromethoxy)nicotinamide (40 mg, crude) in DCM (2 mL) was added TFA (0.5 mL). The mixture was stirred at 20° C. for 2 h. Then the solvent was removed at reduced pressure to give a residue that was purified by reverse phase chromatography (52-100% MeCN in water with 0.1% TFA, C18 column) to give the title compound. LRMS m/z (M+H): calculated 522.1, observed 522.1. $^1$H NMR δ (ppm) (400 MHz, $CD_3OD$): 8.57 (d, J=5.6 Hz, 1H), 8.39 (d, J=1.6 Hz, 1H), 7.85 (dd, J=5.6, 2.0 Hz, 1H), 7.64 (s, 1H), 3.47 (t, J=5.6 Hz, 4H), 1.90-2.10 (m, 5H), 0.95-1.03 (m, 2H), 0.68-0.76 (m, 2H).

Example 183

2-(4,4-difluoropiperidin-1-yl)-6-methyl-N-(2-sulfamoylpyridin-4-yl)-5-(2,2,2-trifluoroethoxy)nicotinamide

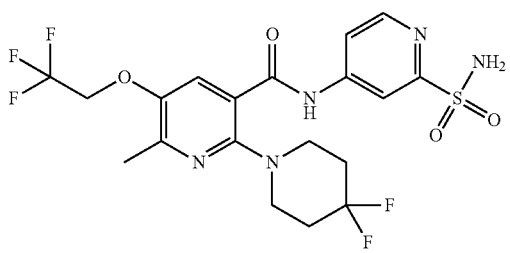 [SMILES: Cc1nc(N2CCC(F)(F)CC2)c(C(=O)Nc2ccnc(S(N)(=O)=O)c2)cc1OCC(F)(F)F]

Step 1: 6-iodo-2-methyl-3-(2,2,2-trifluoroethoxy)pyridine To a solution of 6-iodo-2-methylpyridin-3-ol (0.40 g, 1.7 mmol) in DMF (10 mL) was added 2,2,2-trifluoroethyl trifluoromethanesulfonate (0.51 g, 2.2 mmol) dropwise at 0° C. The mixture was stirred at 20° C. for 3 h, then washed with water and extracted with EtOAc. The organic layer was washed with brine, dried over $Na_2SO_4$, filtered and concentrated under reduced pressure to give a residue that was purified by silica gel chromatography (petroleum ether/ethyl acetate=5:1) to give the title compound.

Step 2: 6-(4,4-difluoropiperidin-1-yl)-2-methyl-3-(2,2,2-trifluoroethoxy)pyridine To a solution of 6-iodo-2-methyl-3-(2,2,2-trifluoroethoxy)pyridine (0.30 g, 0.95 mmol) in dioxane (3 mL) was added 4,4-difluoropiperidine hydrochloride (0.18 g, 1.1 mmol), Ruphos-Pd-G3 (79 mg, 0.095 mmol) and sodium 2-methylpropan-2-olate (0.27 g, 2.8 mmol) under nitrogen. The mixture was stirred at 60° C. for 12 h. Then the mixture was washed with water and extracted with EtOAc. The organic layer was washed with brine, dried over $Na_2SO_4$, filtered and concentrated under reduced pressure to give a residue that was purified by silica gel chromatography (petroleum ether/ethyl acetate=5:1) to give the title compound.

Step 3: 2-(4,4-difluoropiperidin-1-yl)-3-iodo-6-methyl-5-(2,2,2-trifluoroethoxy)pyridine To a solution of 6-(4,4-difluoropiperidin-1-yl)-2-methyl-3-(2,2,2-trifluoroethoxy)pyridine (10 mg, 0.032 mmol) in dichloromethane (2 mL) was added NIS (18 mg, 0.081 mmol). The mixture was stirred at 20° C. for 5 h. Then the mixture was concentrated under reduced pressure to give a residue that was purified by silica gel chromatography (petroleum ether/ethyl acetate=5:1) to give the title compound.

Step 4: 2-(4,4-difluoropiperidin-1-yl)-6-methyl-5-(2,2,2-trifluoroethoxy)nicotinonitrile To a solution of 2-(4,4-difluoropiperidin-1-yl)-3-iodo-6-methyl-5-(2,2,2-trifluoroethoxy)pyridine (0.20 g, 0.46 mmol) in DMA (3 mL) was added dicyanozinc (0.16 g, 1.4 mmol), dppf (51 mg, 0.092 mmol) and $Pd_2(dba)_3$ (42 mg, 0.046 mmol). The mixture was degassed and backfilled with nitrogen three times. Then the mixture was stirred at 130° C. for 1 h, diluted with water and extracted with EtOAc. The organic layer was washed with brine, dried over $Na_2SO_4$, filtered and concentrated under reduced pressure to give a residue that was purified by silica gel chromatography (0-30% ethyl acetate/petroleum ether) to give the title compound.

Step 5: 2-(4,4-difluoropiperidin-1-yl)-6-methyl-5-(2,2,2-trifluoroethoxy)nicotinamide To a solution of 2-(4,4-difluoropiperidin-1-yl)-6-methyl-5-(2,2,2-trifluoroethoxy)nicotinonitrile (0.10 g, 0.30 mmol) and KOH (84 mg, 1.5 mmol) in DMSO (3 mL) was added $H_2O_2$ (0.52 mL, 6.0 mmol). The mixture was stirred at 20° C. for 1 h. The mixture was diluted with $Na_2SO_3$ and extracted with EtOAc. The organic layer was washed with brine, dried over $Na_2SO_4$, filtered and concentrated to a residue that was purified by silica gel chromatography (petroleum ether:EtOAc=1:1) to give the title compound.

Step 6: N-(2-(N,N-bis(2,4-dimethoxybenzyl)sulfamoyl)pyridin-4-yl)-2-(4,4-difluoropiperidin-1-yl)-6-methyl-5-(2,2,2-trifluoroethoxy)nicotinamide To a solution of 2-(4,4-difluoropiperidin-1-yl)-6-methyl-5-(2,2,2-trifluoroethoxy)nicotinamide (60 mg, 0.17 mmol) in dioxane (1.5 mL) was added $Cs_2CO_3$ (0.17 g, 0.51 mmol), 4-bromo-N,N-bis(2,4-dimethoxybenzyl)pyridine-2-sulfonamide (0.14 g, 0.26 mmol) and XantPhos-Pd-G2 (15 mg, 0.017 mmol). The mixture was degassed and backfilled with nitrogen three times. The mixture was stirred at 100° C. for 13 h. The solution was washed with water and extracted with EtOAc. The organic layer was dried over $Na_2SO_4$, filtered and concentrated to a residue was purified by silica gel chromatography (petroleum ether:EtOAc=1:1) to give the title compound.

Step 7: 2-(4,4-difluoropiperidin-1-yl)-6-methyl-N-(2-sulfamoylpyridin-4-yl)-5-(2,2,2-trifluoroethoxy)nicotinamide (183) A solution of N-(2-(N,N-bis(2,4-dimethoxybenzyl)sulfamoyl)pyridin-4-yl)-2-(4,4-difluoropiperidin-1-yl)-6-methyl-5-(2,2,2-trifluoroethoxy)nicotinamide (0.12 g, 0.15 mmol) in TFA (1 mL) and dichloromethane (3 mL) was stirred at 20° C. for 1 h. The mixture was concentrated under reduced pressure to give a residue that was purified by reverse phase chromatography (41-100% MeCN in water with 0.1% TFA, C18 column). LRMS m/z (M+H): calculated 510.1, observed 510.1. $^1$H NMR δ (ppm) (400 MHz, $CD_3OD$): 8.58 (d, J=5.6 Hz, 1H), 8.47 (d, J=1.6 Hz, 1H), 7.84 (dd, J=2.0, 5.6 Hz, 1H), 7.81 (s, 1H), 4.63 (q, J=8.4 Hz, 2H), 3.33-3.40 (m, 4H), 2.46 (s, 3H), 2.04-2.16 (m, 4H).

Example 184

2-(4,4-difluoroazepan-1-yl)-6-methyl-N-(2-sulfamoylpyridin-4-yl)-5-(trifluoromethyl)nicotinamide

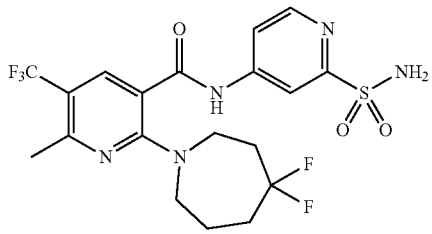 [SMILES: Cc1nc(N2CCCC(F)(F)CC2)c(C(=O)Nc2ccnc(S(N)(=O)=O)c2)cc1C(F)(F)F]

Step 1: 4,4-difluoro-1-(6-methyl-5-(trifluoromethyl)pyridin-2-yl)azepane To a solution of 1-(6-chloro-5-(trifluoromethyl)pyridin-2-yl)-4,4-difluoroazepane (Intermediate 38, 1.8 g, 5.7 mmol) in dioxane (20 mL) and water (5 mL) were added 2,4,6-trimethyl-1,3,5,2,4,6-trioxatriborinane (1.7 mL, 11 mmol), $K_2CO_3$ (1.6 g, 11 mmol) and $PdCl_2(dppf)$ (0.42 g, 0.57 mmol). The mixture was stirred at 100° C. for 10 hours under a nitrogen atmosphere. Then the mixture was diluted with water and extracted with EtOAc. The organic phase was washed with brine, dried over $Na_2SO_4$, and filtered, concentrated to give a residue that was purified by silica gel chromatography (4% ethyl acetate/PE) to give the title compound.

Step 2: 1-(3-bromo-6-methyl-5-(trifluoromethyl)pyridin-2-yl)-4,4-difluoroazepane To a solution of 4,4-difluoro-1-(6-methyl-5-(trifluoromethyl)pyridin-2-yl)azepane (1.2 g, 4.1 mmol) in DMF (10 mL) was added NBS (1.1 g, 6.1 mmol) dropwise with stirring at 20° C. The mixture was stirred at 20° C. for 10 hours, then diluted in EtOAc and water. The organic layer was washed with brine, dried over $Na_2SO_4$, filtered and concentrated under reduced pressure to give a residue that was purified by silica gel chromatography (3% EtOAc/petroleum ether) to give the title compound.

Step 3: N-(2-(N,N-bis(2,4-dimethoxybenzyl)sulfamoyl)pyridin-4-yl)-2-(4,4-difluoroazepan-1-yl)-6-methyl-5-(trifluoromethyl)nicotinamide A mixture of 1-(3-bromo-6-methyl-5-(trifluoro-methyl)pyridin-2-yl)-4,4-difluoroazepane (0.30 g, 0.80 mmol), 4-amino-N,N-bis(2,4-dimethoxy-benzyl)pyridine-2-sulfonamide (0.76 g, 1.6 mmol), DMAP (9.8 mg, 0.080 mmol) and $tBu_3$-Pd-G2 (41 mg, 0.080 mmol) was taken up in DMF (10 mL) and sparged with nitrogen for 10 min. Then $Et_3N$ (0.56 mL, 4.0 mmol) was added. The reaction vial was loaded into a par reactor and degassed three times with nitrogen ($N_2$/vent), followed by three times with carbon monoxide ((120 psi CO)/vent). The mixture was left exposed to 120 psi of CO and heated to 120° C. for 12 hours. Then the mixture was filtered, and the filtrate was diluted with water and extracted with EtOAc. The organic layer was washed with brine, dried over anhydrous $Na_2SO_4$, filtered and concentrated to give a residue that was purified by silica gel chromatography (petroleum ether/ethyl acetate=1/1) to give the title compound.

Step 4: 2-(4,4-difluoroazepan-1-yl)-6-methyl-N-(2-sulfamoylpyridin-4-yl)-5-(trifluoromethyl)-nicotinamide A solution of N-(2-(N,N-bis(2,4-dimethoxybenzyl)sulfamoyl)pyridin-4-yl)-2-(4,4-difluoroazepan-1-yl)-6-methyl-5-(trifluoromethyl)nicotinamide (0.43 g, 0.43 mmol) in DCM (3 mL) and TFA (3 mL) was stirred at 20° C. for 1 hour. Then the mixture was filtered and the filtrate was diluted with water and extracted with EtOAc. The organic layer was washed with brine, dried over anhydrous $Na_2SO_4$, filtered and concentrated to give a residue that was purified by silica gel chromatography (DCM/MeOH=20/1) to give the title compound. LRMS m/z (M+H): calculated 494.1, observed 494.1. $^1$H NMR δ (ppm) (400 MHz, $CD_3OD$): 8.56 (d, J=5.4 Hz, 1H), 8.38 (d, J=1.8 Hz, 1H), 8.16 (d, J=2.8 Hz, 1H), 7.86-7.88 (m, 1H), 7.69 (d, J=2.7 Hz, 1H), 6.50-6.97 (m, 1H), 3.66-3.74 (m, 2H), 3.42 (t, J=5.6 Hz, 2H), 2.24-2.39 (m, 2H), 1.85-2.02 (m, 4H).

Example 185

6-cyclopropyl-2-(4,4-difluoroazepan-1-yl)-N-(2-sulfamoylpyridin-4-yl)-5-(trifluoromethyl)nicotinamide

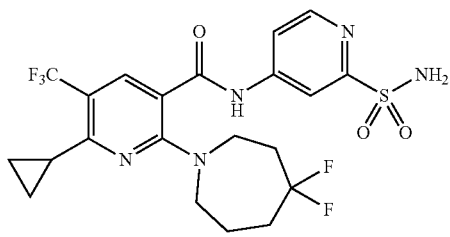 [SMILES: NS(=O)(=O)c1cc(NC(=O)c2cc(C(F)(F)F)c(C3CC3)nc2N2CCCC(F)(F)CC2)ccn1]

Step 1: 1-(6-cyclopropyl-5-(trifluoromethyl)pyridin-2-yl)-4,4-difluoroazepane To a solution of 1-(6-chloro-5-(trifluoromethyl)pyridin-2-yl)-4,4-difluoroazepane (Intermediate 38, 0.70 g, 2.2 mmol) in dioxane (10 mL) and water (2 mL) were added potassium cyclopropyltrifluoroborate (0.66 g, 4.4 mmol), $K_2CO_3$ (0.62 g, 4.4 mmol) and $PdCl_2$(dppf) (0.16 g, 0.22 mmol). The mixture was stirred at 100° C. for 10 hours under nitrogen, then diluted with water and extracted with EtOAc. The organic phase was separated, washed with brine, dried over $Na_2SO_4$, filtered and concentrated to give a residue that was purified by silica gel chromatography (5% ethyl acetate/PE) to give the title compound.

Step 2: 1-(3-bromo-6-cyclopropyl-5-(trifluoromethyl)pyridin-2-yl)-4,4-difluoroazepane To a solution of 1-(6-cyclopropyl-5-(trifluoromethyl)pyridin-2-yl)-4,4-difluoroazepane (0.30 g, 0.94 mmol) in DMF (3 mL) was added NBS (0.25 g, 1.4 mmol) with stirring at 20° C. The mixture was stirred at 20° C. for 10 hours, then extracted with EtOAc and water. The organic layer was separated, washed with brine, dried over $Na_2SO_4$, filtered and concentrated under reduced pressure to give a residue that was purified by silica gel chromatography (petroleum ether/ethyl acetate=5/1) to give the title compound.

Step 3: N-(2-(N,N-bis(2,4-dimethoxybenzyl)sulfamoyl)pyridin-4-yl)-6-cyclopropyl-2-(4,4-difluoroazepan-1-yl)-5-(trifluoromethyl)nicotinamide 1-(3-bromo-6-cyclopropyl-5-(trifluoromethyl)pyridin-2-yl)-4,4-difluoroazepane (70 mg, 0.140 mmol), 4-amino-N,N-bis(2,4-dimethoxybenzyl)pyridine-2-sulfonamide (80 mg, 0.17 mmol), DMAP (1.7 mg, 0.014 mmol), and $P(tBu)_3$-Pd-G2 (7.2 mg, 0.014 mmol) were taken up in DMF (3 mL). The mixture was degassed with nitrogen for 10 minutes, then triethylamine (43 mg, 0.42 mmol) was added. The reaction vial was degassed (3×$N_2$/vent), then (3×CO (120 psi)/vent), and then left exposed to 120 psi of CO and heated to 120° C. for 12 h. Then the reaction mixture was filtered and the filtrate was diluted with water and extracted with EtOAc. The combined organic layers were washed with brine, dried over anhydrous $Na_2SO_4$, filtered and concentrated to give a residue that was purified by silica gel chromatography (petroleum ether/ethyl acetate=1/1) to give the title compound.

Step 4: 6-cyclopropyl-2-(4,4-difluoroazepan-1-yl)-N-(2-sulfamoylpyridin-4-yl)-5-(trifluoromethyl)nicotinamide A solution of N-(2-(N,N-bis(2,4-dimethoxybenzyl)-sulfamoyl)pyridin-4-yl)-6-cyclopropyl-2-(4,4-difluoroazepan-1-yl)-5-(trifluoromethyl)-nicotinamide (60 mg, 0.073 mmol) in TFA (1 mL) and DCM (1 mL) was stirred at 20° C. for 1 hour. Then the mixture was concentrated under reduced pressure and purified by reverse phase chromatography (50-100% MeCN in water with 0.1% TFA, C18 column) to give the title compound. LRMS m/z (M+H): calculated 520.1, observed 519.9. $^1$H NMR δ (ppm) (400 MHz, $CD_3OD$): 8.56 (d, J=5.6 Hz, 1H), 8.39 (d, J=2.0 Hz, 1H), 7.95 (s, 1H), 7.86-7.88 (m, 1H), 3.67-3.77 (m, 2H), 3.42 (t, J=5.6 Hz, 2H), 2.21-2.36 (m, 3H), 1.86-2.00 (m, 4H), 1.15-1.19 (m, 2H), 1.01-1.09 (m, 2H).

Example 186

2-(azepan-1-yl)-N-(5-fluoropyridin-3-yl)-5-(trifluoromethyl)nicotinamide

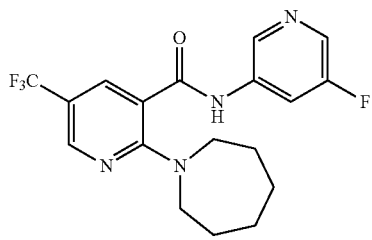 [SMILES: O=C(Nc1cncc(F)c1)c1cc(C(F)(F)F)cnc1N1CCCCCC1]

To a mixture of 2-(azepan-1-yl)-5-(trifluoromethyl)nicotinic acid (Intermediate 17, 10 mg, 0.035 mmol) in pyridine (0.3 mL) was added 3-amino-5-fluoropyridine (11 mg, 0.10 mmol) and EDC (10 mg, 0.052 mmol). The mixture was sonicated and stirred at ambient temperature 16 hours in a sealed vial. Then the mixture was concentrated under a stream of nitrogen, followed by high vacuum. The resulting residue was purified by reverse phase chromatography (30-100% MeCN in water with 0.1% TFA, C18 column) to give the title compound. LRMS m/z (M+H): calculated 383.1, observed 383.1. $^1$H NMR δ (ppm) (500 MHz, DMSO-$d_4$) ☐ 11.04 (s, 1H), 8.65 (s, 1H), 8.53 (m, 1H), 8.35 (d, 1H), 8.12 (dt, 1H), 8.02 (d, 1H), 3.34 (s, 4H), 1.75 (m, 4H), 1.45 (m, 4H).

TABLE 8

The compounds of Exmples 187-200 were prepared according to a synthetic procedure similar to the synthetic procedure for Example 186.

| Example | Compound | Name | Calc'd [M + H]$^+$ | Observed [M + H]$^+$ |
|---|---|---|---|---|
| 187 | | 2-(azepan-1-yl)-5-chloro-N-(2-methoxy-4-pyridyl)-4,6-dimethyl-pyridine-3-carboxamide | 389.2 | 389.2 |
| 188 | | 2-(azepan-1-yl)-5-chloro-4,6-dimethyl-N-(5-sulfamoyl-3-pyridyl)pyridine-3-carboxamide | 438.1 | 438.1 |
| 189 | | 5-chloro-2-(4,4-difluoro-1-piperidyl)-4,6-dimethyl-N-(5-sulfamoyl-3-pyridyl)pyridine-3-carboxamide | 460.1 | 460.1 |
| 190 | | 2-(6-azaspiro[2.5]octan-6-yl)-5-chloro-4,6-dimethyl-N-(5-sulfamoyl-3-pyridyl)pyridine-3-carboxamide | 450.1 | 450.2 |

TABLE 8-continued

The compounds of Exmples 187-200 were prepared according to a synthetic procedure similar to the synthetic procedure for Example 186.

| Example | Compound | Name | Calc'd [M + H]+ | Observed [M + H]+ |
|---|---|---|---|---|
| 191 | | 5-chloro-4,6-dimethyl-2-(1-piperidyl)-N-(5-sulfamoyl-3-pyridyl)pyridine-3-carboxamide | 424.1 | 424.1 |
| 192 | | 2-(4,4-difluoroazepan-1-yl)-6-methoxy-N-(5-sulfamoyl-3-pyridyl)pyridine-3-carboxamide | 442.1 | 442.1 |
| 193 | | 2-(azepan-1-yl)-N-(5-cyano-3-pyridyl)-5-(trifluoromethyl)-pyridine-3-carboxamide | 390.1 | 390.1 |
| 194 | | 2-(azepan-1-yl)-N-(5-methoxy-3-pyridyl)-5-(trifluoromethyl)-pyridine-3-carboxamide | 395.2 | 395.2 |
| 195 | | 2-(azepan-1-yl)-N-(5-methyl-3-pyridyl)-5-(tri-fluoromethyl)-pyridine-3-carboxamide | 379.2 | 379.2 |

TABLE 8-continued

The compounds of Exmples 187-200 were prepared according to a synthetic procedure similar to the synthetic procedure for Example 186.

| Example | Compound | Name | Calc'd [M + H]+ | Observed [M + H]+ |
|---|---|---|---|---|
| 196 | | 2-(azepan-1-yl)-N-[5-(hydroxymethyl)-3-pyridyl]-5-(trifluoromethyl)pyridine-3-carboxamide | 395.2 | 395.2 |
| 197 | | 2-(azepan-1-yl)-N-(2-cyano-4-pyridyl)-5-(trifluoromethyl)pyridine-3-carboxamide | 390.2 | 390.4 |
| 198 | | 2-(azepan-1-yl)-N-(2-ethylsulfonyl-4-pyridyl)-5-(trifluoromethyl)pyridine-3-carboxamide | 457.1 | 457.4 |
| 199 | | 2-(azepan-1-yl)-N-(3-bromoimidazo[1,2-a]pyridin-6-yl)-5-(trifluoromethyl)-pyridine-3-carboxamide | 482.1 | 482.2 |
| 200 | | 2-(azepan-1-yl)-5-(trifluoromethyl)-N-[5-(trifluoromethyl)-3-pyridyl]pyridine-3-carboxamide | 433.1 | 433.3 |

Example 201

2-(azepan-1-yl)-5-chloro-4,6-dimethyl-N-(2-sulfamoylpyridin-4-yl)nicotinamide

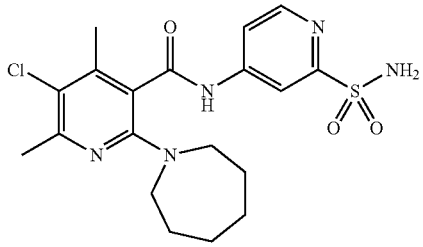 [SMILES: Cc1nc(N2CCCCCC2)c(C(=O)Nc2ccnc(S(N)(=O)=O)c2)c(C)c1Cl]

Step 1: 2-(azepan-1-yl)-5-chloro-4,6-dimethylnicotinic acid To a solution of 2,5-dichloro-4,6-dimethylnicotinic acid (0.50 g, 2.3 mmol) in DMF (5 mL) was added DIPEA (2.0 mL, 11 mmol), $K_2CO_3$ (2.0 g) and hexamethyleneimine (1.1 g, 11 mmol). The reaction vial was sealed and heated at 140° C. for 16 hours. Then the reaction mixture was cooled to rt and diluted in EtOAc. The organic layer was washed with 5% AcOH in water, brine, dried over $MgSO_4$, filtered and concentrated to give a residue that was purified via silica gel chromatography (0-75% EtOAc/hexanes) to give the title compound.

Step 2: 2-(azepan-1-yl)-5-chloro-4,6-dimethyl-N-(2-sulfamoylpyridin-4-yl)nicotinamide To a solution of 2-(azepan-1-yl)-5-chloro-4,6-dimethylnicotinic acid (35 mg, 0.12 mmol) in pyridine (1 mL) was added EDC (36 mg, 0.19 mmol) and 4-aminopyridine-2-sulfonamide (54 mg, 0.31 mmol). The mixture was stirred at 80° C. for 16 h, then concentrated under reduced pressure to give a residue that was purified reverse phase chromatography (5-95% MeCN in water with 0.1% TFA, C18 column) to give the title compound. LRMS m/z (M+H): calculated 438.1, observed 438.5. $^1$H NMR δ (ppm) (600 MHz, $CD_3OD$): 8.57 (d, J=5.5 Hz, 4H), 8.36 (d, J=1.6 Hz, 4H), 7.84 (dd, J=5.5, 1.9 Hz, 4H), 3.58-3.53 (m, 18H), 2.49 (s, 13H), 2.33 (s, 13H), 1.93 (s, 1H), 1.75 (s, 15H), 1.52 (s, 16H).

Example 202

5-chloro-4,6-dimethyl-2-(6-azaspiro[2.5]octan-6-yl)-N-(2-sulfamoylpyridin-4-yl)nicotinamide

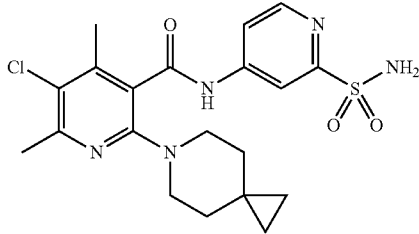 [SMILES: Cc1nc(N2CCC3(CC2)CC3)c(C(=O)Nc2ccnc(S(N)(=O)=O)c2)c(C)c1Cl]

Step 1: 2-(azepan-1-yl)-5-chloro-4,6-dimethylnicotinic acid To a mixture of 2,5-dichloro-4,6-dimethylnicotinic acid (0.50 g, 2.3 mmol) and $K_2CO_3$ (0.31 g, 2.3 mmol) in a vial was added DMF and hexamethyleneimine (0.56 g, 5.7 mmol). The vial was sealed and stirred at 135° C. for 16 h, then the mixture was dissolved in EtOAc. The organic layer was washed with 5% AcOH in water, brine, dried over $MgSO_4$, filtered and concentrated under reduced pressure to give a residue that was purified by silica gel chromatography (20% EtOAc/hexanes) to give the title compound.

Step 2: 5-chloro-4,6-dimethyl-2-(6-azaspiro[2.5]octan-6-yl)-N-(2-sulfamoylpyridin-4-yl)nicotinamide To a solution of 5-chloro-4,6-dimethyl-2-(6-azaspiro[2.5]octan-6-yl)nicotinic acid (35 mg, 0.12 mmol) in pyridine (1 mL) was added EDC (34 mg, 0.18 mmol) and 4-aminopyridine-2-sulfonamide (51 mg, 0.30 mmol). The mixture was stirred at 80° C. for 16 h, then concentrated and purified by reverse phase chromatography (5-95% MeCN in water with 0.1% TFA, C18 column) to give the title compound. LRMS m/z (M+H): calculated 450.1, observed 450.4. $^1$H NMR δ (ppm) (600 MHz, $CD_3OD$): 8.58 (d, J=5.3 Hz, 3H), 8.40 (s, 3H), 7.84 (d, J=5.3 Hz, 3H), 3.36-3.31 (m, 14H), 2.54 (s, 10H), 2.38 (s, 9H), 1.93 (s, 1H), 1.36-1.31 (m, 12H), 0.28 (s, 11H).

Example 203

4-(2-(azepan-1-yl)-5-(trifluoromethyl)nicotinamido)picolinamide

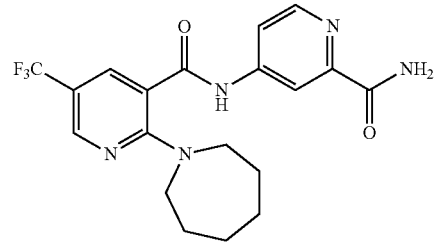 [SMILES: NC(=O)c1cc(NC(=O)c2cc(C(F)(F)F)cnc2N2CCCCCC2)ccn1]

Step 1: 2-(azepan-1-yl)-N-(2-cyanopyridin-4-yl)-5-(trifluoromethyl)nicotinamide The title compound was synthesized according to the synthetic procedure for Example 202 starting from Intermediate 17.

Step 2: 4-(2-(azepan-1-yl)-5-(trifluoromethyl)nicotinamido)picolinamide A mixture of 2-(azepan-1-yl)-3-((2-cyanopyridin-4-yl)carbamoyl)-5-(trifluoromethyl)pyridin-1-ium 2,2,2-trifluoroacetate (11 mg, 0.021 mmol) and NaOH (7.2 µl, 0.043 mmol) in MeOH (500 µl) was heated to 80° C. for 1 hour. Then the mixture was concentrated under reduced pressure and purified by reverse phase chromatography (5-9% MeCN in water with 0.1% TFA, C18 column) to give the title compound. LRMS m/z (M+H): calculated 408.2, observed 408.4. $^1$H NMR δ (ppm) (600 MHz, $CD_3OD$): 8.60 (d, J=5.7 Hz, 2H), 8.54 (s, 2H), 8.47 (s, 2H), 8.06 (d, J=5.9 Hz, 2H), 8.02 (s, 2H), 4.09 (s, 1H), 3.58 (q, J=8.5, 7.0 Hz, 10H), 3.30 (s, 24H), 1.83 (s, 8H), 1.53 (s, 9H).

Example 204

5-bromo-2-(4,4-difluoropiperidin-1-yl)-N-(2-sulfamoylpyridin-4-yl)nicotinamide

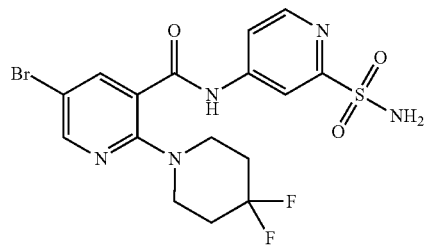 [SMILES: NS(=O)(=O)c1cc(NC(=O)c2cc(Br)cnc2N2CCC(F)(F)CC2)ccn1]

The title compound was a synthesized according to the synthetic procedure for Example 203 starting from 2-chloro-5-bromo-nicotinic acid. LRMS m/z (M, M+2): calculated 476.0/478.0, observed 476.2/478.2.

Example 205

2-(4,4-difluoropiperidin-1-yl)-5-phenyl-N-(2-sulfamoylpyridin-4-yl)nicotinamide

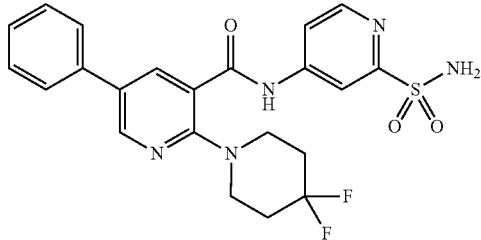 [SMILES: NS(=O)(=O)c1cc(NC(=O)c2cc(-c3ccccc3)cnc2N2CCC(F)(F)CC2)ccn1]

Step 1: tert-butyl tert-butyl((4-(2-(4,4-difluoropiperidin-1-yl)-5-phenylnicotinamido)pyridin-2-yl)sulfonyl)carbamate A mixture of phenylboronic acid (14 mg, 0.12 mmol), tert-butyl ((4-(5-bromo-2-(4,4-difluoropiperidin-1-yl)nicotinamido)pyridin-2-yl)sulfonyl)(tert-butyl)carbamate (Intermediate 39, 50 mg, 0.08 mmol), potassium phosphate tribasic (50 mg, 0.24 mmol), and Xphos Pd G2 (6.2 mg, 0.0079 mmol) was suspended in THF (0.80 mL). The reaction vessel was sealed and degassed via vacuum and purged with nitrogen (5×). The reaction mixture was stirred at 60° C. for 5 h, then filtered through a pad of Celite™, rinsed with ethyl acetate and concentrated to give the title compound.

Step 2: 2-(4,4-difluoropiperidin-1-yl)-5-phenyl-N-(2-sulfamoylpyridin-4-yl)nicotinamide To a solution of crude tert-butyl tert-butyl((4-(2-(4,4-difluoropiperidin-1-yl)-5-phenylnicotinamido)-pyridin-2-yl)sulfonyl)carbamate (50 mg, 0.079 mmol), in DCM (0.8 mL) at 0° C. was added TFA (0.31 mL, 4.0 mmol). The mixture was stirred at rt for 1.5 h and then concentrated by blowing air over the mixture. The residue was purified by reverse phase chromatography (5-95% MeCN in water with 0.1% TFA, C18 column) to give the title compound. LRMS m/z (M+H): calculated 474.1, observed 474.4.

Example 206

2-(4,4-difluoropiperidin-1-yl)-5-(piperidin-1-yl)-N-(2-sulfamoylpyridin-4-yl)nicotinamide

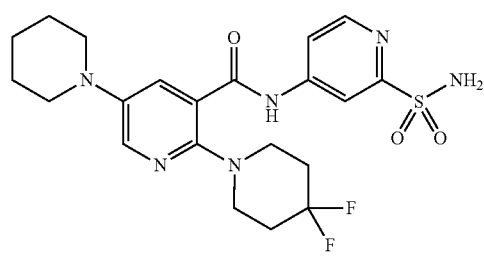 [SMILES: NS(=O)(=O)c1cc(NC(=O)c2cc(N3CCCCC3)cnc2N2CCC(F)(F)CC2)ccn1]

Step 1: tert-butyl ((4-(2-(4,4-difluoropiperidin-1-yl)-5-(piperidin-1-yl)nicotinamido)pyridin-2-yl)sulfonyl)carbamate A mixture of tert-butyl ((4-(5-bromo-2-(4,4-difluoropiperidin-1-yl)nicotinamido)pyridin-2-yl)sulfonyl)(tert-butyl)carbamate (Intermediate 39, 50 mg, 0.08 mmol), cesium carbonate (0.13 g, 0.40 mmol), and Ruphos Pd G2 (12 mg, 0.016 mmol) was suspended in dioxane (0.80 mL). Then piperidine (23 uL, 0.24 mmol) was added and the reaction vessel was sealed and degassed via vacuum and purged with N₂ (5×). The reaction mixture was stirred at 80° C. for 5 h then 100° C. for 15 h, then filtered through a pad of Celite™, rinsed with ethyl acetate, and concentrated to give the title compound.

Step 2: 2-(4,4-difluoropiperidin-1-yl)-5-(piperidin-1-yl)-N-(2-sulfamoylpyridin-4-yl)nicotinamide To a solution of tert-butyl ((4-(2-(4,4-difluoropiperidin-1-yl)-5-(piperidin-1-yl)nicotinamido)pyridin-2-yl)sulfonyl)carbamate (46 mg, 0.079 mmol), in DCM (0.8 mL) at 0° C. was added TFA (0.30 mL, 4.0 mmol). The mixture was stirred at rt for 2 h then concentrated by blowing air over top. The residue was purified by reverse phase chromatography (5-95% MeCN in water with 0.1% TFA, C18 column) to give the title compound. LRMS m/z (M+H): calculated 481.2, observed 481.5.

Example 207

2-(4,4-difluoropiperidin-1-yl)-5-(1H-pyrazol-1-yl)-N-(2-sulfamoylpyridin-4-yl)nicotinamide

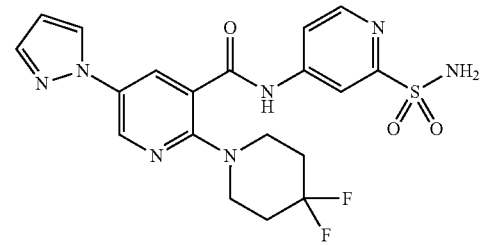 [SMILES: NS(=O)(=O)c1cc(NC(=O)c2cc(-n3cccn3)cnc2N2CCC(F)(F)CC2)ccn1]

Step 1: tert-butyl ((4-(2-(4,4-difluoropiperidin-1-yl)-5-(1H-pyrazol-1-yl)nicotinamido)pyridin-2-yl)sulfonyl)carbamate A mixture of 1H-pyrazole (16 mg, 0.24 mmol), tert-butyl ((4-(5-bromo-2-(4,4-difluoropiperidin-1-yl)nicotinamido)pyridin-2-yl)sulfonyl)(tert-butyl)carbamate (Intermediate 39, 50 mg, 0.08 mmol), cesium carbonate (51 mg, 0.16 mmol), and copper (I) iodide (12 mg, 0.063 mmol) was suspended in DMSO (0.80 mL). Then (1R,2R)—N,N'-dimethyl-1,2-cyclohexanediamine (12 uL, 0.079 mmol) was added and the reaction vessel was sealed and degassed via vacuum and purged with nitrogen (5×). The reaction mixture was stirred at 120° C. for 5 h, then partitioned between water and ethyl acetate. The organic layer was separated and washed with water, dried over $Na_2SO_4$, filtered, and concentrated to give the title compound.

Step 2: 2-(4,4-difluoropiperidin-1-yl)-5-(1H-pyrazol-1-yl)-N-(2-sulfamoylpyridin-4-yl)-nicotinamide To a solution of crude tert-butyl ((4-(2-(4,4-difluoropiperidin-1-yl)-5-(1H-pyrazol-1-yl)nicotinamido)pyridin-2-yl)sulfonyl)carbamate (44 mg, 0.079 mmol) in DCM (0.8 mL) at 0° C. was added TFA (0.30 mL, 4.0 mmol). The mixture was stirred at rt for 2 h and then concentrated by blowing air over top. The resulting residue was purified by reverse phase chromatography (5-95% MeCN in water with 0.1% TFA, C18 column) to give the title compound. LRMS m/z (M+H): calculated 464.1, observed 464.4.

Example 208

N-(2-oxo-1,2-dihydropyridin-4-yl)-2-(6-azaspiro[2.5]octan-6-yl)-5-(trifluoromethyl)nicotinamide

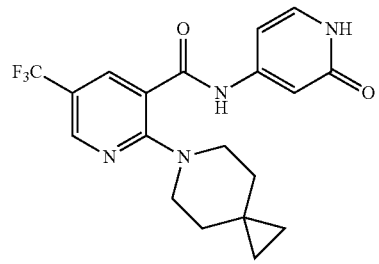 [SMILES: O=C(Nc1cc[nH]c(=O)c1)c1cc(C(F)(F)F)cnc1N1CCC2(CC1)CC2]

To a mixture of N-(2-methoxypyridin-4-yl)-2-(6-azaspiro[2.5]octan-6-yl)-5-(trifluoromethyl)-nicotinamide (Example 143, 131 mg, 0.322 mmol) in DMF (0.3 mL) was added pyridine hydrochloride (0.19 g, 1.6 mmol) and the resulting mixture was heated at 105° C. in a sealed vial for 16 h. Additional pyridine hydrochloride (250 mg) was added and the mixture was heated at 105° C. for 3 hours. The mixture was then diluted with EtOAc, washed with saturated aqueous $NaHCO_3$, water, brine, dried over $MgSO_4$ and concentrated to give a residue. The residue was swished with $CHCl_3$ and filtered to give the title compound. LRMS m/z (M+H): calculated 393.2, observed 393.1. $^1$H NMR δ (ppm) (500 MHz, DMSO-$d_4$) ☐ 11.26 (s, 1H), 10.56 (s, 1H), 8.56 (m, 1H), 7.97 (d, 1H), 7.33 (d, 1H), 6.79 (s, 1H), 6.41 (s, 1H), 3.52 (m, 4H), 1.38 (m, 4H), 0.33 (s, 4H).

TABLE 9

The compounds of Exmples 209-213 were prepared according to a synthetic procedure similar to the synthetic procedure for Example 208.

| Example | Compound | Name | Calc'd [M + H]$^+$ | Observed [M + H]$^+$ |
|---|---|---|---|---|
| 209 | | 5-chloro-4,6-dimethyl-N-(2-oxo-1,2-dihydropyridin-4-yl)-2-(6-azaspiro[2.5]octan-6-yl)nicotinamide | 387.2 | 387.2 |
| 210 | | 2-(4,4-difluoroazepan-1-yl)-N-(2-oxo-1,2-dihydropyridin-4-yl)-5-(trifluoromethyl)-nicotinamide | 417.1 | 417.1 |

TABLE 9-continued

The compounds of Exmples 209-213 were prepared according to a synthetic procedure similar to the synthetic procedure for Example 208.

| Example | Compound | Name | Calc'd [M + H]+ | Observed [M + H]+ |
|---|---|---|---|---|
| 211 | | 5-chloro-4,6-dimethyl-N-(2-oxo-1,2-dihydropyridin-4-yl)-2-(piperidin-1-yl)-nicotinamide | 361.1 | 361.2 |
| 212 | | 2-(azepan-1-yl)-N-(2-oxo-1,2-dihydropyridin-4-yl)-5-(trifluoromethyl)nicotinamide | 381.1 | 381.2 |
| 213 | | 2-(azepan-1-yl)-5-chloro-4,6-dimethyl-N-(2-oxo-1,2-diydropyridin-4-yl)nicotinamide | 375.2 | 375.2 |

Example 214

5-chloro-2-(4,4-difluoroazepan-1-yl)-N,4,6-trimethyl-N-(2-sulfamoylpyridin-4-yl)nicotinamide

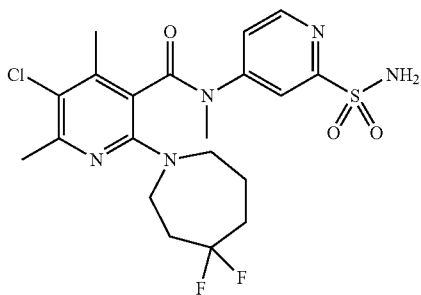 [SMILES: Cc1nc(N2CCCC(F)(F)CC2)c(C(=O)N(C)c2ccnc(S(N)(=O)=O)c2)c(C)c1Cl]

Step 1: 2,5-dichloro-N,4,6-trimethylnicotinamide A mixture of 2,5-dichloro-4,6-dimethylnicotinic acid (150 mg, 0.68 mmol) in SOCl$_2$ (2.0 mL, 27 mmol) was stirred at room temperature for 1 hour under a nitrogen atmosphere. The mixture was evaporated under reduced pressure, and the resulting residue was dissolved in THF (2 mL). The solution was added dropwise into a solution of methanamine (2.0 mL, 0.68 mmol) in water at room temperature. The resultant mixture was purified by prep-TLC (petroleum ether:ethyl acetate 1:1) to give the title compound.

Step 2: 5-chloro-2-(4,4-difluoroazepan-1-yl)-N,4,6-trimethylnicotinamide To a mixture of 2,5-dichloro-N,4,6-trimethylnicotinamide (50 mg, 0.21 mmol) and 4,4-difluoroazepane hydrochloride (Intermediate 40, 44 mg, 0.26 mmol) in NMP (2 mL) was added DIPEA (0.11 mL, 0.64 mmol) at 25° C. The reaction mixture was stirred at 100° C. for 18 h, then additional 4,4-difluoroazepane hydrochloride (20 mg, 0.12 mmol) was added, and the reaction mixture was stirred at 220° C. for 2 h in a microwave reactor. The mixture was cooled to room temperature, treated with water and extracted with ethyl acetate. The combined organic layers were washed with brine, dried over Na$_2$SO$_4$, filtered and concentrated under reduced pressure to give a residue that was purified by silica gel chromatography (petroleum ether:ethyl acetate 1:1) to give the title compound.

Step 3: N-(2-(N,N-bis(2,4-dimethoxybenzyl)sulfamoyl)pyridin-4-yl)-5-chloro-2-(4,4-difluoroazepan-1-yl)-N,4,6-trimethylnicotinamide To a mixture of 5-chloro-2-(4,4-difluoroazepan-1-yl)-N,4,6-trimethylnicotinamide (40 mg, 0.12 mmol) and 4-bromo-N,N-bis(2,4-dimethoxybenzyl)pyridine-2-sulfonamide (Intermediate 4, 78 mg, 0.14 mmol) and Cs$_2$CO$_3$ (0.12 g, 0.36 mmol) in dioxane (3 mL) was added Xantphos G3 (11 mg, 0.012 mmol). The reaction mixture was stirred at 100° C. for 18 h under an atmosphere of nitrogen. The mixture was then treated with water and extracted with EtOAc. The combined organic layers were washed with brine, dried over Na$_2$SO$_4$, filtered and concentrated under reduced pressure to give a residue that was purified by silica gel chromatography (petroleum ether:ethyl acetate 1:1) to give the title compound.

Step 4: 5-chloro-2-(4,4-difluoroazepan-1-yl)-N,4,6-trimethyl-N-(2-sulfamoylpyridin-4-yl)nicotinamide To a solution of N-(2-(N,N-bis(2,4-dimethoxybenzyl)sulfamoyl)pyridin-4-yl)-5-chloro-2-(4,4-difluoroazepan-1-yl)-N,4,6-trimethylnicotinamide (30 mg, 0.038 mmol) in DCM (1 mL) was added TFA (0.8 mL) with stirring at 25° C. The reaction mixture was stirred at 25° C. for 1 h. Then the mixture was concentrated under reduced pressure and purified by reverse phase chromatography (45-75% MeCN in water with 0.1% TFA, C18 column) to give the title compound. LRMS m/z (M+H): calculated 488.1, observed 488.2. $^1$H NMR δ (500 MHz, CD$_3$OD): 8.46 (d, J=5.0 Hz, 1H), 7.44 (d, J=1.5 Hz, 1H), 7.11 (dd, J=2.0, 5.0 Hz, 1H), 3.54 (s, 3H), 3.41-3.47 (m, 1H), 3.22-3.29 (m, 1H), 3.14-3.21 (m, 1H), 3.05-3.14 (m, 1H), 2.44 (s, 3H), 2.39 (s, 3H), 1.74-2.15 (m, 6H).

Example 215

5-chloro-4,6-dimethyl-2-(4-methylcyclohexyl)-N-(2-sulfamoylpyridin-4-yl)nicotinamide

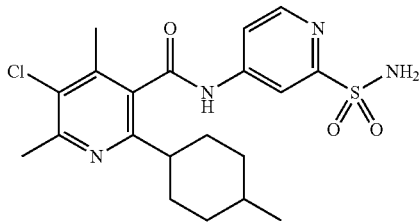 [SMILES: Cc1nc(C2CCC(C)CC2)c(C(=O)Nc2ccnc(S(N)(=O)=O)c2)c(C)c1Cl]

To a vial was added nickel(II) iodide (17 mg, 0.053 mmol), pyridine-2,6-bis(carboximidamide) (13 mg, 0.053 mmol) and zinc (70 mg, 1.1 mmol), and the vial was evacuated and backfilled with nitrogen. Then DMA (1.0 mL) was added to the vial with stirring for 5 minutes at room temperature. A solution of 2,5-dichloro-4,6-dimethyl-N-(2-sulfamoylpyridin-4-yl)nicotinamide (100 mg, 0.27 mmol), NaI (80 mg, 0.53 mmol) and 1-bromo-4-methylcyclohexane (94 mg, 0.53 mmol) in DMA (2 mL) was added to the vial containing the above mixture. The reaction mixture was heated to 80° C. for 12 h, then the mixture was diluted with DMF (2 mL), filtered and purified by reverse phase chromatography (38-58% MeCN in water with 0.1% TFA, C18 column) to give the title compound. LRMS m/z (M+H): calculated 437.1, observed 437.2. $^1$H NMR δ (500 MHz, CD$_3$OD) 8.62 (d, J=5.5 Hz, 1H), 8.37 (d, J=1.5 Hz, 1H), 7.82-7.90 (m, 1H), 2.67 (s, 3H), 2.64-2.66 (m, 1H), 2.39 (s, 3H), 1.67-1.95 (m, 6H), 1.37-1.49 (m, 1H), 0.91-1.03 (m, 2H), 0.89 (d, J=6.5 Hz, 3H).

Example 216

5-chloro-3-(4,4-difluoroazepan-1-yl)-N-(2-sulfamoylpyridin-4-yl)pyrazine-2-carboxamide

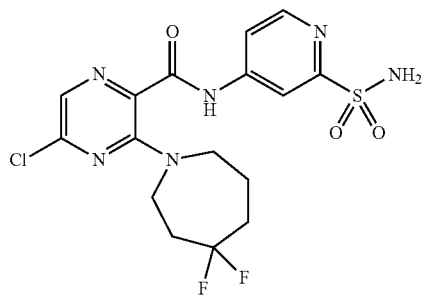 [SMILES: NS(=O)(=O)c1cc(NC(=O)c2ncc(Cl)nc2N2CCCC(F)(F)CC2)ccn1]

Step 1: 1-(6-chloro-3-iodopyrazin-2-yl)-4,4-difluoroazepane To a mixture of 3,5-dichloro-2-iodopyrazine (4.0 g, 8.7 mmol) and CsF (4.0 g, 26 mmol) in DMSO (10 mL) was added 4,4-difluoroazepane hydrochloride (2.2 g, 13 mmol). The reaction mixture was stirred at 50° C. for 10 hours, then the solvent was removed under reduced pressure. The resulting residue was diluted with water, and extracted with EtOAc. The combined organic layers were washed with brine, dried over anhydrous Na$_2$SO$_4$, filtered and concentrated to give a residue that was purified by silica gel chromatography (petroleum ether/ethyl acetate 5/1) to give the title compound.

Step 2: 1-(6-chloro-3-vinylpyrazin-2-yl)-4,4-difluoroazepane To a solution of 1-(6-chloro-3-iodopyrazin-2-yl)-4,4-difluoroazepane (2.4 g, 6.4 mmol) in THF (20 mL) and water (5 mL) was added Cs$_2$CO$_3$ (6.3 g, 19 mmol), Pd(dppf)Cl$_2$ (0.47 g, 0.64 mmol) and potassium vinyltrifluoroborate (1.3 g, 9.6 mmol). The reaction mixture was degassed and backfilled with nitrogen (three times), then the reaction mixture was stirred at 55° C. for 13 hours. The mixture was filtered, diluted with water and extracted with EtOAc. The combined organic layers were washed with brine, dried over anhydrous Na$_2$SO$_4$, filtered and concentrated to give a residue that was purified by silica gel chromatography (petroleum ether/ethyl acetate 10/1) to provide the title compound.

Step 3: 5-chloro-3-(4,4-difluoroazepan-1-yl)pyrazine-2-carbaldehyde To a mixture of 1-(6-chloro-3-vinylpyrazin-2-yl)-4,4-difluoroazepane (1.2 g, 4.4 mmol) in THF (15 mL) and water (3 mL) was added 4-methylmorpholine N-oxide (1.0 g, 8.8 mmol) and OsO$_4$ (0.014 mL, 0.044 mmol). The reaction mixture was stirred at 20° C. for 12 hours, then NaIO$_4$ (4.7 g, 22 mmol) was added. The reaction mixture was stirred at 20° C. for an additional 2 hours. Then the mixture was diluted with water and extracted with DCM. The combined organic layers were dried over Na$_2$SO$_4$, filtered and concentrated under reduced pressure to give a residue that was purified by silica gel chromatography (5% EtOAc/hexanes) to give the title compound.

Step 4: 5-chloro-3-(4,4-difluoroazepan-1-yl)pyrazine-2-carboxylic acid To a stirred mixture of 5-chloro-3-(4,4-difluoroazepan-1-yl)pyrazine-2-carbaldehyde (0.10 g, 0.36 mmol), 2-methylbut-2-ene (0.10 g, 1.5 mmol) and NaH$_2$PO$_4$ (0.65 g, 5.4 mmol) in tBuOH (3 mL) and water (2 mL) was added in one portion NaClO$_2$ (0.20 g, 2.2 mmol) at 0° C. The reaction mixture was stirred at 20° C. for 12 hours. The organic layer was freeze-dried to give the title compound.

Step 5: tert-butyl tert-butyl((4-(5-chloro-3-(4,4-difluoro-azepan-1-yl)pyrazine-2-carboxamido)pyridin-2-yl)sulfonyl)carbamate To a solution of 5-chloro-3-(4,4-difluoroazepan-1-yl)pyrazine-2-carboxylic acid (100 mg crude) and tert-butyl ((4-aminopyridin-2-yl)sulfonyl)(tert-butyl)carbamate (Intermediate 8, 0.17 g, 0.51 mmol) in pyridine (2 mL) was added POCl$_3$ (0.064 mL, 0.69 mmol) at 0° C. The reaction mixture was stirred at 0° C. for 1 hour. The mixture was concentrated under reduced pressure to a residue that was diluted with water and extracted with EtOAc. The combined organic layers were dried over Na$_2$SO$_4$, filtered and concentrated under reduced pressure to give a residue that was purified by silica gel chromatography (50% petroleum ether/EtOAc) to give the title compound.

Step 6: 5-chloro-3-(4,4-difluoroazepan-1-yl)-N-(2-sulfamoylpyridin-4-yl)pyrazine-2-carboxamide A solution of tert-butyl tert-butyl((4-(5-chloro-3-(4,4-difluoroazepan-1-yl)pyrazine-2-carboxamido)pyridin-2-yl)sulfonyl)carbamate (0.19 g, 0.25 mmol) in TFA (2 mL) and DCM (2 mL) was stirred at 20° C. for 2 hours. Then the reaction mixture was concentrated under reduced pressure. The resulting residue was dissolved in DMF and purified by reverse phase chromatography (39-59% MeCN in water with 0.1% TFA, C18 column) to give the title compound. LRMS m/z (M+H): calculated 447.1, observed 447.1. $^1$H NMR δ (500 MHz, CD$_3$OD) 8.57 (d, J=5.5 Hz, 1H), 8.47 (d, J=2.0 Hz, 1H), 7.92-7.96 (m, 2H), 3.72-3.82 (m, 2H), 3.47 (t, J=5.5 Hz, 2H), 2.29-2.40 (m, 2H), 1.91-2.07 (m, 4H).

Example 217

5-chloro-2-cycloheptyl-4,6-dimethyl-N-(2-sulfamoylpyridin-4-yl)nicotinamide

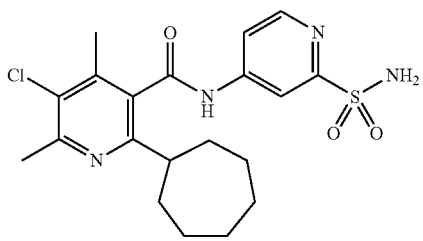 [SMILES: Cc1nc(C2CCCCCC2)c(C(=O)Nc2ccnc(S(N)(=O)=O)c2)c(C)c1Cl]

To a vial was added nickel(II) iodide (17 mg, 0.053 mmol), pyridine-2,6-bis(carboximidamide) (13 mg, 0.053 mmol) and zinc (70 mg, 1.1 mmol), and the vial was evacuated and backfilled with nitrogen. Then DMA (1.0 mL) was added to the vial with stirring for 5 minutes at room temperature. A solution of 2,5-dichloro-4,6-dimethyl-N-(2-sulfamoylpyridin-4-yl)nicotinamide (100 mg, 0.27 mmol), NaI (40 mg, 0.27 mmol) and bromocycloheptane (94 mg, 0.53 mmol) in DMA (1.5 mL) was added to the vial containing the above mixture. The reaction mixture was heated to 80° C. for 12 h, then the mixture was diluted with DMF (2 mL), filtered and purified by reverse phase chromatography (39-69% MeCN in water with 0.1% TFA, C18 column) to give the title compound. LRMS m/z (M+H): calculated 437.1, observed 437.2. $^1$H NMR δ (500 MHz, CD$_3$OD) 8.63 (d, J=5.5 Hz, 1H), 8.37 (d, J=1.5 Hz, 1H), 7.87-7.88 (m, 1H), 2.82-2.90 (m, 1H), 2.65 (s, 3H), 2.40 (s, 3H), 1.80-1.92 (m, 6H), 1.38-1.67 (m, 6H).

Example 218

5-chloro-2-(4,4-difluorocyclohexyl)-4,6-dimethyl-N-(2-sulfamoylpyridin-4-yl)nicotinamide

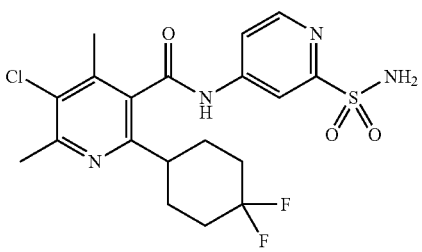 [SMILES: Cc1nc(C2CCC(F)(F)CC2)c(C(=O)Nc2ccnc(S(N)(=O)=O)c2)c(C)c1Cl]

To a vial was added nickel(II) iodide (17 mg, 0.053 mmol), pyridine-2,6-bis(carboximidamide) (13 mg, 0.053 mmol) and zinc (70 mg, 1.1 mmol), and the vial was evacuated and backfilled with nitrogen. Then DMA (1.0 mL) was added to the vial with stirring for 5 minutes at room temperature. A solution of 2,5-dichloro-4,6-dimethyl-N-(2-sulfamoylpyridin-4-yl)nicotinamide (100 mg, 0.27 mmol), NaI (40 mg, 0.27 mmol) and 4-bromo-1,1-difluorocyclohexane (106 mg, 0.53 mmol) in DMA (1.5 mL) was added to the vial containing the above mixture. The reaction mixture was heated to 80° C. for 12 h, then the mixture was diluted with DMF (2 mL), filtered and purified by reverse phase chromatography (43-63% MeCN in water with 0.1% TFA, C18 column) to give the title compound. LRMS m/z (M+H): calculated 459.1, observed 459.1. $^1$H NMR δ (500 MHz, CD$_3$OD) 8.61 (d, J=5.5 Hz, 1H), 8.37 (d, J=1.5 Hz, 1H), 7.86-7.88 (m, 1H), 2.74-2.83 (m, 1H), 2.63 (m, 3H), 2.38 (s, 3H), 2.07-2.23 (m, 4H), 1.75-1.96 (m, 4H).

Example of a Pharmaceutical Composition

As a specific embodiment of an oral pharmaceutical composition, a 100 mg potency tablet is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Qube® Assay Experimental Procedure

Compounds were tested on human Nav1.8 and Nav1.5 channels stably expressed in human embryo kidney (HEK) 293 cells. Sodium current measurements on Qube® were conducted as follows: automated 384-well patch-clamp assays on the Qube® platform (Sophion Biosciences) were used to measure the inhibition of sodium flow through human Nav1.8 and Nav1.5 channels. Whole-cell voltage-clamp recordings were performed in QChips® (Sophion Biosciences) at room temperature. Nav1.8 current measurements on Qube® were obtained as follows: Nav1.8 currents were elicited with a 10 second 1 Hertz (Hz) pulse train from a holding potential of −90 millivolts (mV), delivered to the cells once per minute in the control condition (DMSO only) and after compound addition. The 1 hertz pulse train stimulation consisted of ten test pulses to 10 millivolt (mV) for 20 milliseconds (ms), each of which was followed by a 980 millisecond repolarization to −67 millivolts. At the end of the 10 second pulse train stimulation, a 5 second hyperpolarization step to −100 millivolt (mV) was used to recover Nav1.8 from fast inactivation. The peak currents elicited by the $1^{st}$ and $10^{th}$ test pulses were used to determine $IC_{50}$ values for resting inhibition and inactivated state inhibition. Nav1.5 current measurements on Qube® were obtained as follows: Nav1.5 currents were elicited with a 20 second 3 Hertz pulse train in the control condition (DMSO only) and after compound addition. The pulse train consisted of sixty 20 millisecond test pulses to 0 millivolt from a holding potential of −80 millivolt (mV). The average peak currents elicited by the last 3 test pulses were used to determine $IC_{50}$ values for Nav1.5 inhibition.

The following buffers were used for the Qube® recordings: External buffer for Nav1.8 Qube® recording: 150 NaCl, 2 $CaCl_2$), 5 KCl, 1 Mg $Cl_2$, 10 HEPES, 12 Dextrose; External buffer for Qube® Nav1.5 recording: 120 N-Methyl-D-Glucamine, 40 NaCl, 1 KCl, 2.7 $CaCl_2$), 5 HEPES, 0.5 $MgCl_2$; and Internal buffer for Qube® recording: 120 CsF, 30 CsCl, 10 EGTA, 5 HEPES, 5 NaF, 2 $MgCl_2$.

For all Qube® experiments offline analysis was used to determine percent inhibition as a function of drug concentration. $IC_{50}$ values were determined by fitting to the Hill equation.

The compounds of the present invention have $Na_v1.8$ $IC_{50}$ values in the Qube® Assay of less than 10 micromolar. Specific $IC_{50}$ values of the compounds of Examples 1-218 in the Qube® Assay are listed in Table I.

TABLE I $IC_{50}$ values (nM) for Examples in the $Na_v$ 1.8 Qube ® Assay

| Example | $IC_{50}$ (nM) |
|---|---|
| 1 | 406 |
| 2 | 2189 |
| 3 | 2377 |
| 4 | 5431 |
| 5 | 820 |
| 6 | 355 |
| 7 | 2827 |
| 8 | 2354 |
| 9 | 816 |
| 10 | 174 |
| 11 | 212 |
| 12 | 94 |
| 13 | 4.1 |
| 14 | 45 |
| 15 | 6.5 |
| 16 | 12 |
| 17 | 3.1 |
| 18 | 0.9 |
| 19 | 1.6 |
| 20 | 67 |
| 21 | 4.5 |
| 22 | 3.0 |
| 23 | 2.6 |
| 24 | 2.1 |
| 25 | 5.4 |
| 26 | 1856 |
| 27 | 31 |
| 28 | 1303 |
| 29 | 31 |
| 30 | 4.0 |
| 31 | 4.1 |
| 32 | 4.3 |
| 33 | 35 |
| 34 | 50 |
| 35 | 74 |
| 36 | 147 |
| 37 | 1247 |
| 38 | 24 |
| 39 | 441 |
| 40 | 4.1 |
| 41 | 5.1 |
| 42 | 341 |
| 43 | 37 |
| 44 | 59 |
| 45 | 1793 |
| 46 | 1.0 |
| 47 | 3.9 |
| 48 | 12 |
| 49 | 1.4 |
| 50 | 14 |
| 51 | 6.6 |
| 52 | 2.8 |
| 53 | 0.8 |
| 54 | 2.1 |
| 55 | 1.4 |
| 56 | 9.1 |
| 57 | 31 |
| 58 | 10 |
| 59 | 116 |
| 60 | 14 |
| 61 | 15 |
| 62 | 105 |
| 63 | 20 |
| 64 | 23 |
| 65 | 94 |
| 66 | 88 |
| 67 | 25 |
| 68 | 29 |
| 69 | 82 |
| 70 | 41 |
| 71 | 60 |
| 72 | 714 |
| 73 | 225 |
| 74 | 319 |
| 75 | 233 |
| 76 | 389 |
| 77 | 2978 |
| 78 | 5077 |
| 79 | 21 |
| 80 | 31 |
| 81 | 39 |
| 82 | 54 |
| 83 | 114 |
| 84 | 147 |
| 85 | 152 |
| 86 | 172 |
| 87 | 223 |
| 88 | 275 |
| 89 | 275 |
| 90 | 294 |
| 91 | 616 |
| 92 | 659 |
| 93 | 707 |
| 94 | 745 |
| 95 | 1419 |
| 96 | 1621 |
| 97 | 1896 |
| 98 | 2366 |
| 99 | 2558 |
| 100 | 4629 |
| 101 | 3.9 |
| 102 | 27 |
| 103 | 166 |
| 104 | 56 |
| 105 | 696 |
| 106 | 103 |
| 107 | 139 |
| 108 | 191 |
| 109 | 289 |
| 110 | 505 |
| 111 | 633 |
| 112 | 8413 |
| 113 | 9332 |
| 114 | 95 |

TABLE I-continued

IC$_{50}$ values (nM) for Examples in the Na$_v$ 1.8 Qube ® Assay

| Example | IC$_{50}$ (nM) |
|---|---|
| 115 | 1.6 |
| 116 | 32 |
| 117 | 18 |
| 118 | 54 |
| 119 | 30 |
| 120 | 2.9 |
| 121 | 58 |
| 122 | 20 |
| 123 | 28 |
| 124 | 50 |
| 125 | 144 |
| 126 | 21 |
| 127 | 220 |
| 128 | 94 |
| 129 | 753 |
| 130 | 3877 |
| 131 | 2.0 |
| 132 | 5.3 |
| 133 | 12 |
| 134 | 155 |
| 135 | 57 |
| 136 | 494 |
| 137 | 26 |
| 138 | 5.8 |
| 139 | 16 |
| 140 | 91 |
| 141 | 245 |
| 142 | 29 |
| 143 | 1540 |
| 144 | 36 |
| 145 | 161 |
| 146 | 177 |
| 147 | 22 |
| 148 | 26 |
| 149 | 57 |
| 150 | 77 |
| 151 | 89 |
| 152 | 155 |
| 153 | 310 |
| 154 | 84 |
| 155 | 60 |
| 156 | 58 |
| 157 | 82 |
| 158 | 41 |
| 159 | 1627 |
| 160 | 9.2 |
| 161 | 63 |
| 162 | 22 |
| 163 | 10 |
| 164 | 3.3 |
| 165 | 2.1 |
| 166 | 13 |
| 167 | 52 |
| 168 | 17 |
| 169 | 6.9 |
| 170 | 24 |
| 171 | 9.2 |
| 172 | 0.3 |
| 173 | 199 |
| 174 | 4.1 |
| 175 | 53 |
| 176 | 1094 |
| 177 | 2.8 |
| 178 | 13 |
| 179 | 102 |
| 180 | 14 |
| 181 | 17 |
| 182 | 62 |
| 183 | 82 |
| 184 | 0.5 |
| 185 | 3.8 |
| 186 | 1288 |
| 187 | 141 |
| 188 | 5.9 |
| 189 | 13 |

TABLE I-continued

IC$_{50}$ values (nM) for Examples in the Na$_v$ 1.8 Qube ® Assay

| Example | IC$_{50}$ (nM) |
|---|---|
| 190 | 31 |
| 191 | 124 |
| 192 | 163 |
| 193 | 654 |
| 194 | 1555 |
| 195 | 2774 |
| 196 | 5186 |
| 197 | 244 |
| 198 | 425 |
| 199 | 5071 |
| 200 | 9665 |
| 201 | 1.3 |
| 202 | 1.9 |
| 203 | 139 |
| 204 | 55 |
| 205 | 71 |
| 206 | 363 |
| 207 | 1081 |
| 208 | 287 |
| 209 | 12 |
| 210 | 86 |
| 211 | 357 |
| 212 | 570 |
| 213 | 80 |
| 214 | 347 |
| 215 | 6.6 |
| 216 | 80 |
| 217 | 3.2 |
| 218 | 2.4 |

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:

1. A compound of structural Formula I:

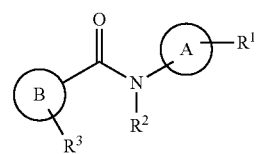

I or a pharmaceutically acceptable salt thereof, wherein
A is selected from:
  (1) pyridine,
  (2) pyrimidine,
  (3) pyrazine,
  (4) indazole,
  (5) imidazo[1,2-a]pyridine,
  (6) pyrrolo[3,2-c]pyridine,
  (7) pyrrolo[2,3-b]pyridine,
  (8) pyrazole,
  (9) thiophene, and
  (10) 1,2,4-oxadiazole,
wherein A is unsubstituted or substituted with one to four substituents selected from $R^a$, provided that both A and B are not pyridine;
B is selected from:
  (1) pyrazine,
  (2) pyridine,
  (3) pyrimidine, and
  (4) pyridazine,
wherein each B is unsubstituted or substituted with one to three substituents selected from $R^b$;
$R^1$ is selected from:
  (1) —$SO_3H$,
  (2) —$SO_2NH_2$,
  (3) —$SO_2C_{1-6}$alkyl,
  (4) —$SO_2NH$—$C_{1-6}$alkyl,
  (5) —$SO_2C_{3-6}$cycloalkyl,
  (6) —$C(O)NH_2$,
  (7) —$CO_2H$,
  (8) —CN,
  (9) halogen,
  (10) —OH, and
  (11) —$OC_{1-6}$alkyl,
wherein each alkyl, and cycloalkyl is unsubstituted or substituted with one to three substituents selected from $R^d$;
$R^2$ is hydrogen;
$R^3$ is selected from:
  (1) cyclohexane,
  (2) cycloheptane,
  (3) pyrrolidine,
  (4) azetidine,
  (5) piperidine,
  (6) piperazine,
  (7) azepane,
  (8) morpholine,
  (9) thiomorpholine,
  (10) oxazepane,
  (11) isoindoline,
  (12) dihydroisoquinoline,
  (13) azabicyclo[2.2.1]heptane,
  (14) azabicyclo[3.1.1]heptane,
  (15) azabicyclo[4.1.0]heptane,
  (16) azabicyclo[3.2.1]octane,
  (17) azabicyclo[3.2.0]heptane,
  (18) azaspiro[2.5]octane,
  (19) dihydrothieno[3,2-c]pyridine,
  (20) dihydroimidazo[1,2-a]pyrazine, and
  (21) hexahydrofuro[3,2-b]pyrrole,
wherein $R^3$ is unsubstituted or substituted with one to eight substituents selected from $R^c$;
each $R^a$ is selected from:
  (1) —$OC_{1-6}$alkyl,
  (2) halogen,
  (3) —OH,
  (4) oxo,
  (5) —CN,
  (6) —$C_{3-6}$cycloalkyl, and
  (7) —$C_{2-5}$cycloheteroalkyl,
wherein halogen is F or $C_1$, and wherein each alkyl, cycloalkyl and cycloheteroalkyl is unsubstituted or substituted with one to six substituents selected from halogen, OH, $NH_2$, $NH(C_{1-6}$alkyl) and $N(C_{1-6}$alkyl$)_2$;
each $R^b$ is independently selected from the group consisting of:
  (1) —$CF_3$,
  (2) —$CHF_2$,
  (3) —$OCHF_2$,
  (4) $OCH_2CF_3$,
  (5) —$OCF_3$,
  (6) CN,
  (7) halogen,
  (8) —$Si(C_{1-6}$alkyl$)_3$,
  (9) —$C_{1-6}$alkyl,
  (10) —$OC_{1-6}$alkyl,
  (11) —$C_{3-6}$cycloalkyl,
  (12) —$C_{2-6}$cycloheteroalkyl,
  (13) —$C_{2-6}$alkyl-$C_{3-6}$cycloalkyl,
  (14) —$C_{2-6}$alkynyl-$C_{3-6}$cycloalkyl, and
  (15) heteroaryl,
wherein each $R^b$ is unsubstituted or substituted with one to five substituents selected from $R^f$;
each $R^c$ is independently selected from:
  (1) —$CF_3$,
  (2) —$CH_2CF_3$,
  (3) —$CHF_2$,
  (4) —$OCHF_2$,
  (5) —$OCF_3$,
  (6) CN,
  (7) OXO,
  (8) —OH,
  (9) halogen,
  (10) —$C_{1-6}$alkyl,
  (11) —$C_{2-6}$alkenyl,
  (12) —$C_{2-6}$alkynyl,
  (13) —$C_{3-6}$cycloalkyl,
  (14) —$C_{2-6}$cycloheteroalkyl,
  (15) —$C_{1-6}$alkyl-$C_{3-6}$cycloalkyl,
  (16) —$C_{1-6}$alkyl-$C_{2-6}$cycloheteroalkyl,
  (17) —$C_{1-6}$alkyl-aryl,
  (18) —$C_{1-6}$alkyl-heteroaryl,
  (19) —$C_{1-6}$alkenyl-$C_{3-6}$cycloalkyl,
  (20) —$C_{1-6}$alkenyl-aryl,
  (21) —$C_{1-6}$alkenyl heteroaryl,
  (22) —$C_{1-6}$alkenyl-$C_{2-6}$cycloheteroalkyl,
  (23) —$C_{2-6}$alkynyl-$C_{3-6}$cycloalkyl,
  (24) —$C_{2-6}$alkynyl-$C_{2-6}$cycloheteroalkyl,
  (25) —$C_{2-6}$alkynyl-aryl,
  (26) —$C_{2-6}$alkynyl heteroaryl,
  (27) —$OC_{1-6}$alkyl,
  (28) —$OC_{2-6}$ alkenyl,
  (29) —$OC_{2-6}$ alkynyl,
  (30) —$OC_{3-6}$ cycloalkyl,
  (31) —$OC_{2-6}$ heterocycloalkyl,
  (32) —$OC_{1-6}$alkyl-cycloalkyl,
  (33) —$OC_{1-6}$alkyl-cycloheteroalkyl,
  (34) —$OC_{1-6}$alkyl-aryl,
  (35) —$OC_{1-6}$ alkyl-heteroaryl,
  (36) —$S(O)_m R^L$,
  (37) —$S(O)R^L$,
  (38) —S—$R^L$,
  (39) —$C_{1-6}$alkyl-$S(O)_m R^L$,
  (40) —$C(O)R^L$,

(41) —C(O)C$_{1-6}$alkyl-R$^L$,
(42) —OC(O)R$^L$,
(43) —CO$_2$R$^L$,
(44) aryl, and
(45) heteroaryl,
wherein each R$^c$ is unsubstituted or substituted with one to five substituents selected from R$^g$;
R$^d$ is independently selected from:
  (1) hydrogen,
  (2) halogen,
  (3) OH,
  (4) OXO,
  (5) —C$_{1-6}$alkyl,
  (6) —OC$_{1-6}$alkyl,
  (7) NH$_2$,
  (8) NH(C$_{1-6}$alkyl), and
  (9) N(C$_{1-6}$alkyl)$_2$;
each R$^f$ is selected from:
  (1) halogen,
  (2) —C$_{1-6}$alkyl,
  (3) —OH,
  (4) —OC$_{1-6}$alkyl,
  (5) —OC$_{3-6}$cycloalkyl,
  (6) —OC$_{2-6}$cycloheteroalkyl,
  (7) CN,
  (8) —NH$_2$,
  (9) —NH(C$_{1-6}$alkyl),
  (10) —NH(C$_{3-6}$cycloalkyl),
  (11) —NH(C$_{2-6}$cycloheteroalkyl),
  (12) —N(C$_{1-6}$alkyl)$_2$,
  (13) —N(C$_{3-6}$cycloalkyl)$_2$, and
  (14) —N(C$_{2-6}$cycloheteroalkyl)$_2$,
wherein each alkyl, cycloalkyl, and cycloheteroalkyl is unsubstituted or substituted with one to three substituents independently selected from: —OH, halogen, cyano, and —S(O)$_2$CH$_3$;
each R$^g$ is selected from:
  (1) halogen,
  (2) C$_{1-6}$alkyl,
  (3) —OH,
  (4) —OC$_{1-6}$alkyl,
  (5) —S(O)m-C$_{1-6}$alkyl,
  (6) —CN,
  (7) —CF$_3$,
  (8) —OCHF$_2$, and
  (9) —OCF$_3$,
wherein each alkyl is unsubstituted or substituted with one to three substituents independently selected from: —OH, halogen, cyano, and —S(O)$_2$CH$_3$;
each R$^L$ is selected from:
  (1) —C$_{1-6}$alkyl,
  (2) —C$_{2-6}$alkenyl,
  (3) —C$_{3-6}$cycloalkyl,
  (4) —C$_{2-6}$cycloheteroalkyl,
  (5) aryl, and
  (6) heteroaryl,
wherein each alkyl, alkenyl, cycloalkyl, cycloheteroalkyl, aryl and heteroaryl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$; and
and each m is independently 0, 1 or 2.

2. The compound according to claim 1 wherein A is pyridine, wherein pyridine is unsubstituted or substituted with one to four substituents selected from R$^a$,
provided that both A and B are not pyridine;
or a pharmaceutically acceptable salt thereof.

3. The compound according to claim 1 wherein B is selected from:
  (1) pyridine,
  (2) pyrimidine, and
  (3) pyridazine,
wherein each B is unsubstituted or substituted with one to three substituents selected from R$^b$;
or a pharmaceutically acceptable salt thereof.

4. The compound according to claim 1 wherein B is pyridine, wherein pyridine is unsubstituted or substituted with one to three substituents selected from R$^b$; or a pharmaceutically acceptable salt thereof.

5. The compound according to claim 1 wherein R$^1$ is selected from:
  (1) —SO$_2$NH$_2$,
  (2) —C(O)NH$_2$, and
  (3) —OH;
or a pharmaceutically acceptable salt thereof.

6. The compound according to claim 1 wherein R$^3$ is selected from:
  (1) pyrrolidine,
  (2) azetidine,
  (3) piperidine,
  (4) piperazine,
  (5) azepane,
  (6) morpholine,
  (7) thiomorpholine,
  (8) oxazepane,
  (9) isoindoline,
  (10) dihydroisoquinoline,
  (11) azabicyclo[2.2.1]heptane,
  (12) azabicyclo[3.1.1]heptane,
  (13) azabicyclo[4.1.0]heptane,
  (14) azabicyclo[3.2.1]octane,
  (15) azabicyclo[3.2.0]heptane,
  (16) azaspiro[2.5]octane,
  (17) dihydrothieno[3,2-c]pyridine,
  (18) dihydroimidazo[1,2-a]pyrazine, and
  (19) hexahydrofuro[3,2-b]pyrrole,
wherein R$^3$ is unsubstituted or substituted with one to eight substituents selected from R$^c$;
or a pharmaceutically acceptable salt thereof.

7. The compound according to claim 1 wherein R$^3$ is selected from:
  (1) piperidine,
  (2) azepane, and
  (3) morpholine,
wherein R$^3$ is unsubstituted or substituted with one to six substituents selected from R$^c$;
or a pharmaceutically acceptable salt thereof.

8. The compound according to claim 1 wherein
A is selected from:
  (1) pyridine,
  (2) pyrimidine,
  (3) pyrazine,
  (4) indazole,
  (5) imidazo[1,2-a]pyridine,
  (6) pyrrolo[3,2-c]pyridine,
  (7) pyrrolo[2,3-b]pyridine,
  (8) pyrazole,
  (9) thiophene, and
  (10) 1,2,4-oxadiazole, wherein A is unsubstituted or substituted with one to four substituents selected from $R^a$, provided that both A and B are not pyridine;

B is selected from:
(1) pyridine,
(2) pyrimidine, and
(3) pyridazine, wherein each B is unsubstituted or substituted with one to four substituents selected from $R^b$;

$R^1$ is selected from:
(1) —$SO_3H$,
(2) —$SO_2NH_2$,
(3) —$SO_2C_{1-6}$alkyl,
(4) —$SO_2NH$—$C_{1-6}$alkyl,
(5) —$SO_2C_{3-6}$cycloalkyl,
(6) —$C(O)NH_2$,
(7) —$CO_2H$,
(8) —CN,
(9) halogen,
(10) —OH, and
(11) —$OC_{1-6}$alkyl, wherein each alkyl, and cycloalkyl is unsubstituted or substituted with one to three substituents selected from $R^d$;

$R^2$ is hydrogen;

$R^3$ is selected from:
(1) pyrrolidine,
(2) azetidine,
(3) piperidine,
(4) piperazine,
(5) azepane,
(6) morpholine,
(7) thiomorpholine,
(8) oxazepane,
(9) isoindoline,
(10) dihydroisoquinoline,
(11) azabicyclo[2.2.1]heptane,
(12) azabicyclo[3.1.1]heptane,
(13) azabicyclo[4.1.0]heptane,
(14) azabicyclo[3.2.1]octane,
(15) azabicyclo[3.2.0]heptane,
(16) azaspiro[2.5]octane,
(17) dihydrothieno[3,2-c]pyridine,
(18) dihydroimidazo[1,2-a]pyrazine, and
(19) hexahydrofuro[3,2-b]pyrrole, wherein $R^3$ is unsubstituted or substituted with one to eight substituents selected from $R^c$;

or a pharmaceutically acceptable salt thereof.

9. The compound according to claim 8 wherein
B is pyridine, wherein pyridine is unsubstituted or substituted with one to three substituents selected from $R^b$;

$R^1$ is selected from:
(1) —$SO_2NH_2$,
(2) —$C(O)NH_2$, and
(3) —OH;

$R^2$ is hydrogen;

$R^3$ is selected from:
(1) piperidine,
(2) azepane, and
(3) morpholine, wherein $R^3$ is unsubstituted or substituted with one to six substituents selected from $R^c$;

or a pharmaceutically acceptable salt thereof.

10. A compound selected from:
1) 2-(4,4-difluoropiperidin-1-yl)-N-(6-sulfamoylpyrazin-2-yl)-5-(trifluoromethyl)-nicotinamide;
2) 2-(4,4-difluoropiperidin-1-yl)-N-(4-hydroxypyrimidin-2-yl)-5-(trifluoromethyl)-nicotinamide;
3) 2-(4,4-difluoroazepan-1-yl)-N-[1-(methylsulfonyl)-1H-pyrrolo[2,3-b]pyridin-3-yl]-5-(trifluoromethyl) pyridine-3-carboxamide;
4) 5-chloro-2-(4,4-difluoroazepan-1-yl)-6-methyl-N-[1-(methylsulfonyl)-1H-pyrazol-4-yl]pyridine-3-carboxamide;
5) 5-chloro-2-(4,4-difluoroazepan-1-yl)-4,6-dimethyl-N-[1-(methylsulfonyl)-1H-pyrazol-4-yl]pyridine-3-carboxamide;
6) N-{1-[(2-aminoethyl)sulfonyl]-1H-pyrazol-4-yl}-5-chloro-2-(4,4-difluoroazepan-1-yl)-6-methylpyridine-3-carboxamide;
7) 2-(4,4-difluoroazepan-1-yl)-N-[1-(methylsulfonyl)-1H-indazol-3-yl]-5-(trifluoromethyl)-pyridine-3-carboxamide;
8) 2-(4,4-difluoroazepan-1-yl)-N-[1-(methylsulfonyl)-1H-pyrrolo[3,2-c]pyridin-3-yl]-5-(trifluoromethyl) pyridine-3-carboxamide;
9) N-[1-(cyclopropylsulfonyl)-1H-pyrazol-4-yl]-2-(4,4-difluoroazepan-1-yl)-5-(trifluoro-methyl)pyridine-3-carboxamide;
10) N-[5-cyclopropyl-1-(methylsulfonyl)-1H-pyrazol-4-yl]-2-(4,4-difluoroazepan-1-yl)-5-(trifluoromethyl) pyridine-3-carboxamide;
11) 2-cyclopropyl-4-(4,4-difluoroazepan-1-yl)-N-(2-sulfamoylpyridin-4-yl)pyrimidine-5-carboxamide;
12) 6-cyclopropyl-3-(4,4-difluoroazepan-1-yl)-N-(2-sulfamoylpyridin-4-yl)pyridazine-4-carboxamide;
13) 2-(azepan-1-yl)-N-(3-cyano-1,2,4-oxadiazol-5-yl)-5-(trifluoromethyl)pyridine-3-carboxamide;
14) 2-(azepan-1-yl)-N-(2-methyl-5-sulfamoylthiophen-3-yl)-5-(trifluoro-methyl)pyridine-3-carboxamide;
15) 4-(4,4-difluoroazepan-1-yl)-2-methyl-N-(2-sulfamoylpyridin-4-yl)pyrimidine-5-carboxamide;
16) 3-(4,4-difluoroazepan-1-yl)-N-(2-sulfamoylpyridin-4-yl)-6-(trifluoromethyl)-pyridazine-4-carboxamide; and
17) 2-(azepan-1-yl)-N-(3-bromoimidazo[1,2-a]pyridin-6-yl)-5-(trifluoromethyl)-pyridine-3-carboxamide;

or a pharmaceutically acceptable salt thereof.

11. A pharmaceutical composition comprising a compound of claim 1, or a pharmaceutically acceptable salt thereof, and a pharmaceutically acceptable carrier.

12. A method of treating a disorder, condition or disease that is responsive to the inhibition of Nav1.8 channel activity in a patient in need thereof comprising administration of a therapeutically effective amount of a compound according to claim 1, or a pharmaceutically acceptable salt thereof.

13. The method of claim 12 wherein the disorder is selected from: pain disorder, a cough disorder, an acute itch disorder or chronic itch disorder.

14. The method of claim 13 wherein the disorder is a pain disorder.

15. The method of claim 14 wherein the pain disorder is selected from: acute pain, inflammatory pain, or neuropathic pain.

* * * * *